US009951064B2

(12) United States Patent
Bryan et al.

(10) Patent No.: US 9,951,064 B2
(45) Date of Patent: Apr. 24, 2018

(54) AZAINDAZOLE COMPOUNDS AS INHIBITORS OF T790M CONTAINING EGFR MUTANTS

(71) Applicant: Genentech, Inc., South San Francisco, CA (US)

(72) Inventors: Marian C. Bryan, San Francisco, CA (US); Bryan Chan, Foster City, CA (US); Francois Diederich, Basel (CH); Jennafer Dotson, Belmont, CA (US); Emily Hanan, Redwood City, CA (US); Timothy Heffron, Burlingame, CA (US); Michael Lainchbury, Harlow (GB); Robert Heald, Harlow (GB); Eileen M. Seward, Harlow (GB)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 15/152,947

(22) Filed: May 12, 2016

(65) Prior Publication Data

US 2016/0257682 A1 Sep. 8, 2016

Related U.S. Application Data

(63) Continuation of application No. PCT/US2014/044401, filed on Jun. 26, 2014.

(60) Provisional application No. 61/950,497, filed on Mar. 10, 2014, provisional application No. 61/840,716, filed on Jun. 28, 2013.

(51) Int. Cl.
| | |
|---|---|
| *C07D 471/04* | (2006.01) |
| *C07D 519/00* | (2006.01) |
| *A61K 31/517* | (2006.01) |
| *A61K 31/5386* | (2006.01) |
| *A61K 31/506* | (2006.01) |
| *A61K 31/5377* | (2006.01) |
| *A61K 45/06* | (2006.01) |
| *A61K 31/541* | (2006.01) |

(52) U.S. Cl.
CPC .......... *C07D 471/04* (2013.01); *A61K 31/506* (2013.01); *A61K 31/517* (2013.01); *A61K 31/5377* (2013.01); *A61K 31/5386* (2013.01); *A61K 31/541* (2013.01); *A61K 45/06* (2013.01); *C07D 519/00* (2013.01)

(58) Field of Classification Search
CPC .. C07D 471/04; C07D 519/00; A61K 31/517; A61K 31/5386; A61K 31/506; A61K 31/5377; A61K 31/541; A61K 45/06
USPC .................................................. 514/210.18
See application file for complete search history.

(56) References Cited

U.S. PATENT DOCUMENTS 6,268,391 B1    7/2001   Dickerson et al.

FOREIGN PATENT DOCUMENTS

| WO | 2004/006846 A2 | 1/2004 | |
|---|---|---|---|
| WO | 2011/079231 A1 | 6/2011 | |
| WO | 2013/014448 A1 | 1/2013 | |
| WO | WO 2013017480 A1 * | 2/2013 | ........... C07D 471/04 |
| WO | 2014/081718 A1 | 5/2014 | |

OTHER PUBLICATIONS

Alexander Levitzki, Annu Rev Pharmacol Toxicol, (2013), 53, p. 161-185.*
(Author Not Identified) Ansel's Pharmaceutical Dosage Forms and Drug Delivery Systems (Table of Contents only, in 6 pages), Allen et al., Ed., 8th edition, Philadelphia, PA:Lippincott Williams & Wilkins (2004).
(Author Not Identified) Handbook of Pharmaceuticals Excipients (Cover and Table of Contents only, total in 6 pages), Rowe et al., Ed., 5th edition, Grayslake, IL:Pharmaceutical Press (2005).
(Author Not Identified) Remington: The Science and Practice of Pharmacy (Cover and Table of Contents only, total in 4 pages), Gennaro et al., 20th edition, Philadelphia, PA:Lippincott Williams & Wilkins (2000).
Abraham "Phosphatidylinositol 3-kinase related kinases", Curr Opin Immunol, 8(3):412-418 (1996).
Adams et al., "Development of the Proteasome Inhibitor Velcade™ (Bortezomib)", Cancer Investigation, 22(2):304-311 (2004).
Alli et al., "Fatty acid synthase inhibitors are chemopreventive for mammary cancer in neu-N transgenic mice", Oncogene, 24(1):39-46 (2005).
Ashby, "CaaX converting enzymes", Current Opinion in Lipidology, 9(2):99-102 (1998).
Balasubramanian et al., "Isoform-specific histone deacetylase inhibitors: The next step?", Cancer Lett, 280(2):211-221 (2009).
Ball, "p21: structure and functions associated with cyclin-CDK binding", Progress in Cell Cycle Research, 3:125-134( 1997).
Bertrand, "Inside HDAC with HDAC inhibitors", Eur J Med Chem, 45:2095-2116 (2010).
Bolen et al., "Leukocyte Protein Tyrosine Kinases: Potential Targets for Drug Discovery", Annu Rev Immunol ,15:371-404 (1997).
Bouma et al., "Activity of disulfiram (bis(diethylthiocarbamoyl)disulphide) and ditiocarb (diethyldithiocarbamate) against metronidazole-sensitive and -resistant Trichomonas vaginalis and Tritrichomonas foetus", J Antimicrob Chemother, 42(6):817-820 (1998).
Brekken et al., "Selective inhibition of vascular endothelial growth factor (VEGF) receptor 2 (KDR/Flk-1) activity by a monoclonal anti-VEGF antibody blocks tumor growth in mice", Cancer Res, 60:5117-5124 (2000).
Brodt et al., "Inhibition of the Type I Insulin-like Growth Factor Receptor Expression and Signaling: Novel Strategies for Antimetastatic Therapy", Biochemical Pharmacology, 60:1101-1107 (2000).

(Continued)

*Primary Examiner* — Yong L Chu

(57) ABSTRACT

This invention relates to novel compounds which are inhibitors of T790M containing EGFR mutants, to pharmaceutical compositions containing them, to processes for their preparation, and to their use in therapy for the prevention or treatment of cancer.

15 Claims, No Drawings

(56) References Cited

OTHER PUBLICATIONS

Bruns et al., "Blockade of the Epidermal Growth Factor Receptor Signaling by a Novel Tyrosine Kinase Inhibitor Leads to Apoptosis of Endothelial Cells and Therapy of Human Pancreatic Carcinoma", Cancer Res, 60(11):2926-2935 ( 2000).
Canman et al., "The role of ATM in DNA damage responses and cancer", Oncogene, 17(25):3301-3308 (1998).
Chen et al., "DNA Vaccines Encoding Full-Length or Truncated Neu Induce Protective Immunity against Neu-expressing Mammary Tumors", Cancer Res, 58(9):1965-1971 (1998).
Ciardiello et al., "EGFR antagonists in cancer treatment", N Engl J Med, 358(11):1160-1174 (2008).
Einzig et al., "'Randomized Phase II Trial of Either Fluorouracil (F), Parenterai Hydroxyurea (H), lnterferon-α-2a (I) and Filgrastim (G) or Doxorubicin/Docetaxel (AD) in Patients (PTS) with Advanced Gastric Cancer: Eastern Cooperative Oncology Group (ECOG) Study EST 6296' & 'Impact of Highly Active Antiretroviral Therapy (HAART) on Prognosis in Patients with HIV-Associated Non-Hodgkin's Lymphoma: An Analysis of ECOG Trial E1494'", Poster (in 4 pages), San Francisco, CA, pp. 166a & 294a (May 12-15, 2001).
Fantin et al., "Attenuation of LDH-A expression uncovers a link between glycolysis, mitochondrial physiology, and tumor maintenance", Cancer Cell, 9(6):425-434 (2006).
Feling et al., "Salinosporamide A: A Highly Cytotoxic Proteasome Inhibitor from a Novel Microbial Source, a Marine Bacterium of the New Genus *Salinospora*", Angew Chem Int Ed Engl. 42(3):355-357 (2003).
Forastiere, "Use of Paclitaxel (TAXOL®) in Squamous Cell Carcinoma of the Head and Neck", Seminars in Oncology, 20(4 Suppl 3):56-60 (1993).
Gorre et al., "Clinical Resistance to STI-571 Cancer Therapy Caused by BCR-ABL Gene Mutation or Amplification", Science, 293(5531):876-880 (2001).
Göttlicher et al., "Valproic acid defines a novel class of HDAC inhibitors inducing differentiation of transformed cells", EMBO J, 20(24):6969-6978 (2001).
Green et al., "Monoclonal antibody therapy for solid tumors", Cancer Treat Rev, 26(4):269-286 (2000).
Holmes et al., "Phase II Trial of Taxol, an Active Drug in the Treatment of Metastatic Breast Cancer", Journal of the National Cancer Institute, 83(24):1797-1805 ( 1991).
Hynes et al., "ErbB receptors and signaling pathways in cancer", Curr Opin Cell Biol, 321:177-184 (2009).
Ignoffo et al., Cancer Chemotherapy Pocket Guide (Cover and Table of Contents only, total in 7 pages), Bernstein, Philadelphia, PA:Lippincott-Raven Publishers (1998).
International Preliminary Report on Patentability issued in International Application No. PCT/US2014/044401, dated Dec. 29, 2015, in 7 pages.
International Search Report issued in International Application No. PCT/US2014/044401, dated Aug. 22, 2014, in 5 pages.
Jackson, "DNA-dependent Protein Kinase", Int J Biochem Cell Biol, 29(7):935-938 (1997).
Jia et al., "Synergistic antileukemic interactions between 17-AAG and UCN-01 involve interruption of RAF/MEK- and AKT-related pathways", Blood, 102(5):1824-1832 (2003).
Kath, "Patent focus: inhibitors of tumour cell growth", Expert Opinion on Therapeutic Patents, 10(6):803-818 (2000).
Kearns et al., "Paclitaxel Pharmacokinetics and Pharmacodynamics", Seminars in Oncology, 22(3 Suppl 6):16-23 (1995).
Kingston et al., "New Trends in Natural Products Chemistry / Synthesis and Structure-Activity Relationships of Taxol Derivatives as Anticancer Agents", Studies in Organic Chemistry, 26:219-235 (1986).
Kitada et al., "Reversal of Chemoresistance of Lymphoma Cells by Antisense-Mediated Reduction of bcl-2 Gene Expression", Antisense Research and Development, 4:71-79 (1994).

Kuhn et al., "Potent activity of carfilzomib, a novel, irreversible inhibitor of the ubiquitin-proteasome pathway, against preclinical models of multiple myeloma", Blood, 110(9):3281-3290 (2007).
Kumar, "Taxol-induced Polymenization of Purified Tubulin", J Biol Chem, 256(20):10435-10441 (1981).
Lackey et al., "The Discovery of Potent eRaf1 Kinase Inhibitors", Bioorganic & Medicinal Chemistry Letters, 10(3):223-226 (2000).
Lee et al., "Radicicol represses the transcriptional function of the estrogen receptor by suppressing the stabilization of the receptor by heat shock protein 90", Molecular and Cellular Endocrinology, 188:47-54 (2002).
Liotta et al., Cancer—Principles and Practice of Ooncology (Cover and Table of Contents only, total in 48 pages), Devita et al., Ed., 6th edition, Philadelphia, PA: Lippineott Williams & Wilkins (2001).
Liu et al., "Discovery of Small Molecule Mer Kinase Inhibitors for the Treatment of Pediatric Acute Lymphoblastic Leukemia", ACS Med Chem Lett, 3(2):129-134 (2012).
Lofts et al. New Molecular Targets for Cancer Chemotherapy ", Growth Factor Receptors Targets" (with Cover and Table of Contents, total in 25 pages), Kerr et al., Ed., Salem, MA:CRC Press, Inc., 45-57 (1994).
Lynch et al., "Activating Mutations in the Epidermal Growth Factor Receptor Underlying Responsiveness of Non-Small-Cell Lung cancer to Gefitinib", N. Engl. J. Med., 350(21):2129-2139 (2004).
Markman, "Taxol: An Important New Drug in the Management of Epithelial Ovanian Cancer", Yale J Biol Med, 64(6):583-590 (1991).
Marks et al., "Dimethyl sulfoxide to vorinostat: development of this histone deacetylase inhibitor as an anticancer drug", Nat Biotechnol, 25(1):84-90 (2007).
Martínez-Lacac et al., "RAS transformation causes sustained activation of epidermal growth factor receptor and elevation of mitogen-activated protein kinase in human mammary epithelial cells", Int. J. Cancer, 88:44-52 (2000).
Massagué et al., "Serine/Threonine Kinase Receptors: Mediators of Transforming Growth Factor Beta Family Signals", Cancer Surveys, 27:41-64 (1996).
McGuire et al., "Taxol: A Unique Antineoplastic Agent with Significant Activity in Advanced Ovarian Epithelial Neoplasms", Annals of Internal Medicine, 111(4):273-279 (1989).
Miller et al., "Bronchioloalveolar pathologic subtype and smoking history predict sensitivity to gefitinib in advanced non-small-cell lung cancer", J Clin Oncol, 22(6):1103-1109 (2004).
Oliff, "Farnesyltransferase inhibitors: targeting the molecular basis of cancer", Biochimica et Biophysica Acta, 1423:C19-C30 (1999).
Paez et al., "EGFR Mutations in Lung Cancer: Correlation with Clinical Response to Gefitinib Therapy", Science, 304: 1497-1500 (Jun. 4, 2004).
Pao et al., "EGF receptor gene mutations are common in lung cancers from 'never smokers' and are associated with sensitivity of tumors to gefitimb and erlotinib", P Natl Acad Sci USA, 101(36):13306-13311 (Sep. 7, 2004).
Pao et al., "Rational, biologically based treatment of EGFR-mutant non-small-cell lung cancer", Nat Rev Cancer, 10(11):760-774 (2010).
Philip et al., "Potential for protein kinase C inhibitors in cancer therapy", Cancer Treatment and Research, 78:3-27 (1995).
Reilly et al., "HER-2/neu Is a Tumor Rejection Target in Tolerized HER-2/neu Transgenic Mice", Cancer Res, 60:3569-3576 (2000).
Revill et al., "Panobinostat", Drugs of the Future, 32(4):315-322 (2007).
Richon et al., "Histone deacetylase inhibitor selectively induces p21WAF1 expression and gene-associated histone acetylation", Proc Natl Acad Sci U S A, 97(18): 10014-10019 (2000).
Rosania et al., "Targeting hyperproliferative disorders with cyclin dependent kinase inhibitors", Expert Opinion on Therapeutic Patents, 10(2):215-230 (2000).
Scharovsky et al., "Inhibition of ras Oncogene: A Novel Approach to Antineoplastic Therapy" Journal of Biomedical Science 7:292-298 (2000).
Schiff et al., "Promotion of microtubule assembly in vitro by taxol", Nature, 277(5698):665-667(1979).

(56) References Cited

OTHER PUBLICATIONS

Schiff et al., "Taxol stabilizes microtubules in mouse fibroblast cells", Proc Natl Acad Sci USA, 77(3):1561-1565 (1980).
Schreiber et al., "Transforming Growth Factor-α: A More Potent Angiogenic Mediator Than Epidermal Growth Factor", Science, 232(4755):1250-1253 (1986).
Sharma et al., Epidermal growth factor receptor mutations in lung cancer, Nat Rev Cancer, 7(3):169-181 (2007).
Shawver et al., "Receptor tyrosine kinases as targets for inhibition of angiogenesis", Drug Discovery Today, 2(2):50-63 (1997).
Sinha et al., "Implications for Src Kinases in Hematopoiesis: Signal Transduction Therapeutics", Journal of Hematotherapy & Stem Cell Research, 8(5):465-480 (1999).
Smithgall, "SH2 and SH3 domains: Potential targets for anti-cancer drug design", J Pharmacol Toxicol Methods, 34(3):125-132 (1995).
Stenger et al., "Vorinostat in cutaneous T-cell lymphoma", Community Oncology, 4:384-386 (2007).
Stern, "Tyrosine kinase signalling in breast cancer ErbB family receptor tyrosine kinases", Breast Cancer Res, 2:176-183 (2000).
Tamborini et al., "A New Mutation in the KIT ATP Pocket Causes Acquired Resistance to Imatinib in a Gastrointestinal Stromal Tumor Patient", Gastroenterology, 127(1):294-299 (2004).
Tennant et al., "Targeting metabolic transformation for cancer therapy", Nat Rev Cancer, 10:267-277 (2010).
Vinodhkumar et al., "Romidepsin (depsipeptide) induced cell cycle arrest, apoptosis and histone hyperacetylation in lung carcinoma cells (A549) are associated with increase in p21 and hypophosphorylated retinoblastoma proteins expression", Biomed Pharmacother, 62(2):85-93 (2008).
Wani et al., "Plant antitumor agents. VI. The isolation and structure of taxol, a novel antileukemic and antitumor agent from Taxus brevifolia", J Am Chem Soc, 93(9):2325-2327 (1971).
Waters et al., "Phase I Clinical and Pharmacokinetic Study of Bcl-2 Antisense Oligonucleotide Therapy in Patients With Non-Hodgkin's Lymphoma", J Clin Oncol, 18(9):1812-1823 (2000).
Williamson et al., "Epigallocatechin gallate, the main polyphenol in green tea, binds to the T-cell receptor, CD4: Potential for HIV-1 therapy", J Allergy Clin Immunol, 118(6):1369-1374 (2006).
Woo et al., "Taxol inhibits progression of congenital polycystic kidney disease", Nature, 368(6473):750-753 (1994).
Written Opinion of the International Searching Authority issued in International Application No. PCT/US2014/044401, dated Aug. 22, 2014, in 6 pages.
Yamamoto et al., "Ras-Induced Transformation and Signaling Pathway", J. Biochem, 126(5):799-803 (1999).
Yarden et al., "Untangling the ErbB signalling network", Nat Rev Mol Cell Biol, 2: 127-137 (Feb. 2001).
Yen et al., "Heregulin selectively upregulates vascular endothelial growth factor secretion in cancer cells and stimulates angiogenesis", Oncogene, 19(31):3460-3469 (2000).
Yun et al., "The T7 90M mutation in EGFR kinase causes drug resistance by increasing the affinity for ATP", Proc Natl Acad Sci USA, 105(6):2070-2075 (2008).
Zhong et al., "Modulation of Hypoxia-inducible Factor 1α Expression by the Epidermal Growth Factor/Phosphatidylinositol 3-Kinase/PTEN/AKT/FRAP Pathway in Human Prostate Cancer Cells: Implications for Tumor Angiogenesis and Therapeutics", Cancer Res, 60(6):1541-1545 (2000).
Zhou et al., "Novel mutant-selective EGFR kinase inhibitors against EGFR T790M", Nature, 462(7276):1070-1074 (2009).
The European Communication, dated Apr. 4, 2017, in the corresponding European Patent Application No. 14740116.0.

\* cited by examiner

AZAINDAZOLE COMPOUNDS AS INHIBITORS OF T790M CONTAINING EGFR MUTANTS

CROSS-REFERENCE TO RELATED APPLICATIONS

This application is a continuation of International Application No. PCT/US2014/044401 having an international filing date of Jun. 26, 2014, and which claims benefit under U.S.C. § 119 to U.S. Provisional Application No. 61/950, 497 filed on Mar. 10, 2014, and U.S. Provisional Application No. 61/840,716 filed on Jun. 28, 2013, both of which are hereby incorporated by reference in their entirety.

FIELD OF INVENTION

This invention relates to novel compounds which are inhibitors of T790M containing EGFR mutants, to pharmaceutical compositions containing them, to processes for their preparation, and to their use in therapy for the prevention or treatment of cancer in a human.

BACKGROUND OF THE INVENTION

The HER family receptor tyrosine kinases are important mediators of cell growth, differentiation and survival. The receptor family includes four distinct members including epidermal growth factor receptor (EGFR, ErbB1, or HER1) HER2 (ErbB2), HER3 (ErbB3) and HER4 (ErbB4). Upon ligand binding the receptors form homo and heterodimers and subsequent activation of the intrinsic tyrosine kinase activity leads to receptor auto-phosphorylation and the activation of downstream signaling molecules (Yarden and Sliwkowski). De-regulation of EGFR by overexpression or mutation has been implicated in many types of human cancer including colorectal, pancreatic, gliomas, head and neck and lung cancer and several EGFR targeting agents have been developed over the years (Ciardiello, Hynes). Erlotinib (Tarceva®), a reversible inhibitor of the EGFR tyrosine kinase was approved by the United States Food and Drug Administration (FDA) for the treatment of recurrent NSCLC and pancreatic cancer. Other reversible EGFR tyrosine kinase inhibitors ("TKI") include gefitinib and lapatinib.

The most impressive single agent activity of EGFR tyrosine kinase inhibitors is observed in a subset of non-small cell lung cancer (NSCLC) patients whose tumors harbor somatic kinase domain mutations, whereas clinical benefit in wild-type EGFR patients is greatly diminished (Lynch 2004, Paez 2004). The most common somatic mutations of EGFR are exon 19 deletions with delta 746-750 the most prevalent mutation and the exon 21 amino acid substitutions with L858R the most frequent mutation (Sharma). Intriguingly, this is a subset of patients characterized by high prevalence of adenocarcinomas, females, never-smokers and Asians (Miller, Pao 2004).

Patients with EGFR-mutant lung cancer eventually develop disease progression after 10-14 months on EGFR tyrosine kinase inhibitors (Pao 2010). Over 50% of patients that progress on tyrosine kinase inhibitors acquire a secondary mutation in the kinase domain at position 790 that is known as the gatekeeper residue. Replacement of threonine by the bulkier residue methionine (T790M mutation) leads to an increase in the affinity for ATP relative to mutant forms of EGFR associated with clinical benefits from EGFR TKI treatment and to a reduced affinity for TKIs which taken together confers drug resistance (Yun). Similar gatekeeper mutations in the kinase domain that cause drug resistance are seen in Abl and Kit (Tamborini, Gone). The present invention demonstrates the generation of selective molecules that specifically inhibit T790M containing EGFR mutants.

REFERENCES

Yarden, Y., Sliwkowski, M X. Untangling the ErbB signalling network. Nature Review Mol Cell Biol. 2001 February; 2(2):127-37.

Ciardiello, F., and Tortora, G. (2008). EGFR antagonists in cancer treatment. The New England journal of medicine 358, 1160-1174.

Hynes N E, MacDonald G. ErbB receptors and signaling pathways in cancer. Curr Opin Cell Biol. 2009 April; 21(2):177-84.

Lynch, T. J., Bell, D. W., Sordella, R., Gurubhagavatula, S., Okimoto, R. A., Brannigan, B. W., Harris, P. L., Haserlat, S. M., Supko, J. G., Haluska, F. G., et al. (2004). Activating mutations in the epidermal growth factor receptor underlying responsiveness of non-small-cell lung cancer to gefitinib. The New England journal of medicine 350, 2129-2139.

Paez, J. G., Janne, P. A., Lee, J. C., Tracy, S., Greulich, H., Gabriel, S., Herman, P., Kaye, F. J., Lindeman, N., Boggon, T. J., et al. (2004). EGFR mutations in lung cancer: correlation with clinical response to gefitinib therapy. Science (New York, N.Y. 304, 1497-1500.

Sharma S V, Bell D W, Settleman J, Haber D A. Epidermal growth factor receptor mutations in lung cancer. Nat Rev Cancer. 2007 March; 7(3):169-81.

Miller V A, Kris M G, Shah N, Patel J, Azzoli C, Gomez J, Krug L M, Pao W, Rizvi N, Pizzo B, Tyson L, Venkatraman E, Ben-Porat L, Memoli N, Zakowski M, Rusch V, Heelan R T. Bronchioloalveolar pathologic subtype and smoking history predict sensitivity to gefitinib in advanced non-small-cell lung cancer. J Clin Oncol. 2004 Mar. 15; 22(6):1103-9.

Pao W, Miller V, Zakowski M, Doherty J, Politi K, Sarkaria I, Singh B, Heelan R, Rusch V, Fulton L, Mardis E, Kupfer D, Wilson R, Kris M, Varmus H. EGF receptor gene mutations are common in lung cancers from "never smokers" and are associated with sensitivity of tumors to gefitinib and erlotinib. Proc Natl Acad Sci USA. 2004 Sep. 7; 101(36):13306-11.

Pao W, Chmielecki J. Rational, biologically based treatment of EGFR-mutant non-small-cell lung cancer. Nat Rev Cancer. 2010 November; 10(11):760-74.

Yun C H, Mengwasser K E, Toms A V, Woo M S, Greulich H, Wong K K, Meyerson M, Eck M J. The T790M mutation in EGFR kinase causes drug resistance by increasing the affinity for ATP. Proc Natl Acad Sci USA. 2008 Feb. 12; 105(6):2070-5.

Tamborini E, Bonadiman L, Greco A, Albertini V, Negri T, Gronchi A, Bertulli R, Colecchia M, Casali P G, Pierotti M A, Pilotti S. A new mutation in the KIT ATP pocket causes acquired resistance to imatinib in a gastrointestinal stromal tumor patient. Gastroenterology. 2004 July; 127 (1):294-9.

Gone M E, Mohammed M, Ellwood K, Hsu N, Paquette R, Rao P N, Sawyers C L. Clinical resistance to STI-571 cancer therapy caused by BCR-ABL gene mutation or amplification. Science. 2001 Aug. 3; 293(5531):876-80.

SUMMARY OF THE INVENTION

1. A compound of Formula (I)

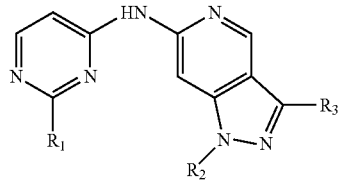

wherein, $R_1$ is $C_3$-$C_7$heterocycloalkyl, heteroaryl, —O($C_1$-$C_6$alkyl), or —$NR_aR_b$, wherein said $C_3$-$C_7$heterocycloalkyl and heteroaryl may be further substituted with one to five $R_f$ groups;

$R_2$ is hydrogen, $C_1$-$C_6$alkyl, $C_3$-$C_7$cycloalkyl or $C_3$-$C_7$heterocycloalkyl;

$R_3$ is $C_1$-$C_6$alkyl, $C_3$-$C_7$heterocycloalkyl, $C_3$-$C_7$cycloalkyl, —O($C_1$-$C_6$alkyl), CN, —$NR_aR_b$, —NHC(O)($C_1$-$C_3$alkyl), —C(O)$NR_aR_b$ or heteroaryl;

wherein each $R_f$ is independently selected from the group consisting of $C_1$-$C_3$alkyl, alkoxy, amino, hydroxy, alkylamino, amide, urea, oxo, halo, pyrazolyl, imidazolyl, triazolyl, CN, —NHC(O)($C_1$-$C_3$alkyl), acyl, sulfonyl, sulfoxide, sulfonamide, sulfoximinyl, —$(CH_2)_mC_3$-$C_7$heterocycloalkyl, —O($C_1$-$C_6$alkyl), and C(O)$OR_a$;

wherein each $R_a$ is independently H or $C_1$-$C_6$alkyl, each $R_b$ is independently H, $C_1$-$C_6$alkyl, alkoxy, amino, —$(CH_2)_mC(O)NH_2$, —$(CH_2)_mC_3$-$C_7$cycloalkyl, —$(CH_2)_mC_3$-$C_7$heterocycloalkyl or —$(CH_2)_m$heteroaryl, or $R_a$ and $R_b$ together may form a $C_3$-$C_7$cycloalkyl, $C_3$-$C_7$heterocycloalkyl or heteroaryl ring, wherein said $C_3$-$C_7$cycloalkyl, $C_3$-$C_7$heterocycloalkyl and heteroaryl may each be further substituted with one to three groups selected from the group consisting of halo, hydroxy, $C_1$-$C_3$alkyl, amino, oxo, amide, sulfonyl, sulfoxide, sulfoximinyl, sulfonamide, alkoxy, CN and acyl;

each m is independently 0, 1, 2 or 3;

or a pharmaceutically acceptable salt thereof.

This invention also relates to pharmaceutical compositions of compounds of Formula (I).

This invention also relates to a method of inhibiting T790M containing EGFR mutants.

This invention also relates to a method of treating cancer, use of compounds of Formula (I) in therapy, and use of compounds of Formula (I) in manufacturing a medicament for treating cancer. This invention also relates to method of preparing compounds of Formula (I).

DETAILED DESCRIPTION OF THE INVENTION

Definitions

As used herein, unless defined otherwise in a claim, the term "acyl" refers to the group —C(O)R', where R' is alkyl, $C_3$-$C_6$cycloalkyl, or heterocyclyl, as each is defined herein.

As used herein, unless defined otherwise in a claim, the term "alkoxy" refers to the group —OR', where R' is $C_1$-$C_4$alkyl or $C_3$-$C_6$cycloalkyl as defined above. Examples of "alkoxy" include methoxy, ethoxy, isopropoxy, propoxy, butoxy, t-butoxy, isobutoxy, cyclopropoxy, and cyclobutoxy, and halogenated forms thereof, e.g. fluoromethoxy and difluoromethoxy.

As used herein, unless defined otherwise in a claim, the term "alkyl" (or "alkylene") refers to a straight or branched hydrocarbon chain having from one to twelve carbon atoms, which may be unsubstituted or substituted, saturated or unsaturated with multiple degrees of substitution, for example one, two or three, included within the present invention. Examples of substituents are selected from the group consisting of halo, trifluoromethyl, difluoromethyl, amino, alkylamino, cyano, sulfonyl, sulfonamide, sulfoxide, amide, hydroxy, alkoxy, ester, carboxylic acid and alkylthio. Examples of "alkyl" as used herein include, but are not limited to, methyl, ethyl, propyl, isopropyl, isobutyl, n-butyl, t-butyl, isopentyl, n-pentyl, and the like, as well as substituted versions thereof. Examples of substituted alkyl include but are not limited to, hydroxymethyl, difluoromethyl and trifluoromethyl. Unsaturated alkyl can also be referred to as alkenyl or alkynyl, which may be substituted as described above. Examples of unsaturated alkyl include, but are not limited to, ethenyl or vinyl (—CH═$CH_2$), prop-1-enyl (—CH═$CHCH_3$), prop-2-enyl (—$CH_2$CH═$CH_2$), 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, hexa-1,3-dienyl, ethynyl (—C≡CH), prop-1-ynyl (—C≡$CCH_3$), prop-2-ynyl (propargyl, —$CH_2$C≡CH), but-1-ynyl, but-2-ynyl and but-3-ynyl.

As used herein, unless defined otherwise in a claim, the term "alkylamino" refers to the group —NR'R", wherein R' is H, $C_1$-$C_6$alkyl or $C_3$-$C_6$cycloalkyl, and R" is $C_1$-$C_6$alkyl or $C_3$-$C_6$cycloalkyl, examples of alkylamino include, but are not limited to, methylamino, dimethylamino, ethylamino, diethylamino, propylamino and cyclopropylamino.

As used herein, unless defined otherwise in a claim, the term "amide" refers to the group —C(O)NR'R", wherein R' and R" are each independently H, $C_1$-$C_6$alkyl, or $C_3$-$C_6$cycloalkyl; examples of amide include, but are not limited to, —C(O)$NH_2$, —C(O)$NHCH_3$, and —C(O)N$(CH_3)_2$.

As used herein, unless defined otherwise in a claim, the term "aryl" refers to an aromatic, hydrocarbon, ring system. The ring system may be monocyclic or fused polycyclic (e.g., bicyclic, tricyclic, etc.), substituted or unsubstituted. In various embodiments, the monocyclic aryl ring is $C_5$-$C_{10}$, or $C_5$-$C_7$, or $C_5$-$C_6$, where these carbon numbers refer to the number of carbon atoms that form the ring system. A $C_6$ ring system, i.e. a phenyl ring, is an aryl group. In various embodiments, the polycyclic ring is a bicyclic aryl group, where examples of bicyclic aryl groups include are $C_8$-$C_{12}$, or $C_9$-$C_{10}$. A naphthyl ring, which has 10 carbon atoms, is a polycyclic aryl group. Examples of substituents for aryl are described below in the definition of "optionally substituted".

As used herein, unless defined otherwise in a claim, the term "cyano" refers to the group —CN.

As used herein, unless defined otherwise in a claim, "cycloalkyl" refers to a non-aromatic, substituted or unsubstituted, saturated or partially unsaturated hydrocarbon ring group. Examples of substituents are described in the definition of "optionally substituted". In one example, the cycloalkyl group is 3 to 12 carbon atoms ($C_3$-$C_{12}$). In other examples, cycloalkyl is $C_3$-$C_8$, $C_3$-$C_{10}$ or $C_5$-$C_{10}$. In other examples, the cycloalkyl group, as a monocycle, is $C_3$-$C_8$, $C_3$-$C_6$ or $C_5$-$C_6$. In another example, the cycloalkyl group, as a bicycle, is $C_7$-$C_{12}$. In another example, the cycloalkyl group, as a spiro system, is $C_5$-$C_{12}$. Examples of monocyclic cycloalkyl include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl and cyclododecyl. Exemplary arrangements of bicyclic cycloalkyls having 7 to 12 ring atoms include, but are not limited to, [4,4], [4,5], [5,5], [5,6] or [6,6] ring systems. Exemplary bridged bicyclic cycloalkyls include, but are not limited to, bicyclo[2.2.1]heptane, bicyclo[2.2.2]octane and bicyclo[3.2.2]nonane. Examples of spiro cycloalkyl include, spiro[2.2]pentane, spiro[2.3]hexane, spiro[2.4]heptane, spiro[2.5]octane and spiro[4.5]decane.

As used herein, unless defined otherwise in a claim, the term "ester" refers to the group —C(O)OR', where R' is $C_1$-$C_6$alkyl, or $C_3$-$C_6$cycloalkyl.

As used herein, unless defined otherwise in a claim, the term "heterocycle" "heterocycloalkyl" or "heterocyclyl" refers to unsubstituted and substituted mono- or polycyclic non-aromatic ring system containing 2 to 12 ring carbon atoms and 1 to 3 ring hetero atoms. Polycyclic ring systems can be fused bi- or tri-cyclic, spiro or bridged. Examples of heteroatoms include N, O, and S, including N-oxides, sulfur oxides, and dioxides. In one embodiment, the ring is three to eight-membered and is either fully saturated or has one or more degrees of unsaturation. Multiple degrees of substitution are included within the present definition. Examples of substituents are defined hereunder. Examples of "heterocyclic" groups include, but are not limited to tetrahydrofuranyl, pyranyl, 1,4-dioxanyl, 1,3-dioxanyl, oxolanyl, oxetanyl, 2-oxa-6-azaspiro[3.3]heptan-6-yl, piperidinyl, pyrrolidinyl, morpholinyl, azetidinyl, piperazinyl, pyrrolidinonyl, piperazinonyl, pyrazolidinyl, imidazolinyl, imidazolidinyl, and their various tautomers.

As used herein, unless defined otherwise in a claim, the term "heteroaryl", unless defined otherwise in a claim, refers to an aromatic ring system containing 1 to 9 carbon(s) and at least one heteroatom. Examples of heteroatoms include N, O, and S. Heteroaryl may be monocyclic or polycyclic, substituted or unsubstituted. A monocyclic heteroaryl group may have 2 to 6 ring carbon atoms and 1 to 3 ring hetero atoms in the ring, while a polycyclic heteroaryl may contain 3 to 9 ring carbon atoms and 1 to 5 ring hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include but are not limited to: benzofuranyl, benzothiophenyl, furanyl, imidazolyl, indolyl, azaindolyl, azabenzimidazolyl, benzoxazolyl, benzthiazolyl, benzothiadiazolyl, benzotriazolyl, benzoimidazolyl, tetrazinyl, tetrazolyl, isothiazolyl, oxazolyl, isoxazolyl, pyrazinyl, pyrazolyl, pyridazinyl, pyridinyl, pyrimidinyl, pyrrolyl, quinolinyl, quinazolinyl, quinoxalinyl, triazinyl, thiazolyl and thiophenyl. Examples of substituents for heteroaryl are described below in the definition of "optionally substituted".

As used herein, unless defined otherwise in a claim, the term "sulfoximinyl" refers to the group —S(O)(NH)R, wherein R is $C_1$-$C_6$alkyl, or $C_3$-$C_6$cycloalkyl.

As used herein, unless defined otherwise in a claim, the term "urea" refers to the group —NR'C(O)NR", wherein R' and R" are each independently H, $C_1$-$C_6$alkyl, or $C_3$-$C_6$cycloalkyl.

As used herein, unless defined otherwise in a claim, the term "optionally" means that the subsequently described event(s) may or may not occur, and includes both event(s) that occur and event(s) that do not occur.

As used herein, unless defined otherwise in a claim, the phrase "optionally substituted" or variations thereof denote an optional substitution, including multiple degrees of substitution, with one or more substituent group, for example, one, two or three. The phrase should not be interpreted as duplicative of the substitutions herein described and depicted. Exemplary optional substituent groups include acyl, sulfonyl, amino, sulfonamide, sulfoxide, alkoxy, cyano, halo, urea, ester, carboxylic acid, amide, hydroxy, oxo, and nitro.

As used herein, unless defined otherwise in a claim, the term "treatment" refers to alleviating the specified condition, eliminating or reducing one or more symptoms of the condition, slowing or eliminating the progression of the condition As used herein, unless defined otherwise in a claim, the term "effective amount" means that amount of a drug or pharmaceutical agent that will elicit the biological or medical response of a tissue, system, animal, or human that is being sought, for instance, by a researcher or clinician.

As used herein, unless defined otherwise in a claim, the term "therapeutically effective amount" means any amount which, as compared to a corresponding subject who has not received such amount, results in treatment of a disease, disorder, or side effect, or a decrease in the rate of advancement of a disease or disorder. The term also includes within its scope amounts effective to enhance normal physiological function. For use in therapy, therapeutically effective amounts of a compound of Formula I, as well as salts thereof, may be administered as the raw chemical. Additionally, the active ingredient may be presented as a pharmaceutical composition.

The present invention also relates to compounds of Formula (I), wherein $R_1$ is $C_3$-$C_7$heterocycloalkyl; or a pharmaceutically acceptable salt thereof.

The present invention also relates to compounds of Formula (I), wherein $R_1$ is heteroaryl; or a pharmaceutically acceptable salt thereof.

The present invention also relates to compounds of Formula (I), wherein $R_1$ is —$NR_aR_b$; or a pharmaceutically acceptable salt thereof.

The present invention also relates to compounds of Formula (I), wherein $R_1$ is heteroaryl or $C_3$-$C_7$heterocycloalkyl, $R_f$ is sulfonyl or alkoxy, $R_3$ is —$NR_aR_b$ or heteroaryl, $R_2$ is $C_1$-$C_6$alkyl, or a pharmaceutically acceptable salt thereof.

The present invention also relates to compounds of Formula (I), wherein $R_1$ is piperdinyl or pyrazolyl, or a pharmaceutically acceptable salt thereof.

The present invention also relates to any of the above compounds, wherein $R_f$—$SO_2$(cyclopropyl), halo, hydroxy, $C_1$-$C_6$alkyl or methoxy, or a pharmaceutically acceptable salt thereof.

The present invention also relates to any of the above compounds, wherein $R_2$ is $C_1$-$C_6$alkyl;

The present invention also relates to any of the above compounds, wherein $R_3$ is $C_1$-$C_3$alkyl, $C_3$-$C_7$heterocycloalkyl, heteroaryl, —$NR_aR_b$ or —$C(O)NR_aR_b$; or a pharmaceutically acceptable salt thereof.

The present invention also relates to any of the above compounds, wherein $R_1$ is a $C_3$-$C_7$heterocycloalkyl or heteroaryl selected from the group consisting of piperidinyl and pyrazolyl, wherein said $C_3$-$C_7$heterocycloalkyl or heteroaryl may be further substituted with one to three $R_f$ groups selected from $C_1$-$C_6$alkyl, alkoxy, hydroxyl, halo, sulfonyl, and sulfonamide; or a pharmaceutically acceptable salt thereof.

The present invention also relates to any of the above compounds, wherein $R_2$ is isopropyl, sec-butyl, or 1,1,1-trifluoropropan-2-yl; or a pharmaceutically acceptable salt thereof.

The present invention also relates to a pharmaceutical composition comprising any of the above compounds and a pharmaceutically acceptable carrier.

The present invention also relates to a method of treating cancer comprising administering to a human in need thereof an effective amount of any of the above compounds or a pharmaceutically acceptable salt thereof in a pharmaceutical composition.

The present invention also relates to a use of any of the above compounds in the preparation of a medicament for the treatment of cancer.

The present invention also relates to any of the above compounds or a pharmaceutically acceptable salt thereof for use in therapy.

The present invention also relates to a method of treating cancer comprising co-administering to a human in need thereof a combination of an effective amount of an anti-neoplastic agent in a pharmaceutical composition and any of the above compounds or a pharmaceutically acceptable salt thereof in a pharmaceutical composition.

The present invention also relates to a use of a combination of an anti-neoplastic agent and any of the above compounds or a pharmaceutically acceptable salt thereof in preparation of a medicament for the treatment of cancer.

The present invention also relates to any of the above methods, wherein said cancer is non-small cell lung cancer.

The present invention also relates to any of the above uses, wherein said cancer is non-small cell lung cancer.

This invention also relates to any one of the examples in the Experimental section.

Typically, but not absolutely, the salts of the present invention are pharmaceutically acceptable salts. Salts encompassed within the term "pharmaceutically acceptable salts" refer to non-toxic salts of the compounds of this invention. Salts of the disclosed compounds containing a basic amine or other basic functional group may be prepared by any method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, choline, quinine, quinoline, and basic amino acid such as lysine and arginine.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

The compound of Formula (I) may exist in solid or liquid form. In the solid state, it may exist in crystalline or noncrystalline form, or as a mixture thereof. The skilled artisan will appreciate that pharmaceutically acceptable solvates may be formed for crystalline or noncrystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compound of Formula (I) or a salt thereof may exist in stereoisomeric forms (e.g., it contains one or more asymmetric carbon atoms). The individual stereoisomers (enantiomers and diastereomers) and mixtures of these are included within the scope of the present invention. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as 2H, 3H, 11C, 13C, 14C, 15N, 17O, 18O, 31P, 32P, 35S, 18F, 36Cl, 123I and 125I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as 3H, 14C are incorporated, are useful in drug and/or substrate tissue distribution assays. Tritiated, i.e., 3H, and carbon-14, i.e., 14C, isotopes are commonly used for their ease of preparation and detectability. 11C and 18F isotopes are useful in PET (positron emission tomography), and 125I isotopes are useful in SPECT (single photon emission computerized tomography), all useful in brain imaging. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Pharmaceutical Compositions

The invention further provides a pharmaceutical composition (also referred to as pharmaceutical formulation) comprising a compound of Formula I or pharmaceutically acceptable salt, thereof and one or more excipients (also referred to as carriers and/or diluents in the pharmaceutical arts). The excipients are acceptable in the sense of being compatible with the other ingredients of the formulation and not deleterious to the recipient thereof (i.e., the patient).

In accordance with another aspect of the invention there is provided a process for the preparation of a pharmaceutical composition comprising mixing (or admixing) a compound of Formula I or salt thereof with at least one excipient.

Pharmaceutical compositions may be in unit dose form containing a predetermined amount of active ingredient per unit dose. Such a unit may contain a therapeutically effective dose of the compound of Formula I or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

The compounds of the invention may be administered by any acceptable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

Such compositions may be prepared by any method known in the art of pharmacy, for example, by bringing into association the active ingredient with the excipient(s). A typical formulation is prepared by mixing a compound of the present invention and a carrier or excipient. Examples of carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to an acceptable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, binders, lubricants, disintegrating agents, and coloring agents can also be incorporated into the mixture. Examples of binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In one embodiment, tablets and capsules are used for delivery of the pharmaceutical composition.

The present invention provides a method of treatment in a mammal, for example, a human, suffering from cancer, for example, lung cancer and pancreatic cancer. Such treatment comprises the step of administering a therapeutically effective amount of a compound of Formula I or salt thereof to said mammal, for example, a human. Treatment can also comprise the step of administering a therapeutically effective amount of a pharmaceutical composition containing a compound of Formula I or salt thereof to said mammal, for example, a human.

While it is possible that, for use in therapy, a therapeutically effective amount of a compound of Formula I or salt thereof may be administered as the raw chemical, it is typically presented as the active ingredient of a pharmaceutical composition or formulation.

The precise therapeutically effective amount of a compound or salt thereof of the invention will depend on a number of factors, including, but not limited to, the age and weight of the subject (patient) being treated, the precise disorder requiring treatment and its severity, the nature of the pharmaceutical formulation/composition, and route of administration, and will ultimately be at the discretion of the attending physician or veterinarian. Typically, a compound of Formula I or salt thereof will be given for the treatment in the range of about 0.1 to 100 mg/kg body weight of recipient (patient, mammal) per day and more usually in the range of 0.1 to 10 mg/kg body weight per day. Acceptable daily dosages may be from about 1 to about 2000 mg/day, and for example, from about 1 to about 100 mg/day. This amount may be given in a single dose per day or in a number (such as two, three, four, five, or more) of sub-doses per day such that the total daily dose is the same. An effective amount of a salt thereof may be determined as a proportion of the effective amount of the compound of Formula I per se. Similar dosages should be appropriate for treatment (including prophylaxis) of the other conditions referred herein for treatment. In general, determination of appropriate dosing can be readily arrived at by one skilled in medicine or the pharmacy art.

Indications and Methods of Treatment

The compounds of the present invention inhibit the activity of T790M containing EGFR mutants. The compositions and methods provided herein can potentially be useful for the treatment of cancer including tumors such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can potentially be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, meduUoblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplasia syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of or related to the above identified conditions.

In one embodiment, the compositions and methods provided herein are useful for the treatment of lung cancer and pancreatic cancer, most specifically, non-small cell lung cancer (NSCLC).

Combinations

When a compound of Formula (I) is administered for the treatment of cancer, the term "co-administering" and derivatives thereof as used herein refers to either simultaneous administration or any manner of separate sequential administration of a T790M inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. If the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracycline, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors including non-receptor tyrosine kinase inhibitors, receptor tyrosine kinase inhibitors, angiogenesis inhibitors; immunotherapeutic agents; proapoptotic agents; and cell cycle signaling inhibitors.

Examples of a further active ingredient or ingredients for use in combination or co-administered with the present T790M inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine, N-tert-butyl ester, β-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, for example, non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2-)O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethy)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S, 10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl) methyl] methylamino] benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

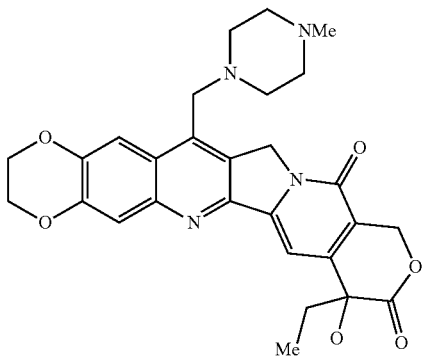

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFR), platelet derived growth factor receptor (PDGFR), erbB2, erbB4, vascular endothelial growth factor receptor (VEGFR), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

Erlotinib (Tareva®) is an EGFR inhibitor. Gefitinib (Iressa®) is another drug of this type. Erlotinib specifically targets the epidermal growth factor receptor (EGFR) tyrosine kinase, which is highly expressed and occasionally mutated in various forms of cancer. It binds in a reversible fashion to the adenosine triphosphate (ATP) binding site of the receptor. For the signal to be transmitted, two EGFR molecules need to come together to form a homodimer. These then use the molecule of ATP to trans-phosphorylate each other on tyrosine residues, which generates phospho-tyrosine residues, recruiting the phosphotyrosine-binding proteins to EGFR to assemble protein complexes that transduce signal cascades to the nucleus or activate other cellular biochemical processes. By inhibiting the binding of ATP, formation of phosphotyrosine residues in EGFR is not possible and the signal cascades are not initiated.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed erb family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development.

For instance, examples of cyclin dependent kinases, including CDK2, CDK4, and CDK6 and inhibitors for the same are described in, for instance, Rosania et al, Exp. Opin. Ther. Patents (2000) 10(2):215-230. Further, p21WAF1/CIP1 has been described as a potent and universal inhibitor of cyclin-dependent kinases (Cdks) (Ball et al., *Progress in Cell Cycle Res.*, 3: 125 (1997)). Compounds that are known to induce expression of p21WAF1/CIP1 have been implicated in the suppression of cell proliferation and as having tumor suppressing activity (Richon et al., *Proc. Nat Acad. Sci. U.S.A.* 97(18): 10014-10019 (2000)), and are included as cell cycle signaling inhibitors.

Modulators of the Retinoid Acid Receptor have been used to treat leukemias. The pathology of the leukemia is associated with the abnormal accumulation of immature progenitor cells that are sensitive to retinoc acid therapy. The majority of cases of acute promyelocytic leukemia (APL), also called acute myeloid leukemia subtype M3, involve a chromosomal translocation of chromosomes 15 and 17 that causes genetic fusion of the retinoic acid receptor (RAR) gene to the promyelocytic leukemia (PML) gene. This fusion PML-RAR protein is responsible for preventing immature myeloid cells from differentiating into more mature cells. This block in differentiation is and subsequent accumulation of less differentiated cells is thought to cause leukemia. ATRA, Tretinoin, acts on PML-RAR to lift this block, causing the immature promyelocytes to differentiate to normal mature blood cells thus decreasing promyelocytes and promoting a population of terminally differentiated cells with a restricted lifespan. Talazorole is an experimental drug in the same class as Tretinoin.

Epigenetic alterations have been implicated in virtually all types of human cancers. Cancer specific changes are often associated with silencing of tumor suppressor genes via histone modifications and modifications to DNA including DNA hypermethylation. Epigenetic pharmaceuticals control regulatory regions associated with tumor suppressor genes by causing conformational changes in histones and removing repressive modifications to DNA. These changes directly affect the formation and progression of cancer. Examples of epigenetic agents include histone deacetylase inhibitors and DNA methylation inhibitors.

Histone deacetylase inhibitors (HDAC inhibitors, HDI) are a class of compounds that interfere with the function of histone deacetylases Inhibitors of histone deacetylases have been shown to be useful in the treatment of cutaneous T-cell lymphoma. They are being investigated in the clinic for multiple other tumor types. Examples of HDAC inhibitors approved for use are Vorinostat and Romidepsin. These compounds are thought to inhibit the activity of HDACs and result in the accumulation of acetylation to histones promoting gene expression.

Azacitidine (INN) or 5-azacytidine, sold under the trade name Vidaza, is a chemical analogue of cytidine, a nucleoside present in DNA and RNA. Azacitidine and its deoxy derivative, decitabine (also known as 5-aza-2'deoxycytidine), are used in the treatment of myelodysplastic syndrome and are currently under study for other tumor indications. Azacitidine acts as a false substrate and potent inhibitor of DNA methyltransferases leading to reduction of DNA methylation. DNA methyltransferases incorporate azacitidine into DNA during replication and into RNA during transcription in the cell Inhibition of DNA methylation occurs through the formation of stable complexes between the molecule and DNA methyltransferases, thereby saturating cell methylation machinery. This results in a loss of DNA methylation and can affect the way cell regulation proteins, such as transcriptional machinery, are able to associate with the DNA.

Examples of such HDAC inhibitors include:
1. Vorinostat, including pharmaceutically acceptable salts thereof. Marks et al., Nature Biotechnology 25, 84 to 90 (2007); Stenger, Community Oncology 4, 384-386 (2007).

Vorinostat has the following chemical structure and name:

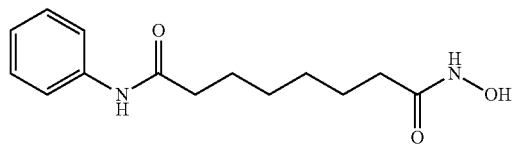 [SMILES: O=C(CCCCCCC(=O)Nc1ccccc1)NO]

N-hydroxy-N'-phenyl-octanediamide

2. Romidepsin, including pharmaceutically acceptable salts thereof.

Vinodhkumar et al., Biomedicine & Pharmacotherapy 62 (2008) 85-93.

Romidepsin, has the following chemical structure and name:

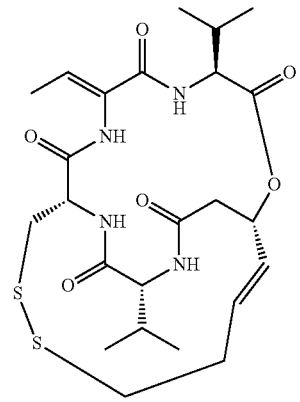 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

(1S,4S,7Z,10S,16E,21R)-7-ethylidene-4,21-di(propan-2-yl)-2-oxa-12,13-dithia-5,8,20,23-tetrazabicyclo[8.7.6]tricos-16-ene-3,6,9,19,22-pentone 3. Panobinostat, including pharmaceutically acceptable salts thereof. Drugs of the Future 32(4): 315-322 (2007).

Panobinostat, has the following chemical structure and name:

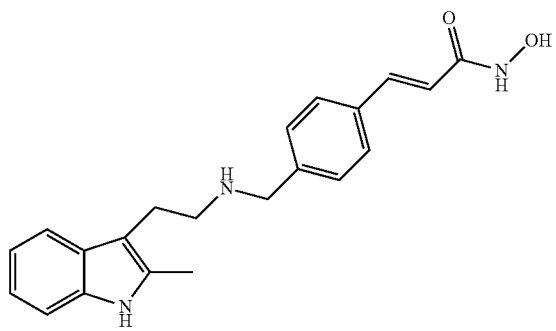 [SMILES: Cc1[nH]c2ccccc2c1CCNCc1ccc(/C=C/C(=O)NO)cc1]

(2E)-N-hydroxy-3-[4-([{2-(2-methyl-1H-indol-3-yl)ethyl]amino}methyl)phenyl]acrylamide 4. Valproic acid, including pharmaceutically acceptable salts thereof. Gottlicher, et al., EMBO J. 20(24): 6969-6978 (2001).

Valproic acid, has the following chemical structure and name:

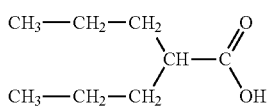

2-propylpentanoic acid

5. Mocetinostat (MGCD0103), including pharmaceutically acceptable salts thereof. Balasubramanian et al., Cancer Letters 280: 211-221 (2009).

Mocetinostat, has the following chemical structure and name:

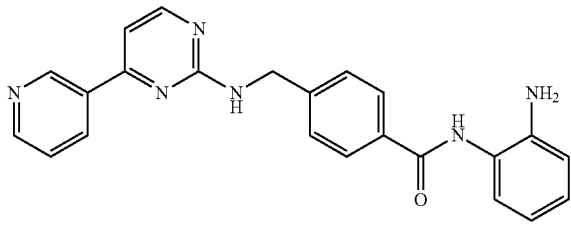 [SMILES: Nc1ccccc1NC(=O)c1ccc(CNc2nccc(-c3cccnc3)n2)cc1]

N-(2-Aminophenyl)-4-[[(4-pyridin-3-ylpyrimidin-2-yl)amino]methyl] benzamide

Further examples of such HDAC inhibitors are included in Bertrand European Journal of Medicinal Chemistry 45, (2010) 2095-2116.

Proteasome inhibitors are drugs that block the action of proteasomes, cellular complexes that break down proteins, like the p53 protein. Several proteasome inhibitors are marketed or are being studied in the treatment of cancer. Examples of proteasome inhibitors for use in combination herein include:

1. Bortezomib (Velcade®), including pharmaceutically acceptable salts thereof. Adams J, Kauffman M (2004), Cancer Invest 22 (2): 304-11.

Bortezomib has the following chemical structure and name.

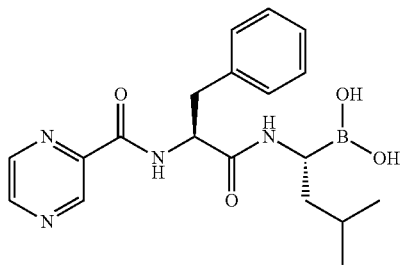 [SMILES: CC(C)C[C@H](NC(=O)[C@H](Cc1ccccc1)NC(=O)c1cnccn1)B(O)O]

[(1R)-3-methyl-1-({(2S)-3-phenyl-2-[(pyrazin-2-ylcarbonyl)amino]propanoyl}amino)butyl]boronic acid 2. Disulfiram, including pharmaceutically acceptable salts thereof.

Bouma et al. (1998). J. Antimicrob. Chemother. 42 (6): 817-20.

Disulfiram has the following chemical structure and name.

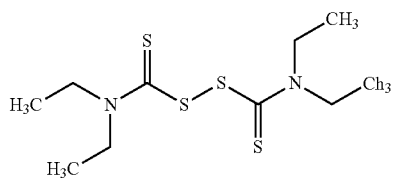

1,1',1'',1'''-[disulfanediylbis(carbonothioylnitrilo)]tetraethane

3. Epigallocatechin gallate (EGCG), including pharmaceutically acceptable salts thereof. Williamson et al., (December 2006), The Journal of Allergy and Clinical Immunology 118 (6): 1369-74.

Epigallocatechin gallate has the following chemical structure and name.

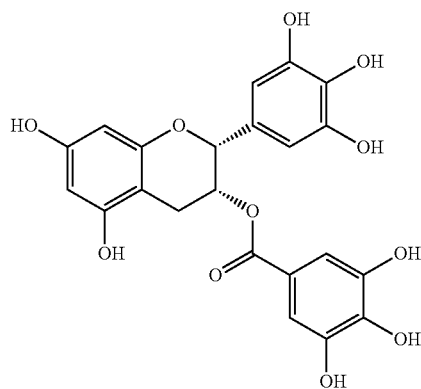 [SMILES: O=C(O[C@@H]1Cc2c(O)cc(O)cc2O[C@@H]1c1cc(O)c(O)c(O)c1)c1cc(O)c(O)c(O)c1]

[(2R,3R)-5,7-dihydroxy-2-(3,4,5-trihydroxyphenyl)chroman-3-yl]3,4,5-trihydroxybenzoate 4. Salinosporamide A, including pharmaceutically acceptable salts thereof. Feling et at., (2003), Angew. Chem. Int. Ed. Engl. 42 (3): 355-7.

Salinosporamide A has the following chemical structure and name.

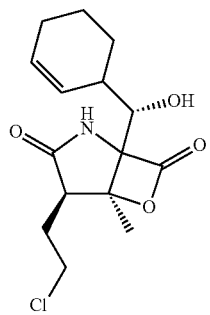 [SMILES: C[C@@]12OC(=O)C1([C@@H](O)C1C=CCCC1)NC(=O)[C@@H]2CCCl]

(4R,5S)-4-(2-chloroethyl)-1-((1S)-cyclohex-2-enyl(hydroxy)methyl)-5-methyl-6-oxa-2-azabicyclo3.2.0heptane-3,7-dione 5. Carfilzomib, including pharmaceutically acceptable salts thereof. Kuhn D J, et al, Blood, 2007, 110:3281-3290.

Carfilzomib has the following chemical structure and name.

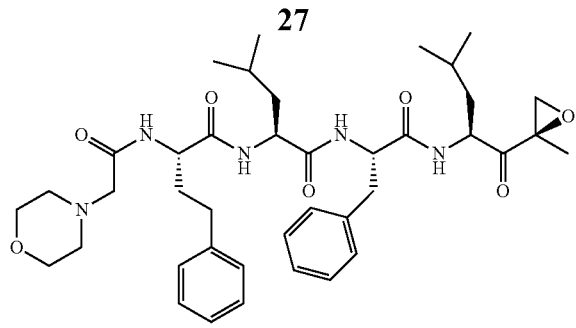

(S)-4-methyl-N—((S)-1-(((S)-4-methyl-1-((R)-2-methyl-oxiran-2-yl)-1-oxopentan-2-yl)amino)-1-oxo-3-phenyl-propan-2-yl)-2-((S)-2-(2-morpholinoacetamido)-4-phenylbutanamido)pentanamide The 70 kilodalton heat shock proteins (Hsp70s) and 90 kilodalton heat shock proteins (Hsp90s) are a families of ubiquitously expressed heat shock proteins. Hsp70s and Hsp90s are over expressed certain cancer types. Several Hsp70s and Hsp90s inhibitors are being studied in the treatment of cancer. Examples of Hsp70s and Hsp90s inhibitors for use in combination herein include:

1. 17-AAG(Geldanamycin), including pharmaceutically acceptable salts thereof. Jia W et al. Blood. 2003 Sep. 1; 102(5):1824-32.

17-AAG(Geldanamycin) has the following chemical structure and name.

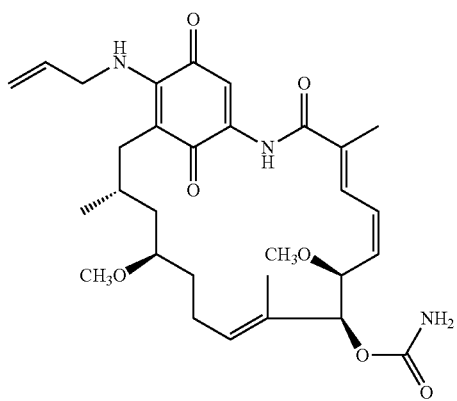

17-(Allylamino)-17-demethoxygeldanamycin

2. Radicicol, including pharmaceutically acceptable salts thereof (Lee et al., Mol Cell Endocrinol. 2002, 188, 47-54)

Radicicol has the following chemical structure and name.

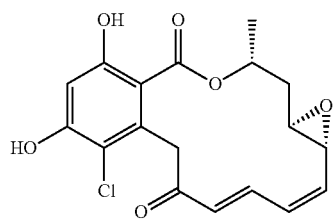 [SMILES: C[C@@H]1C[C@H]2O[C@@H]2/C=C\C=C\C(=O)Cc2c(Cl)c(O)cc(O)c2C(=O)O1]

(1aR,2Z,4E,14R,15aR)-8-chloro-9,11-dihydroxy-14-methyl-15,15a-dihydro-1aH-benzo[c]oxireno[2,3-k][1]oxacyclotetradecine-6,12(7H,14H)-dione Inhibitors of cancer metabolism—Many tumor cells show a markedly different metabolism from that of normal tissues. For example, the rate of glycolysis, the metabolic process that converts glucose to pyruvate, is increased, and the pyruvate generated is reduced to lactate, rather than being further oxidized in the mitochondria via the tricarboxylic acid (TCA) cycle. This effect is often seen even under aerobic conditions and is known as the Warburg Effect.

Lactate dehydrogenase A (LDH-A), an isoform of lactate dehydrogenase expressed in muscle cells, plays a pivotal role in tumor cell metabolism by performing the reduction of pyruvate to lactate, which can then be exported out of the cell. The enzyme has been shown to be upregulated in many tumor types. The alteration of glucose metabolism described in the Warburg effect is critical for growth and proliferation of cancer cells and knocking down LDH-A using RNA-1 has been shown to lead to a reduction in cell proliferation and tumor growth in xenograft models.

D. A. Tennant et. al., Nature Reviews, 2010, 267.

P. Leder, et. al., Cancer Cell, 2006, 9, 425.

High levels of fatty acid synthase (FAS) have been found in cancer precursor lesions. Pharmacological inhibition of FAS affects the expression of key oncogenes involved in both cancer development and maintenance Alli et al. Oncogene (2005) 24, 39-46. doi:10.1038

Inhibitors of cancer metabolism, including inhibitors of LDH-A and inhibitors of fatty acid biosynthesis (or FAS inhibitors), are acceptable for use in combination with the compounds of this invention.

In one embodiment, the cancer treatment method of the claimed invention includes the co-administration a compound of Formula (I) and/or a pharmaceutically acceptable salt thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors including non-receptor tyrosine kinase, tyrosine kinase inhibitors, angiogenesis inhibitors, immunotherapeutic agents, proapoptotic agents, cell cycle signaling inhibitors; HDAC inhibitors, proteasome inhibitors; and inhibitors of cancer metabolism.

In another embodiment, the present invention relates to co-administering a compound of the present invention in combination with erlotinib and/or gefitinib for the treatment of cancer.

In another embodiment, the present invention relates to co-administering a compound of the present invention in combination with erlotinib and/or gefitinib for the treatment of non-small cell lung cancer.

In one embodiment, the present invention relates to a use of a combination of erlotinib and/or gefitinib and a compound of the present invention or a pharmaceutically acceptable salt thereof in preparation of a medicament for the treatment of cancer.

In one embodiment, the present invention relates to a use of a combination of erlotinib and/or gefitinib and a compound of the present invention or a pharmaceutically acceptable salt thereof in preparation of a medicament for the treatment of non-small cell lung cancer.

EXPERIMENTALS

General Experimental Conditions $^1$H NMR spectra were recorded at ambient temperature using either a Varian Unity Inova (400 MHz) spectrometer with a triple resonance 5 mm probe, an Avance III (300 MHz) spectrometer or a Bruker Ultrashield (400 MHz or 500 MHz) spectrometer. Chemical shifts are expressed in ppm relative to tetramethylsilane. The following abbreviations have been used: br=broad signal, s=singlet, d=doublet, dd=double doublet, t=triplet, q=quartet, m=multiplet.

Microwave experiments were carried out using a CEM Discover, Smith Synthesiser or a Biotage Initiator 60™, which uses a single-mode resonator and dynamic field tuning, both of which give reproducibility and control. Temperatures from 40-250° C. can be achieved and pressures of up to 30 bar can be reached.

High Pressure Liquid Chromatography-Mass Spectrometry (LCMS) experiments to determine retention times (RT) and associated mass ions were performed using one of the following methods. The spectrometers have an electrospray source operating in positive and negative ion mode. Additional detection was achieved using a Sedex 85 evaporative light scattering detector.

Method A:

Experiments performed on an Agilent 1100 HPLC with Agilent MSD mass spectrometer using ESI as ionization source using an Agilent ZORBAX SB-C18 100×3.0 mm column and a 0.7 mL/min flow rate. The solvent system was a gradient starting with 98% water with 0.05% TFA (solvent A) and 2% acetonitrile with 0.05% TFA (solvent B), ramping up to 2% solvent A and 98% solvent B over 25.5 min. The final solvent system was held constant for a further 2.5 min.

Method B:

Experiments performed on an Agilent 1200 HPLC with Agilent MSD mass spectrometer using ESI as ionization source using an Agilent ZORBAX SB-C18 30×2.1 mm column and a 0.4 mL/min flow rate. The solvent system was a gradient starting with 97% water with 0.05% TFA (solvent A) and 3% acetonitrile with 0.05% TFA (solvent B), ramping up to 5% solvent A and 95% solvent B over 7 min. The final solvent system was held constant for a further 1.5 min.

Method C:

Experiments performed on a Waters Acquity UHPLC with Waters-LCT Premier XE mass spectrometer using ESI as ionization source using an Acquity UPLC BEH C18, 1.7 um, 2.1*50 mm column and a 0.6 mL/min flow rate. The solvent system was a gradient starting with 98% water with 0.05% TFA (solvent A) and 2% acetonitrile with 0.05% TFA (solvent B), ramping up to 2% solvent A and 98% solvent B over 17 min. The final solvent system was held constant for a further 1.5 min.

Method D:

Experiments performed on a Waters Acquity UHPLC with Waters-LCT Premier XE mass spectrometer using ESI as ionization source using an Acquity UPLC BEH C18, 1.7 um, 2.1*50 mm column and a 0.6 mL/min flow rate. The solvent system was a gradient starting with 98% water with 0.05% TFA (solvent A) and 2% acetonitrile with 0.05% TFA (solvent B), ramping up to 2% solvent A and 98% solvent B over 7.5 min. The final solvent system was held constant for a further 1.0 min.

Method E:

Experiments performed on a Waters Micromass ZQ2000 quadrupole mass spectrometer linked to a Waters Acquity UPLC system with a PDA UV detector.

LC Column—Acquity BEH C18 1.7 µm 100×2.1 mm, maintained at 40° C. and a 0.4 mL/min flow rate. The mobile phase consisted of formic acid 0.1% in water (solvent A) and formic acid 0.1% in acetonitrile (solvent B).

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Method F:

Experiments performed on a Waters Micromass ZQ2000 quadrupole mass spectrometer linked to a Waters Acquity UPLC system with a PDA UV detector.

LC Column—Acquity Shield RP18 1.7 µm, 100×2.1 mm or Acquity HSS T3 1.8 µm, 100×2.1 mm, maintained at 40° C. and a 0.4 mL/min flow rate. The mobile phase consisted of formic acid 0.1% in water (solvent A) and formic acid 0.1% in acetonitrile (solvent B).

| Gradient - Time | flow mL/min | % A | % B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Method G:

Experiments performed on an Shimadzu 1100 HPLC with Shimadzu MSD mass spectrometer using ESI as ionization source using an SHIMADU XR-ODS 50×3.0 mm column and a 0.9 mL/min flow rate. The solvent system was a gradient starting with 95% water with 0.1% formic acid (solvent A) and 5% acetonitrile (solvent B), ramping up to 100% solvent B over 2 min. The final solvent system was held constant for a further 1.1 min.

Method H:

Experiments performed on an Shimadzu 1100 HPLC with Shimadzu MSD mass spectrometer using ESI as ionization source using an Phenomenex Gemini-NX C18 50×3.0 mm column and a 0.9 mL/min flow rate. The solvent system was a gradient starting with 90% water with 0.04% NH3 (solvent A) and 10% acetonitrile (solvent B), ramping up to 35% solvent A and 65% solvent B over 4 min. The final solvent system was held constant for a further 0.2 min.

Method I:

Experiments performed on an Shimadzu 1100 HPLC with Shimadzu MSD mass spectrometer using ESI as ionization source using an Shimadzu Shim-pack XR-ODS III 50×2.0 mm column and a 0.7 mL/min flow rate. The solvent system was a gradient starting with 95% water with 0.1% FA (solvent A) and 5% acetonitrile (solvent B), ramping up to 60% solvent A and 40% solvent B over 1 min. The final solvent system was held constant for a further 1 min.

Method J:

Experiments performed on an Shimadzu 1100 HPLC with Shimadzu MSD mass spectrometer using ESI as ionization source using an SHIMADU XR-ODS 50×3.0 mm column and a 1 mL/min flow rate. The solvent system was a gradient starting with 95% water with 0.05% TFA (solvent A) and 5% acetonitrile with 0.05% TFA (solvent B), ramping up to 5% solvent A and 95% solvent B over 4.2 min. The final solvent system was held constant for a further 1 min.

Method K:

Experiments performed on an Shimadzu 1100 HPLC with Shimadzu MSD mass spectrometer using ESI as ionization source using an SHIMADU XR-ODS 50×3.0 mm column and a 1 mL/min flow rate. The solvent system was a gradient starting with 95% water with 0.05% TFA (solvent A) and 5% acetonitrile with 0.05% TFA (solvent B), ramping up to 25% solvent A and 75% solvent B over 2 min. The final solvent system was held constant for a further 1.2 min.

Method L:

Experiments performed on an Shimadzu 1100 HPLC with Shimadzu MSD mass spectrometer using ESI as ionization source using an SHIMADU XR-ODS 50×3.0 mm column and a 1 mL/min flow rate. The solvent system was a gradient starting with 95% water with 0.05% TFA (solvent A) and 5% acetonitrile with 0.05% TFA (solvent B), ramping up to 35% solvent A and 65% solvent B over 4.5 min. The final solvent system was held constant for a further 0.7 min.

Method M:

Experiments performed on an Shimadzu 1100 HPLC with Shimadzu MSD mass spectrometer using ESI as ionization source using an SHIMADU XR-ODS 50×3.0 mm column and a 1 mL/min flow rate. The solvent system was a gradient starting with 95% water with 0.05% TFA (solvent A) and 5% acetonitrile with 0.05% TFA (solvent B), ramping up to 30% solvent A and 70% solvent B over 4 min. The final solvent system was held constant for a further 1.9 min.

Method N:

Experiments performed on an Shimadzu 1100 HPLC with Shimadzu MSD mass spectrometer using ESI as ionization source using an SHIMADU XR-ODS 50×3.0 mm column and a 1 mL/min flow rate. The solvent system was a gradient starting with 95% water with 0.05% TFA (solvent A) and 5% acetonitrile with 0.05% TFA (solvent B), ramping up to 100% solvent B over 2 min. The final solvent system was held constant for a further 1.1 min.

Method O:

Experiments performed on an Agilent 1100 HPLC with Agilent quadrupole LC/MSD SL mass spectrometer using ESI as ionization source using an Agilent XBridge C18 30×3.0 mm column and a 2 mL/min flow rate. The solvent system was a gradient starting with 98% water with 0.05% TFA (solvent A) and 2% acetonitrile with 0.05% TFA (solvent B), ramping up to 5% solvent A and 95% solvent B over 2.2 min. The final solvent system was held constant for a further 0.3 min.

Method P:

Experiments performed on a Waters Acquity UHPLC with Waters SQ mass spectrometer using ESI as ionization source using an Acquity UPLC BEH C18, 1.7 um, 2.1*50 mm column and a 0.7 mL/min flow rate. The solvent system was a gradient starting with 95% water with 0.05% TFA (solvent A) and 5% acetonitrile with 0.05% TFA (solvent B), ramping up to 5% solvent A and 95% solvent B over 1.4 min. The final solvent system was held constant for a further 0.3 min.

Method Q:

Experiments performed on a Shimadzu 1100 HPLC with Shimadzu MSD mass spectrometer using ESI as ionization source using a Shim-pack XR-ODS50×3.0 mm column and a 1 mL/min flow rate. The solvent system was a gradient starting with 95% water with 0.05% TFA (solvent A) and 5% acetonitrile with 0.05% TFA (solvent B), ramping up to 100% solvent B over 2.2 min. The final solvent system was held constant for a further 1 min.

Method R:

Experiments performed on a Shimadzu 1100 HPLC with Shimadzu MSD mass spectrometer using ESI as ionization source using a Shim-pack XBridge C18 50×3.0 mm column and a 1.1 mL/min flow rate. The solvent system was a gradient starting with 95% water with 0.05% ammonium bicarbonate (solvent A) and 5% acetonitrile (solvent B), ramping up to 95% solvent B over 2.2 min. The final solvent system was held constant for a further 1 min.

Schemes:

Compounds of the invention can be prepared as shown in Scheme A below. A methyl 4,6-dihalo nicotinate compound a is reduced to the corresponding aldehyde b. Cyclization of compound b with hydrazine affords azaindazole c. Iodination of compound c provides compound d, which is alkylated to provide intermediate e. Coupling of an optionally substituted amine $R_1R_2NH$ with compound e in the presence of palladium or copper affords compound f. Palladium-mediated coupling of compound f with intermediate g then provides final compound h. Alternatively, palladium-mediated coupling of intermediate e with an optionally substituted alkenyl borate affords compound i. A second palladium-mediated coupling with intermediate g then provides compound j. Reduction of compound j affords final compound k.

Scheme A:

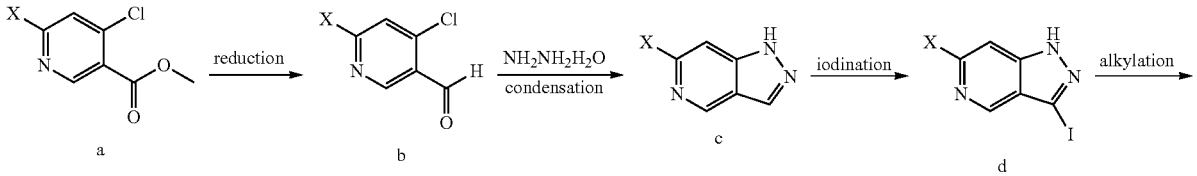

-continued

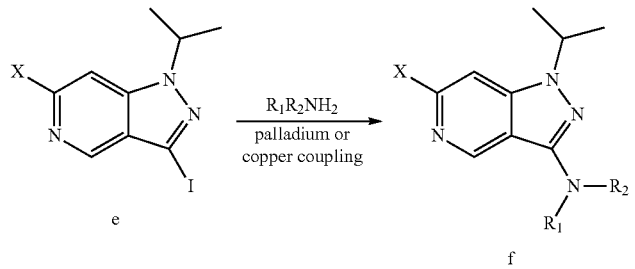

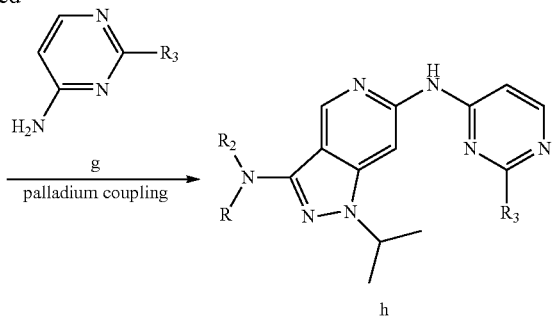

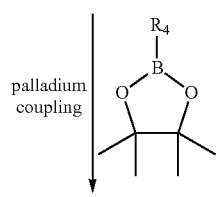

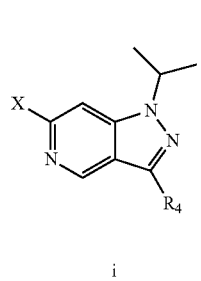

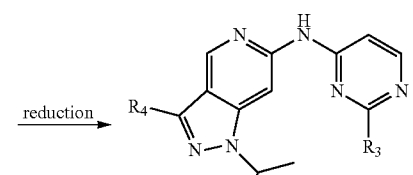

EXAMPLES

Example 1: 4-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)thiomorpholine 1,1-dioxide

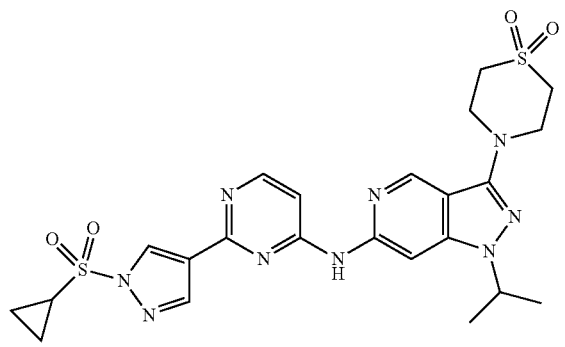 [SMILES: CC(C)n1nc(N2CCS(=O)(=O)CC2)c2cnc(Nc3ccnc(-c4cnn(S(=O)(=O)C5CC5)c4)n3)cc21]

Step 1: 1-(Cyclopropylsulfonyl)-4-(4,4,5,5-tetramethyl-1,3,2-dioxaborolan-2-yl)-1H-pyrazole

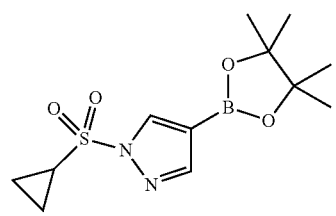 [SMILES: CC1(C)OB(c2cnn(S(=O)(=O)C3CC3)c2)OC1(C)C]

To a solution of 4-pyrazoleboronic acid pinacol ester (1.02 g, 5.26 mmol) in N,N-dimethylformamide (15 mL) was added sodium hydride (60 wt % dispersion in mineral oil)(0.32 g, 8 mmol) and cyclopropylsufonyl chloride (0.8 g, 5.78 mmol). The reaction was stirred at room temperature for 5 h. The mixture was then diluted with brine and extracted with EtOAc (3×). The combined organic extracts were washed with brine, dried over anhydrous sodium sulfate, filtered and concentrated in vacuo. The crude material was purified via flash chromatography on silica gel (solvent gradient: 0%-100% EtOAc in heptane) to give 1-(cyclopropylsulfonyl)-4-(4,4,5,5-tetramethyl-1,3,2-dioxaborolan-2-yl)-1H-pyrazole (0.8 g, 50%).

Step 2: 2-(1-(cyclopropylsulfonyl)-1H-pyrazol-4-yl)pyrimidin-4-amine

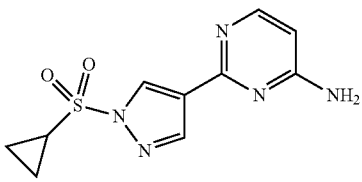 [SMILES: Nc1ccnc(-c2cnn(S(=O)(=O)C3CC3)c2)n1]

To a reaction vessel was added bis(di-tert-butyl(4-dimethylaminophenyl)phosphine)dichloropalladium(II) (370 mg, 0.50 mmol), 1-(cyclopropylsulfonyl)-4-(4,4,5,5-tetramethyl-1,3,2-dioxaborolan-2-yl)-1H-pyrazole (1500 mg, 4.256 mmol), 2-bromopyrimidin-4-amine (880 mg, 5.0 mmol), 2M sodium carbonate in water (5.0 mL, 10 mmol) and acetonitrile (8.4 mL, 160 mmol). The reaction was sealed and heated to 100° C. thermally. After 2 h, the reaction was cooled to room temperature, diluted with saturated aqueous sodium bicarbonate, and extracted with EtOAc (3×). The combined organic extracts were washed with brine, dried over anhydrous sodium sulfate, filtered and concentrated in vacuo. The crude product was then purified via flash chromatography on silica gel (0%-10% methanol in dichloromethane) to provide 2-(1-(cyclopropylsulfonyl)-1H-pyrazol-4-yl)pyrimidin-4-amine (1129 g, 85%) as a yellow solid. LCMS (ESI) [M+H]$^+$=266.1; $^1$H NMR (400 MHz, DMSO-d$_6$) δ 8.86 (s, 1H), 8.44 (s, 1H), 8.27 (d, J=5.1 Hz, 1H), 7.06 (d, J=5.1 Hz, 1H), 6.63 (s, 2H), 3.22 (tt, J=7.8, 4.6 Hz, 1H), 1.38-1.29 (m, 2H), 1.28-1.19 (m, 2H).

Step 3: Methyl 4,6-dihydroxynicotinate

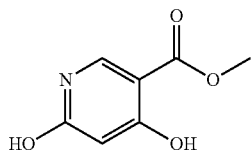

A solution containing dimethyl-1, 3-acetonedicarboxylate (2000 g, 11.5 mol), ethyl orthoformate (1947 mL, 11.5 mol), and acetic anhydride (2168 mL, 23.0 mol) was heated at 130° C. for 2 h. The reaction was allowed to be cooled to room temperature then concentrated in vacuo to 1500 mL. The crude reaction was cooled in ice bath and aqueous ammonia (2 L) was added in portions with stirring. After 30 min, the mixture was acidified with concentrated HCl (~300 mL) and the suspension was filtered. The crude product was dried under vacuum to give methyl 4,6-dihydroxynicotinate (900 g, 46%) which was taken on directly into the next step.

Step 4: Methyl 4,6-dichloronicotinate

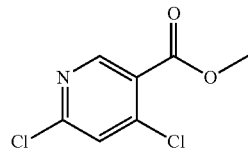

To a solution of methyl 4, 6-dihydroxynicotinate (900 g, 5.3 mol) in phosphoryl chloride (4000 mL) was added N,N-diethyl aniline (1035 mL, 6.4 mol). The reaction was heated to 120° C. for 2 h and then allowed to cool to room temperature. The reaction mixture was reduced in vacuo and poured slowly onto ice portionwise. The mixture was extracted with EtOAc (2×). The combined organic extracts were dried over anhydrous sodium sulfate and concentrated in vacuo. The crude product was purified via flash chromatography on silica gel (solvent gradient: 0%-5% EtOAc in petroleum ether) to afford methyl 4,6-dichloronicotinate (400 g, yield 42%). LCMS (ESI) [M+H]$^+$=206.1; $^1$H NMR (400 MHz, DMSO-d$_6$) δ 8.84 (s, 1H), 7.98 (s, 1H), 3.90 (s, 3H).

Step 5: 4,6-Dichloronicotinaldehyde

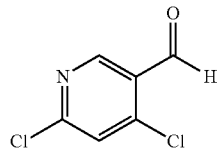

To a solution of methyl 4,6-dichloronicotinate (370 g, 1.8 mol) in dichloromethane (4500 mL) was added diisobutylaluminum hydride (1.00 M in dichloromethane, 1974 mL) at −70° C. The reaction was stirred at −70° C. for 30 min, quenched with 2M HCl, and extracted with dichloromethane (2×). The combined organic layers were dried over anhydrous sodium sulfate, filtered, and concentrated in vacuo. The crude material was purified via flash chromatography on silica gel (eluent: 30% EtOAc in heptane) to give 4,6-dichloronicotinaldehyde (76.8 g, yield 45%). LCMS (ESI) [M+H]$^+$=177.9; $^1$H NMR (400 MHz, CDCl$_3$): δ 10.44 (d, J=1.6 Hz, 1H), 8.84 (d, J=2.0 Hz, 1H), 7.50 (s, 1H).

Step 6: 6-Chloro-1H-pyrazolo[4,3-c]pyridine

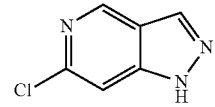

To a reaction vessel containing a mixture of 4,6-dichloronicotinaldehyde (300 g, 1.7 mol) in 1,4-dioxane (1200 mL) was added hydrazine (50% in water)(360 mL, 3.6 mol). The reaction vessel was sealed and heated at 150° C. over 18 h. The mixture was cooled to room temperature, concentrated in vacuo, poured over water and filtered. The filter cake was washed with 20% EtOAc in hexanes and dried to afford 6-chloro-1H-pyrazolo[4,3-c]pyridine (101.4 g, 38%) as a light-yellow solid. LCMS (ESI) [M+H]$^+$=154.

Step 7: 6-Chloro-3-iodo-1H-pyrazolo[4,3-c]pyridine

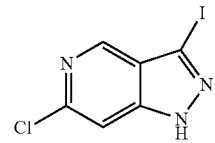 [SMILES: Clc1cc2[nH]nc(I)c2cn1]

To a solution of 6-chloro-1H-pyrazolo[4,3-c]pyridine (5.2 g, 34 mmol) in N,N-dimethylformamide (75 mL) was added potassium carbonate (5.7 g, 41 mmol) and iodine (4.3 g, 41 mmol). The reaction was stirred at room temperature. After 4 h, additional iodine (4.3 g, 17 mmol) and potassium carbonate (2.3 g, 17 mmol) were added. After 16 h, the reaction was diluted with saturated aqueous sodium bicarbonate and extracted with EtOAc (3×). The combined organic extracts were washed with brine, dried over anhydrous sodium sulfate, filtered, concentrated in vacuo and purified via flash chromatography on silica gel (solvent gradient: 0%-100% EtOAc in heptane) to give 6-chloro-3-iodo-1H-pyrazolo[4,3-c]pyridine (7.5 g, 79%). LCMS (ESI)

[M+H]+=280; 1H NMR (400 MHz, DMSO-d6) δ 14.02 (br, 1H), 8.63 (br, 1H), 7.69 (s, 1H).

Step 8: 6-Chloro-3-iodo-1-isopropyl-1H-pyrazolo[4,3-c]pyridine

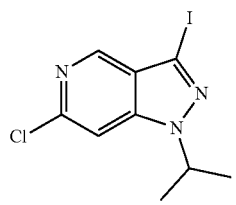

To a solution of 6-chloro-3-iodo-1H-pyrazolo[4,3-c]pyridine (1.5 g, 5.4 mmol) in N,N-dimethylformamide (8 mL) was added sodium hydride (60 wt % dispersion in mineral oil)(260 mg, 6.4 mmol) at 0° C. The reaction was stirred at 0° C. for 5 min before adding 2-bromopropane (0.76 mg, 8.1 mmol). The reaction was warmed to room temperature and stirred for 2 h, after which the reaction was diluted with saturated aqueous ammonium chloride, and extracted with EtOAc (3×). The combined organic extracts were washed with brine, dried over anhydrous sodium sulfate, filtered, and concentrated. The crude product was purified via flash chromatography on silica gel (solvent gradient: 0%-100% EtOAc in heptanes) to provide compound 6-chloro-3-iodo-1-isopropyl-1H-pyrazolo[4,3-c]pyridine (1390 mg, 81%) as a pale yellow solid. LCMS (ESI) [M+H]+=322.1; 1H NMR (400 MHz, CDCl3) δ 8.56 (s, 1H), 7.34 (s, 1H), 4.78-4.71 (m, 1H), 1.60 (d, J=6.8 Hz, 6H).

Step 9: 4-(6-Chloro-1-isopropyl-1H-pyrazolo[4,3-c]pyridin-3-yl)thiomorpholine 1,1-dioxide

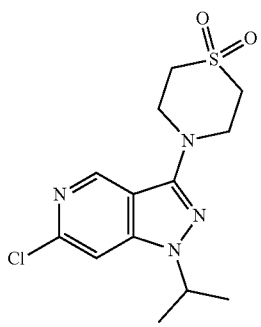 [SMILES: CC(C)n1nc(N2CCS(=O)(=O)CC2)c2cnc(Cl)cc21]

A solution of 6-chloro-3-iodo-1-isopropyl-1H-pyrazolo[4,3-c]pyridine (400 mg, 1 mmol), cesium carbonate (800 mg, 2 mmol), 4,5-bis(diphenylphosphino)-9,9-dimethylxanthene (70 mg, 0.1 mmol), palladium (II) acetate (30 mg, 0.1 mmol), 1,4-thiazinane 1,1-dioxide (200 mg, 1 mmol) and 1,4-dioxane (2.5 mL) was purged with nitrogen gas for 20 min. The reaction was sealed and stirred at 110° C. for 20 h. Additional palladium (II) acetate (30 mg, 0.1 mmol) and 4,5-bis(diphenylphosphino)-9,9-dimethylxanthene (70 mg, 0.1 mmol) were added and the reaction was heated to 130° C. in the microwave for 60 min. The reaction was cooled to room temperature, filtered and the filtrate was concentrated in vacuo and purified via flash chromatography on silica gel (solvent gradient: 0%-100% EtOAc in heptanes) to afford 4-(6-chloro-1-isopropyl-1H-pyrazolo[4,3-c]pyridin-3-yl)thiomorpholine 1,1-dioxide (49.2 mg, 10%) as an orange solid. LCMS (ESI) [M+H]+=329.1.

Step 10: 4-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)thiomorpholine 1,1-dioxide

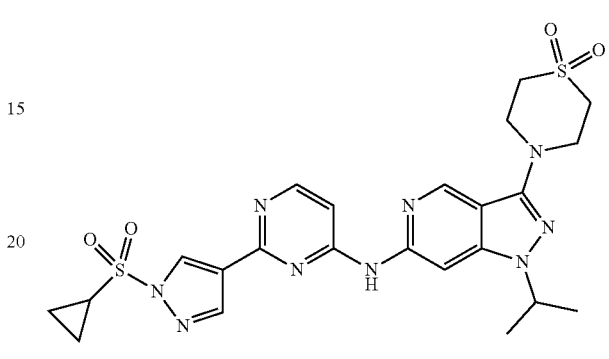

To a reaction vial was added cesium carbonate (41 mg, 0.126 mmol), 2-dicyclohexylphosphino-2',4',6'-triisopropylbiphenyl (9.3 mg, 0.0189 mmol), tris(dibenzylideneacetone)dipalladium(0) (5.9 mg, 0.00630 mmol), 4-(6-chloro-1-isopropyl-1H-pyrazolo[4,3-c]pyridin-3-yl)thiomorpholine 1,1-dioxide (20.7 mg, 0.0630 mmol), 2-(1-(cyclopropylsulfonyl)-1H-pyrazol-4-yl)pyrimidin-4-amine (33.4 mg, 0.126 mmol) and 1,4-dioxane (1.5 mL). The reaction was then heated at 100° C. for 18 h, cooled to room temperature, filtered and the filtrate was concentrated in vacuo. The crude product was purified by preparatory reverse-phase HPLC to provide 4-(6-((2-(1-(cyclopropylsulfonyl)-1H-pyrazol-4-yl)pyrimidin-4-yl)amino)-1-isopropyl-1H-pyrazolo[4,3-c]pyridin-3-yl)thiomorpholine 1,1-dioxide (10.0 mg, 29%) as a white solid. LCMS (ESI): $R_T$ (min)=5.136, [M+H]+=558.2, method=B; 1H NMR (400 MHz, DMSO-d6) δ 9.78 (s, 1H), 9.00 (s, 1H), 8.86 (d, J=1.0 Hz, 1H), 8.64 (d, J=5.1 Hz, 1H), 8.62 (s, 1H), 8.36 (d, J=1.0 Hz, 1H), 7.45 (d, J=5.2 Hz, 1H), 4.74 (p, J=6.6 Hz, 1H), 3.96 (m, 4H), 3.27 (m, 5H), 1.47 (d, J=6.6 Hz, 6H), 1.41-1.20 (m, 4H).

Example 2: 1-Isopropyl-N-(2-(4-methoxypiperdin-1-yl)pyrimidin-4-yl)-3-(2-oxa-6-azaspiro[3.3] heptan-6-yl)-1H-pyrazolo[4,3-c]pyridine-6-amine

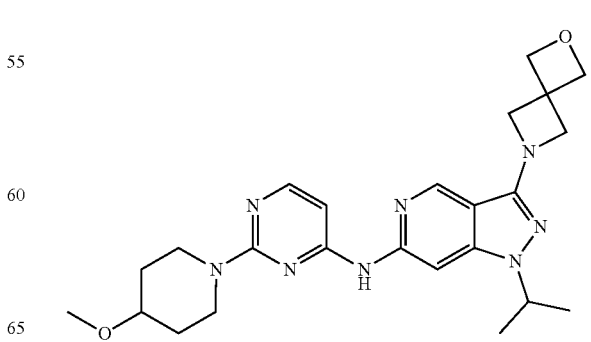

Step 1: 6-(6-Chloro-1-isopropyl-1H-pyrazolo[4,3-c]pyridin-3-yl)-2-oxa-6-azaspiro[3.3]heptane

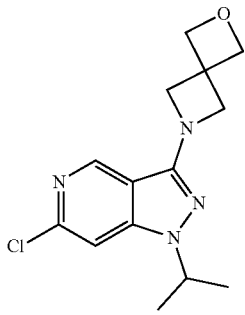 [SMILES: CC(C)n1nc(N2CC3(COC3)C2)c2cnc(Cl)cc21]

To a reaction vessel was added 6-chloro-3-iodo-1-isopropyl-1H-pyrazolo[4,3-c]pyridine (Example 1, Step 8) (2.16 g, 6.72 mmol), 2-oxa-6-azaspiro[3.3]heptane (0.69 g, 6.72 mmol), cesium carbonate (4.82 g, 14.8 mmol), 4,5-bis(diphenylphosphino)-9,9-dimethylxanthene (0.40 g, 0.67 mmol), palladium (II) acetate (0.15 g, 0.67 mmol) and 1,4-dioxane (5 mL). After purging with nitrogen for 5 min, the vessel was sealed and heated at 110° C. After 17 h, the reaction mixture was cooled to room temperature, filtered and concentrated in vacuo. The residue was purified by reverse phase column chromatography (0%-100% acetonitrile in water) to afford 6-(6-chloro-1-isopropyl-1H-pyrazolo[4,3-c]pyridin-3-yl)-2-oxa-6-azaspiro[3.3]heptane (1.06 g, 54%) as a yellow solid. LCMS (ESI): [M+H]+=295.1; $^1$H NMR (400 MHz, CDCl$_3$) δ 8.53 (s, 1H), 7.11 (s, 1H), 4.87 (s, 4H), 4.51 (h, J=6.7 Hz, 1H), 4.33 (s, 4H), 1.49 (d, J=6.6 Hz, 6H).

Step 2: 2-(4-Methoxypiperidin-1-yl)pyrimidin-4-amine

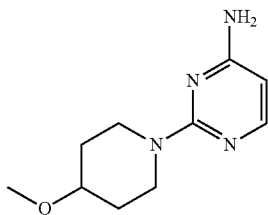

2-Chloropyrimidin-4-ylamine (3.5 g, 27.0 mmol), 4-methoxypiperidine hydrochloride (4.09 g, 27.0 mmol) and cesium carbonate (26.4 g, 81.0 mmol) were suspended in N,N-dimethylformamide (60 mL) and heated at 120° C. for 18 h. The reaction mixture was cooled to room temperature and partitioned between water and EtOAc. The aqueous phase was washed with EtOAc (×2) and the combined organic phases were washed with brine, dried over anhydrous magnesium sulfate, and concentrated in vacuo affording the title compound as a solid (2.5 g). The aqueous phase was concentrated in vacuo and the slurry was extracted with EtOAc. The volatiles were removed in vacuo and the resulting residue was purified via flash chromatography on silica gel (solvent gradient: 0%-100% EtOAc in cyclohexane) and then triturated with cyclohexane affording a second batch of 2-(4-methoxypiperidin-1-yl)pyrimidin-4-amine (2.38 g, 87% combined yield). LCMS (ESI): [M+H]+=209.2; $^1$H NMR (400 MHz, CDCl$_3$) δ: 7.94 (1H, d, J=5.60 Hz), 5.74 (1H, d, J=5.60 Hz), 4.53 (2H s), 4.33-4.24 (2H, m), 3.47-3.37 (4H, m), 3.33-3.24 (2H, m), 1.98-1.87 (2H, m), 1.60-1.47 (2H, m).

Step 3: 1-Isopropyl-N-(2-(4-methoxypiperdin-1-yl)pyrimidin-4-yl)-3-(2-oxa-6-azaspiro[3.3] heptan-6-yl)-1H-pyrazolo[4,3-c]pyridine-6-amine

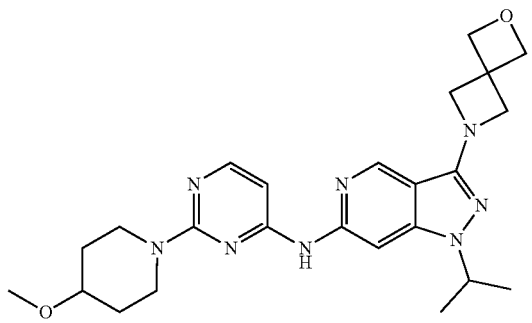 [SMILES: COC1CCN(c2nccc(Nc3cc4c(cn3)c(N3CC5(COC5)C3)nn4C(C)C)n2)CC1]

To a reaction vessel was added 6-(6-chloro-1-isopropyl-1H-pyrazolo[4,3-c]pyridin-3-yl)-2-oxa-6-azaspiro[3.3]heptane (33.8 mg, 0.115 mmol), 2-(4-methoxy-1-piperidyl)pyrimidin-4-amine, (24.0 mg, 0.115 mmol), cesium carbonate (75.2 mg, 0.231 mmol), 2-(dicyclohexylphosphino)-2',4',6'-triisopropylbiphenyl (5.67 mg, 0.0115 mmol), tris(dibenzylideneacetone)dipalladium(0) (16.3 mg, 0.0173 mmol) and 1,4-dioxane (3 mL). After purging with nitrogen for 15 min, the vessel was sealed and heated at 105° C. After 18 h, the reaction mixture was cooled to room temperature, filtered and concentrated in vacuo. The crude product was purified by preparatory reverse-phase HPLC to afford 1-isopropyl-N-(2-(4-methoxypiperdin-1-yl)pyrimidin-4-yl)-3-(2-oxa-6-azaspiro[3.3]heptan-6-yl)-1H-pyrazolo[4,3-c]pyridine-6-amine (21.6 mg, 40%). LCMS (ESI): R$_T$ (min)=4.33, [M+H]+=465.3, method=B; $^1$H NMR (400 MHz, DMSO-d$_6$) δ 9.81 (s, 1H), 8.55 (d, J=1.2 Hz, 1H), 8.12 (s, 1H), 7.98 (d, J=5.6 Hz, 1H), 6.37 (d, J=5.7 Hz, 1H), 4.74 (s, 4H), 4.51 (p, J=6.7 Hz. 1H), 4.29-4.25 (m, 4H), 4.26-4.17 (m, 2H), 3.50-3.44 (m, 1H), 3.43-3.33 (m, 2H), 3.29 (s, 3H), 3.27 (s, 2H), 1.96-1.84 (m, 2H), 1.41 (d, J=6.7 Hz, 6H).

Example 3: 1-(4-((1-Isopropyl-3-(2-oxa-6-azaspiro[3.3]heptan-6-yl)-1H-pyrazolo[4,3-c]pyridin-6-yl)amino)pyrimidin-2-yl)-3,3-dimethylpiperidin-4-ol

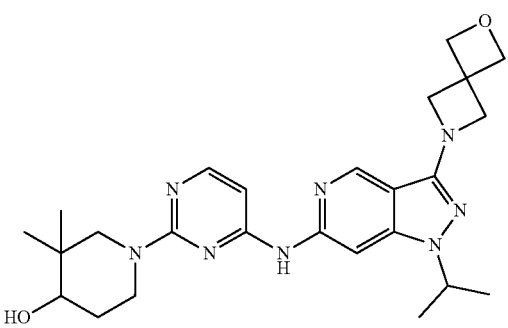 [SMILES: CC(C)n1nc(N2CC3(COC3)C2)c2cnc(Nc3ccnc(N4CCC(O)C(C)(C)C4)n3)cc21]

Step 1: 1-(4-Aminopyrimidin-2-yl)-3,3-dimethyl-piperdin-4-ol

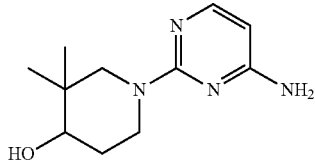 [SMILES: CC1(C)CN(c2nccc(N)n2)CCC1O]

To a reaction vessel was added 2-chloropyrimidin-4-amine (1.0 g, 8.0 mmol, 1.1 equiv), 3,3-dimethylpiperidin-4-ol (1.0 g, 9.0 mmol, 1.0 equiv), triethylamine (3.0 g, 30 mmol, 4.0 equiv), and 2-propanol (5 mL). The sealed reaction vessel was heated under microwave irradiation at 150° C. for 45 min. The reaction mixture was cooled to room temperature, diluted with saturated aqueous sodium bicarbonate and extracted with dichloromethane. The organic layer was dried over magnesium sulfate, filtered and concentrated in vacuo to afford 1-(4-aminopyrimidin-2-yl)-3,3-dimethyl-piperdin-4-ol (1.24 g, 70%). LCMS (ESI): [M+H]$^+$=223.2; $^1$H NMR (300 MHz, DMSO-d$_6$) δ 7.69 (d, J=5.6 Hz, 1H), 6.28 (s, 2H), 5.64 (d, J=5.6 Hz, 1H), 4.55 (d, J=4.7 Hz, 1H), 4.33-4.22 (m, 1H), 4.02 (dd, J=12.8, 1.7 Hz, 1H), 3.25 (dd, J=9.4, 4.6 Hz, 1H), 3.08-2.96 (m, 1H), 2.75 (d, J=13.0 Hz, 1H), 1.66-1.54 (m, 1H), 1.47-1.35 (m, 1H), 0.87 (s, 3H), 0.74 (s, 3H).

Step 2: 1-(4-((1-Isopropyl-3-(2-oxa-6-azaspiro[3.3]heptan-6-yl)-1H-pyrazolo[4,3-c]pyridin-6-yl)amino)pyrimidin-2-yl)-3,3-dimethylpiperidin-4-ol

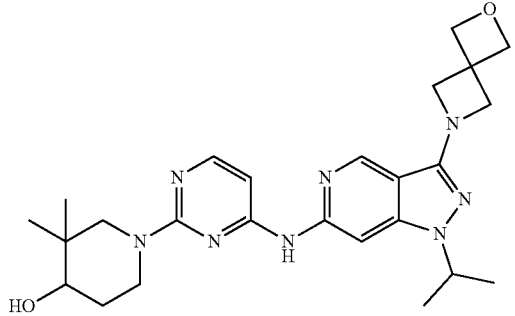 [SMILES: CC(C)n1nc(N2CC3(COC3)C2)c2cnc(Nc3ccnc(N4CCC(O)C(C)(C)C4)n3)cc21]

To a reaction vessel was added 6-(6-chloro-1-isopropyl-1H-pyrazolo[4,3-c]pyridin-3-yl)-2-oxa-6-azaspiro[3.3]heptane (Example 2, Step 1) (114 mg, 0.389 mmol), 1-(-aminopyrimidin-2-yl)-3,3-dimethyl-piperdin-4-ol (103.9 mg, 0.467 mmol), cesium carbonate (253.7 mg, 0.779 mmol), 2-(dicyclohexylphospino)-2',4',6'-triisopropylbiphenyl (75.9 mg, 0.154 mmol), palladium(II)acetate (22.3 mg, 0.097 mmol) and 1,4-dioxane (3 mL). After purging with nitrogen for 15 min, the vessel was sealed and heated at 110° C. After 22 h, the reaction mixture was cooled to room temperature, filtered and concentrated in vacuo. The residue was purified by preparatory reverse-phase HPLC to afford 1-(4-((1-isopropyl-3-(2-oxa-6-azaspiro[3.3]heptan-6-yl)-1H-pyrazolo[4,3-c]pyridin-6-yl)amino)pyrimidin-2-yl)-3,3-dimethylpiperidin-4-ol (58.4 mg, 31%). LCMS (ESI): R$_T$ (min)=7.4, [M+H]$^+$=479.3, method=C; $^1$H NMR (400 MHz, DMSO-d$_6$) δ 9.80-9.72 (m, 1H), 8.54 (s, 1H), 8.12 (s, 1H), 7.94 (d, J=5.6 Hz, 1H), 6.32 (d, J=5.5 Hz, 1H), 4.74 (s, 4H), 4.62 (d, J=5.4 Hz, 1H), 4.54 (p, J=6.7 Hz, 1H), 4.35 (d, J=13.3 Hz, 1H), 4.27 (s, 4H), 4.06 (d, J=13.0 Hz, 1H), 3.35 (dt, J=8.7, 4.3 Hz, 1H), 3.24 (m, 1H), 3.00 (d, J=13.0 Hz, 1H), 1.70 (dt, J=13.2, 4.2 Hz, 1H), 1.53 (t, J=11.6 Hz, 1H), 1.41 (d, J=6.6 Hz, 6H), 0.93 (s, 3H), 0.81 (s, 3H).

Example 4: N-(2-(1-(Cyclopropylmethyl)-1H-pyrazol-4-yl)pyrimidin-4-yl)-1-isopropyl-3-(2-oxa-6-azaspiro[3.3]heptan-6-yl)-1H-pyrazolo[4,3-c]pyridin-6-amine

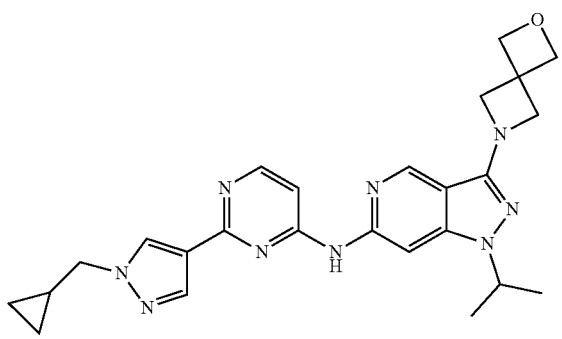 [SMILES: CC(C)n1nc(N2CC3(COC3)C2)c2cnc(Nc3ccnc(-c4cnn(CC5CC5)c4)n3)cc21]

Step 1: 1-(Cyclopropylmethyl)-4-(4,4,5,5-tetramethyl-1,3,2-dioxaborolan-2-yl)-1H-pyrazole

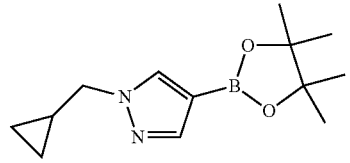 [SMILES: CC1(C)OB(c2cnn(CC3CC3)c2)OC1(C)C]

To a reaction vessel containing sodium hydride (60 wt % dispersion in mineral oil)(3.09 g, 77.32 mmol) was added N,N-dimethylformamide (30 mL) under a stream of nitrogen followed by 4-(4,4,5,5-tetramethyl-1,3,2-dioxaborolan-2-yl)-1H-pyrazole (10 g, 51.55 mmol) and the reaction mixture was stirred for 20 min at room temperature. Cyclopropylmethylbromide (8.7 g, 61.86 mmol) was then added and the reaction mixture was stirred for 24 h under an atmosphere of nitrogen. The reaction mixture was slowly poured over saturated aqueous ammonium chloride and extracted with EtOAc. The organic layer was then washed with brine, dried over anhydrous sodium sulfate, filtered and concentrated in vacuo. The residue was purified via flash chromatography on silica gel (solvent gradient: 0%-100% EtOAc in cyclohexane) to afford 1-(cyclopropylmethyl)-4-(4,4,5,5-tetramethyl-1,3,2-dioxaborolan-2-yl)-1H-pyrazole (6.29 g, 49%). LCMS (ESI): [M+H]$^+$=249.2; $^1$H NMR (400 MHz, CDCl$_3$) δ 7.80 (d, J=7.4 Hz, 2H), 3.99 (d, J=7.0 Hz, 2H), 1.32 (s, 12H), 1.29-1.26 (m, 1H), 0.69-0.60 (m, 2H), 0.41-0.33 (m, 2H).

Step 2: 2-(1-(Cyclopropylmethyl)-1H-pyrazol-4-yl)pyrimidin-4-amine

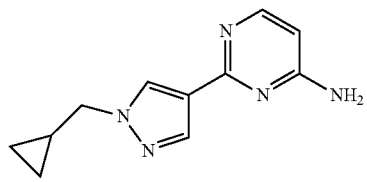 [SMILES: Nc1ccnc(-c2cnn(CC3CC3)c2)n1]

To a reaction vessel was added 1-(cyclopropylmethyl)-4-(4,4,5,5-tetramethyl-1,3,2-dioxaborolan-2-yl)-1H-pyrazole (1.0 g, 4.0 mmol), 2-chloropyrimidin-4-amine (550 mg, 4.2 mmol), bis(di-tert-butyl(4-dimethylaminophenyl)phosphine)dichloropalladium(II) (290 mg. 0.40 mmol), 1M sodium carbonate in water (8 mL) and acetonitrile (10 mL). The vessel was sealed and heated at 80° C. After 24 h, the reaction mixture was cooled to room temperature, filtered and concentrated in vacuo. The residue was purified via flash chromatography on an amine-functionalized column (solvent gradient: 0%-20% methanol in dichloromethane) to provide 2-(1-(cyclopropylmethyl)-1H-pyrazol-4-yl)pyrimidin-4-amine (0.6 g, 70%) as a yellow solid. LCMS (ESI): [M+H]$^+$=216.1; $^1$H NMR (400 MHz, DMSO-d$_6$) δ 8.19 (s, 1H), 8.03 (d, J=5.8 Hz, 1H), 7.88 (s, 1H), 6.75 (s, 2H), 6.22 (d, J=5.8 Hz, 1H), 4.00 (d, J=7.2 Hz, 2H), 1.26 (s, 1H), 0.63-0.47 (m, 2H), 0.38 (dd, J=4.5, 1.8 Hz, 2H).

Step 3: N-(2-(1-(Cyclopropylmethyl)-1H-pyrazol-4-yl)pyrimidin-4-yl)-1-isopropyl-3-(2-oxa-6-azaspiro[3.3]heptan-6-yl)-1H-pyrazolo[4,3-c]pyridin-6-amine

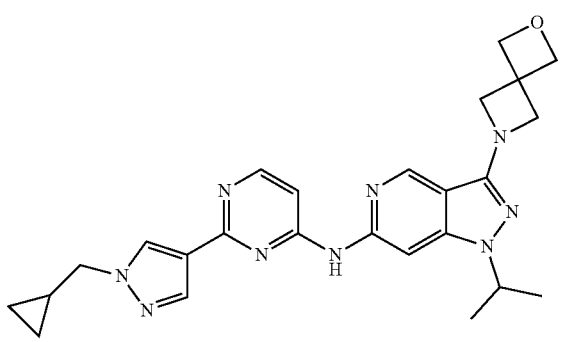 [SMILES: CC(C)n1nc(N2CC3(COC3)C2)c2cnc(Nc3ccnc(-c4cnn(CC5CC5)c4)n3)cc21]

To a reaction vessel was added 6-(6-chloro-1-isopropyl-1H-pyrazolo[4,3-c]pyridin-3-yl)-2-oxa-6-azaspiro[3.3]heptane (Example 2, Step 1) (513.6 mg, 1.75 mmol), 2-(1-(cyclopropylmethyl)-1H-pyrazol-4-yl)pyrimidin-4-amine (453.1 mg, 2.105 mmol), sodium tert-butoxide (516 mg, 5.262 mmol), 2-(dicyclohexylphosphino)3,6-dimethoxy-2',4',6'-triisopropyl-1,1'-biphenyl (96.08 mg, 0.174 mmol), chloro[2-(dicyclohexylphosphino)-3,6-dimethoxy-2'-4'-6'-tri-1-propyl-1,1'-biphenyl][2-(2-aminoethyl)phenyl]palladium(II) (151.6 mg, 0.175 mmol) and tert-butyl alcohol (20 mL). The vessel was sealed and heated at 100° C. After 22 h, the reaction mixture was cooled to room temperature, filtered and concentrated in vacuo. The residue was purified by C18-reverse phase silica gel chromatography (eluent: 15% methanol with 0.1% ammonium hydroxide) to afford N-(2-(1-(cyclopropylmethyl)-1H-pyrazol-4-yl)pyrimidin-4-yl)-1-isopropyl-3-(2-oxa-6-azaspiro[3.3]heptan-6-yl)-1H-pyrazolo[4,3-c]pyridin-6-amine (585.2 mg, 71%). LCMS (ESI): R$_T$ (min)=3.87, [M+H]$^+$=472.3, method=B; $^1$H NMR (400 MHz, DMSO-d$_6$) δ 10.07 (s, 1H), 8.59 (s, 1H), 8.33 (s, 1H), 8.31 (s, 1H), 8.16 (s, 1H), 8.01 (s, 1H), 7.06 (d, J=5.9 Hz, 1H), 4.75 (s, 4H), 4.65 (p, J=6.7 Hz, 1H), 4.29 (s, 4H), 4.05 (d, J=7.0 Hz, 2H), 1.46 (d, J=6.5 Hz, 6H), 1.34-1.26 (m, 1H), 0.61-0.51 (m, 2H), 0.40 (dd, J=6.0 Hz, 2H).

Example 5: N-(2-(1-(Cyclopropylsulfonyl)-1H-pyrazol-4-yl)pyrimidin-4-yl)-1-isopropyl-3-(2-oxa-6-azaspiro[3.3]heptan-6-yl)-1H-pyrazolo[4,3-c]pyridin-6-amine

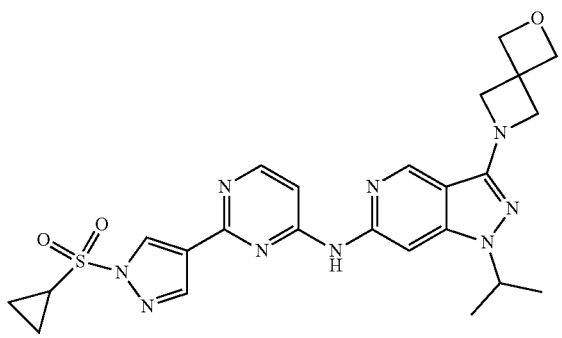 [SMILES: CC(C)n1nc(N2CC3(COC3)C2)c2cnc(Nc3ccnc(-c4cnn(S(=O)(=O)C5CC5)c4)n3)cc21]

To a reaction vessel was added 6-(6-chloro-1-isopropyl-1H-pyrazolo[4,3-c]pyridin-3-yl)-2-oxa-6-azaspiro[3.3]heptane (Example 2, Step 1) (150.0 mg, 0.512 mmol), 2-(1-(cyclopropylsulfonyl)-1H-pyrazol-4-yl)pyrimidin-4-amine (Example 1, Step 2) (149.5 mg, 0.564 mmol), cesium carbonate (333.8 mg, 1.03 mmol), 2-(dicyclohexylphosphino)-2',4',6'-triisopropylbiphenyl (75.53 mg, 0.154 mmol), tris(dibenzylideneacetone)dipalladium(0) (187.6 mg, 0.205 mmol) and 1,4-dioxane (5 mL). After purging with nitrogen for 15 min, the reaction vessel was sealed and heated at 110° C. After 22 h, the reaction mixture was cooled to room temperature, filtered and concentrated in vacuo. The residue was purified by reverse phase column chromatography (solvent gradient: 0%-100% acetonitrile in water) followed by preparatory reverse-phase HPLC to afford N-(2-(1-(cyclopropylsulfonyl)-1H-pyrazol-4-yl)pyrimidin-4-yl)-1-isopropyl-3-(2-oxa-6-azaspiro[3.3]heptan-6-yl)-1H-pyrazolo[4,3-c]pyridin-6-amine (14 mg, 5%). LCMS (ESI): R$_T$ (min)=4.686, [M+H]$^+$=522.2, method=B; $^1$H NMR (400 MHz, DMSO-d$_6$) δ 10.30 (s, 1H), 8.68 (s, 1H), 8.61 (d J=1.0 Hz, 1H), 8.46 (s, 1H), 8.41 (d, J=5.8 Hz, 1H), 8.27 (s, 1H), 7.14 (d, J=5.9 Hz, 1H), 4.75 (s, 4H), 4.70 (p, J=6.6 Hz, 1H), 4.29 (s, 4H), 3.28-3.24 (m, 1H), 1.46 (d, J=6.6 Hz, 6H), 1.38-1.32 (m, 2H), 1.30-1.24 (m, 2H).

Example 6: 2-((6-((2-(1-(Cyclopropylsulfonyl)-1H-pyrazol-4-yl)pyrimidin-4-yl)amino)-1-isopropyl-1H-pyrazolo[4,3-c]pyridin-3-yl)amino)ethanol

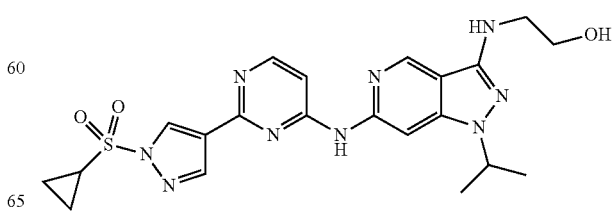

Step 1: 2-((tert-Butyldiphenylsilyl)oxy)ethanamine

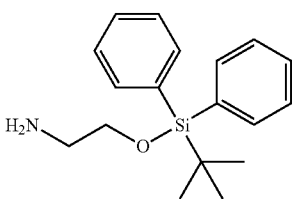 [SMILES: CC(C)(C)[Si](OCCN)(c1ccccc1)c1ccccc1]

To a solution of ethanolamine (5 mL, 80.0 mmol) and dichloromethane (100 mL) was added triethylamine (25 mL, 180 mmol) and 4-dimethylaminopyridine (100 mg, 0.83 mmol). The reaction mixture was cooled to 0° C. and stirred for 15 min prior to addition of tert-butylchlorodiphenylsilane (23.7 mL, 91.1 mmol). The reaction mixture was then allowed to warm to room temperature. After 24 h, the reaction mixture was washed with brine and the organic layer was concentrated in vacuo. The crude product was then purified by silica gel chromatography (solvent gradient: 10%-90% EtOAc in heptanes) to afford 2-((tert-butyldiphenylsilyl)oxy)ethanamine (15 g, 75%). LCMS (ESI): [M+H]$^+$=300.3; $^1$H NMR (500 MHz, CDCl$_3$) δ 7.68 (d, J=7.2 Hz, 4H), 7.43 (t, J=7.2 Hz, 2H), 7.39 (t, J=7.2 Hz, 4H), 3.70 (t, J=5.4 Hz, 2H), 2.83 (t, J=5.4 Hz, 2H), 2.41 (br, 2H), 1.07 (s, 9H).

Step 2: N-(2-((tert-Butyldiphenylsilyl)oxy)ethyl)-6-chloro-1-isopropyl-1H-pyrazolo[4,3-c]pyridin-3-amine

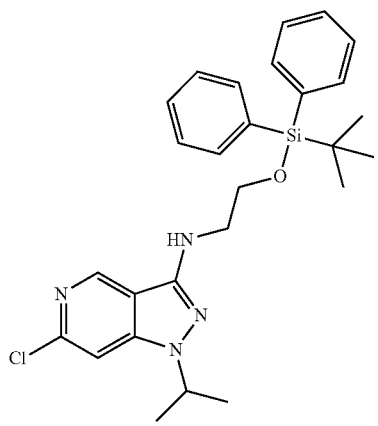 [SMILES: CC(C)n1nc(NCCO[Si](c2ccccc2)(c2ccccc2)C(C)(C)C)c2cnc(Cl)cc21]

To a reaction vessel was added 6-chloro-3-iodo-1-isopropyl-1H-pyrazolo[4,3-c]pyridine (Example 1, Step 8) (568 mg, 1.77 mmol), 2-((tert-butyldiphenylsilyl)oxy)ethanamine (1.058 g, 3.53 mmol), cesium carbonate (1.27 g, 3.89 mmol), 4,5-bis(diphenylphosphino)-9,9-dimethylxanthene (210.75 mg, 0.353 mmol), tris(dibenzylideneacetone)dipalladium(0) (323.5 mg, 0.353 mmol) and 1,4-dioxane (2.5 mL). After purging with nitrogen for 15 min, the reaction vessel was sealed and heated to 100° C. After 20 h, the reaction mixture was cooled to room temperature, filtered and concentrated in vacuo. The residue was purified by silica flash chromatography (solvent gradient: 0%-50% EtOAc in heptanes) to afford N-(2-((tert-butyldiphenylsilyl)oxy) ethyl)-6-chloro-1-isopropyl-1H-pyrazolo[4,3-c]pyridin-3-amine (120 mg, 14%). LCMS (ESI): [M+H]$^+$=493.3.

Step 3: 2-((6-((2-(1-(Cyclopropylsulfonyl)-1H-pyrazol-4-yl)pyrimidin-4-yl)amino)-1-isopropyl-1H-pyrazolo[4,3-c]pyridin-3-yl)amino)ethanol

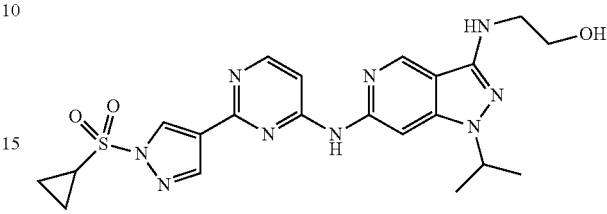

To a reaction vessel was added N-(2-((tert-butyldiphenylsilyl)oxy)ethyl)-6-chloro-1-isopropyl-1H-pyrazolo[4,3-c]pyridin-3-amine (120 mg, 0.243 mmol), 2-(1-(cyclopropylsulfonyl)-1H-pyrazol-4-yl)pyrimidin-4-amine (Example 1, Step 2, 71.02 mg, 0.268 mmol), cesium carbonate (166.5 mg, 0.511 mmol), 2-(dicyclohexylphosphino)-2',4',6'-triisopropylbiphenyl (23.92 mg, 0.049 mmol), tris(dibenzylideneacetone)dipalladium (0) (91.9 mg, 0.097 mmol) and 1,4-dioxane (5 mL). After purging with nitrogen for 15 min, the reaction vessel was sealed and heated to 110° C. After 18 h, the reaction mixture was cooled to room temperature, filtered and concentrated in vacuo. The residue was purified by silica flash chromatography (solvent gradient: 0%-50% EtOAc in heptanes) to afford N$^3$-(2-((tert-butyldiphenylsilyl)oxy)ethyl)-N$^6$-(2-(1-(cyclopropylsulfonyl)-1H-pyrazol-4-yl)pyrimidin-4-yl)-1-isopropyl-1H-pyrazolo[4,3-c]pyridine-3,6-diamine (50 mg, 28%), which was brought up in methanol (10 mL, 247 mmol) and treated with acetic acid (0.02 mL, 0.35 mmol) while stirring. After 18 h, the reaction mixture was concentrated in vacuo and purified by preparatory reverse-phase HPLC to afford 2-((6-((2-(1-(cyclopropylsulfonyl)-1H-pyrazol-4-yl)pyrimidin-4-yl)amino)-1-isopropyl-1H-pyrazolo[4,3-c]pyridin-3-yl)amino)ethanol (15.4 mg, 12%). LCMS (ESI): R$_T$ (min)=4.42, [M+H]$^+$=484.2, method=B; $^1$H NMR (400 MHz, DMSO-d$_6$) δ 10.21 (s, 1H), 8.73 (d, J=1.0 Hz, 1H), 8.68 (s, 1H), 8.46 (s, 1H), 8.40 (d, J=5.9 Hz, 1H), 7.15 (d, J=6.0 Hz, 1H), 6.99-6.94 (m, 1H), 6.41 (t, J=5.8 Hz, 1H), 4.68 (t, J=5.4 Hz, 1H), 4.66-4.59 (m, 1H), 3.64 (q, J=5.8 Hz, 2H), 3.35 (q, J=5.9 Hz, 2H), 1.53 (s, 1H), 1.45 (d, J=6.6 Hz, 6H), 1.37-1.31 (m, 2H), 1.30-1.22 (m, 2H).

Example 7: N-(2-(1-(Cyclopropylsulfonyl)-1H-pyrazol-4-yl)pyrimidin-4-yl)-3-fluoro-1-isopropyl-1H-pyrazolo[4,3-c]pyridin-6-amine

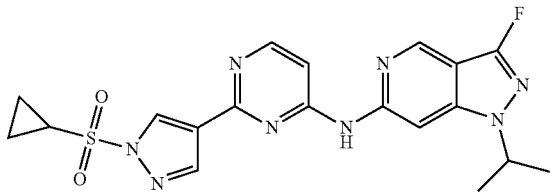 [SMILES: CC(C)n1nc(F)c2cnc(Nc3ccnc(-c4cnn(S(=O)(=O)C5CC5)c4)n3)cc21]

Step 1: 6-Chloro-1-isopropyl-1H-pyrazolo[4,3-c]pyridine

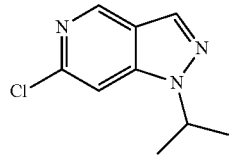

To a solution of 6-chloro-1H-pyrazolo[4,3-c]pyridine (1.0116 g, 6.5872 mmol) in N,N-dimethylformamide (12.0 mL) at 0° C. was added sodium hydride (60 wt % dispersion in mineral oil)(297.4 mg, 7.436 mmol). After stirring for 5 min at 0° C., 2-bromopropane (0.75 mL, 7.9 mmol) was added and the reaction allowed to warm to room temperature. After 2 h, additional sodium hydride (250.4 mg, 6.26 mmol) and 2-bromopropane (0.75 mL, 7.9 mmol) were added and the reaction mixture stirred at room temperature for 18 h. The reaction mixture was diluted with EtOAc, washed with water (2×) and brine, dried over magnesium sulfate, filtered, and concentrated in vacuo. The crude product was purified via flash chromatography on silica gel (solvent gradient: 0%-50% EtOAc in dichloromethane) to yield 6-chloro-1-isopropyl-1H-pyrazolo[4,3-c]pyridine (649.9 mg, 50.4%). LCMS (ESI) [M+H]$^+$=196.2; $^1$H NMR (400 MHz, DMSO-d$_6$) δ 8.91 (d, J=1.0 Hz, 1H), 8.35 (d, J=0.8 Hz, 1H), 7.93 (t, J=1.0 Hz, 1H), 5.08-4.95 (m, 1H), 1.47 (d, J=6.6 Hz, 6H).

Step 2: 6-Chloro-3-fluoro-1-isopropyl-1H-pyrazolo[4,3-c]pyridine

A mixture of 6-chloro-1-isopropyl-1H-pyrazolo[4,3-c]pyridine (575 mg, 2.9 mmol), 1-chloromethyl-4-fluoro-1,4-diazoniabicyclo[2.2.2]octane bis(tetrafluoroborate) (1.53 g, 4.15 mmol), and acetonitrile (8.0 mL, 150 mmol) was heated in a sealed vial at 90° C. for 24 h. The reaction mixture was cooled to room temperature, diluted with EtOAc, washed with water and brine, dried over magnesium sulfate, filtered, and concentrated in vacuo. The crude product was purified via flash chromatography on silica gel (solvent gradient: 0%-80% EtOAc in heptanes) to yield 6-chloro-3-fluoro-1-isopropyl-1H-pyrazolo[4,3-c]pyridine (153.8 mg, 17%). LCMS (ESI) [M+H]$^+$=214.2; $^1$H NMR (400 MHz, DMSO-d$_6$) δ 8.78 (d, J=1.2 Hz, 1H), 8.44 (dd, J=2.2, 0.6 Hz, 1H), 5.03 (p, J=6.6 Hz, 1H), 1.59-1.47 (m, 6H).

Step 3: N-(2-(1-(Cyclopropylsulfonyl)-1H-pyrazol-4-yl)pyrimidin-4-yl)-3-fluoro-1-isopropyl-1H-pyrazolo[4,3-c]pyridin-6-amine

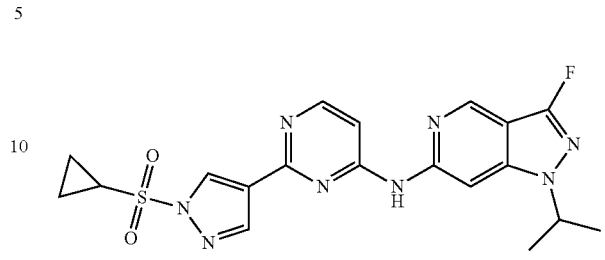

A mixture of 6-chloro-3-fluoro-1-isopropyl-pyrazolo[4,3-c]pyridine (63.3 mg, 0.207 mmol), 2-(1-(cyclopropylsulfonyl)-1H-pyrazol-4-yl)pyrimidin-4-amine (Example 1, Step 2) (81.8 mg, 0.308 mmol), palladium(II) acetate (10.0 mg, 0.0445 mmol), 4,5-bis(diphenylphosphino)-9,9-dimethylxanthene (38.0 mg, 0.0657 mmol), cesium carbonate (137.0 mg, 0.4205 mmol) and 1,4-dioxane (1.5 mL, 18 mmol) was purged with nitrogen for 20 min and heated under microwave irradiation at 110° C. for 30 min. Additional palladium (II) acetate (10.0 mg, 0.0445 mmol) and 4,5-bis(diphenylphosphino)-9,9-dimethylxanthene (26.0 mg, 0.0449 mmol) were added and the reaction mixture was heated under microwave irradiation at 110° C. for 90 min. The reaction mixture was cooled to room temperature, diluted with dichloromethane, filtered through a PFTE frit, and concentrated. The crude product was purified via flash chromatography on silica gel (solvent gradient: 0%-10% methanol in dichloromethane) followed by preparatory reverse-phase HPLC and lyophilized to yield N-(2-(1-(cyclopropylsulfonyl)-1H-pyrazol-4-yl)pyrimidin-4-yl)-3-fluoro-1-isopropyl-1H-pyrazolo[4,3-c]pyridin-6-amine (25.9 mg, 28%). LCMS (ESI): RT (min)=4.275, [M+H]$^+$=443.2, method=B; $^1$H NMR (400 MHz, DMSO-d$_6$) δ 9.95 (s, 1H), 8.78 (d, J=1.3 Hz, 1H), 8.50 (s, 1H), 8.41 (d, J=6.0 Hz, 1H), 8.37 (d, J=2.0 Hz, 1H), 8.35 (s, 1H), 7.11 (d, J=5.8 Hz, 1H), 5.04 (p, J=6.6 Hz, 1H), 3.26-3.18 (m, 1H), 1.55 (d, J=6.6 Hz, 6H), 1.35-1.27 (m, 2H), 1.27-1.19 (m, 2H).

Example 8: 1-(4-((1-Isopropyl-3-(pyrrolidin-1-yl)-1H-pyrazolo[4,3-c]pyridin-6-yl)amino) pyrimidin-2-yl)-3,3-dimethylpiperidin-4-ol

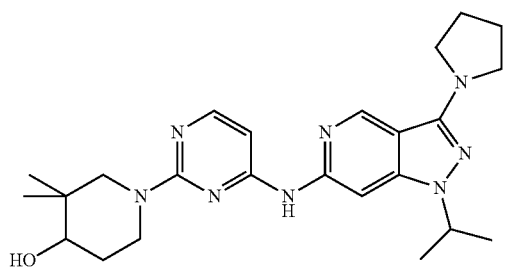 [SMILES: CC(C)n1nc(N2CCCC2)c2cnc(Nc3ccnc(N4CCC(O)C(C)(C)C4)n3)cc21]

Step 1: 6-Chloro-1-isopropyl-3-(pyrrolidin-1-yl)-1H-pyrazolo[4,3-c]pyridine

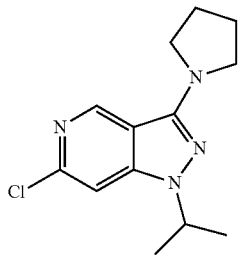 [SMILES: CC(C)n1nc(N2CCCC2)c2cnc(Cl)cc21]

To a reaction vessel was added 6-chloro-3-iodo-1-isopropyl-1H-pyrazolo[4,3-c]pyridine (Example 1, Step 8) (1.02 g, 3.17 mmol), pyrrolidine (0.43 g, 6.0 mmol), copper (I) iodide (191.1 mg, 1.0 mmol), L-proline (116.9 mg, 1,015 mmol), potassium carbonate (1.33 g, 9.64 mmol) and N,N-dimethylformamide (8 mL). After purging with nitrogen for 15 min, the reaction vessel was sealed and heated at 70° C. After 24 h, the reaction mixture was cooled to room temperature, diluted with EtOAc, washed with water (2×) and brine, dried over magnesium sulfate, filtered and concentrated in vacuo. The crude product was purified via flash chromatography on silica gel (solvent gradient: 0%-80% EtOAc in dichloromethane) to afford 6-chloro-1-isopropyl-3-(pyrrolidin-1-yl)-1H-pyrazolo[4,3-c]pyridine (520.4 mg, 62%). LCMS (ESI): [M+H]$^+$=265.1; $^1$H NMR (400 MHz, CDCl$_3$) δ 8.72 (d, J=0.9 Hz, 1H), 7.07 (d, J=0.9 Hz, 1H), 4.51 (p, J=6.7 Hz, 1H), 3.68-3.58 (m, 4H), 2.10-2.00 (m, 4H), 1.50 (d, J=6.6 Hz, 6H).

Step 2: 1-(4-((1-Isopropyl-3-(pyrrolidin-1-yl)-1H-pyrazolo[4,3-c]pyridin-6-yl)amino)pyrimidin-2-yl)-3,3-dimethylpiperidin-4-ol

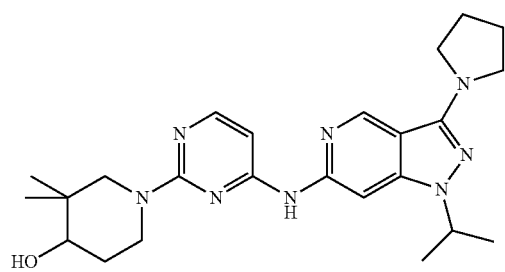 [SMILES: CC(C)n1nc(N2CCCC2)c2cnc(Nc3ccnc(N4CCC(O)C(C)(C)C4)n3)cc21]

A mixture of 6-chloro-1-isopropyl-3-pyrrolidin-1-yl-1H-pyrazolo[4,3-c]pyridine (153.6 mg, 0.5801 mmol), 1-(4-aminopyrimidin-2-yl)-3,3-dimethyl-piperidin-4-ol (Example 3, Step 1) (157.1 mg, 0.7067 mmol), chloro{[BrettPhos][2-(2-aminoethylphenyl)palladium(II)]}/[BrettPhos] admixture (37.3 mg, 0.0279 mmol) (PdP/P ratio 1:1), sodium tert-butoxide (165.8 mg, 1.73 mmol) and tert-butanol (2.5 mL, 26 mmol) was purged with nitrogen for 15 min and heated in a sealed vial at 100° C. for 2 h. The reaction mixture was cooled to room temperature, diluted with EtOAc, filtered through a PFTE frit, washed with water and brine, dried over magnesium sulfate, and concentrated in vacuo. The crude product was purified via reverse-phase HPLC and lyophilized to yield 1-(4-((1-isopropyl-3-(pyrrolidin-1-yl)-1H-pyrazolo[4,3-c]pyridin-6-yl)amino)pyrimidin-2-yl)-3,3-dimethylpiperidin-4-ol (109.3 mg, 42%). LCMS (ESI): R$_T$ (min)=3.750, [M+H]$^+$=451.3, method=B; $^1$H NMR (400 MHz, DMSO-d$_6$) δ 9.73 (s, 1H), 8.71 (d, J=0.9 Hz, 1H), 8.09 (s, 1H), 7.94 (d, J=5.6 Hz, 1H), 6.32 (d, J=5.6 Hz, 1H), 4.65 (d, J=4.4 Hz, 1H), 4.53 (p, J=6.6 Hz, 1H), 4.43-4.32 (m, 1H), 4.13-4.01 (m, 1H), 3.61-3.48 (m, 4H), 3.42-3.32 (m, 1H), 3.28-3.22 (m, 1H), 3.00 (d, J=12.9 Hz, 1H), 2.03-1.89 (m, 4H), 1.76-1.65 (m, 1H), 1.59-1.47 (m, 1H), 1.42 (d, J=6.6 Hz, 6H), 0.94 (s, 3H), 0.81 (s, 3H).

Example 9: N-(2-(1-(Cyclopropylmethyl)-1H-pyrazol-4-yl)pyrimidin-4-yl)-1-isopropyl-3-morpholino-1H-pyrazolo[4,3-c]pyridin-6-amine

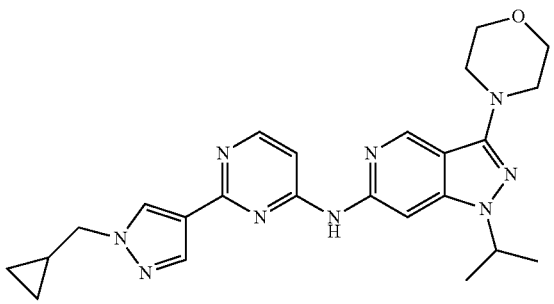 [SMILES: CC(C)n1nc(N2CCOCC2)c2cnc(Nc3ccnc(-c4cnn(CC5CC5)c4)n3)cc21]

Step 1: 4-(6-Chloro-1-isopropyl-pyrazolo[4,3-c]pyridin-3-yl)morpholine

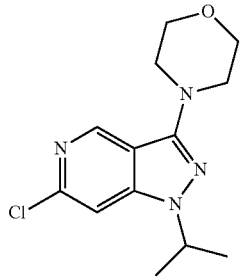 [SMILES: CC(C)n1nc(N2CCOCC2)c2cnc(Cl)cc21]

4-(6-Chloro-1-isopropyl-pyrazolo[4,3-c]pyridin-3-yl)morpholine was prepared following a similar experimental procedure to Example 8, Step 1 to afford 4-(6-chloro-1-isopropyl-pyrazolo[4,3-c]pyridine-3-yl)morpholine (278.8 mg, 32%). LCMS (ESI): [M+H]$^+$=281.1; $^1$H NMR (400 MHz, DMSO-d$_6$) δ 8.93 (d, J=0.9 Hz, 1H), 7.68 (d, J=0.9 Hz, 1H), 4.81 (p, J=6.6 Hz, 1H), 3.82-3.74 (m, 4H), 3.43-3.36 (m, 4H), 1.39 (d, J=6.6 Hz, 6H).

Step 2: N-(2-(1-(Cyclopropylmethyl)-1H-pyrazol-4-yl)pyrimidin-4-yl)-1-isopropyl-3-morpholino-1H-pyrazolo[4,3-c]pyridin-6-amine

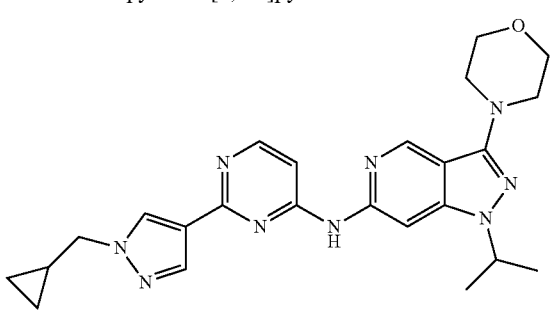

A mixture of 4-(6-chloro-1-isopropyl-pyrazolo[4,3-c]pyridin-3-yl)morpholine (75.5 mg, 0.269 mmol), 2-(1-(cyclopropylmethyl)-1H-pyrazol-4-yl)pyrimidin-4-amine (Example 4, Step 2, 74.8 mg, 0.348 mmol), chloro{[BrettPhos][2-(2-aminoethylphenyl)palladium(II)]}/[BrettPhos] admixture (37.3 mg, 0.0279 mmol) (PdP/P ratio 1:1), sodium tert-butoxide (83.2 mg, 0.866 mmol) and tert-butanol (2.0 mL, 21 mmol) was purged with nitrogen for 15 min and heated in a sealed vial at 100° C. for 3 h. The reaction mixture was cooled to room temperature, diluted with EtOAc, filtered through a PFTE frit, washed with water and brine, dried over magnesium sulfate, and concentrated. The crude product was purified via reverse-phase HPLC and lyophilized to yield N-(2-(1-(cyclopropylmethyl)-1H-pyrazol-4-yl)pyrimidin-4-yl)-1-isopropyl-3-morpholino-1H-pyrazolo[4,3-c]pyridin-6-amine (66.5 mg, 54%). LCMS (ESI): $R_T$ (min)=4.1882, $[M+H]^+$=460.3, method=B; $^1$H NMR (400 MHz, DMSO-$d_6$) δ 10.16 (s, 1H), 8.89 (s, 1H), 8.34 (s, 1H), 8.33 (d, J=6.0 Hz, 1H), 8.24 (s, 1H), 8.03 (s, 1H), 7.04 (d, J=5.9 Hz, 1H), 4.70 (p, J=6.7 Hz, 1H), 4.05 (d, J=7.1 Hz, 2H), 3.79 (t, J=4.8 Hz, 4H), 3.40 (t, J=4.8 Hz, 4H), 1.48 (d, J=6.6 Hz, 6H), 1.31 (ddd, J=12.3, 7.9, 4.9 Hz, 1H), 0.62-0.53 (m, 2H), 0.45-0.36 (m, 2H).

Example 10: 1-(4-((1-Isopropyl-3-(4-methyl-1H-pyrazol-5-yl)-1H-pyrazolo[4,3-c]pyridin-6-yl)amino)pyrimidin-2-yl)-3,3-dimethylpiperidin-4-ol

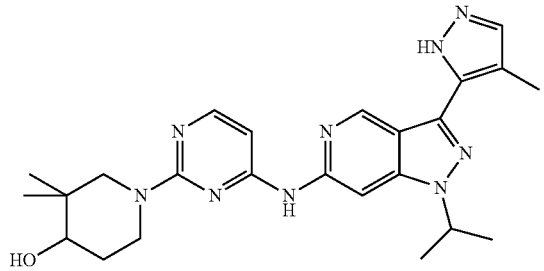

Step 1: 6-Chloro-1-isopropyl-3-(4-methyl-1-(tetrahydro-2H-pyran-2-yl)-1H-pyrazol-5-yl)-1H-pyrazolo[4,3-c]pyridine

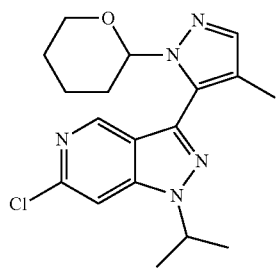 [SMILES: Cc1cnn(C2CCCCO2)c1-c1nn(C(C)C)c2cc(Cl)ncc12]

A mixture of 6-chloro-3-iodo-1-isopropyl-1H-pyrazolo[4,3-c]pyridine (Example 1, Step 8) (407.9 mg, 1.269 mmol), 4-methyl-1-(tetrahydro-2H-pyran-2-yl)-1H-pyrazole-5-boronic acid pinacol ester (475.7 mg, 1.547 mmol), [1,1'-bis(diphenylphosphino)ferrocene]palladium(II) chloride, complex with dichloromethane (1:1) (104.8 mg, 0.1283 mmol), and acetonitrile (4.0 mL, 76 mmol) was purged with nitrogen for 15 min and heated at 90° C. for 18 h. Sodium carbonate (2M in water)(1.3 mL, 2.6 mmol) was added and the reaction mixture was heated under microwave irradiation at 130° C. for 45 min. The reaction mixture was cooled to room temperature, filtered and concentrated onto celite. The crude product was purified via flash chromatography on silica gel (solvent gradient: 0%-10% methanol in dichloromethane) to yield 6-chloro-1-isopropyl-3-(4-methyl-1-(tetrahydro-2H-pyran-2-yl)-1H-pyrazol-5-yl)-1H-pyrazolo[4,3-c]pyridine (390.6 mg, 86%). LCMS (ESI) $[M+H]^+$=360.3.

Step 2: 1-(4-((1-Isopropyl-3-(4-methyl-1H-pyrazol-5-yl)-1H-pyrazolo[4,3-c]pyridin-6-yl)amino)pyrimidin-2-yl)-3,3-dimethylpiperidin-4-ol

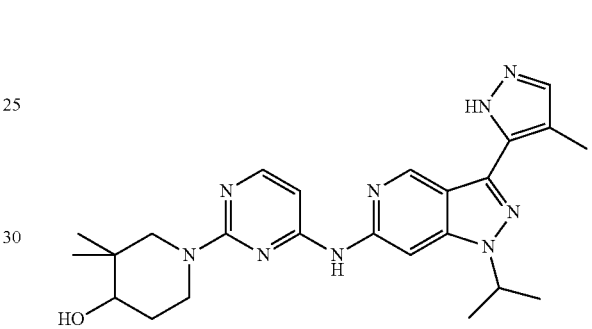

A mixture of 6-chloro-1-isopropyl-3-(4-methyl-1-(tetrahydro-2H-pyran-2-yl)-1H-pyrazol-5-yl)-1H-pyrazolo[4,3-c]pyridine (155.3 mg, 0.4316 mmol), 1-(4-aminopyrimidin-2-yl)-3,3-dimethyl-piperidin-4-ol (Example 3, Step 1) (125.4 mg, 0.5641 mmol), chloro{[BrettPhos][2-(2-aminoethylphenyl)palladium(II)]}/[BrettPhos] admixture (29.6 mg, 0.02 mmol), sodium tert-butoxide (131.1 mg, 1.36 mmol) and tert-butanol (2.0 mL, 21 mmol) was heated in a sealed vial under a nitrogen atmosphere at 100° C. for 2 h. The reaction mixture was cooled to room temperature, filtered through a PFTE frit, diluted with EtOAc, washed with water and brine, dried over magnesium sulfate, and concentrated. The resulting material was dissolved in methanol (3.0 mL, 70 mmol), treated with HCl (4M in 1,4-dioxane) (1.0 mL, 4.0 mmol), and stirred at room temperature for 4 h. This mixture was concentrated in vacuo, and the crude product was purified via reverse-phase HPLC and lyophilized to yield 1-(4-((1-isopropyl-3-(4-methyl-1H-pyrazol-5-yl)-1H-pyrazolo[4,3-c]pyridin-6-yl)amino)pyrimidin-2-yl)-3,3-dimethylpiperidin-4-ol (55.9 mg, 26%). LCMS (ESI): $R_T$ (min)=4.039, $[M+H]^+$=462.3, method=B; $^1$H NMR (400 MHz, DMSO-$d_6$) δ 12.81 (s, 1H), 9.94 (s, 1H), 9.19 (s, 1H), 8.38 (s, 1H), 7.97 (d, J=5.6 Hz, 1H), 7.67 (s, 1H), 6.33 (d, J=5.6 Hz, 1H), 4.80 (p, J=6.6 Hz, 1H), 4.65 (d, J=4.7 Hz, 1H), 4.46-4.34 (m, 1H), 4.18-4.06 (m, 1H), 3.42-3.35 (m, 1H), 3.35-3.30 (m, 1H), 3.04 (d, J=12.9 Hz, 1H), 2.37 (s, 3H), 1.79-1.66 (m, 1H), 1.63-1.46 (m, 7H), 0.96 (s, 3H), 0.84 (s, 3H).

Example 11: 1-Isopropyl-6-((2-(4-methoxypiperidin-1-yl)pyrimidin-4-yl)amino)-1H-pyrazolo[4,3-c]pyridine-3-carboxamide

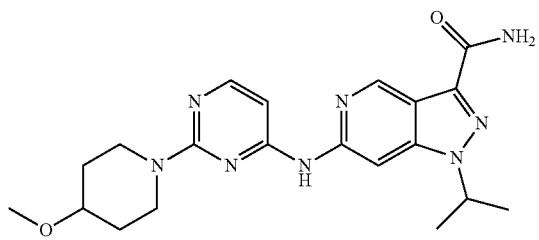 [SMILES: COC1CCN(c2nccc(Nc3cc4c(cn3)c(C(N)=O)nn4C(C)C)n2)CC1]

Step 1: Methyl 6-chloro-1-isopropyl-1H-pyrazolo[4,3-c]pyridine-3-carboxylate

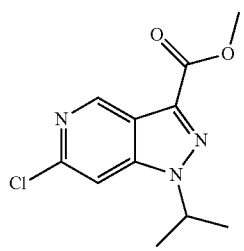 [SMILES: COC(=O)c1nn(C(C)C)c2cc(Cl)ncc12]

A mixture of 6-chloro-3-iodo-1-isopropyl-1H-pyrazolo[4,3-c]pyridine (Example 1, Step 8) (0.50 g, 1.6 mmol), palladium (II) acetate (17 mg, 0.078 mmol) and triethylamine (0.65 mL, 4.7 mmol) in methanol (5 mL) was bubbled with CO for 5 min. The reaction was then stirred under CO at 65° C. for 3 h. The reaction mixture was then cooled to room temperature, filtered and concentrated in vacuo. The crude product was purified via flash chromatography on silica gel (solvent gradient: 0%-100% EtOAc in heptane) to give methyl 6-chloro-1-isopropyl-1H-pyrazolo[4,3-c]pyridine-3-carboxylate (0.157 g, 40%). LCMS (ESI): $R_T$ (min)=1.08 min, $[M+H]^+$=322.0, method=P.

Step 2: 6-Chloro-1-isopropyl-1H-pyrazolo[4,3-c]pyridine-3-carboxamide

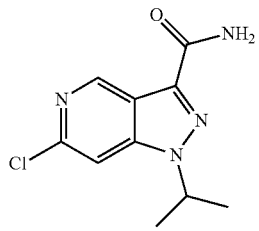 [SMILES: CC(C)n1nc(C(N)=O)c2cnc(Cl)cc21]

To a solution of methyl 6-chloro-1-isopropyl-1H-pyrazolo[4,3-c]pyridine-3-carboxylate (0.397 g, 1.56 mmol) in dichloroethane (10 mL) was added trimethyltin hydroxide (0.87 g, 4.7 mmol). The reaction was stirred at 60° C. for 4 h, cooled to room temperature, diluted with 0.1 M HCl and extracted with EtOAc (3×). The combined organic extracts were washed with brine, dried over anhydrous sodium sulfate, filtered and concentrated to give crude 6-chloro-1-isopropyl-1H-pyrazolo[4,3-c]pyridine-3-carboxylic acid which was taken on directly.

To a solution of crude 6-chloro-1-isopropyl-1H-pyrazolo[4,3-c]pyridine-3-carboxylic acid (0.25 g, 1.0 mmol) in N,N-dimethylformamide (10 mL) was added O-benzotriazole-N,N,N',N'-tetramethyluronium hexafluorophosphate (0.62 g, 1.6 mmol) and N,N-diisopropylethylamine (0.28 mL, 1.6 mmol). The reaction was stirred at room temperature for 20 min, ammonium hydroxide (10 mL) was added, and the reaction was stirred for an additional 20 min. The reaction was then diluted with saturated aqueous sodium bicarbonate and extracted with EtOAc (3×). The combined organic extracts were washed with brine, dried over anhydrous sodium sulfate, filtered and concentrated in vacuo. The crude product was purified via flash chromatography on silica gel (solvent gradient: 0%-100% EtOAc in heptane) to give 6-chloro-1-isopropyl-1H-pyrazolo[4,3-c]pyridine-3-carboxamide (95 mg, 38%). LCMS (ESI): $R_T$ (min)=0.63, $[M+H]^+$=240.1, method=P.

Step 3: 1-Isopropyl-6-((2-(4-methoxypiperidin-1-yl)pyrimidin-4-yl)amino)-1H-pyrazolo[4,3-c]pyridine-3-carboxamide

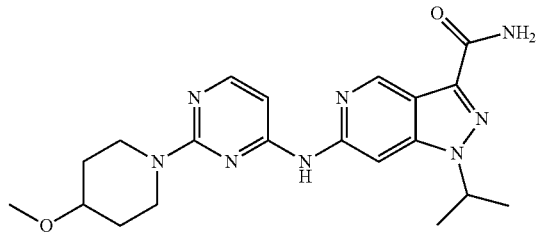 [SMILES: COC1CCN(c2nccc(Nc3cc4c(cn3)c(C(N)=O)nn4C(C)C)n2)CC1]

To a reaction vessel was added 6-chloro-1-isopropyl-1H-pyrazolo[4,3-c]pyridine-3-carboxamide (65 mg, 0.27 mmol), 2-(4-methoxypiperidin-1-yl)pyrimidin-4-amine (Example 2, Step 2) (57 mg, 0.27 mmol), sodium tert-butoxide (80 mg, 0.82 mmol), chloro{[BrettPhos][2-(2-aminoethylphenyl]palladium(II)]}/[Brettphos] admixture (PdP/P=1:1, 50 mg), and tert-butanol (2.5 mL). The mixture was degassed by nitrogen bubbling for 20 min. The reaction vessel was sealed and heated at 120° C. After 3 h, the reaction was cooled, filtered through celite and concentrated in vacuo. The crude product was then purified via reverse-phase HPLC and lyophilized to yield 1-isopropyl-6-((2-(4-methoxypiperidin-1-yl)pyrimidin-4-yl)amino)-1H-pyrazolo[4,3-c]pyridine-3-carboxamide (5.9 mg, 5.3%). LCMS (ESI): $R_T$ (min)=3.98, $[M+H]^+$=411.2, method=B; $^1$H NMR (400 MHz, DMSO-$d_6$) δ 10.07 (s, 1H), 9.10 (d, J=1.1 Hz, 1H), 8.44 (d, J=0.9 Hz, 1H), 8.01 (d, J=5.6 Hz, 1H), 7.71 (s, 1H), 7.52 (s, 1H), 6.37 (d, J=5.6 Hz, 1H), 4.82 (m, 1H), 4.37-4.15 (m, 2H), 3.61-3.37 (m, 3H), 1.91 (s, 2H), 1.64-1.36 (m, 8H).

Example 12: 1-(4-((1-(sec-Butyl)-3-(3-(2-hydroxy-propan-2-yl)azetidin-1-yl)-1H-pyrazolo[4,3-c]pyridin-6-yl)amino)pyrimidin-2-yl)-3,3-dimethylpiperidin-4-ol

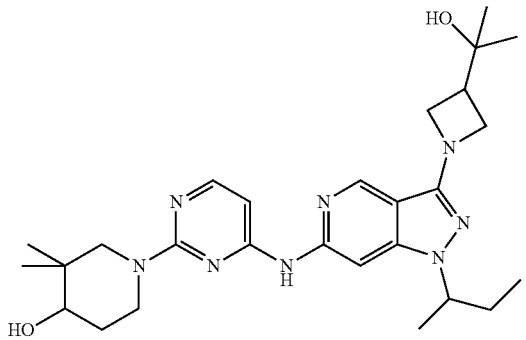 [SMILES: CCC(C)n1nc(N2CC(C(C)(C)O)C2)c2cnc(Nc3ccnc(N4CCC(O)C(C)(C)C4)n3)cc21]

Step 1: 1-(sec-Butyl)-6-chloro-3-iodo-1H-pyrazolo[4,3-c]pyridine

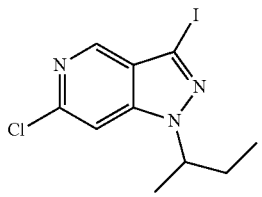

To a solution of 6-chloro-3-iodo-1H-pyrazolo[4,3-c]pyridine (3.5 g, 13 mmol) in N,N-dimethylformamide (25 mL) was added sodium hydride (60 wt % dispersion in mineral oil)(0.6 g, 15 mmol). The reaction mixture was stirred at room temperature for 10 min prior to the addition of 2-bromobutane (2.7 mL, 25 mmol). The reaction was stirred at room temperature for 5 h, diluted with brine and extracted with EtOAc (3×). The combined organic extracts were washed with brine, dried over anhydrous sodium sulfate, filtered and concentrated in vacuo. The crude product was purified via flash chromatography on silica gel (solvent gradient: 0%-100% EtOAc in heptane) to give 1-(sec-butyl)-6-chloro-3-iodo-1H-pyrazolo[4,3-c]pyridine (3.6 g, 86%). LCMS (ESI): $R_T$(min)=1.16, [M+H]$^+$=336.1, method=P. $^1$H NMR (400 MHz, CDCl$_3$) δ 8.56 (s, 1H), 7.31 (s, 1H), 4.54-4.35 (m, 1H), 2.15-1.99 (m, 1H), 1.98-1.81 (m, 1H), 1.61-1.49 (m, 3H), 0.79 (t, J=7.4 Hz, 3H).

Step 2: 2-[1-(6-Chloro-1-sec-butyl-pyrazolo[4,3-c]pyridin-3-yl)azetidin-3-yl)propan-2-ol

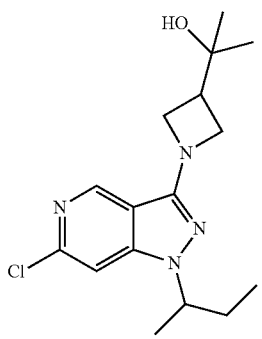 [SMILES: CCC(C)n1nc(N2CC(C(C)(C)O)C2)c2cnc(Cl)cc21]

To a reaction vessel was added 6-chloro-3-iodo-1-isopropyl-1H-pyrazolo[4,3-c]pyridine (1.0 g, 1.4 mmol), 2-(azetidin-3-yl)propan-2-ol (0.41 g, 3.6 mmol), potassium carbonate (1.4 g, 10 mmol), L-proline (0.17 g, 1.5 mmol), copper(I) iodide (0.28 g, 1.5 mmol) and N,N-dimethylformamide (8 mL). The reaction was degassed by nitrogen bubbling for 20 min. The reaction vessel was sealed and stirred at 90° C. After 3.5 h, the reaction was cooled to room temperature, filtered and extracted with EtOAc (3×). The combined organic extracts were washed with brine, dried over anhydrous sodium sulfate, filtered and concentrated in vacuo. The crude product was purified via flash chromatography on silica gel (solvent gradient: 0%-100% EtOAc in heptane) to give 2-[1-(6-chloro-1-sec-butyl-pyrazolo[4,3-c]pyridin-3-yl)azetidin-3-yl]propan-2-ol (0.45 g, 47%). LCMS (ESI): $R_T$(min)=0.93, [M+H]$^+$=323.3, method=P.

Step 3: 1-(4-((1-(sec-Butyl)-3-(3-(2-hydroxypropan-2-yl)azetidin-1-yl)-1H-pyrazolo[4,3-c]pyridin-6-yl)amino)pyrimidin-2-yl)-3,3-dimethylpiperidin-4-ol

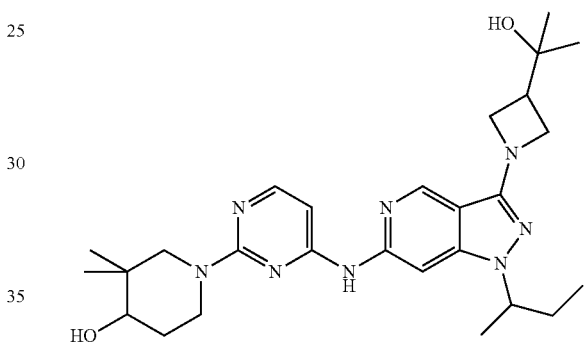

To a reaction vessel was added 2-[1-(6-chloro-1-sec-butyl-pyrazolo[4,3-c]pyridin-3-yl)azetidin-3-yl]propan-2-ol (0.20 g, 0.55 mmol) and 1-(4-aminopyrimidin-2-yl)-3,3-dimethyl-piperdin-4-ol (Example 3, Step 1) (0.12 g, 0.55 mmol), sodium tert-butoxide (160 mg, 1.6 mmol), chloro{[BrettPhos][2-(2-aminoethylphenyl]palladium(II)]}/[Brettphos] admixture (PdP/P=1:1, 60 mg) and tert-butanol (4 mL). The mixture was degassed by nitrogen bubbling for 15 min and heated at 120° C. for 90 min. The reaction was then cooled to room temperature, filtered and concentrated in vacuo. The crude product was purified via reverse-phase HPLC and lyophilized to yield a diastereomeric mixture of 1-(4-((1-(sec-butyl)-3-(3-(2-hydroxypropan-2-yl)azetidin-1-yl)-1H-pyrazolo[4,3-c]pyridin-6-yl)amino)pyrimidin-2-yl)-3,3-dimethylpiperidin-4-ol (116.5 mg, 42%). LCMS (ESI): $R_T$(min)=3.70, [M+H]$^+$=509.4. $^1$H NMR (400 MHz, DMSO-d$_6$) δ 9.81 (s, 1H), 8.55 (d, J=0.7 Hz, 1H), 8.13 (d, J=5.4 Hz, 1H), 7.94 (d, J=5.6 Hz, 1H), 6.30 (d, J=5.6 Hz, 1H), 4.69 (d, J=3.8 Hz, 1H), 4.49-4.30 (m, 2H), 4.30-4.15 (m, 1H), 4.14-3.95 (m, 5H), 3.00 (m, 1H), 2.82 (m, 1H), 2.00-1.84 (m, 1H), 1.83-1.67 (m, 2H), 1.53 (s, 1H), 1.40 (d, J=6.6 Hz, 3H), 1.08 (s, 6H), 0.94 (d, J=2.8 Hz, 3H), 0.81 (d, J=6.0 Hz, 3H), 0.69 (m, 3H).

Example 13: 2-(1-(1-(sec-Butyl)-6-((2-(1-(cyclopropylsulfonyl)-1H-pyrazol-4-yl)pyrimidin-4-yl)amino)-1H-pyrazolo[4,3-c]pyridin-3-yl)azetidin-3-yl)propan-2-ol

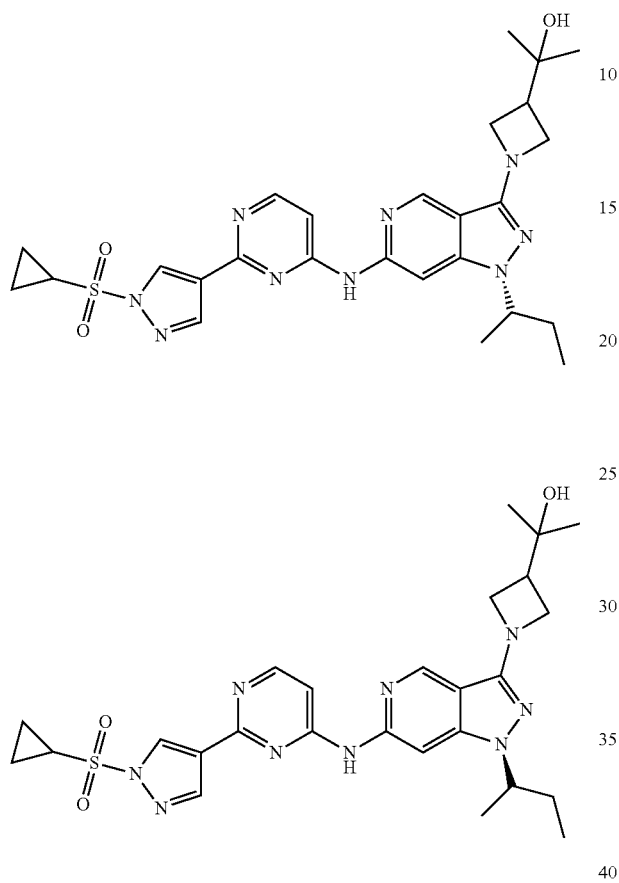

To a reaction vessel was added 2-[1-(6-chloro-1-sec-butyl-pyrazolo[4,3-c]pyridin-3-yl)azetidin-3-yl]propan-2-ol (Example 12, Step 2) (0.25 g, 0.68 mmol), 2-(1-(cyclopropylsulfonyl)-1H-pyrazol-4-yl)pyrimidin-4-amine (Example 1, Step 2) (0.18 g, 0.68 mmol), cesium carbonate (0.44 g, 1.4 mmol), 2-dicyclohexylphosphino-2',4',6'-triisopropylbiphenyl (66 mg, 0.14 mmol), tris(dibenzylideneacetone)dipalladium(0) (31 mg, 0.034 mmol) and 1,4-dioxane (3 mL). The reaction was degassed by nitrogen bubbling for 20 min and heated at 100° C. for 3 h. The reaction mixture was cooled to room temperature, filtered and concentrated in vacuo. The crude product was purified by chiral supercritical fluid chromatography to give the enantiomers of the title compound. Enantiomer 1 (43.4 mg, 12%): LCMS (ESI): $R_T$ (min)=4.40, [M+H]$^+$=552.3, method=B. $^1$H NMR (400 MHz, DMSO-d$_6$) δ 10.26 (s, 1H), 8.68 (s, 1H), 8.61 (s, 1H), 8.46 (s, 1H), 8.40 (d, J=5.9 Hz, 1H), 8.22 (s, 1H), 7.14 (d, J=5.8 Hz, 1H), 4.40 (s, 3H), 4.05 (m, 4H), 2.89-2.77 (m, 1H), 1.99-1.87 (m, 1H), 1.85-1.73 (m, 1H), 1.45 (d, J=6.6 Hz, 3H), 1.30 (m, 4H), 1.09 (s, 6H), 0.73 (t, J=7.3 Hz, 3H). Enantiomer 2 (40.1 mg, 11%): $R_T$ (min)=4.45, [M+H]$^+$=552.3, method=B. $^1$H NMR (400 MHz, DMSO-d$_6$) δ 10.27 (s, 1H), 8.68 (s, 1H), 8.61 (d, J=0.9 Hz, 1H), 8.53-8.43 (m, 1H), 8.40 (d, J=5.9 Hz, 1H), 8.23 (s, 1H), 7.13 (d, J=5.7 Hz, 1H), 4.39 (d, J=14.9 Hz, 3H), 4.11-3.98 (m, 4H), 2.88-2.78 (m, 1H), 2.00-1.88 (m, 1H), 1.85-1.73 (m, 1H), 1.45 (d, J=6.6 Hz, 3H), 1.34 (m, 2H), 1.26 (m, 2H), 1.09 (s, 6H), 0.73 (t, J=7.3 Hz, 3H).

Example 14: 1-(sec-Butyl)-N-(2-(1-(cyclopropylsulfonyl)-1H-pyrazol-4-yl)pyrimidin-4-yl)-3-(2-oxa-6-azaspiro[3.3]heptan-6-yl)-1H-pyrazolo[4,3-c]pyridin-6-amine

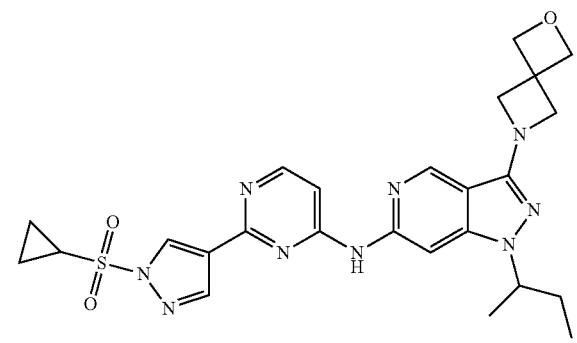 [SMILES: CCC(C)n1nc(N2CC3(COC3)C2)c2cnc(Nc3ccnc(-c4cnn(S(=O)(=O)C5CC5)c4)n3)cc21]

Step 1: 6-(1-(sec-Butyl)-6-chloro-1H-pyrazolo[4,3-c]pyridin-3-yl)-2-oxa-6-azaspiro[3.3]heptane

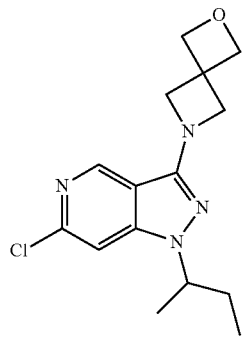 [SMILES: CCC(C)n1nc(N2CC3(COC3)C2)c2cnc(Cl)cc21]

To a reaction vessel was added 6-chloro-3-iodo-1-isopropyl-1H-pyrazolo[4,3-c]pyridine (Example 12, Step 1) (1.0 g, 3.0 mmol), 2-oxa-6-azaspiro[3.3]heptane (0.36 g, 3.6 mmol), cesium carbonate (1.9 g, 10 mmol), 4,5-bis(diphenylphosphino)-9,9-dimethylxanthene (0.17 g, 0.30 mmol), palladium(II) acetate (67 mg, 0.3 mmol) and 1,4-dioxane (3 mL). The reaction was degassed by nitrogen bubbling for 20 min and stirred at 120° C. After 3 h, the reaction was cooled to room temperature, filtered and concentrated in vacuo. The crude product was purified via flash chromatography on silica gel (solvent gradient: 0%-100% EtOAc in heptane) to give the title compound (0.2 g, 20%). LCMS (ESI): $R_T$ (min)=0.89, [M+H]$^+$=307.2, method=P.

Step 2: 1-(sec-Butyl)-N-(2-(1-(cyclopropylsulfonyl)-1H-pyrazol-4-yl)pyrimidin-4-yl)-3-(2-oxa-6-azaspiro[3.3]heptan-6-yl)-1H-pyrazolo[4,3-c]pyridin-6-amine

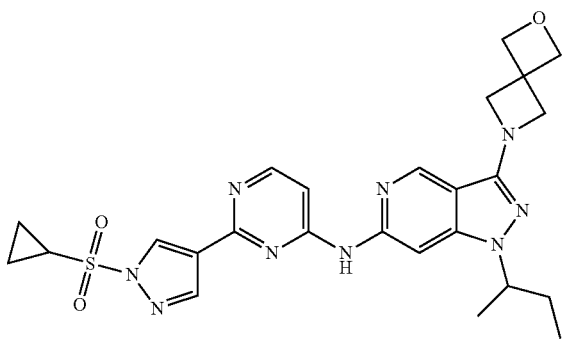 [SMILES: CCC(C)n1nc(N2CC3(COC3)C2)c2cnc(Nc3ccnc(-c4cnn(S(=O)(=O)C5CC5)c4)n3)cc21]

To a reaction vessel was added 6-(1-(sec-butyl)-6-chloro-1H-pyrazolo[4,3-c]pyridin-3-yl)-2-oxa-6-azaspiro[3.3]heptane (0.20 g, 0.65 mmol), 2-(1-(cyclopropylsulfonyl)-1H-pyrazol-4-yl)pyrimidin-4-amine (Example 1, Step 2) (0.17 g, 0.65 mmol), cesium carbonate (0.42 g, 1.3 mmol), 2-dicyclohexylphosphino-2',4',6'-triisopropylbiphenyl (63 mg, 0.13 mmol), tris(dibenzylideneacetone)dipalladium(0) (30 mg, 0.033 mmol) and 1,4-dioxane (3 mL). The reaction was degassed with nitrogen for 20 min and heated at 100° C. After 3 h, the reaction mixture was cooled to room temperature filtered and concentrated in vacuo. The crude product was purified by supercritical fluid chromatography to give a racemic mixture of 1-(sec-butyl)-N-(2-(1-(cyclopropylsulfonyl)-1H-pyrazol-4-yl)pyrimidin-4-yl)-3-(2-oxa-6-azaspiro[3.3]heptan-6-yl)-1H-pyrazolo[4,3-c]pyridin-6-amine (42 mg, 12%). LCMS (ESI): $R_T$ (min)=4.24, [M+H]$^+$=536.2, method=B; $^1$H NMR (400 MHz, DMSO-$d_6$) δ 10.28 (s, 1H), 8.68 (s, 1H), 8.61 (d, J=0.8 Hz, 1H), 8.46 (s, 1H), 8.41 (d, J=5.9 Hz, 1H), 8.24 (s, 1H), 7.14 (d, J=5.8 Hz, 1H), 4.75 (s, 4H), 4.48-4.34 (m, 1H), 4.29 (s, 4H), 3.35-3.22 (m, 1H), 2.00-1.86 (m, 1H), 1.86-1.72 (m, 1H), 1.44 (d, J=6.6 Hz, 3H), 1.39-1.18 (m, 4H), 0.72 (t, J=7.3 Hz, 3H).

Example 15: 1-Isopropyl-N-(2-(4-methoxypiperidin-1-yl)pyrimidin-4-yl)-3-(pyrrolidin-1-yl)-1H-pyrazolo[4,3-c]pyridin-6-amine

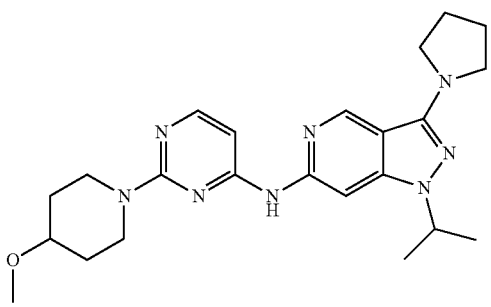 [SMILES: COC1CCN(c2nccc(Nc3cc4c(cn3)c(N3CCCC3)nn4C(C)C)n2)CC1]

To a reaction vessel was added 6-chloro-1-isopropyl-3-(pyrrolidin-1-yl)-1H-pyrazolo[4,3-c]pyridine (Example 8, Step 1) (75 mg, 0.28 mmol), 1-(4-aminopyrimidin-2-yl)-3,3-dimethyl-piperdin-4-ol (Example 2, Step 2) (59 mg, 0.28 mmol), sodium tert-butoxide (84 mg, 0.85 mmol), chloro{[BrettPhos][2-(2-aminoethylphenyl]palladium(II)]}/[Brettphos] admixture (PdP/P=1:1, 50 mg) and tert-butanol (5 mL). The mixture was degassed by nitrogen bubbling for 20 min. The reaction vessel was sealed and heated at 125° C. After 1 h, the reaction was cooled to room temperature, filtered through celite and concentrated in vacuo. The crude product was then purified via reverse-phase HPLC and lyophilized to yield 1-isopropyl-N-(2-(4-methoxypiperidin-1-yl)pyrimidin-4-yl)-3-(pyrrolidin-1-yl)-1H-pyrazolo[4,3-c]pyridin-6-amine (37 mg, 30%). LCMS (ESI): $R_T$ (min)=4.76, [M+H]$^+$=437.3, method=B. $^1$H NMR (400 MHz, DMSO-$d_6$) δ 9.76 (s, 1H), 8.71 (d, J=0.9 Hz, 1H), 8.08 (s, 1H), 7.97 (d, J=5.6 Hz, 1H), 6.37 (d, J=5.7 Hz, 1H), 4.61-4.42 (m, 1H), 4.23 (m, 2H), 3.54 (m, 4H), 3.47 (m, 1H), 3.44-3.33 (m, 2H), 1.94 (m, 6H), 1.42 (m, 8H).

Example 16: N$^6$-(2-(1-(Ethylsulfonyl)-1H-pyrazol-4-yl)pyrimidin-4-yl)-1-isopropyl-N$^3$-(oxetan-3-yl)-1H-pyrazolo[4,3-c]pyridine-3,6-diamine

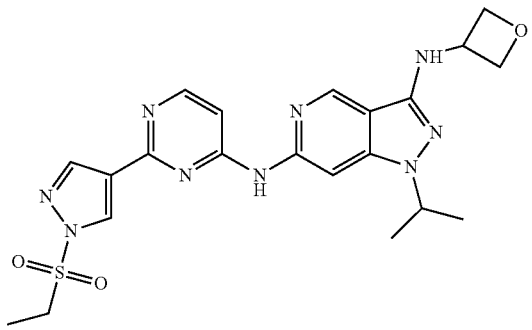 [SMILES: CCS(=O)(=O)n1cc(-c2nccc(Nc3cc4c(cn3)c(NC3COC3)nn4C(C)C)n2)cn1]

Step 1: 2-Bromo-5-iodopyridin-4-amine

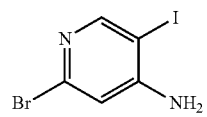

To a 3-necked round-bottom flask containing 2-bromopyridin-4-amine (100 g, 578 mmol), acetic acid (1 L) and sodium acetate (118 g, 1.44 mol) was added a solution of iodine monochloride (103 g, 635 mmol) in acetic acid (0.5 L) dropwise with stirring at 50° C. The resulting solution was stirred for 3 h at 75° C. The reaction mixture was cooled to room temperature and concentrated in vacuo. The resulting solution was diluted with brine (1 L) and extracted with EtOAc (3×1 L). The combined organic layers were washed with saturated aqueous sodium bicarbonate (2×0.5 L), saturated aqueous sodium sulfite (0.2 L), and brine (0.3 L), dried over anhydrous sodium sulfate and concentrated in vacuo. The crude product was purified via flash chromatography on silica gel (eluent: 5% EtOAc in dichloromethane) to afford 2-bromo-5-iodopyridin-4-amine (50 g, 29%) as a white solid. LCMS (ESI): $R_T$ (min)=1.114, [M+H]$^+$=299, method=L.

Step 2: 2-Bromo-4-chloro-5-iodopyridine

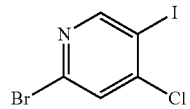

To a 3-necked round-bottom flask containing acetonitrile (1.5 L), 2-bromo-5-iodopyridin-4-amine (125 g, 418 mmol) and copper (I) chloride (61.0 g, 622 mmol) was added tert-butyl nitrite (86.0 g, 835 mmol) dropwise with stirring at 50° C. The resulting solution was heated to reflux for 1 h. The reaction mixture was cooled to room temperature and concentrated in vacuo. The crude product was purified via flash chromatography on silica gel (solvent gradient: 1%-10% EtOAc in petroleum ether) to afford 2-bromo-4-chloro-5-iodopyridine (96 g, 72%) as a yellow solid.

Step 3: Methyl 6-bromo-4-chloropyridine-3-carboxylate

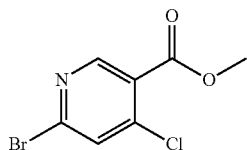

To a 2 L pressure tank reactor was placed 2-bromo-4-chloro-5-iodopyridine (30.0 g, 94.2 mmol), methanol (500 L), triethylamine (28.6 g, 282 mmol), and palladium (II) acetate (2.10 g, 9.35 mmol). The resulting solution was stirred at 60° C. under an atmosphere of CO (1-2 atm). After 18 h, the reaction was cooled to room temperature, filtered and concentrated in vacuo. The crude product was purified via flash chromatography on silica gel (solvent gradient: 2%-20% EtOAc in petroleum ether) to afford methyl 6-bromo-4-chloropyridine-3-carboxylate (11 g, 47%) as a white solid. LCMS (ESI): $R_T$ (min)=3.243, $[M+H]^+$=250, method=L; $^1$H NMR (300 MHz, DMSO-$d_6$): δ 8.14 (s, 1H), 7.64 (s, 1H), 3.98 (s, 3H).

Step 4: 6-Bromo-4-chloropyridine-3-carbaldehyde

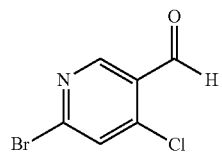

To a 3-necked round-bottom flask under nitrogen containing methyl 6-bromo-4-chloropyridine-3-carboxylate (35.0 g, 139 mmol) in dichloromethane (700 mL) was added diisobutylaluminum hydride (1M in hexanes) (153 mL) dropwise with stirring at −78° C. The resulting solution was maintained at −78° C. for 1 h and then warmed to room temperature. After 1 h, the reaction was quenched by addition of HCl (2N in water, 100 mL) followed by water (500 mL). The resulting solution was extracted with dichloromethane (3×500 mL) and the combined organic layers were washed with brine, dried over anhydrous sodium sulfate and concentrated in vacuo. The crude product was purified via flash chromatography on silica gel (solvent gradient: 1%-10% EtOAc in petroleum ether) to afford 6-bromo-4-chloropyridine-3-carbaldehyde (17 g, 55%) as a white solid. LCMS (ESI): $R_T$ (min)=1.404, $[M+H]^+$=220, method=L.

Step 5: 6-Bromo-1H-pyrazolo[4,3-c]pyridine

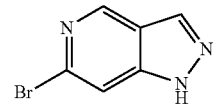

To a reaction vessel, was added 6-bromo-4-chloropyridine-3-carbaldehyde (24.0 g, 109 mmol), 1,4-dioxane (600 mL), triethylamine (22.0 g, 217 mmol), hydrazine hydrate (9.50 g, 131 mmol) and the reaction mixture was heated to reflux for 3 days. The reaction was cooled to room temperature and concentrated in vacuo. The crude product was purified via flash chromatography on silica gel (solvent gradient: 1%-5% methanol in dichloromethane) to afford 6-bromo-1H-pyrazolo[4,3-c]pyridine (7.4 g, 34%) as a yellow solid. LCMS (ESI): $R_T$ (min)=1.195, $[M+H]^+$=198, method=L; $^1$H NMR (400 MHz, DMSO-$d_6$): δ 13.62 (br, 1H), 8.93 (s, 1H), 8.35 (s, 1H), 7.81 (s, 1H).

Step 6: 6-Bromo-3-iodo-1H-pyrazolo[4,3-c]pyridine

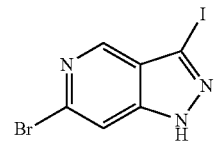

To a reaction vessel, was added a solution of 6-bromo-1H-pyrazolo[4,3-c]pyridine (5.50 g, 27.8 mmol) in N,N-dimethylformamide (100 mL), potassium hydroxide (3.60 g, 64.2 mmol) and iodine (14.2 g, 55.9 mmol) and the resulting mixture was stirred for 16 h at 40° C. The reaction was cooled to room temperature and diluted with water (500 mL). The resulting suspension was filtered and the solids were collected and dried in an oven under reduced pressure to afford 6-bromo-3-iodo-1H-pyrazolo[4,3-c]pyridine (10.5 g) as a yellow solid. LCMS (ESI): $R_T$ (min)=1.390, $[M+H]^+$=324, method=M; $^1$H NMR (400 MHz, DMSO-$d_6$): δ 14.00 (s, 1H), 8.61 (s, 1H), 7.88 (s, 1H).

Step 7: 6-Bromo-3-iodo-1-isopropyl-1H-pyrazolo[4,3-c]pyridine

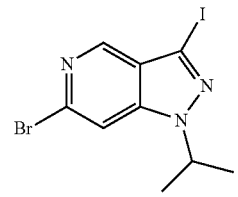

To a solution of 6-bromo-3-iodo-1H-pyrazolo[4,3-c]pyridine (10.4 g, 32.1 mmol) in N,N-dimethylformamide (100 mL) under nitrogen was added sodium hydride (2.10 g, 52.5 mmol) and 2-iodopropane (21.0 g, 123 mmol) and the reaction mixture was stirred at room temperature. After 16 h, the reaction was quenched with water (400 mL) and extracted with EtOAc (2×300 mL). The combined organic layers were washed with brine, dried over anhydrous sodium sulfate and concentrated in vacuo. The crude product was purified via flash chromatography on silica gel (eluent: 10% EtOAc in petroleum ether) to afford 6-bromo-3-iodo-1-isopropyl-1H-pyrazolo[4,3-c]pyridine (5.2 g, 44%) as a white solid. LCMS (ESI): $R_T$ (min)=1.598, M+H$^+$=366, method=M; $^1$H NMR (400 MHz, DMSO-d$_6$): δ 8.57 (s, 1H), 8.13 (s, 1H), 5.07-5.00 (m, 1H), 1.46-1.45 (d, J=6.8 Hz, 6H).

Step 8: 6-Bromo-1-isopropyl-N-(oxetan-3-yl)-1H-pyrazolo[4,3-c]pyridin-3-amine

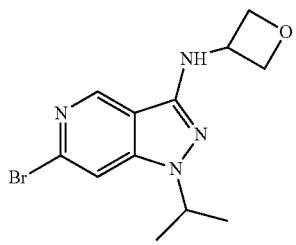 [SMILES: CC(C)n1nc(NC2COC2)c2cnc(Br)cc21]

To a solution of 6-bromo-3-iodo-1-isopropyl-1H-pyrazolo[4,3-c]pyridine (400 mg, 1.09 mmol, 1.00 equiv) in 1.4-dioxane (10 mL) under nitrogen was added palladium (II) acetate (24.3 mg, 0.110 mmol), 4,5-bis(diphenylphosphino)-9,9-dimethylxanthene (94.7 mg, 0.160 mmol), cesium carbonate (891 mg, 2.73 mmol) and oxetan-3-amine (95.7 mg, 1.31 mmol). The reaction mixture was stirred at 80° C. After 90 min, the reaction mixture was cooled to room temperature and concentrated in vacuo. The crude product was purified via flash chromatography on silica gel (eluent: 5% methanol in dichloromethane) to afford 6-bromo-1-isopropyl-N-(oxetan-3-yl)-1H-pyrazolo[4,3-c]pyridin-3-amine (120 mg, 35%) as a yellow solid. LCMS (ESI): $R_T$ (min)=1.395, M+H$^+$=311, method=N.

Step 9: 2-(1-(Ethylsulfonyl)-1H-pyrazol-4-yl)pyrimidin-4-amine

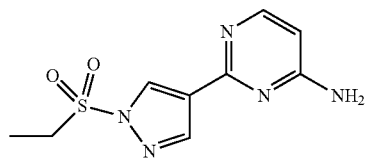 [SMILES: CCS(=O)(=O)n1cc(-c2nccc(N)n2)cn1]

2-(1-(Ethylsulfonyl)-1H-pyrazol-4-yl)pyrimidin-4-amine was prepared in a method analogous to Example 1, Step 2. LCMS (ESI): $R_T$ (min)=0.358, M+H$^+$=254, method=M.

Step 10: N$^6$-(2-(1-(Ethylsulfonyl)-1H-pyrazol-4-yl) pyrimidin-4-yl)-1-isopropyl-N$^3$-(oxetan-3-yl)-1H-pyrazolo[4,3-c]pyridine-3,6-diamine

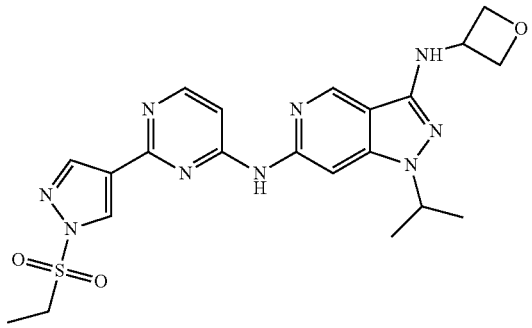 [SMILES: CCS(=O)(=O)n1cc(-c2nccc(Nc3cc4c(cn3)c(NC3COC3)nn4C(C)C)n2)cn1]

A solution of 6-bromo-1-isopropyl-N-(oxetan-3-yl)-1H-pyrazolo[4,3-c]pyridin-3-amine (50.0 mg, 0.160 mmol) in 1,4-dioxane (2 mL) under nitrogen was treated with tris(dibenzylideneacetone)dipalladium(0) (14.7 mg, 0.020 mmol), 4,5-bis(diphenylphosphino)-9,9-dimethylxanthene (18.6 mg, 0.030 mmol), cesium carbonate (105 mg, 0.320 mmol), and 2-[1-(ethanesulfonyl)-1H-pyrazol-4-yl]-4-methylpyrimidine (40.7 mg, 0.160 mmol) and stirred for 2 h at 90° C. The reaction was cooled to room temperature and concentrated in vacuo. The crude product was purified via flash chromatography on silica gel (eluent: 5% methanol in dichloromethane) to afford N$^6$-(2-(1-(ethylsulfonyl)-1H-pyrazol-4-yl)pyrimidin-4-yl)-1-isopropyl-N$^3$-(oxetan-3-yl)-1H-pyrazolo[4,3-c]pyridine-3,6-diamine (5 mg, 6%) as a yellow solid. LCMS (ESI): RT (min)=1.504, M+H$^+$=484, method=N; $^1$H NMR (300 MHz, CDCl$_3$) δ 9.00 (br, 1H), 8.76 (s, 1H), 8.73 (s, 1H), 8.49 (s, 1H), 8.46 (s, 1H), 8.44 (s, 1H), 6.90-6.88 (d, J=6 Hz, 1H), 5.20 (br, 1H), 5.07-4.98 (m, 3H), 4.71-4.69 (m, 2H), 4.68-4.58 (m, 1H), 3.63-3.55 (m, 2H), 1.57-1.50 (s, 6H), 1.35-1.30 (m, 3H)

Example 17: 1-(6-(2-(1-(Ethylsulfonyl)-1H-pyrazol-4-yl) pyrimidin-4-ylamino)-1-isopropyl-1H-pyrazolo [4,3-c] pyridin-3-yl)-N, N-dimethylazetidine-3-carboxamide

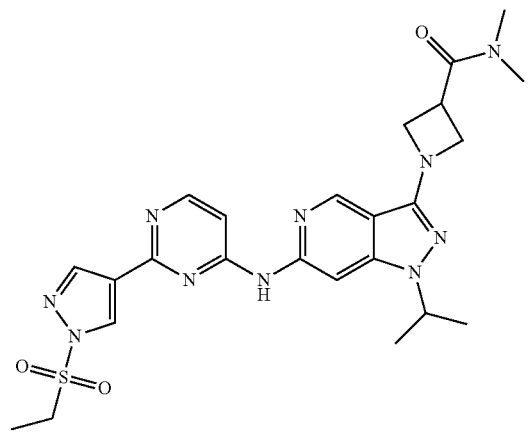 [SMILES: CCS(=O)(=O)n1cc(-c2nccc(Nc3cc4c(cn3)c(N3CC(C(=O)N(C)C)C3)nn4C(C)C)n2)cn1]

Step 1: 1-(6-Bromo-1-isopropyl-1H-pyrazolo [4,3-c] pyridin-3-yl)-N, N-dimethylazetidine-3-carboxamide

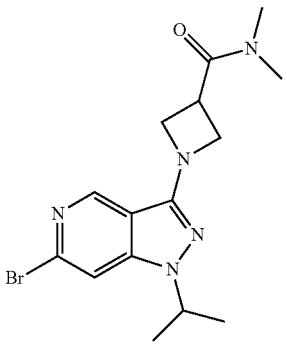 [SMILES: CC(C)n1nc(N2CC(C(=O)N(C)C)C2)c2cnc(Br)cc21]

To a reaction vessel purged and maintained under nitrogen was added 6-bromo-3-iodo-1-isopropyl-1H-pyrazolo[4,3-c]pyridine (Example 16, Step 7) (250 mg, 0.680 mmol), tris(dibenzylideneacetone)dipalladium(0) (62.0 mg, 0.0680 mmol), 4,5-bis(diphenylphosphino)-9,9-dimethylxanthene (38.8 mg, 0.0680 mmol), N,N-dimethylazetidine-3-carboxamide hydrochloride (146 mg, 0.890 mmol), cesium carbonate (669 mg, 2.05 mmol) and 1,4-dioxane (6 mL). The resulting mixture was stirred for 3 h at 95° C. The reaction was cooled to room temperature and extracted with EtOAc. The organic layer was washed with brine, dried over anhydrous sodium sulfate and concentrated in vacuo. The crude product was purified via flash chromatography on silica gel (eluent: 25% EtOAc in petroleum ether) to provide 1-(6-bromo-1-isopropyl-1H-pyrazolo[4,3-c] pyridin-3-yl)-N, N-dimethylazetidine-3-carboxamide (140 mg, 56%) as a yellow solid. LCMS (ESI): $R_T$ (min)=1.288, M+H$^+$=366, method=N.

Step 2: 1-(6-(2-(1-(Ethylsulfonyl)-1H-pyrazol-4-yl) pyrimidin-4-ylamino)-1-isopropyl-1H-pyrazolo[4,3-c] pyridin-3-yl)-N, N-dimethylazetidine-3-carboxamide

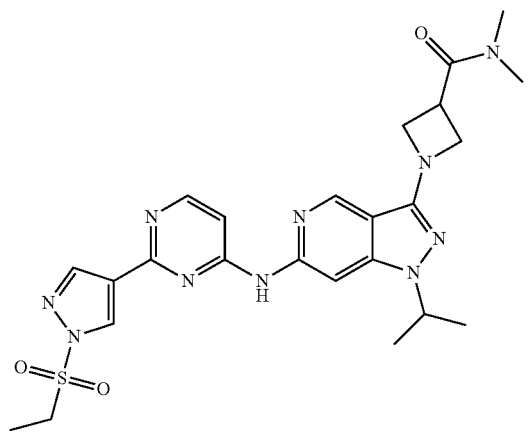 [SMILES: CCS(=O)(=O)n1cc(-c2nccc(Nc3cc4c(cn3)c(N3CC(C(=O)N(C)C)C3)nn4C(C)C)n2)cn1]

To a reaction vessel purged and maintained under nitrogen was added 1-(6-bromo-1-isopropyl-1H-pyrazolo[4,3-c] pyridin-3-yl)-N, N-dimethylazetidine-3-carboxamide (140 mg, 0.380 mmol), tris(dibenzylideneacetone)dipalladium(0) (35.0 mg, 0.0380 mmol), 4,5-bis(diphenylphosphino)-9,9-dimethylxanthene (21.7 mg, 0.0380 mmol), 2-(1-(ethylsulfonyl)-1H-pyrazol-4-yl)pyrimidin-4-amine (Example 16, Step 9) (116 mg, 0.460 mmol), cesium carbonate (250 mg, 0.770 mmol), and 1,4-dioxane (4 mL). The reaction mixture was stirred for 2 h at 90° C. The reaction was cooled to room temperature, extracted with EtOAc, and the organic layer was washed with brine, dried over anhydrous sodium sulfate and concentrated in vacuo. The crude product was purified via reverse-phase HPLC and lyophilized to yield 1-(6-(2-(1-(ethylsulfonyl)-1H-pyrazol-4-yl) pyrimidin-4-ylamino)-1-isopropyl-1H-pyrazolo[4,3-c] pyridin-3-yl)-N, N-dimethylazetidine-3-carboxamide (30 mg, 15%) as a off-white solid. LCMS (ESI): $R_T$ (min)=1.585, M+H$^+$=539, method=P; $^1$H NMR (400 MHz, DMSO-d$_6$): δ 10.35 (s, 1H), 8.69 (s, 1H), 8.64 (s, 1H), 8.48 (s, 1H), 8.41 (d, J=6 Hz, 1H), 8.30 (s, 1H), 7.13 (d, J=5.6 Hz, 1H), 4.72 (m, 1H), 4.31-4.35 (m, 2H), 4.16-4.19 (m, 2H), 3.93 (m, 1H), 3.83 (m, 2H), 2.91 (s, 3H), 2.86 (s, 3H), 1.45 (s, 6H), 1.31 (m, 3H)

Example 18: 1-(6-(2-(1-(Cyclopropylsulfonyl)-1H-pyrazol-4-yl) pyrimidin-4-ylamino)-1-isopropyl-1H-pyrazolo[4,3-c] pyridin-3-yl) pyrrolidin-3-ol

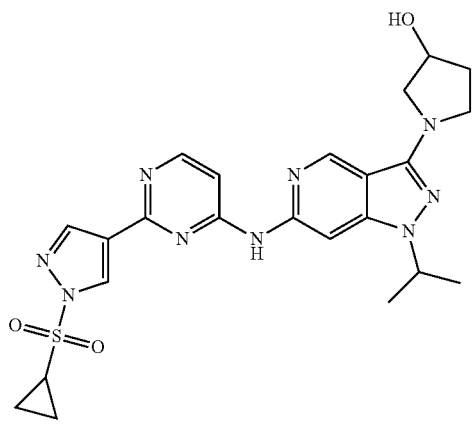 [SMILES: CC(C)n1nc(N2CCC(O)C2)c2cnc(Nc3ccnc(-c4cnn(S(=O)(=O)C5CC5)c4)n3)cc21]

Step 1: 1-(6-Bromo-1-isopropyl-1H-pyrazolo[4,3-c] pyridin-3-yl) pyrrolidin-3-ol

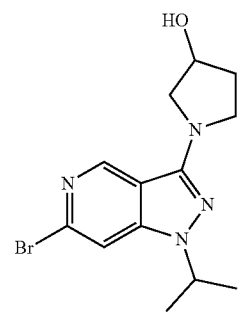 [SMILES: CC(C)n1nc(N2CCC(O)C2)c2cnc(Br)cc21]

To a microwave reaction vessel containing 6-bromo-3-iodo-1-isopropyl-1H-pyrazolo[4,3-c]pyridine (Example 16, Step 7) (400 mg, 1.09 mmol) in N,N-dimethylformamide (20 mL) was added pyrrolidin-3-ol hydrochloride (300 mg, 2.43 mmol), copper (I) iodide (64.0 mg, 0.340 mmol), L-proline (40.0 mg, 0.350 mmol), and potassium carbonate (480 mg, 3.47 mmol). The reaction vessel was sealed and irradiated in the microwave for 90 min at 100° C. Upon cooling to room temperature, the reaction mixture was diluted with water and extracted with EtOAc. The organic layer was washed with brine, dried over anhydrous sodium sulfate and concentrated in vacuo. The crude product was purified via flash chromatography on silica gel (eluent: 60% EtOAc in petroleum ether) to provide to afford 1-(6-bromo-1-isopropyl-1H-pyrazolo[4,3-c] pyridin-3-yl) pyrrolidin-3-ol (110 mg, 31%) as brown oil. LCMS (ESI): $R_T$ (min)=1.341, M+H$^+$=325, method=N.

Step 2: 1-(6-(2-(1-(Cyclopropylsulfonyl)-1H-pyrazol-4-yl) pyrimidin-4-ylamino)-1-isopropyl-1H-pyrazolo[4,3-c] pyridin-3-yl) pyrrolidin-3-ol

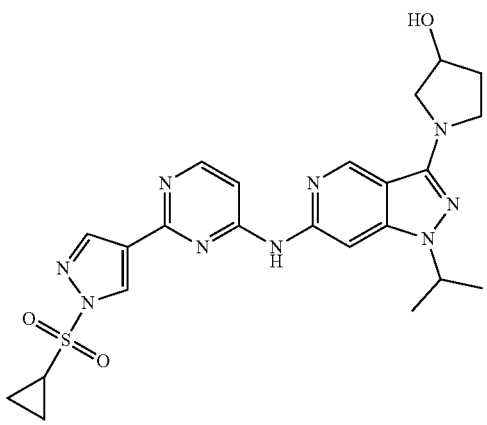 [SMILES: CC(C)n1nc(N2CCC(O)C2)c2cnc(Nc3ccnc(-c4cnn(S(=O)(=O)C5CC5)c4)n3)cc21]

The title compound was prepared in a method analogous to Example 17, Step 2 to provide 1-(6-(2-(1-(cyclopropylsulfonyl)-1H-pyrazol-4-yl) pyrimidin-4-ylamino)-1-isopropyl-1H-pyrazolo[4,3-c] pyridin-3-yl) pyrrolidin-3-ol (39.9 mg, 25%) as a yellow solid. LCMS (ESI): $R_T$ (min)=1.489, M+H$^+$=510, method=L; $^1$H NMR (400 MHz, DMSO-d$_6$): δ 10.29 (s, 1H), 8.77 (s, 1H), 8.70 (s, 1H), 8.48 (s, 1H), 8.41 (d, J=6.0 Hz, 1H), 8.24 (s, 1H), 7.14 (d, J=5.6 Hz, 1H), 4.96 (s, 1H), 4.72-4.65 (m, 1H), 4.43 (m, 1H), 3.72-3.60 (m, 3H), 3.45-3.43 (m, 1H), 3.29-3.26 (m, 1H), 2.10-2.04 (m, 1H), 1.94-1.90 (m, 1H), 1.47 (d, J=6.6 Hz, 6H), 1.37-1.34 (m, 2H), 1.28-1.24 (m, 2H)

Example 19: N-(2-(1-(Cyclopropylsulfonyl)-1H-pyrazol-4-yl) pyrimidin-4-yl)-1-isopropyl-3-(tetrahydrofuran-3-yl)-1H-pyrazolo[4,3-c] pyridin-6-amine

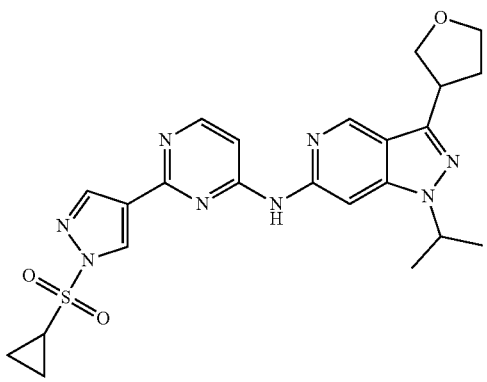 [SMILES: CC(C)n1nc(C2CCOC2)c2cnc(Nc3ccnc(-c4cnn(S(=O)(=O)C5CC5)c4)n3)cc21]

Step 1: 6-Bromo-3-(2, 5-dihydrofuran-3-yl)-1-isopropyl-1H-pyrazolo[4,3-c] pyridine

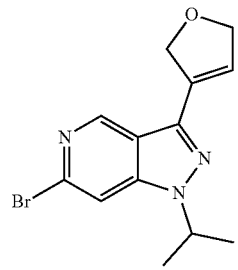 [SMILES: CC(C)n1nc(C2=CCOC2)c2cnc(Br)cc21]

To a microwave reaction vessel was added 6-bromo-3-iodo-1-isopropyl-1H-pyrazolo[4,3-c]pyridine (Example 16, Step 7) (517 mg, 1.41 mmol), 2-(2,5-dihydrofuran-3-yl)-4,4,5,5-tetramethyl-1,3,2-dioxaborolane (300 mg, 1.53 mmol), [1,1'-bis(diphenylphosphino)ferrocene] dichloropalladium(II), complex with dichloromethane (80.7 mg, 0.100 mmol), sodium carbonate (1M in water, 2.5 mL), potassium acetate (1 M in water, 2.5 mL) and acetonitrile (10 mL). The reaction mixture was irradiated in the microwave for 15 min at 100° C., cooled to room temperature, diluted with water and extracted with EtOAc. The organic layer was washed with brine, dried over anhydrous sodium sulfate and concentrated in vacuo. The crude product was purified via flash chromatography on silica gel (eluent: 5% EtOAc in petroleum ether) to afford 6-bromo-3-(2, 5-dihydrofuran-3-yl)-1-isopropyl-1H-pyrazolo[4,3-c] pyridine (300 mg, 34%) as a yellow solid. LCMS (ESI): $R_T$ (min)=1.530, M+H$^+$=308, method=M.

Step 2: N-(2-(1-(Cyclopropylsulfonyl)-1H-pyrazol-4-yl)pyrimidin-4-yl)-3-(2,5-dihydrofuran-3-yl)-1-isopropyl-1H-pyrazolo[4,3-c]pyridin-6-amine

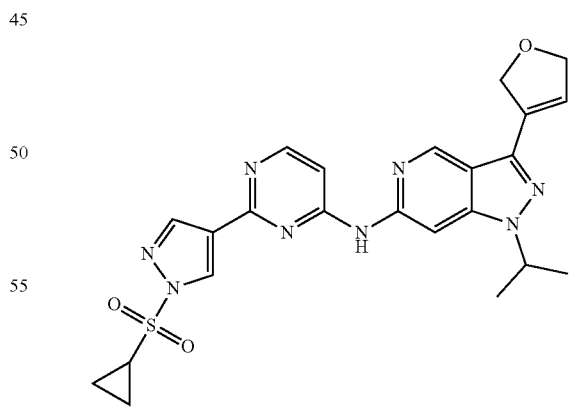

The title compound was prepared in a method analogous to Example 17, Step 2 to afford N-(2-(1-(cyclopropylsulfonyl)-1H-pyrazol-4-yl)pyrimidin-4-yl)-3-(2,5-dihydrofuran-3-yl)-1-isopropyl-1H-pyrazolo[4,3-c]pyridin-6-amine (100 mg, 21%) as a yellow solid. LCMS (ESI): $R_T$ (min)=1.335, M+H$^+$=493, method=N.

Step 3: N-(2-(1-(Cyclopropylsulfonyl)-1H-pyrazol-4-yl)pyrimidin-4-yl)-1-isopropyl-3-(tetrahydrofuran-3-yl)-1H-pyrazolo[4,3-c] pyridin-6-amine

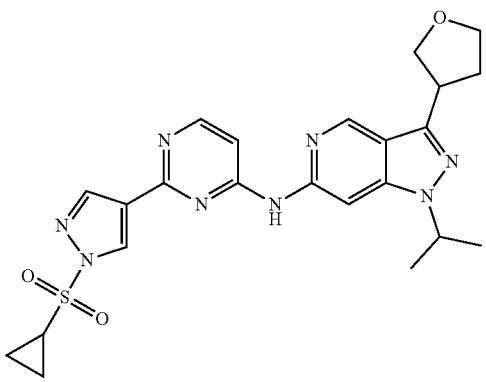 [SMILES: CC(C)n1nc(C2CCOC2)c2cnc(Nc3ccnc(-c4cnn(S(=O)(=O)C5CC5)c4)n3)cc21]

To a 3-necked round-bottom flask purged and maintained under nitrogen was placed a solution of N-(2-(1-(cyclopropylsulfonyl)-1H-pyrazol-4-yl)pyrimidin-4-yl)-3-(2,5-dihydrofuran-3-yl)-1-isopropyl-1H-pyrazolo[4,3-c]pyridin-6-amine (220 mg, 0.450 mmol, 1.00 equiv) and palladium hydroxide (110 mg, 0.780 mmol, 0.700 equiv) in a mixture of methanol and EtOAc (1:1, 10 mL). The atmosphere was exchanged for hydrogen gas and the reaction mixture was stirred for 5 h at room temperature. The reaction mixture was filtered and concentrated in vacuo. The crude product was purified via reverse-phase HPLC and lyophilized to yield N-(2-(1-(cyclopropylsulfonyl)-1H-pyrazol-4-yl)pyrimidin-4-yl)-1-isopropyl-3-(tetrahydrofuran-3-yl)-1H-pyrazolo[4,3-c]pyridin-6-amine (11 mg, 5%) as a white solid. LCMS (ESI): RT (min)=1.805, M+H$^+$=495, method=P; $^1$H NMR (400 MHz, DMSO-d$_6$): δ 10.45 (s, 1H), 8.88 (s, 1H), 8.72 (s, 1H), 8.48 (d, J=6.0 Hz, 2H), 8.42 (d, J=6.0 Hz, 1H), 7.13 (d, J=5.6 Hz, 1H), 4.90-4.87 (m, 1H), 4.18-4.14 (m, 1H), 4.02-3.91 (m, 1H), 3.90-3.81 (m, 3H), 3.32-3.27 (m, 1H), 2.47-2.42 (m, 1H), 2.25-2.22 (m, 1H), 1.54-1.52 (d, J=6.6 Hz, 6H), 1.36-1.34 (m, 2H), 1.29-1.24 (m, 2H)

Example 20: (±)-cis-3-Fluoro-1-[4-(1-isopropyl-3-morpholin-4-yl-1H-pyrazolo[4,3-c]pyridin-6-ylamino)pyrimidin-2-yl]piperidin-4-ol

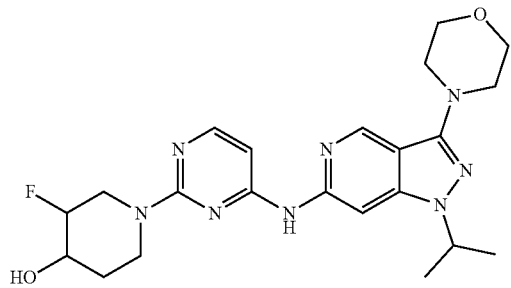 [SMILES: CC(C)n1nc(N2CCOCC2)c2cnc(Nc3ccnc(N4CCC(O)C(F)C4)n3)cc21]

Step 1: 6-Chloro-1-isopropyl-3-morpholin-4-yl-1H-pyrazolo[4,3-c]pyridine

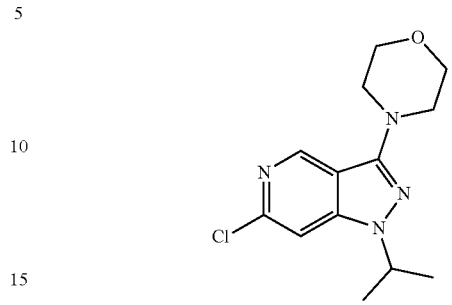

6-Chloro-3-iodo-1-isopropyl-1H-pyrazolo[4,3-c]pyridine (Example 1, Step 8) (0.5 g, 1.55 mmol), morpholine (0.14 mL, 1.55 mmol), 4,5-bis(diphenylphosphino)-9,9-dimethylxanthene (90 mg, 0.16 mmol), tris(dibenzylideneacetone)dipalladium (0) (36 mg, 0.04 mmol) and cesium carbonate (1.0 g, 3.1 mmol) were suspended in 1,4-dioxane (10 mL) and the mixture was degassed by bubbling argon through the mixture under sonication. The reaction was heated to 90° C. under argon for 6 h. The reaction mixture was cooled to room temperature, diluted with water, extracted with EtOAc (3×10 mL) and the combined organic extracts were washed with brine, dried over anhydrous magnesium sulfate, filtered and concentrated in vacuo. The crude product was purified via flash chromatography on silica gel (eluent: 5% EtOAc in cyclohexane) to afford 6-chloro-1-isopropyl-3-morpholin-4-yl-1H-pyrazolo[4,3-c]pyridine (256 mg, 59%) as an off-white solid. LCMS (ESI): [M+H]$^+$=281($^{35}$Cl) 283($^{37}$Cl).

Step 2: (±)-1-(4-Aminopyrimidin-2-yl)-cis-3-fluoropiperidin-4-ol

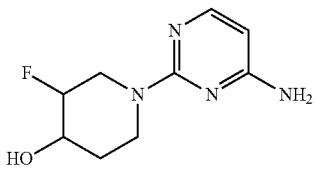 [SMILES: Nc1ccnc(N2CCC(O)C(F)C2)n1]

(±)-cis-3-Fluoro-4-hydroxypiperidine-1-carboxylic acid tert-butyl ester (2.7 g, 12.3 mmol) was dissolved in HCl (4N in 1,4-dioxane, 30 mL) and the mixture was heated at 40° C. for 3 h during which time a white precipitate formed. The reaction mixture was concentrated in vacuo to give a white solid. The solid was dissolved in N,N-dimethylformamide and 4-amino-2-chloropyrimidine (1.59 g, 12.3 mmol) and cesium carbonate (12 g, 36.9 mmol) were added. The reaction mixture was heated at 120° C. for 16 h. The reaction mixture was cooled to room temperature, concentrated in vacuo and the residue suspended in methanol (30 mL) and stirred at room temperature for 5 min. The mixture was filtered and the filtrate was concentrated in vacuo. The resultant residue was purified via flash chromatography on silica gel (solvent gradient: 0%-5% methanol in EtOAc). The product was then triturated with a mixture of methanol and EtOAc to yield (±)-1-(4-aminopyrimidin-2-yl)-cis-3-fluoropiperidin-4-ol (952 mg, 36%) as an off-white solid. LCMS (ESI): [M+H]$^+$=213.

Step 3: (±)-cis-3-Fluoro-1-[4-(1-isopropyl-3-morpholin-4-yl-1H-pyrazolo[4,3-c]pyridin-6-ylamino)pyrimidin-2-yl]piperidin-4-ol

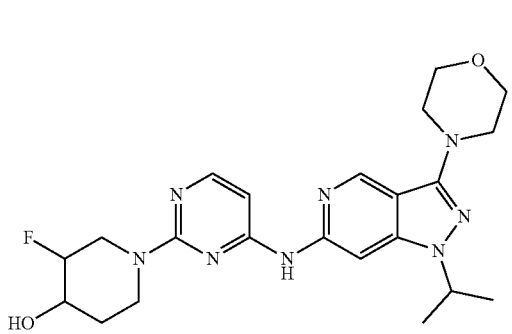 [SMILES: CC(C)n1nc(N2CCOCC2)c2cnc(Nc3ccnc(N4CCC(O)C(F)C4)n3)cc21]

6-Chloro-1-isopropyl-3-morpholin-4-yl-1H-pyrazolo[4,3-c]pyridine (0.2 g, 0.71 mmol), (±)-1-(4-aminopyrimidin-2-yl)-cis-3-fluoropiperidin-4-ol (0.15 g, 0.71 mmol), 2-dicyclohexylphosphino-2',4',6'-triisopropylbiphenyl (68 mg, 0.14 mmol), tris(dibenzylideneacetone)dipalladium (33 mg, 0.04 mmol) and cesium carbonate (0.46 g, 1.42 mmol) were suspended in 1,4-dioxane (10 mL) and the mixture degassed by bubbling argon through the mixture under sonication. The reaction mixture was heated to 90° C. under argon for 1 h, cooled to room temperature, diluted with water and extracted with EtOAc (3×). The combined organic extracts were washed with brine, dried over anhydrous magnesium sulfate, filtered and concentrated in vacuo. The resultant residue was purified via flash chromatography on silica gel (solvent gradient: 0%-10% methanol in EtOAc). The product was then triturated with acetonitrile to yield (±)-cis-3-fluoro-1-[4-(1-isopropyl-3-morpholin-4-yl-1H-pyrazolo[4,3-c]pyridin-6-ylamino)pyrimidin-2-yl]piperidin-4-ol (138 mg, 42%) as a white solid. LCMS (ESI) $R_T$=2.67 min, [M+H]$^+$=457, Method F; $^1$H NMR 400 MHz δ (CDCl$_3$): 8.63 (d, J=1.0 Hz, 1H), 8.04 (d, J=1 Hz, 1H), 8.02 (d, J=5.6 Hz, 1H), 7.35 (br, 1H), 6.05 (d, J=5.6 Hz, 1H), 4.78-4.74 (m, 0.5H), 4.66-4.62 (m, 0.5H), 4.54 (sept, J=6.7 Hz, 1H), 4.32-4.23 (m, 1H), 4.13-3.97 (m, 3H), 3.91-3.85 (m, 4H), 3.83-3.74 (m, 1H), 3.48-3.42 (m, 4H), 2.17 (brs, 1H), 1.99-1.90 (m, 1H), 1.88-1.79 (m, 1H), 1.48 (d, J=6.7 Hz, 6H).

Example 21: (±)-cis-3-Fluoro-1-{4-[1-isopropyl-3-(2-oxa-6-azaspiro[3.3]hept-6-yl)-1H-pyrazolo[4,3-c]pyridin-6-ylamino]-pyrimidin-2-yl}piperidin-4-ol

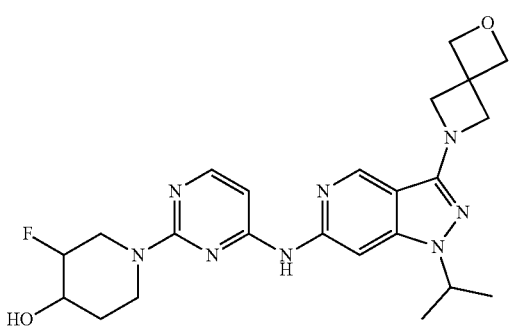 [SMILES: CC(C)n1nc(N2CC3(COC3)C2)c2cnc(Nc3ccnc(N4CCC(O)C(F)C4)n3)cc21]

Step 1: 6-Chloro-1-isopropyl-3-(2-oxa-6-azaspiro[3.3]hept-6-yl)-1H-pyrazolo[4,3-c]pyridine

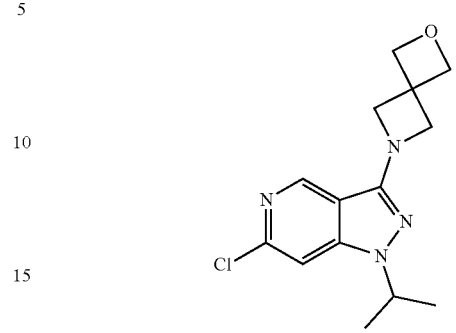

6-Chloro-1-isopropyl-3-(2-oxa-6-azaspiro[3.3]hept-6-yl)-1H-pyrazolo[4,3-c]pyridine was prepared in a method analogous to Example 20, Step 1 to provide the title compound as an off-white solid (358 mg, 79%). LCMS (ESI): [M+H]$^+$=293 ($^{35}$Cl) 295 ($^{37}$Cl).

Step 2: (±)-cis-3-Fluoro-1-{4-[1-isopropyl-3-(2-oxa-6-azaspiro[3.3]hept-6-yl)-1H-pyrazolo[4,3-c]pyridin-6-ylamino]-pyrimidin-2-yl}piperidin-4-ol

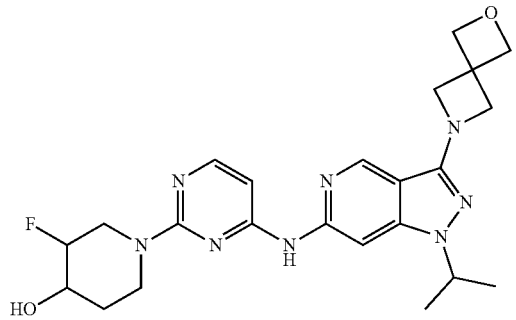 [SMILES: CC(C)n1nc(N2CC3(COC3)C2)c2cnc(Nc3ccnc(N4CCC(O)C(F)C4)n3)cc21]

(±)-cis-3-Fluoro-1-{4-[1-isopropyl-3-(2-oxa-6-azaspiro[3.3]hept-6-yl)-1H-pyrazolo[4,3-c]pyridin-6-ylamino]-pyrimidin-2-yl}piperidin-4-ol was prepared in a method analogous to Example 20, Step 3 to provide the title compound as a pale yellow solid (158 mg, 55%). LCMS (ESI): $R_T$=2.37 min, [M+H]$^+$=469, Method F; $^1$H NMR 400 MHz δ (CDCl$_3$): 8.43 (d, J=0.9 Hz, 1H), 8.02 (d, J=5.7 Hz, 1H), 7.99 (d, J=0.9 Hz, 1H), 7.28 (br, 1H), 6.06 (d, J=5.7 Hz, 1H), 4.85 (s, 4H), 4.77-4.73 (m, 0.5H), 4.65-4.61 (m, 0.5H), 4.52 (sept, J=6.7 Hz, 1H), 4.31 (s, 4H), 4.29-4.23 (m, 1H), 4.13-3.96 (m, 3H), 3.82-3.73 (m, 1H), 2.10-2.06 (m, 1H), 1.99-1.89 (m, 1H), 1.88-1.79 (m, 1H), 1.48 (d, J=6.7 Hz, 6H).

Example 22: (±)-1-(6-((2-(cis-3-Fluoro-4-hydroxypiperidin-1-yl)pyrimidin-4-yl)amino)-1-isopropyl-1H-pyrazolo[4,3-c]pyridin-3-yl)imidazolidin-2-one

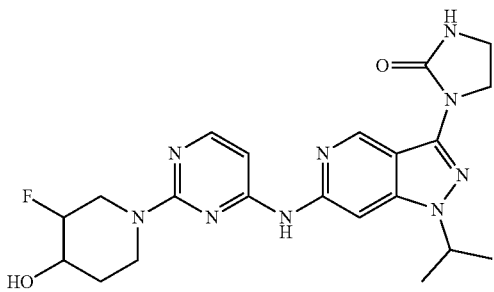 [SMILES: CC(C)n1nc(N2CCNC2=O)c2cnc(Nc3ccnc(N4CCC(O)C(F)C4)n3)cc21]

Step 1: 1-(6-Chloro-1-isopropyl-1H-pyrazolo[4,3-c]pyridin-3-yl)imidazolidin-2-one

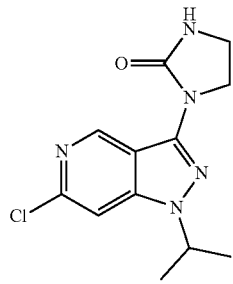 [SMILES: CC(C)n1nc(N2CCNC2=O)c2cnc(Cl)cc21]

A reaction vessel was charged with 6-chloro-3-iodo-1-isopropyl-1H-pyrazolo[4,3-c]pyridine (800 mg, 2.48 mmol), imidazolidin-2-one (321.0 mg, 3.73 mmol), tris(dibenzylideneacetone)dipalladium (0) (455.6 mg, 0.50 mmol), 4,5-bis(diphenylphosphino)-9,9-dimethylxanthene (236.9 mg, 0.50 mmol), cesium carbonate (1.62 g, 5.0 mmol) and suspended in 1,4-dioxane (10.0 ml). The reaction was heated at 60° C. for 7 h, filtered, concentrated in vacuo. The resulting residue was purified by silica gel chromatography (solvent gradient: 0%-100% EtOAc in hexane) to afford 1-(6-chloro-1-isopropyl-1H-pyrazolo[4,3-c]pyridin-3-yl)imidazolidin-2-one (236.2 mg, 34%). LCMS (ESI): [M+H]$^+$=280.7; $^1$H NMR (400 MHz, CDCl$_3$) δ 9.54 (s, 1H), 7.19 (s, 1H), 5.11 (s, 1H), 4.67-4.56 (m, 1H), 4.15 (t, J=8.0 Hz, 2H), 3.70 (t, J=8.0 Hz, 2H), 1.51 (d, J=6.7 Hz, 6H).

Step 2: 3-(6-Chloro-1-isopropyl-1H-pyrazolo[4,3-c]pyridin-3-yl)-2-oxoimidazolidine-1-carboxylic acid tert-butyl ester

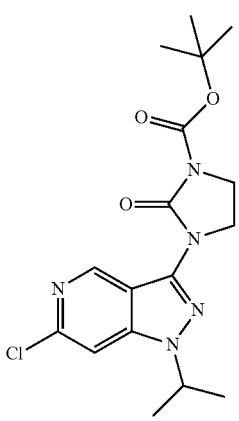 [SMILES: CC(C)n1nc(N2CCN(C(=O)OC(C)(C)C)C2=O)c2cnc(Cl)cc21]

A reaction vessel was charged with 1-(6-chloro-1-isopropyl-1H-pyrazolo[4,3-c]pyridin-3-yl)imidazolidin-2-one (236.2 mg, 0.845 mmol), di-tert-butyl dicarbonate (221.0 mg, 1.01 mmol), dimethylpyridin-4-yl-amine (20.6 mg, 0.17 mmol) and suspended in dichloromethane (9 mL). The reaction was stirred at room temperature for 24 h. The reaction was partitioned with distilled water and the organic layer was separated, dried over anhydrouse magnesium sulfate, filtered, and concentrated in vacuo. The resulting residue was purified by silica gel chromatography (solvent gradient: 0%-100% EtOAc in hexane) to afford 3-(6-chloro-1-isopropyl-1H-pyrazolo[4,3-c]pyridin-3-yl)-2-oxoimidazolidine-1-carboxylic acid tert-butyl ester (237.4 mg, 74%). LCMS (ESI): [M+H]$^+$=380.7.

Step 3: (±)-3-{6-[2-(cis-3-Fluoro-4-hydroxypiperidin-1-yl)pyrimidin-4-ylamino]-1-isopropyl-1H-pyrazolo[4,3-c]pyridin-3-yl}-2-oxoimidazolidine-1-carboxylic acid tert-butyl ester

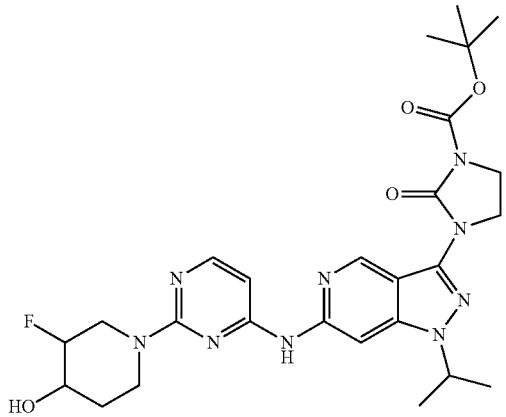 [SMILES: CC(C)n1nc(N2CCN(C(=O)OC(C)(C)C)C2=O)c2cnc(Nc3ccnc(N4CCC(O)C(F)C4)n3)cc21]

A reaction vessel was charged with 3-(6-chloro-1-isopropyl-1H-pyrazolo[4,3-c]pyridin-3-yl)-2-oxoimidazolidine-1-carboxylic acid tert-butyl ester (237.4 mg, 0.625 mmol), (±)-1-(4-aminopyrimidin-2-yl)-cis-3-fluoropiperidin-4-ol (Example 20, Step 2) (132.6 mg, 0.625 mmol), tris(dibenzylideneacetone)dipalladium (0) (59.5 mg, 0.125 mmol), 2-dicyclohexylphosphino-2',4',6'-triisopropylbiphenyl (28.6 mg, 0.031 mmol), and cesium carbonate (407.2 mg, 1.24 mmol) suspended in 1,4-dioxane (5.0 mL). The reaction was heated at 85° C. for 3 h. The reaction was allowed to cool to room temperature and concentrated in vacuo. The resulting residue was purified by silica gel chromatography (solvent gradient: 0%-100% EtOAc in methanol) to afford (±)-3-{6-[2-(cis-3-fluoro-4-hydroxypiperidin-1-yl)pyrimidin-4-ylamino]-1-isopropyl-1H-pyrazolo[4,3-c]pyridin-3-yl}-2-oxoimidazolidine-1-carboxylic acid tert-butyl ester (143.2 mg, 41%). LCMS (ESI): [M+H]$^+$=556.6.

Step 4: (±)-1-{6-[2-(cis-3-Fluoro-4-hydroxypiperidin-1-yl)pyrimidin-4-ylamino]-1-isopropyl-1H-pyrazolo[4,3-c]pyridin-3-yl}imidazolidin-2-one

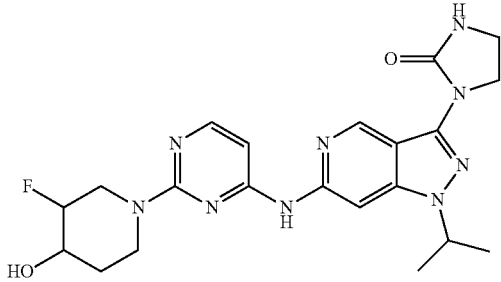 [SMILES: CC(C)n1nc(N2CCNC2=O)c2cnc(Nc3ccnc(N4CCC(O)C(F)C4)n3)cc21]

A reaction vessel was charged with (±)-3-{6-[2-(cis-3-fluoro-4-hydroxypiperidin-1-yl)pyrimidin-4-ylamino]-1-isopropyl-1H-pyrazolo[4,3-c]pyridin-3-yl}-2-oxoimidazolidine-1-carboxylic acid tert-butyl ester (143.2 mg, 0.257 mmol) and suspended in dichloromethane (5 ml). Trifluoroacetic acid (0.5 ml) was added and the reaction stirred at room temperature for 30 min. The reaction was partitioned between dichloromethane and saturated aqueous sodium bicarbonate. The organic layer was separated, dried over anhydrous magnesium sulfate, filtered and concentrated in vacuo. The residue was subjected to reverse phase HPLC to afford (±)-1-{6-[2-(cis-3-fluoro-4-hydroxypiperidin-1-yl)pyrimidin-4-ylamino]-1-isopropyl-1H-pyrazolo[4,3-c]pyridin-3-yl}imidazolidin-2-one. LCMS (ESI): $R_T$ (min)=2.37, $[M+H]^+$=456.2, method F. $^1$H NMR (400 MHz, DMSO-$d_6$) δ 9.89 (s, 1H), 9.25 (s, 1H), 8.17 (s, 1H), 7.94 (d, J=5.7 Hz, 1H), 7.14 (s, 1H), 6.33 (d, J=5.7 Hz, 1H), 5.07 (d, J=5.3 Hz, 1H), 4.71-4.58 (m, 2H), 4.49-4.42 (m, 1H), 4.23-4.19 (m, 1H), 3.94 (t, J=7.9 Hz, 2H), 3.88-3.76 (m, 1H), 3.60-3.53 (m, 1H), 3.47 (t, J=7.9 Hz, 2H), 3.37-3.31 (m, 1H), 1.69-1.65 (m, 2H), 1.42 (2×d, J=6.8 Hz, 6H).

Example 23: (±)-2-(cis-3-Fluoro-4-methoxypiperidin-1-yl)pyrimidin-4-yl]-[1-isopropyl-3-(2-oxa-6-azaspiro[3.3]hept-6-yl)-1H-pyrazolo[4,3-c]pyridin-6-yl]amine

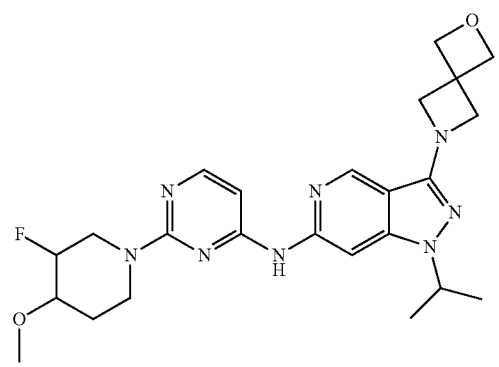 [SMILES: COC1CCN(c2nccc(Nc3cc4c(cn3)c(N3CC5(COC5)C3)nn4C(C)C)n2)CC1F]

Step 1: (±)-tert-Butyl-cis-3-fluoro-4-methoxypiperidine-1-carboxylate

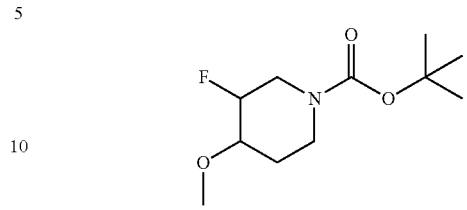

(±)-tert-Butyl cis-3-fluoro-4-hydroxypiperidine-1-carboxylate (54 mg, 0.24 mmol) was dissolved in tetrahydrofuran (450 mL) and sodium hydride ((60 wt % dispersion in mineral oil)(35 mg, 0.89 mol) was added followed by 15-crown-5 (10 drops). The mixture was stirred for 15 min until all gas evolution ceased. Dimethyl sulphate (100 mg, 0.89 mmol) was added and the mixture was stirred at 60° C. for 3 h. Aqueous ammonia (30%, 200 mL) was added slowly to quench the reaction. The reaction mixture was concentrated in vacuo, diluted with brine and extracted with EtOAc (3×). The combined organic extracts were dried over anhydrous magnesium sulfate, filtered, and concentrated in vacuo. The residue was purified by via flash chromatography on silica gel (solvent gradient: 0%-10% EtOAc in cyclohexanes) to give (±)-tert-butyl-cis-3-fluoro-4-methoxypiperidine-1-carboxylate as a colourless oil (51 mg, 88%). LCMS (ESI): $[M+H-^tBu]^+$=178; $^1$H NMR (400 MHz, CDCl$_3$) δ 4.74-4.62 (m, 1H), 4.01-3.97 (m, 1H), 3.77 (s, 1H), 3.43 (m, 4H), 3.33-3.27 (m, 1H), 3.09 (m, 1H), 1.91-1.83 (m, 1H), 1.73-1.61 (m, 1H), 1.45 (s, 9H).

Step 2: (±)-2-(cis-3-Fluoro-4-methoxypiperidin-1-yl)pyrimidin-4-ylamine

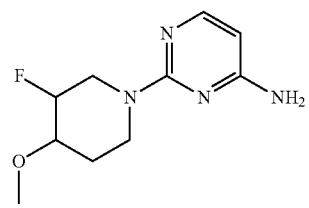 [SMILES: COC1CCN(c2nccc(N)n2)CC1F]

(±)-tert-Butyl-cis-3-fluoro-4-methoxypiperidine-1-carboxylate (530 mg, 2.27 mmol) was dissolved in HCl in 1,4-dioxane (4N, 5 mL) and the reaction mixture was heated at 40° C. for 2 h. The reaction mixture was cooled to room temperature and concentrated in vacuo to give a white solid. To the solid, 2-chloro-4-aminopyrimidine (294 mg, 2.27 mmol), and triethylamine (949 μL, 6.62 mmol) was added isopropanol (5 mL) and the reaction mixture was heated in a sealed tube at 120° C. After 18 h, the reaction mixture was adsorbed onto diatomaceous earth and purified via flash chromatography on silica gel (solvent gradient: 25%-100% EtOAc in cyclohexanes) to give (±)-2-(cis-3-fluoro-4-methoxypiperidin-1-yl)pyrimidin-4-ylamine as a white solid (370 mg, 70%). LCMS (ESI): $[M+H]^+$=227.

Step 3: (±)-2-(cis-3-Fluoro-4-methoxypiperidin-1-yl)pyrimidin-4-yl]-[1-isopropyl-3-(2-oxa-6-azaspiro[3.3]hept-6-yl)-1H-pyrazolo[4,3-c]pyridin-6-yl]amine

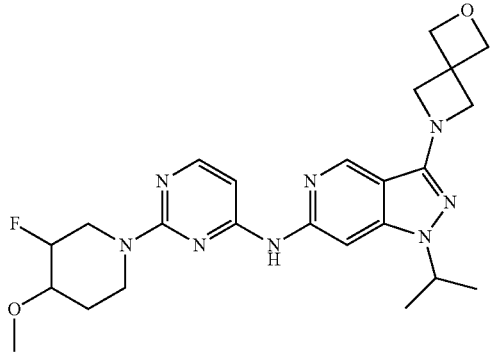 [SMILES: COC1CCN(c2nccc(Nc3cc4c(cn3)c(N3CC5(COC5)C3)nn4C(C)C)n2)CC1F]

A reaction vessel was charged with 6-chloro-1-isopropyl-3-(2-oxa-6-azaspiro[3.3]hept-6-yl)-1H-pyrazolo[4,3-c]pyridine (Example 21, Step 1) (170.0 mg, 0.580 mmol), (±)-2-(cis-3-fluoro-4-methoxypiperidin-1-yl)pyrimidin-4-ylamine (131.0 mg, 0.580 mmol), tris(dibenzylideneacetone)dipalladium (0) (26.5 mg, 0.029 mmol), 2-dicyclohexylphosphino-2',4',6'-triisopropylbiphenyl (55.3 mg, 0.116 mmol), cesium carbonate (378 mg, 1.16 mmol) and 1,4-dioxane (10.0 ml). The reaction mixture was heated at 100° C. for 5 h, cooled to room temperature and concentrated in vacuo. The resulting residue was triturated with methanol and filtered. The solid collected was purified by reverse phase HPLC followed by trituration with methanol to afford (±)-2-(cis-3-fluoro-4-methoxypiperidin-1-yl)pyrimidin-4-yl]-[1-isopropyl-3-(2-oxa-6-azaspiro[3.3]hept-6-yl)-1H-pyrazolo[4,3-c]pyridin-6-yl]amine (55 mg, 20%). LCMS (ESI): $R_T$ (min)=2.70, [M+H]$^+$=483.2, method F. $^1$H NMR (400 MHz, DMSO-d$_6$) δ 8.42 (s, 1H), 8.02 (d, J=5.7 Hz, 1H), 8.00 (s, 1H), 7.36 (s, 1H), 6.04 (d, J=5.7 Hz, 1H), 4.85 (s, 4H), 4.85-4.67 (m, 1H), 4.56-4.59 (m, 1H), 4.43-4.36 (m, 1H), 4.30 (m, 4H), 4.12-4.06 (m, 1H), 3.91-3.81 (m, 1H), 3.68-3.57 (m, 2H), 3.48 (s, 3H), 2.04-1.95 (m, 1H), 1.81-1.74 (1H, m), 1.48 (d, J=7.6 Hz, 6H).

Example 24: 1-(4-(Aminocyclohexyl)methyl)-N$^6$-[2-(4-methoxypiperidin-1-yl)-pyrimidin-4-yl]-1H-pyrazolo[4,3-c]pyridine-3,6-diamine

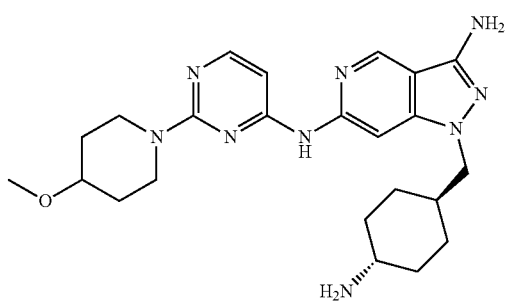 [SMILES: COC1CCN(c2nccc(Nc3cc4c(cn3)c(N)nn4C[C@H]3CC[C@H](N)CC3)n2)CC1]

Step 1: 6-chloro-3-nitro-1H-pyrazolo[4,3-c]pyridine

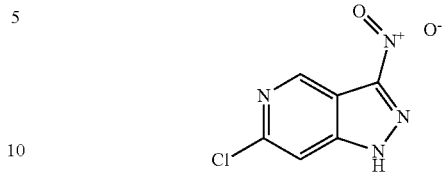

Sulfuric acid (2.0 mL, 38 mmol) was added to a flask at 0° C. containing 6-chloro-1H-pyrazolo[4,3-c]pyridine (Example 1, Step 6) (505.3 mg, 3.290 mmol). Nitric acid (1.5 mL, 30 mmol) was then added dropwise. The reaction vessel was warmed to room temperature, and then heated at 90° C. under a reflux condenser. After 6 h, the reaction mixture was cooled to room temperature, and then allowed to stand at 4° C. for 18 h. The reaction mixture was added dropwise to a flask of 30 mL water cooled in an ice bath. The resulting white precipitate was recovered via filtration, rinsing with a minimal amount of water. The solid was dried under vacuum to yield 167.7 mg. The filtrate was chilled over 3 d at 4° C., and additional precipitate was recovered via filtration and dried under vacuum to yield an additional 219.7 mg (total 387.4 mg, 42%). LCMS (ESI): [M+H]$^+$=199.0; $^1$H NMR (400 MHz, DMSO-d$_6$): δ 9.26 (s, 1H), 7.97 (s, 1H).

Step 2: [4-trans-(6-Chloro-3-nitropyrazolo[4,3-c]pyridin-1-ylmethyl)cyclohexyl]carbamic acid tert-butyl ester

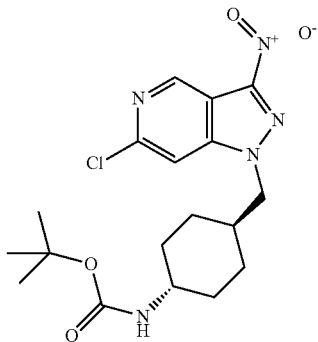

A solution of 6-chloro-3-nitro-1H-pyrazolo[4,3-c]pyridine (200 mg, 1.0 mmol), tert-butyl trans-4-(bromomethyl)cyclohexylcarbamate (*ACS Med. Chem. Lett.*, 2012, 3, 129-134) (353 mg, 1.2 mmol) and cesium carbonate (565 mg, 2.0 mmol) in N,N-dimethylformamide was heated in a sealed tube at 80° C. for 16 h. The reaction mixture was cooled to room temperature, diluted with water (20 mL) and extracted with EtOAc (5×). The organic extracts were combined and concentrated in vacuo. The residue was purified via flash chromatography on silica gel (solvent gradient: 10%-100% EtOAc in cyclohexane) to yield [4-trans-(6-chloro-3-nitropyrazolo[4,3-c]pyridin-1-ylmethyl)cyclohexyl]carbamic acid tert-butyl ester as a white solid (263 mg, 64%). LCMS (ESI): [M+H-$^t$Bu]$^+$=354.

Step 3: (4-trans-{6-[2-(4-Methoxypiperidin-1-yl)pyrimidin-4-ylamino]-3-nitropyrazolo[4,3-c]pyridin-1-ylmethyl}-cyclohexyl)carbamic acid tert-butyl ester

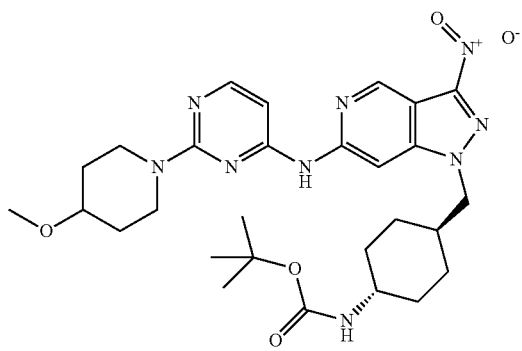

The title compound was prepared by a method analogous to Example 2, Step 3 to afford (4-trans-{6-[2-(4-methoxypiperidin-1-yl)pyrimidin-4-ylamino]-3-nitropyrazolo[4,3-c]pyridin-1-ylmethyl}cyclohexyl)carbamic acid tert-butyl ester as an off-white solid (82 mg, 42%). LCMS (ESI): [M+H]$^+$=582.

Step 4: (4-trans-{3-Amino-6-[2-(4-methoxypiperidin-1-yl)pyrimidin-4-ylamino]pyrazolo[4,3-c]pyridin-1-ylmethyl}cyclohexyl)carbamic acid tert-butyl ester

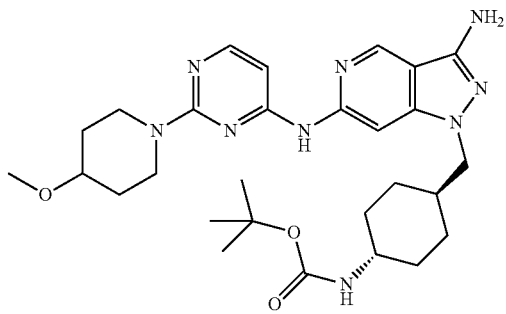 [SMILES: COC1CCN(c2nccc(Nc3cc4c(cn3)c(N)nn4C[C@H]3CC[C@H](NC(=O)OC(C)(C)C)CC3)n2)CC1]

A solution of (4-trans-{6-[2-(4-methoxypiperidin-1-yl)pyrimidin-4-ylamino]-3-nitropyrazolo[4,3-c]pyridin-1-ylmethyl}cyclohexyl)carbamic acid tert-butyl ester (82 mg, 0.14 mmol), iron powder (79 mg, 1.4 mmol) and ammonium chloride (23 mg, 0.42 mmol) in methanol (32 mL) and water (4 mL) was vigorously stirred at 80° C. for 90 min. The reaction mixture was cooled to room temperature and adsorbed onto a 5 g SCX-2 acidic resin column. The column was flushed with methanol (50 mL), followed by elution with 2 M ammonia in methanol (50 mL). The basic eluent was concentrated in vacuo. The residue was purified via flash chromatography on silica gel (solvent gradient: 1%-10% 2M ammonia in methanol solution in dichloromethane) to yield (4-trans-{3-amino-6-[2-(4-methoxypiperidin-1-yl)pyrimidin-4-ylamino]pyrazolo[4,3-c]pyridin-1-ylmethyl}cyclohexyl)carbamic acid tert-butyl ester as a yellow solid (52 mg, 67%). LCMS (ESI): [M+H]$^+$=552.

Step 5: 1-(4-trans-Aminocyclohexylmethyl)-N$^6$-[2-(4-methoxypiperidin-1-yl)-pyrimidin-4-yl]-1H-pyrazolo[4,3-c]pyridine-3,6-diamine

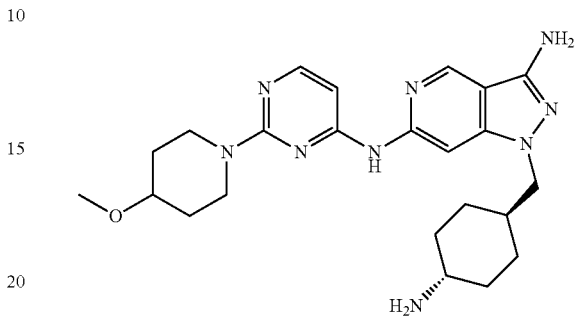

Trifluoroacetic acid (2 mL) was added to a solution of (4-trans-{3-amino-6-[2-(4-methoxypiperidin-1-yl)pyrimidin-4-ylamino]pyrazolo[4,3-c]pyridin-1-ylmethyl}cyclohexyl)carbamic acid tert-butyl ester (52 mg, 0.94 mmol) in dichloromethane (8 mL) and stirred at room temperature for 30 min. The reaction was adsorbed onto a 2 g SCX-2 acidic resin column. The column was flushed with methanol (30 mL), followed by elution with 2 M ammonia in methanol (30 mL). The basic eluent was concentrated in vacuo. The residue was purified via flash chromatography on silica gel (eluent: 10% 2M ammonia in methanol solution in dichloromethane) to yield 1-(4-trans-aminocyclohexylmethyl)-N$^6$-[2-(4-methoxypiperidin-1-yl)pyrimidin-4-yl]-1H-pyrazolo[4,3-c]pyridine-3,6-diamine as a white solid. LCMS (ESI): R$_T$ (min)=1.77, [M+H]$^+$=452, method=F. $^1$H NMR (400 MHz, DMSO-d$_6$) δ 9.80 (s, 1H), 8.63 (s, 1H), 8.04 (s, 1H), 7.97 (d, J=5.6 Hz, 1H), 6.34 (d, J=5.6 Hz, 1H), 5.76, (s, 2H), 4.24-4.18 (m, 2H), 3.77 (d, J=7.0 Hz, 2H), 3.52-3.20 (m, 5H), 3.29 (s, 3H), 2.50-2.38 (m, 1H), 19.5-1.87 (m, 2H), 1.80-1.68 (m, 3H), 1.54-1.41 (m, 4H), 1.01-0.088 (m, 4H).

Example 25: 1-(1-(sec-Butyl)-6-((2-(1-(cyclopropylsulfonyl)-1H-pyrazol-4-yl)pyrimidin-4-yl)amino)-1H-pyrazolo[4,3-c]pyridin-3-yl)imidazolidin-2-one

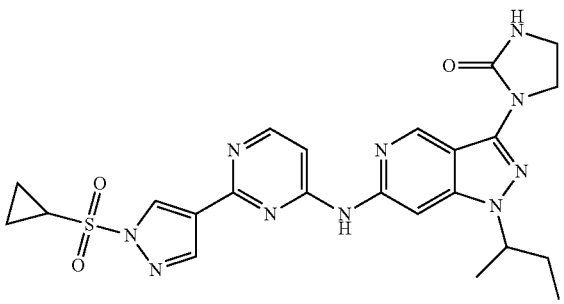 [SMILES: CCC(C)n1nc(N2CCNC2=O)c2cnc(Nc3ccnc(-c4cnn(S(=O)(=O)C5CC5)c4)n3)cc21]

Step 1: 1-(1-(sec-Butyl)-6-chloro-1H-pyrazolo[4,3-c]pyridin-3-yl)imidazolidin-2-one

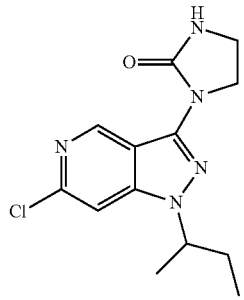 [SMILES: CCC(C)n1nc(N2CCNC2=O)c2cnc(Cl)cc21]

1-(1-(sec-Butyl)-6-chloro-1H-pyrazolo[4,3-c]pyridin-3-yl)imidazolidin-2-one was prepared in a method analogous to Example 20, Step 1 to provide the title compound (0.12 g, 58%). LCMS (ESI): $R_T$ (min)=0.89, [M+H]$^+$=294.2, method=P.

Step 2: 1-(1-(sec-Butyl)-6-((2-(1-(cyclopropylsulfonyl)-1H-pyrazol-4-yl)pyrimidin-4-yl)amino)-1H-pyrazolo[4,3-c]pyridin-3-0)imidazolidin-2-one

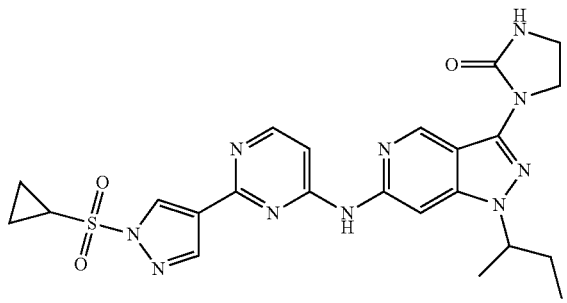 [SMILES: CCC(C)n1nc(N2CCNC2=O)c2cnc(Nc3ccnc(-c4cnn(S(=O)(=O)C5CC5)c4)n3)cc21]

1-(1-(sec-Butyl)-6-((2-(1-(cyclopropylsulfonyl)-1H-pyrazol-4-yl)pyrimidin-4-yl)amino)-1H-pyrazolo[4,3-c]pyridin-3-yl)imidazolidin-2-one was prepared in a method analogous to Example 14, Step 2 to provide the title compound (12 mg, 5.6%). LCMS (ESI): $R_T$ (min)=4.28, [M+H]$^+$=523.2, method=B; $^1$H NMR (400 MHz, DMSO-d$_6$) δ $^1$H NMR (400 MHz, DMSO-d$_6$) δ 10.36 (s, 1H), 9.37 (d, J=0.9 Hz, 1H), 8.82-8.71 (m, 1H), 8.48 (s, 1H), 8.42 (d, J=5.9 Hz, 1H), 8.37 (s, 1H), 7.20 (s, 1H), 7.13 (d, J=6.0 Hz, 1H), 4.55 (m, 1H), 4.07-3.92 (m, 2H), 3.60-3.47 (m, 2H), 2.05-1.78 (m, 2H), 1.50 (d, J=6.6 Hz, 3H), 1.34 (m, 2H), 1.28 (m, 2H), 0.76 (t, J=7.3 Hz, 3H).

Example 26: (±)-1-(1-(sec-Butyl)-6-((2-(cis-3-fluoro-4-methoxypiperidin-1-yl)pyrimidin-4-yl)amino)-1H-pyrazolo[4,3-c]pyridin-3-yl)imidazolidin-2-one

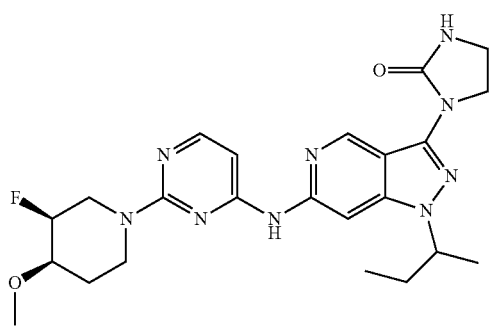 [SMILES: CCC(C)n1nc(N2CCNC2=O)c2cnc(Nc3ccnc(N4CC[C@@H](OC)[C@@H](F)C4)n3)cc21]

(±)-1-(1-(sec-Butyl)-6-((2-(cis-3-fluoro-4-methoxypiperidin-1-yl)pyrimidin-4-yl)amino)-1H-pyrazolo[4,3-c]pyridin-3-yl)imidazolidin-2-one was prepared in a method analogous to Example 15 to provide the title compound to give the title compound (83.6 mg, 42%). LCMS (ESI): $R_T$ (min)=4.02, [M+H]$^+$=484.3. method=B; $^1$H NMR (400 MHz, DMSO-d$_6$) δ 9.97 (s, 1H), 9.31 (d, J=0.7 Hz, 1H), 8.20 (d, J=2.2 Hz, 1H), 7.99 (d, J=5.6 Hz, 1H), 7.22 (s, 1H), 6.38 (d, J=5.6 Hz, 1H), 4.94 (d, J=49.0 Hz, 1H), 4.64 (s, 1H), 4.38 (m, 2H), 4.04-3.89 (m, 2H), 1.96 (m, 1H), 1.88-1.67 (m, 3H), 1.44 (m, 3H), 0.73 (m, 3H).

Example 27: 1-(sec-Butyl)-N-(2-(1-(cyclopropylsulfonyl)-1H-pyrazol-4-yl)pyrimidin-4-yl)-3-morpholino-1H-pyrazolo[4,3-c]pyridin-6-amine

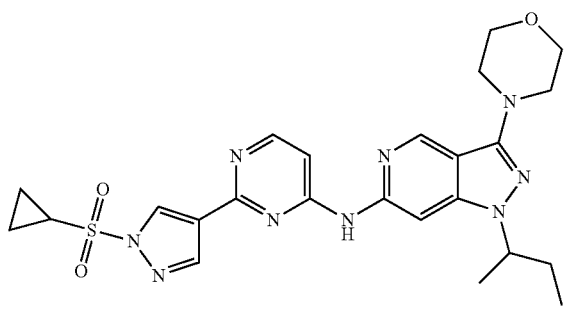 [SMILES: CCC(C)n1nc(N2CCOCC2)c2cnc(Nc3ccnc(-c4cnn(S(=O)(=O)C5CC5)c4)n3)cc21]

Step 1: 4-(1-(sec-Butyl)-6-chloro-1H-pyrazolo[4,3-c]pyridin-3-yl)morpholine

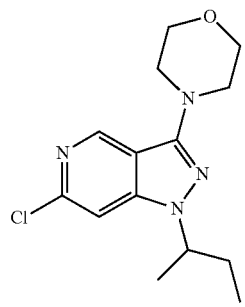 [SMILES: CCC(C)n1nc(N2CCOCC2)c2cnc(Cl)cc21]

4-(1-(sec-Butyl)-6-chloro-1H-pyrazolo[4,3-c]pyridin-3-yl)morpholine was prepared in a method analogous to Example 20, Step 1 to provide the title compound (0.2 g, 30%). LCMS (ESI): $R_T$ (min)=0.89, [M+H]$^+$=295.3, method=P.

Step 2: 1-(sec-Butyl)-N-(2-(1-(cyclopropylsulfonyl)-1H-pyrazol-4-yl)pyrimidin-4-yl)-3-morpholino-1H-pyrazolo[4,3-c]pyridin-6-amine

Example 28: (R)-1-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)pyrrolidine-3-carbonitrile

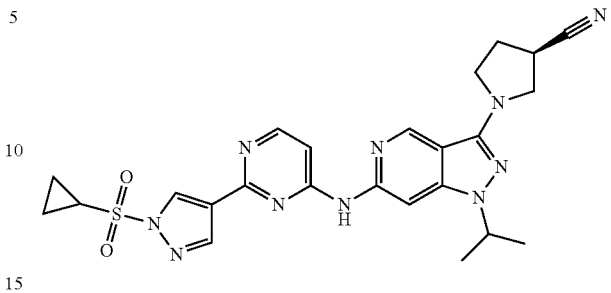

Step 1: (R)-1-(6-Chloro-1-isopropyl-1H-pyrazolo[4,3-c]pyridin-3-yl)pyrrolidine-3-carbonitrile

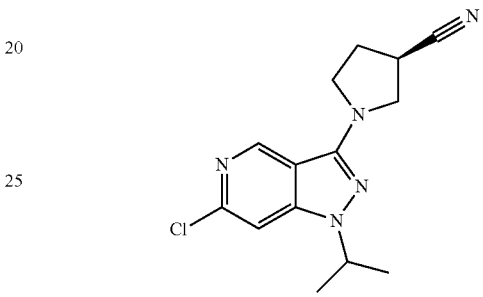

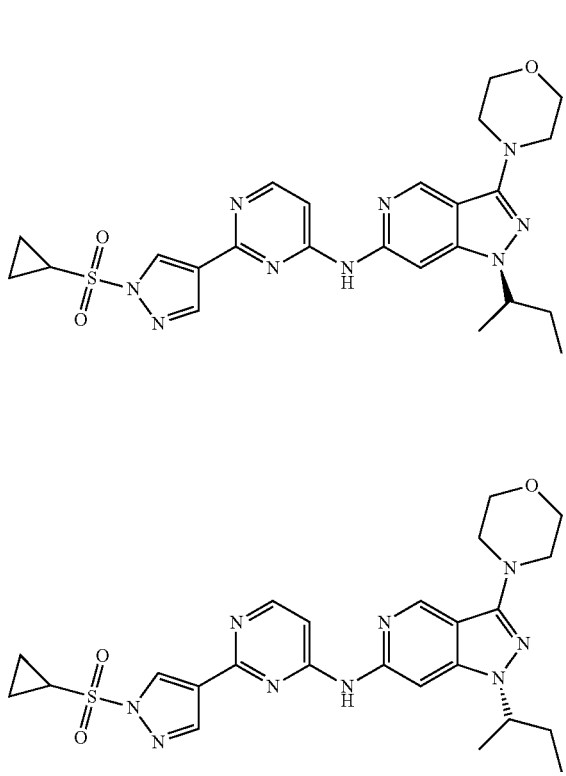

To a reaction vessel was added 6-chloro-3-iodo-1-isopropyl-1H-pyrazolo[4,3-c]pyridine (Example 1, Step 8) (0.90 g, 2.8 mmol), pyrrolidine-3-carbonitrile hydrochloride (390 mg, 2.8 mmol), cesium carbonate (2.0 g, 6.2 mmol), 4,5-bis(diphenylphosphino)-9,9-dimethylxanthene (170 mg, 0.28 mmol), palladium(II) acetate (64 mg, 0.28 mmol) and 1,4-dioxane (5 mL). The reaction was degassed by nitrogen bubbling for 20 min, sealed and stirred at 115° C. for 4 h. The reaction was then cooled to room temperature, filtered and concentrated in vacuo. The crude product was purified via flash chromatography on silica gel (solvent gradient: 0%-10% methanol in dichloromethane) to afford (R)-1-(6-chloro-1-isopropyl-1H-pyrazolo[4,3-c]pyridin-3-yl)pyrrolidine-3-carbonitrile (0.46 g, 57%). LCMS (ESI): $R_T$ (min)=0.91, [M+H]$^+$=290.18, method=P; $^1$H NMR (400 MHz, CDCl$_3$) δ 8.69 (d, J=0.9 Hz, 1H), 7.13 (d, J=0.9 Hz, 1H), 4.53 (m, J=13.3, 6.7 Hz, 1H), 4.00-3.84 (m, 3H), 3.83-3.71 (m, 1H), 3.30 (m, J=13.5, 6.7 Hz, 1H), 2.60-2.36 (m, 2H), 1.49 (d, J=6.7 Hz, 6H).

To a reaction vessel was added 4-(1-(sec-butyl)-6-chloro-1H-pyrazolo[4,3-c]pyridin-3-yl)morpholine (0.12 g, 0.41 mmol), 2-(1-(cyclopropylsulfonyl)-1H-pyrazol-4-yl)pyrimidin-4-amine (Example 1, Step 2) (0.11 g, 0.20 mmol), cesium carbonate (0.27 g, 0.82 mmol), 2-dicyclohexylphosphino-2',4',6'-triisopropylbiphenyl (40 mg, 0.082 mmol), tris(dibenzylideneacetone)dipalladium(0) (19 mg, 0.033 mmol) and 1,4-dioxane (3 mL). The reaction was sealed and degassed under nitrogen for 20 min. The reaction was heated at 100° C. for 3 h, cooled to room temperature, filtered and concentrated in vacuo. The crude product was purified by chiral supercritical fluid chromatography to give the title compound as two single unknown enantiomers. Enantiomer 1 (77.7 mg, 12.5%): LCMS (ESI): $R_T$ (min)=4.58, [M+H]$^+$=524.2, method=B; $^1$H NMR (400 MHz, DMSO-d$_6$) δ 10.33 (s, 1H), 8.90 (s, 1H), 8.69 (s, 1H), 8.47 (s, 1H), 8.41 (d, J=5.9 Hz, 1H), 8.31 (s, 1H), 7.12 (d, J=5.8 Hz, 1H), 4.56-4.36 (m, 1H), 3.87-3.71 (m, 4H), 3.50-3.36 (m, 4H), 2.04-1.88 (m, 1H), 1.88-1.74 (m, 1H), 1.47 (d, J=6.6 Hz, 3H), 1.41-1.18 (m, 4H), 0.74 (t, J=7.3 Hz, 3H). Enantiomer 2 (76.0 mg, 12.3%): LCMS (ESI): $R_T$ (min)=4.63, [M+H]$^+$=524.3, method=B; $^1$H NMR (400 MHz, DMSO-d$_6$) δ 10.33 (s, 1H), 8.90 (s, 1H), 8.69 (s, 1H), 8.47 (s, 1H), 8.41 (d, J=5.9 Hz, 1H), 8.31 (s, 1H), 7.12 (d, J=6.3 Hz, 1H), 4.44 (s, 2H), 3.79 (d, J=4.8 Hz, 4H), 3.41 (d, J=4.5 Hz, 4H), 2.05-1.87 (m, 1H), 1.83 (d, J=5.7 Hz, 1H), 1.47 (d, J=6.6 Hz, 3H), 1.40-1.20 (m, 4H), 0.74 (t, J=7.3 Hz, 3H).

Step 2: (R)-1-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)pyrrolidine-3-carbonitrile

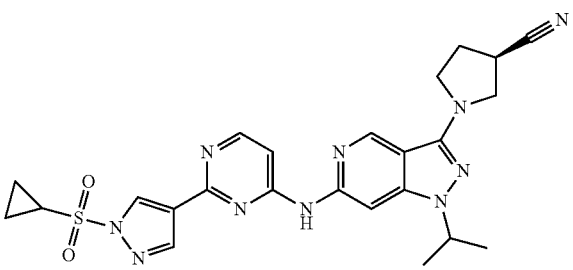 [SMILES: CC(C)n1nc(N2CC[C@@H](C#N)C2)c2cnc(Nc3ccnc(-c4cnn(S(=O)(=O)C5CC5)c4)n3)cc21]

(R)-1-(6-((2-(1-(cyclopropylsulfonyl)-1H-pyrazol-4-yl)pyrimidin-4-yl)amino)-1-isopropyl-1H-pyrazolo[4,3-c]pyridin-3-yl)pyrrolidine-3-carbonitrile was prepared in a method analogous to Example 14, Step 2 to provide the title compound (48.6 mg, 15%). LCMS (ESI): $R_T$ (min)=4.36, [M+H]$^+$=519.2, method=B; $^1$H NMR (400 MHz, DMSO-d$_6$) δ 10.35 (s, 1H), 8.82 (s, 1H), 8.70 (s, 1H), 8.53-8.47 (m, 1H), 8.41 (d, J=5.9 Hz, 1H), 8.30 (s, 1H), 7.13 (d, J=5.5 Hz, 1H), 4.72 (m, 1H), 3.86 (m, 1H), 3.83-3.70 (m, 2H), 3.71-3.53 (m, 2H), 2.41 (dt, J=13.7, 7.6 Hz, 1H), 2.28 (m, 1H), 1.48 (d, J=6.6 Hz, 6H), 1.40-1.20 (m, 4H).

Example 29: N-(2-(1-(Cyclopropylsulfonyl)-1H-pyrazol-4-yl)pyrimidin-4-yl)-1-isopropyl-3-(tetrahydrofuran-3-yloxy)-1H-pyrazolo[4,3-c]pyridin-6-amine

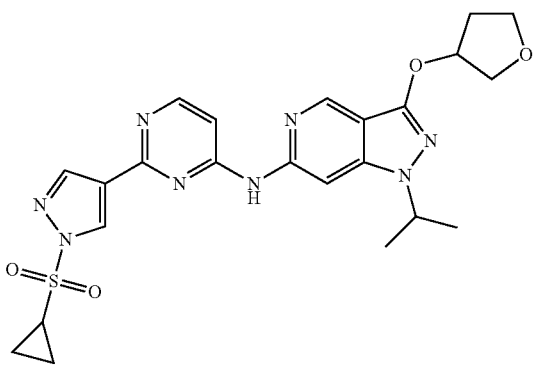 [SMILES: CC(C)n1nc(OC2CCOC2)c2cnc(Nc3ccnc(-c4cnn(S(=O)(=O)C5CC5)c4)n3)cc21]

Step 1: 6-Chloro-1-isopropyl-3-(tetrahydrofuran-3-yloxy)-1H-pyrazolo[4,3-c]pyridine

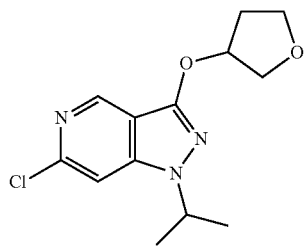 [SMILES: CC(C)n1nc(OC2CCOC2)c2cnc(Cl)cc21]

To a reaction vessel purged and maintained under nitrogen was added 6-chloro-3-iodo-1-isopropyl-1H-pyrazolo[4,3-c]pyridine (Example 1, Step 8) (250 mg, 0.780 mmol), copper (I) iodide (15.0 mg, 0.080 mmol), 2,9-dimethyl-1,10-phenanthroline (33.0 mg, 0.160 mmol), cesium carbonate (520 mg, 1.60 mmol), tetrahydrofuran-3-ol (0.5 mL) and toluene (4 mL). The reaction mixture was stirred for 3 days at 130° C. The reaction mixture was cooled to room temperature, filtered and concentrated in vacuo. The crude product was purified via flash chromatography on silica gel (eluent: 30% EtOAc in petroleum ether) to afford 6-chloro-1-isopropyl-3-(tetrahydrofuran-3-yloxy)-1H-pyrazolo[4,3-c]pyridine (50 mg, 23%) as a white solid. LCMS (ESI): RT (min)=1.528, M+H$^+$=282, method=N.

Step 2: N-(2-(1-(Cyclopropylsulfonyl)-1H-pyrazol-4-yl)pyrimidin-4-yl)-1-isopropyl-3-(tetrahydrofuran-3-yloxy)-1H-pyrazolo[4,3-c]pyridin-6-amine

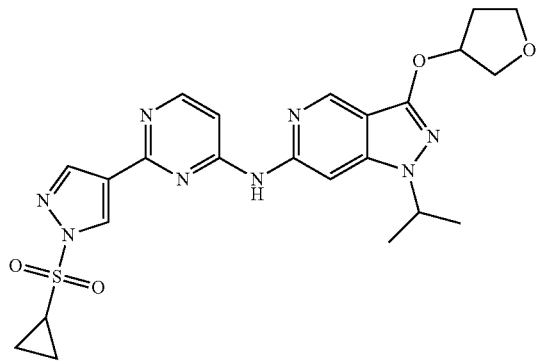 [SMILES: CC(C)n1nc(OC2CCOC2)c2cnc(Nc3ccnc(-c4cnn(S(=O)(=O)C5CC5)c4)n3)cc21]

To a reaction vessel purged and maintained with nitrogen was added 6-chloro-1-isopropyl-3-(tetrahydrofuran-3-yloxy)-1H-pyrazolo[4,3-c]pyridine (100 mg, 0.355 mmol), tris(dibenzylideneacetone)dipalladium(0) (32.5 mg, 0.0355 mmol), 4,5-bis(diphenylphosphino)-9,9-dimethylxanthene (41.0 mg, 0.0709 mmol), 2-(1-(cyclopropylsulfonyl)-1H-pyrazol-4-yl)pyrimidin-4-amine (Example 1, Step 2) (113 mg, 0.426 mmol), cesium carbonate (289 mg, 0.886 mmol) and 1,4-dioxane (4 mL). The reaction mixture was stirred for 30 min at 160° C. under microwave irradiation. The reaction was cooled to room temperature, extracted with EtOAc, and the organic layer was washed with brine, dried over anhydrous sodium sulfate and concentrated in vacuo. The crude product was purified via reverse-phase HPLC and lyophilized to yield N-(2-(1-(cyclopropylsulfonyl)-1H-pyrazol-4-yl)pyrimidin-4-yl)-1-isopropyl-3-(tetrahydrofuran-3-yloxy)-1H-pyrazolo[4,3-c]pyridin-6-amine (29.4 mg, 16%) as a yellow solid. LCMS (ESI): $R_T$ (min)=1.671, M+H$^+$=511, method=N. $^1$H NMR (400 MHz, DMSO-d$_6$): δ 10.40 (s, 1H), 8.71 (s, 1H), 8.66 (s, 1H), 8.48 (s, 1H), 8.437-8.422 (d, J=6.0 Hz, 1H), 8.37 (br, 1H), 7.135-7.120 (d, J=6.0 Hz, 1H), 5.45-5.35 (s, 1H), 4.90-4.55 (m, 1H), 3.95-3.85 (m, 3H), 3.80-3.70 (m, 1H), 3.35-3.20 (m, 1H), 2.20-2.40 (m, 1H), 2.05-2.15 (m, 1H), 1.493-1.477 (d, J=6.4 Hz, 6H), 1.37-1.31 (m, 2H), 1.29-1.24 (m, 2H).

Example 30: 1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-N-(2-methoxyethyl)azetidine-3-carboxamide

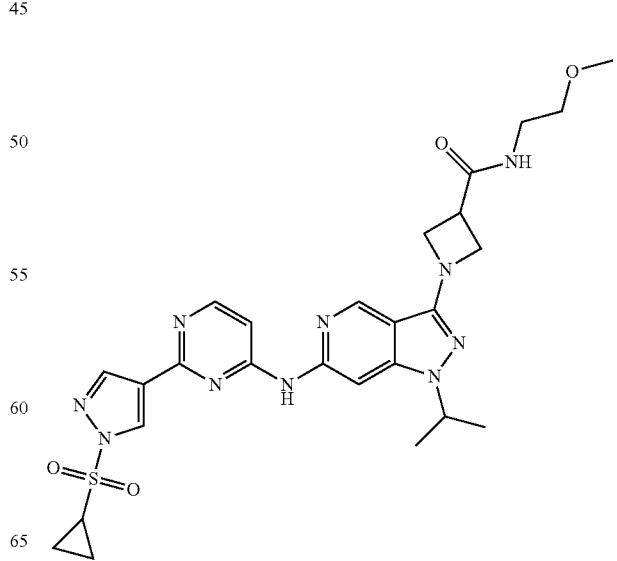

87

Step 1: Ethyl 1-(6-chloro-1-isopropyl-1H-pyrazolo[4,3-c]pyridin-3-yl)azetidine-3-carboxylate

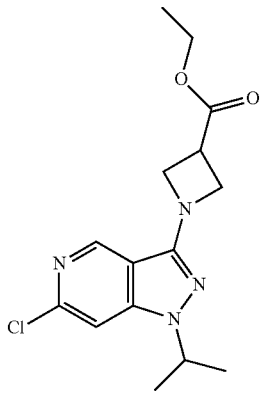 [SMILES: CCOC(=O)C1CN(c2nn(C(C)C)c3cc(Cl)ncc23)C1]

The title compound was prepared in a method analogous to Example 17, Step 1 to provide ethyl 1-(6-chloro-1-isopropyl-1H-pyrazolo[4,3-c]pyridin-3-yl)azetidine-3-carboxylate (1.5 g, 30%) as a yellow solid. LCMS (ESI): $R_T$ (min)=1.488, M+H$^+$=323, method=M.

Step 2: 1-(6-Chloro-1-isopropyl-1H-pyrazolo[4,3-c]pyridin-3-yl)azetidine-3-carboxylic acid

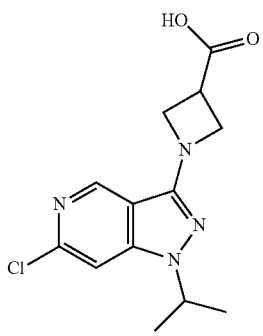 [SMILES: CC(C)n1nc(N2CC(C(=O)O)C2)c2cnc(Cl)cc21]

To a solution of 1-(6-chloro-1-isopropyl-1H-pyrazolo[4,3-c]pyridin-3-yl)azetidine-3-carboxylate (1.50 g, 4.65 mmol) in methanol (30 mL) and tetrahydrofuran (30 mL) was added sodium hydroxide (2 M in water, 15 mL). The reaction mixture was stirred for 1 h at room temperature. The resulting mixture was concentrated in vacuo, diluted with water and extracted with EtOAc (3×). The aqueous layer was acidified to pH 5-6 with aqueous HCl (10 M), filtered, and the solids were collected to afford 1-(6-chloro-1-isopropyl-1H-pyrazolo[4,3-c]pyridin-3-yl)azetidine-3-carboxylic acid (1 g, 73%) as a yellow solid. LCMS (ESI): $R_T$ (min)=1.261, [M+H]$^+$=295, method=M.

88

Step 3: 1-(6-Chloro-1-isopropyl-1H-pyrazolo[4,3-c]pyridin-3-yl)-N-(2-methoxyethyl)azetidine-3-carboxamide

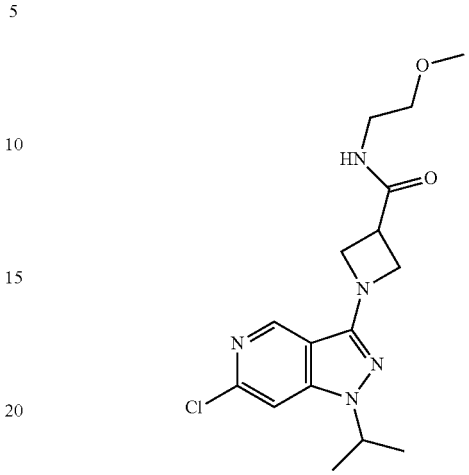

To a reaction vessel purged and maintained under nitrogen was added 1-(6-chloro-1-isopropyl-1H-pyrazolo[4,3-c]pyridin-3-yl)azetidine-3-carboxylic acid (200 mg, 0.680 mmol), 2-methoxyethanamine (101.6 mg, 1.41 mmol), 2-(1H-benzo[d][1,2,3]triazol-1-yl)-1,1,3,3-tetramethylisouronium hexafluorophosphate(V) (309.2 mg, 0.820 mmol), N-ethyl-N-isopropylpropan-2-amine (437 mg, 3.38 mmol) and N,N-dimethylformamide (5 mL). The reaction mixture was stirred for 2 h at room temperature and concentrated in vacuo. The crude product was purified via flash chromatography on silica gel (eluent: 10% methanol in dichloromethane) to afford 1-(6-chloro-1-isopropyl-1H-pyrazolo[4,3-c]pyridin-3-yl)-N-(2-methoxyethyl)azetidine-3-carboxamide (150 mg, 63%) as a white solid. LCMS (ESI): $R_T$ (min)=1.232, M+H$^+$=352, method=M.

Step 4: 1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-N-(2-methoxyethyl)azetidine-3-carboxamide The title compound was prepared in a method analogous to Example 20, Step 2 to provide 1-(6-(2-(1-(cyclopropylsulfonyl)-1H-pyrazol-4-yl)pyrimidin-4-ylamino)-1-isopropyl-1H-pyrazolo[4,3-c]pyridin-3-yl)-N-(2-methoxyethyl)azetidine-3-carboxamide (29.8 mg, 15%) as a off-white solid. LCMS (ESI): $R_T$ (min)=2.358, M+H$^+$=581, method=R; $^1$H NMR (400 MHz, DMSO-d$_6$): δ 10.33 (s, 1H), 8.70 (s, 1H), 8.62 (s, 1H), 8.48 (s, 1H), 8.422-8.408 (d, J=5.6 Hz, 1H), 8.29 (s, 1H), 8.14-8.11 (m, 1H), 7.149-7.135 (d, J=5.6 Hz, 1H), 4.73-4.70 (m, 1H), 4.26-4.22 (m, 2H), 4.14-4.10 (m, 2H), 3.63-3.59 (m, 1H), 3.37-3.25 (m, 8H), 1.476-1.460 (d, J=6.4 Hz, 6H), 1.36-1.34 (m, 2H), 1.28-1.26 (m, 2H).

Each compound in Table 1 below was prepared following a similar experimental procedure (using appropriately substituted reagents) as described in another Example herein, such with the Example being referenced in the Synthesis Method column.

TABLE 1

| Example | Structure/Name | Synthesis Method/ Example # | LCMS R$_T$ (min), M + H$^+$, method | $^1$H NMR (ppm) |
|---|---|---|---|---|
| 31 | N-(2-(1-(cyclopropylmethyl)-1H-pyrazol-4-yl)pyrimidin-4-yl)-1-isopropyl-3-(pyrrolidin-1-yl)-1H-pyrazolo[4,3-c]pyridin-6-amine | 9 | 4.368, 444.3, B | $^1$H NMR (400 MHz, DMSO-d$_6$) δ 10.05 (s, 1H), 8.76 (d, J = 0.9 Hz, 1H), 8.33 (s, 1H), 8.32 (d, J = 5.8 Hz, 1H), 8.13 (s, 1H), 8.02 (s, 1H), 7.07 (d, J = 5.9 Hz, 1H), 4.63 (p, J = 6.6 Hz, 1H), 4.05 (d, J = 7.2 Hz, 2H), 3.61-3.49 (m, 4H), 2.04-1.90 (m, 4H), 1.47 (d, J = 6.6 Hz, 6H), 1.37-1.25 (m, 1H), 0.62-0.53 (m, 2H), 0.46-0.36 (m, 2H). |
| 32 | N-(2-(1-(cyclopropylmethyl)-1H-pyrazol-4-yl)pyrimidin-4-yl)-1-isopropyl-1H-pyrazolo[4,3-c]pyridin-6-amine | 9 | 3.881, 375.2, B | $^1$H NMR (400 MHz, DMSO-d$_6$) δ 10.20 (s, 1H), 8.86 (d, J = 1.0 Hz, 1H), 8.43 (s, 1H), 8.36 (s, 1H), 8.34 (d, J = 5.9 Hz, 1H), 8.19 (s, 1H), 8.05 (s, 1H), 7.06 (d, J = 5.9 Hz, 1H), 4.91 (p, J = 6.6 Hz, 1H), 4.06 (d, J = 7.1 Hz, 2H), 1.56 (d, J = 6.6 Hz, 6H), 1.37-1.25 (m, 1H), 0.62-0.55 (m, 2H), 0.46-0.37 (m, 2H). |
| 33 | 1-(4-((1-isopropyl-1H-pyrazolo[4,3-c]pyridin-6-yl)amino)pyrimidin-2-yl)-3,3-dimethylpiperidin-4-ol | 8 | 3.506, 382.2, B | $^1$H NMR (400 MHz, DMSO-d$_6$) 9.87 (s, 1H), 8.81 (d, J = 0.9 Hz, 1H), 8.36 (s, 1H), 8.16 (s, 1H), 7.96 (d, J = 5.5 Hz, 1H), 6.33 (d, J = 5.6 Hz, 1H), 4.78 (p, J = 6.6 Hz, 1H), 4.65 (s, 1H), 4.43-4.32 (m, 1H), 4.14-4.04 (m, 1H), 3.37 (d, J = 8.7 Hz, 1H), 3.27-3.22 (m, 1H), 3.02 (d, J = 12.9 Hz, 1H), 1.78-1.66 (m, 1H), 1.62-1.53 (m, 1H), 1.51 (d, J = 6.7 Hz, 6H), 0.95 (s, 3H), 0.82 (s, 3H). |
| 34 | 1-(4-((1-isopropyl-3-morpholino-1H-pyrazolo[4,3-c]pyridin-6-yl)amino)pyrimidin-2-yl)-3,3-dimethylpiperidin-4-ol | 8 | 3.724, 467.3, B | $^1$H NMR (400 MHz, DMSO-d$_6$) δ 9.79 (s, 1H), 8.83 (s, 1H), 8.17 (s, 1H), 7.95 (d, J = 5.6 Hz, 1H), 6.32 (d, J = 5.7 Hz, 1H), 4.67-4.51 (m, 2H), 4.42-4.28 (m, 1H), 4.07 (d, J = 12.9 Hz, 1H), 3.79 (t, J = 4.7 Hz, 4H), 3.44-3.33 (m, 5H), 3.01 (d, J = 13.0 Hz, 1H), 1.77-1.65 (m, 1H), 1.58-1.47 (m, 1H), 1.43 (d, J = 6.6 Hz, 6H), 0.94 (s, 3H), 0.82 (s, 3H). |

TABLE 1-continued

| Example | Structure/Name | Synthesis Method/ Example # | LCMS R$_T$ (min), M + H$^+$, method | $^1$H NMR (ppm) |
|---|---|---|---|---|
| 35 | N$^6$-(2-(1-(cyclopropylsulfonyl)-1H-pyrazol-4-yl)pyrimidin-4-yl)-1-isopropyl-N$^3$-(oxetan-3-yl)-1H-pyrazolo[4,3-c]pyridine-3,6-diamine | 16 | 2.876, 495.56, L | $^1$H NMR (300 MHz, CDCl$_3$) □ 8.68 (s, 1H), 8.58 (s, 1H), 8.45 (s, 1H), 8.44-8.41 (d, J = 5.7 Hz, 1H), 8.10 (s, 1H), 7.89 (s, 1H), 6.83-6.81 (d, J = 5.7 Hz, 1H), 5.08-4.98 (m, 3H), 4.69-4.55 (m, 4H), 2.88-2.80 (m, 1H), 1.55-1.49 (m, 8H), 1.31-1.19 (m, 2H) |
| 36 | (1-(6-(2-(1-(ethylsulfonyl)-1H-pyrazol-4-yl)pyrimidin-4-ylamino)-1-isopropyl-1H-pyrazolo[4,3-c]pyridin-3-yl)azetidin-3-yl)methanol | 17 | 1.519, 497.57, R | $^1$H NMR (300 MHz, DMSO-d$_6$): □ 10.24 (s, 1H), 8.72 (s, 1H), 8.68 (s, 1H), 8.47 (s, 1H), 8.40 (d, J = 6.0 Hz, 1H), 8.17 (s, 1H), 7.13 (d, J = 5.7 Hz, 1H), 6.20 (d, J = 7.2 Hz, 1H), 4.68-4.59 (m, 1H), 3.87-3.80 (m, 1H), 3.31-3.25 (m, 1H), 1.45 (d, J = 6.6 Hz, 6H), 1.38-1.27 (m, 4H), 1.24 (d, J = 6.6 Hz, 6H). |
| 37 | 1-(6-(2-(1-(cyclopropylsulfonyl)-1H-pyrazol-4-yl)pyrimidin-4-ylamino)-1-isopropyl-1H-pyrazolo[4,3-c]pyridin-3-yl)azetidin-3-ol | 17 | 1.530, 495.56, R | $^1$H NMR (400 MHz, DMSO-d$_6$): □ 10.31 (s, 1H), 8.69 (s, 1H), 8.61 (d, J = 7.2 Hz, 1H), 8.47 (s, 1H), 8.41 (d, J = 6 Hz, 1H), 8.27 (s, 1H), 7.15 (d, J = 5.6 Hz, 1H), 5.67 (d, J = 6.8 Hz, 1H), 4.62-4.74 (m, 2H), 4.35 (m, 2H), 3.85 (m, 2H), 3.28 (m, 1H), 1.50 (s, 6H), 1.28-1.38 (m, 4H). |

TABLE 1-continued

| Example | Structure/Name | Synthesis Method/ Example # | LCMS R$_T$ (min), M + H$^+$, method | $^1$H NMR (ppm) |
|---|---|---|---|---|
| 38 | N6-(2-(1-(ethylsulfonyl)-1H-pyrazol-4-yl)pyrimidin-4-yl)-1-isopropyl-N3-(tetrahydrofuran-3-yl)-1H-pyrazolo[4,3-c]pyridine-3,6-diamine | 17 | 1.694, 497.57, R | $^1$H NMR (300 MHz, DMSO-d$_6$): ☐ 10.30 (s, 1H), 8.73-8.68 (m, 2H), 8.48 (s, 1H), 8.40 (d, J = 6 Hz, 1H), 8.21 (s, 1H), 7.13 (d, J = 5.7 Hz, 1H), 6.63 (d, J = 6 Hz, 1H), 4.69-4.60 (m, 1H), 4.26-4.24 (m, 1H), 3.94-3.81 (m, 4H), 3.79-3.71 (m, 1H), 3.68-3.64 (m, 1H), 2.25-2.16 (m, 1H), 1.97-1.90 (m, 1H), 1.47-1.45 (d, J = 6.6 Hz, 6H), 1.18-1.14 (m, 3H) |
| 39 | (S)-N6-(2-(1-(cyclopropylsulfonyl)-1H-pyrazol-4-yl)pyrimidin-4-yl)-1-isopropyl-N3-(tetrahydrofuran-3-yl)-1H-pyrazolo[4,3-c]pyridine-3,6-diamine | 18 | 1.554, 509.58, L | $^1$H NMR (400 MHz, DMSO-d$_6$): ☐ 10.27 (s, 1H), 8.74 (s, 1H), 8.69 (s, 1H), 8.48 (s, 1H), 8.41 (d, J = 6.0 Hz, 1H), 8.20 (s, 1H), 7.13 (d, J = 5.2 Hz, 1H), 6.63 (d, J = 5.6 Hz, 1H), 4.67-4.64 (m, 1H), 4.26-4.24 (m, 1H), 3.94-3.85 (m, 2H), 3.79-3.72 (m, 1H), 3.68-3.65 (m, 1H), 3.33-3.27 (m, 1H), 2.24-2.19 (m, 1H), 1.94-1.90 (m, 1H), 1.46 (d, J = 6.6 Hz, 6H), 1.38-1.35 (m, 2H), 1.31-1.24 (m, 2H). |
| 40 | (R)-N6-(2-(1-(cyclopropylsulfonyl)-1H-pyrazol-4-yl)pyrimidin-4-yl)-1-isopropyl-N3-(tetrahydrofuran-3-yl)-1H-pyrazolo[4,3-c]pyridine-3,6-diamine | 18 | 1.549, 509.58, L | $^1$H NMR (400 MHz, DMSO-d$_6$): ☐ 10.27 (s, 1H), 8.73 (s, 1H), 8.69 (s, 1H), 8.47 (s, 1H), 8.40 (d, J = 6.0 Hz, 1H), 8.20 (s, 1H), 7.13 (d, J = 5.2 Hz, 1H), 6.63 (d, J = 5.6 Hz, 1H), 4.66-4.63 (m, 1H), 4.26-4.24 (m, 1H), 3.94-3.85 (m, 2H), 3.78-3.72 (m, 1H), 3.68-3.65 (m, 1H), 3.33-3.27 (m, 1H), 2.24-2.19 (m, 1H), 1.92-1.90 (m, 1H), 1.46 (d, J = 6.6 Hz, 6H), 1.35-1.31 (m, 2H), 1.29-1.26 (m, 2H). |

TABLE 1-continued

| Example | Structure/Name | Synthesis Method/ Example # | LCMS $R_T$ (min), M + H+, method | $^1$H NMR (ppm) |
|---|---|---|---|---|
| 41 | 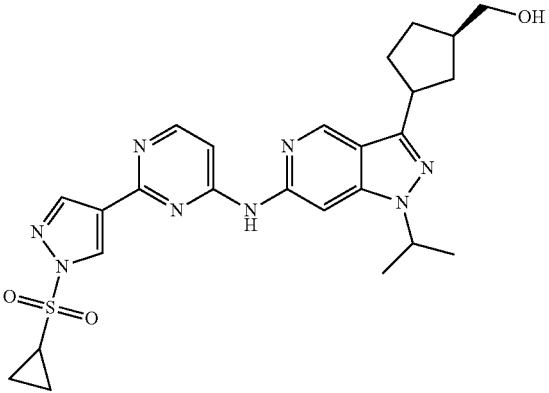 [SMILES: CC(C)n1nc(C2CC[C@@H](CO)C2)c2cnc(Nc3ccnc(-c4cnn(S(=O)(=O)C5CC5)c4)n3)cc21]<br>(R)-(1-(6-(2-(1-(cyclopropylsulfonyl)-1H-pyrazol-4-yl)pyrimidin-4-ylamino)-1-isopropyl-1H-pyrazolo[4,3-c]pyridin-3-yl)pyrrolidin-3-yl)methanol | 18 | 1.555, 523.61, M | $^1$H NMR (300 MHz, CDCl$_3$): □ 8.69 (s, 2H), 8.46 (s, 1H), 8.40 (d, J = 5.7 Hz, 1H), 7.26 (s, 2H), 6.85 (d, J = 5.7 Hz, 1H), 4.64-4.60 (m, 1H), 3.82-3.65 (m, 5H), 3.52-3.46 (m, 1H), 2.89-2.82 (m, 1H), 2.69-2.62 (m, 1H), 2.26-2.15 (m, 1H), 2.01-1.84 (m, 2H), 1.58 (d, J = 6.6 Hz, 6H), 1.55-1.51 (m, 2H), 1.26-1.19 (m, 2H) |
| 42 | 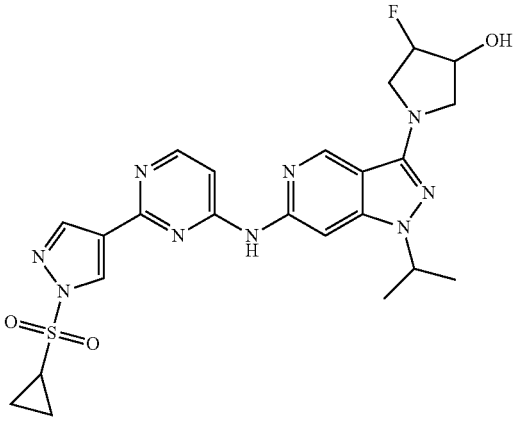 [SMILES: CC(C)n1nc(N2CC(O)C(F)C2)c2cnc(Nc3ccnc(-c4cnn(S(=O)(=O)C5CC5)c4)n3)cc21]<br>1-(6-(2-(1-(cyclopropylsulfonyl)-1H-pyrazol-4-yl)pyrimidin-4-ylamino)-1-isopropyl-1H-pyrazolo[4,3-c]pyridin-3-yl)-trans-4-fluoropyrrolidin-3-ol | 18 | 1.563, 527.57, M | $^1$H NMR (400 MHz, DMSO-d$_6$): □ 10.33 (s, 1H), 8.82 (s, 1H), 8.70 (s, 1H), 8.48 (s, 1H), 8.42 (d, J = 5.6 Hz, 1H), 8.26 (s, 1H), 7.14 (d, J = 5.6 Hz, 1H), 5.57 (s, 1H), 5.10 (s, 1H), 4.74-4.67 (m, 1H), 4.39-4.37 (m, 1H), 3.97-3.75 (m, 3H), 3.59 (d, 1H), 3.34-3.26 (m, 1H), 1.48 (d, J = 6.6 Hz, 6H), 1.38-1.35 (m, 2H), 1.31-1.23 (m, 2H) |

TABLE 1-continued

| Example | Structure/Name | Synthesis Method/ Example # | LCMS $R_T$ (min), M + H+, method | $^1$H NMR (ppm) |
|---|---|---|---|---|
| 43 | 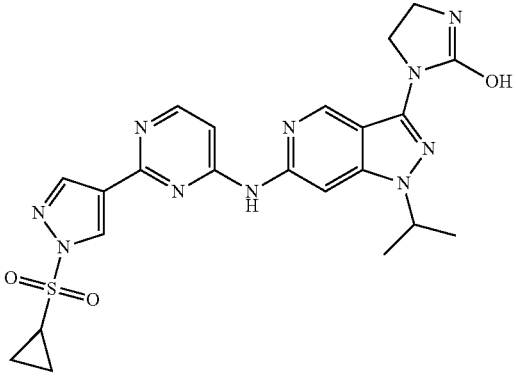 [SMILES: CC(C)n1nc(N2CCN=C2O)c2cnc(Nc3ccnc(-c4cnn(S(=O)(=O)C5CC5)c4)n3)cc21]<br>1-(6-(2-(1-(cyclopropylsulfonyl)-1H-pyrazol-4-yl)pyrimidin-4-ylamino)-1-isopropyl-1H-pyrazolo[4,3-c]pyridin-3-yl)-4,5-dihydro-1H-imidazol-2-ol | 17 | 1.839, 508.56, R | $^1$H NMR (400 MHz, DMSO-$d_6$): ☐ 10.41 (s, 1H), 9.36 (s, 1H), 8.73 (s, 1H), 8.49 (s, 1H), 8.43 (s, 1H), 8.41 (s, 1H), 7.23 (s, 1H), 7.15 (d, J = 5.6 Hz, 1H), 4.86 (m, 1H), 4.00 (m, 2H), 3.53 (m, 2H), 3.28 (m, 1H), 1.50 (s, 6H), 1.28-1.38 (m, 4H) |
| 44 | 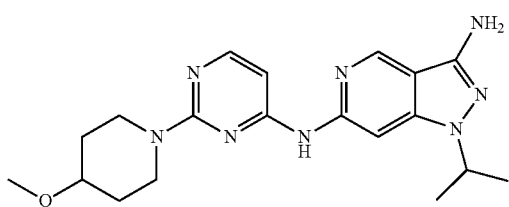 [SMILES: COC1CCN(c2nccc(Nc3cc4c(cn3)c(N)nn4C(C)C)n2)CC1]<br>1-isopropyl-N$^6$-(2-(4-methoxypiperidin-1-yl)pyrimidin-4-yl)-1H-pyrazolo[4,3-c]pyridine-3,6-diamine | 17 | 1.633, 382.46, H | $^1$H NMR (400 MHz, DMSO-$d_6$): ☐ 9.77 (s, 1H), 8.63 (s, 1H), 8.06 (s, 1H), 7.97 (d, J = 5.6 Hz, 1H), 6.35 (d, J = 5.6 Hz, 1H), 5.77 (s, 2H), 4.44-4.50 (m, 1H), 4.20-4.25 (m, 2H), 3.30-3.50 (m, 6H), 1.90-1.92 (m, 2H), 1.45-1.47 (m, 8H) |
| 45 | 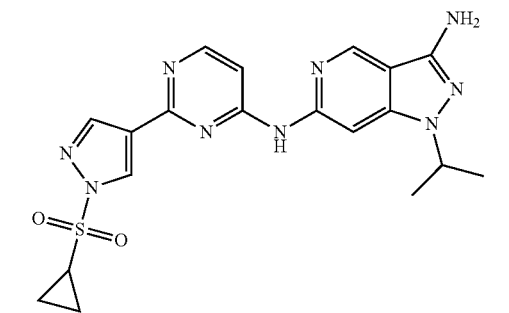 [SMILES: CC(C)n1nc(N)c2cnc(Nc3ccnc(-c4cnn(S(=O)(=O)C5CC5)c4)n3)cc21]<br>N$^6$-(2-(1-(cyclopropylsulfonyl)-1H-pyrazol-4-yl)pyrimidin-4-yl)-1-isopropyl-1H-pyrazolo[4,3-c]pyridine-3,6-diamine | 17 | 1.504, 439.49, R | $^1$H NMR (300 MHz, DMSO-$d_6$): ☐ 10.26 (s, 1H), 8.70 (s, 2H), 8.47 (s, 1H), 8.39 (d, J = 6 Hz, 1H), 8.19 (s, 1H), 7.13 (d, J = 6 Hz, 1H), 5.83 (s, 2H), 4.63 (m, 1H), 3.26 (m, 1H), 1.43 (s, 6H), 1.25-1.35 (m, 4H) |

TABLE 1-continued

| Example | Structure/Name | Synthesis Method/ Example # | LCMS $R_T$ (min), M + H+, method | $^1$H NMR (ppm) |
|---|---|---|---|---|
| 46 | N6-(2-(1-(cyclopropylsulfonyl)-1H-pyrazol-4-yl)pyrimidin-4-yl)-N3, 1-diisopropyl-1H-pyrazolo[4,3-c]pyridine-3,6-diamine | 18 | 2.343, 481.57, M | $^1$H NMR (300 MHz, DMSO-d$_6$): □ 10.24 (s, 1H), 8.72 (s, 1H), 8.68 (s, 1H), 8.47 (s, 1H), 8.40 (d, J = 6.0 Hz, 1H), 8.17 (s, 1H), 7.13 (d, J = 5.7 Hz, 1H), 6.20 (d, J = 7.2 Hz, 1H), 4.68-4.59 (m, 1H), 3.87-3.80 (m, 1H), 3.31-3.25 (m, 1H), 1.45 (d, J = 6.6 Hz, 6H), 1.38-1.27 (m, 4H), 1.24 (d, J = 6.6 Hz, 6H) |
| 47 | 3-(6-(2-(1-(cyclopropylsulfonyl)-1H-pyrazol-4-yl)pyrimidin-4-ylamino)-1-isopropyl-1H-pyrazolo[4,3-c]pyridin-3-ylamino)propanamide | 18 | 1.991, 510.57, M | $^1$H NMR (300 MHz, DMSO-d$_6$): □ 10.24 (s, 1H), 8.71 (s, 1H), 8.68 (s, 1H), 8.47 (s, 1H), 8.40 (d, J = 6.0 Hz, 1H), 8.18 (s, 1H), 7.34 (s, 1H), 7.14 (d, J = 5.7 Hz, 1H), 6.83 (s, 1H), 6.44-6.40 (m, 1H), 4.69-4.60 (m, 1H), 3.50-3.43 (m, 2H), 3.30-3.26 (m, 1H), 2.50-2.43 (m, 2H), 1.46 (d, J = 6.6 Hz, 6H), 1.35-1.26 (m, 4H) |
| 48 | 2-(6-(2-(1-(cyclopropylsulfonyl)-1H-pyrazol-4-yl)pyrimidin-4-ylamino)-1-isopropyl-1H-pyrazolo[4,3-c]pyridin-3-ylamino)acetamide | 18 | 1.927, 496.55, N | $^1$H NMR (300 MHz, DMSO-d$_6$): □ 10.26 (s, 1H), 8.78 (s, 1H), 8.69 (s, 1H), 8.47 (s, 1H), 8.40 (d, J = 6.0 Hz, 1H), 8.19 (s, 1H), 7.40 (s, 1H), 7.15 (d, J = 6.0 Hz, 1H), 7.07 (s, 1H), 6.69-6.65 (m, 1H), 4.69-4.60 (m, 1H), 3.84 (d, J = 6.0 Hz, 2H), 3.29-3.25 (m, 1H), 1.44 (d, J = 6.6 Hz, 6H), 1.34-1.30 (m, 2H), 1.28-1.23 (m, 2H) |

TABLE 1-continued

| Example | Structure/Name | Synthesis Method/ Example # | LCMS R$_T$ (min), M + H$^+$, method | $^1$H NMR (ppm) |
|---|---|---|---|---|
| 49 | 3-((6-(2-(1-(cyclopropylsulfonyl)-1H-pyrazol-4-yl)pyrimidin-4-ylamino)-1-isopropyl-1H-pyrazolo[4,3-c]pyridin-3-yl)(methyl)amino)propane-1,2-diol | 18 | 2.731, 527.60, N | $^1$H NMR (400 MHz, DMSO-d$_6$): ☐ 10.27 (s, 1H), 8.89 (s, 1H), 8.69 (s, 1H), 8.47 (s, 1H), 8.41 (d, J = 6.0 Hz, 1H), 8.21 (s, 1H), 7.15 (d, J = 5.2 Hz, 1H), 4.86 (s, 1H), 4.75-4.72 (m, 1H), 4.70-4.68 (m, 1H), 3.84-3.81 (m, 1H), 3.68-3.63 (m, 1H), 3.42-3.34 (m, 3H), 3.29-3.27 (m, 1H), 3.16 (s, 3H), 1.46 (d, J = 6.4 Hz, 6H), 1.38-1.33 (m, 2H), 1.29-1.24 (m, 2H) |
| 50 | N-(2-(1-(cyclopropylsulfonyl)-1H-pyrazol-4-yl)pyrimidin-4-yl)-1,3-diisopropyl-1H-pyrazolo[4,3-c]pyridin-6-amine | 19 | 2.080, 466.56, R | $^1$H NMR (300 MHz, DMSO-d$_6$): ☐ 10.38 (s, 1H), 8.92 (s, 1H), 8.71 (s, 1H), 8.48-8.40 (m, 3H), 7.15-7.13 (d, J = 6 Hz, 1H), 4.90-4.81 (m, 1H), 3.42-3.31 (m, 1H), 3.26-3.24 (m, 1H), 1.54-1.51 (d, J = 4.2 Hz, 6H), 1.41-1.34 (m, 6H), 1.33-1.25 (m, 4H) |
| 51 | N-(2-(1-(cyclopropylsulfonyl)-1H-pyrazol-4-yl)pyrimidin-4-yl)-1-isopropyl-3-morpholino-1H-pyrazolo[4,3-c]pyridin-6-amine | 18 | 1.673, 510.10, N | $^1$H NMR (300 MHz, DMSO-d$_6$): ☐☐10.37 (s, 1H), 8.91 (s, 1H), 8.70 (s, 1H), 8.47 (s, 1H), 8.42-8.40 (d, J = 6.0 Hz, 1H), 8.34 (s, 1H), 7.12-7.10 (d, J = 6.0 Hz, 1H), 4.77-4.72 (m, 1H), 3.81-3.78 (m, 4H), 3.42-3.39 (m, 4H), 3.31-3.26 (m, 1H), 1.48-1.46 (d, J = 6.6 Hz, 6H,), 1.35-1.32 (m, 2H), 1.29-1.23 (m, 2H) |

TABLE 1-continued

| Example | Structure/Name | Synthesis Method/ Example # | LCMS R$_T$ (min), M + H$^+$, method | $^1$H NMR (ppm) |
|---|---|---|---|---|
| 52 | N$^6$-(2-(1-(cyclopropylsulfonyl)-1H-pyrazol-4-yl)pyrimidin-4-yl)-1-isopropyl-N$^3$-(tetrahydro-2H-pyran-4-yl)-1H-pyrazolo[4,3-c]pyridine-3,6-diamine | 18 | 2.122, 524.25, M | $^1$H NMR (300 MHz, DMSO-d$_6$): □ 10.26 (s, 1H), 8.74 (s, 1H), 8.68 (s, 1H), 8.47 (s, 1H), 8.41-8.39 (d, J = 6.0 Hz, 1H), 8.18 (br, 1H), 7.13-7.12 (d, J = 5.7 Hz, 1H), 6.36-6.34 (d, J = 7.2 Hz, 1H), 4.68-4.59 (m, 1H), 3.92-3.88 (m, 2H), 3.77-3.68 (m, 1H), 3.47-3.44 (m, 2H), 3.32-3.24 (m, 1H), 2.49-2.07 (m, 2H), 1.56-1.48 (m, 8H), 1.45-1.38 (m, 4H) |
| 53 | (4-(6-(2-(1-(cyclopropylsulfonyl)-1H-pyrazol-4-yl)pyrimidin-4-ylamino)-1-isopropyl-1H-pyrazolo[4,3-c]pyridin-3-yl)morpholin-2-yl)methanol | 18 | 2.516, 540.15, R | $^1$H NMR (300 MHz, DMSO-d$_6$): □ 10.37 (s, 1H), 8.90 (s, 1H), 8.70 (s, 1H), 8.48 (s, 1H), 8.42-8.40 (d, J = 6.0 Hz, 1H), 8.35 (br, 1H), 7.131-7.112 (d, J = 5.7 Hz, 1H), 4.83-4.72 (m, 2H), 3.97-3.45 (m, 7H), 3.32-3.26 (m, 1H), 3.00-2.96 (m, 1H), 2.77-2.72 (m, 1H), 1.491-1.469 (d, J = 6.6 Hz, 6H), 1.40-1.20 (m, 4H) |
| 54 | 3-(azetidin-1-yl)-N-(2-(1-(cyclopropylsulfonyl)-1H-pyrazol-4-yl)pyrimidin-4-yl)-1-isopropyl-1H-pyrazolo[4,3-c]pyridin-6-amine | 18 | 2.175, 480.05, R | $^1$H NMR (300 MHz, DMSO-d$_6$): □ 10.31 (s, 1H), 8.69 (s, 1H), 8.60 (s, 1H), 8.47 (s, 1H), 8.418-8.399 (d, J = 5.7 Hz, 1H), 8.27 (br, 1H), 7.153-7.133 (d, J = 6.0 Hz, 1H), 4.72-4.67 (m, 1H), 4.14-4.09 (m, 4H), 3.31-3.26 (m, 1H), 2.46-2.38 (m, 2H), 1.471-1.449 (d, J = 6.6 Hz, 6H), 1.35-1.23 (m, 4H) |

TABLE 1-continued

| Example | Structure/Name | Synthesis Method/ Example # | LCMS $R_T$ (min), M + H+, method | $^1$H NMR (ppm) |
|---|---|---|---|---|
| 55 | 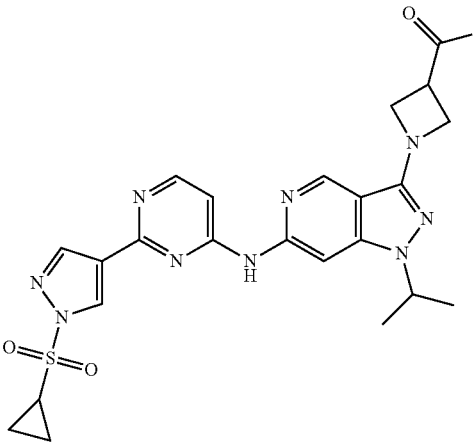<br>1-(6-(2-(1-(cyclopropylsulfonyl)-1H-pyrazol-4-yl)pyrimidin-4-ylamino)-1-isopropyl-1H-pyrazolo[4,3-c]pyridin-3-yl)azetidine-3-carboxamide | 17 | 1.059, 523.35, N | $^1$H NMR (400 MHz, DMSO-d$_6$): □ 10.26 (s, 1H), 8.62 (s, 1H), 8.55 (s, 1H), 8.40 (s, 1H), 8.35-8.336 (d, J = 5.6 Hz, 1H), 8.21 (br, 1H), 7.42 (s, 1H), 7.07 (s, 1H), 6.97 (s, 1H), 4.50-4.80 (m, 1H), 4.19-4.15 (m, 2H), 4.07-4.049 (m, 2H), 3.48 (s, 1H), 3.3 (m, 1H), 1.406-1.391 (d, J = 6.0 Hz, 6H), 1.20-1.19 (m, 4H). |
| 56 | 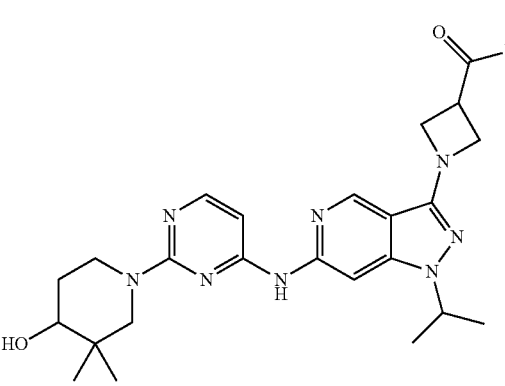<br>1-(6-(2-(4-hydroxy-3,3-dimethylpiperidin-1-yl)pyrimidin-4-ylamino)-1-isopropyl-1H-pyrazolo[4,3-c]pyridin-3-yl)-N,N-dimethylazetidine-3-carboxamide | 17 | 1.295, 508.20, N | $^1$H NMR (300 MHz, DMSO-d$_6$): □ 9.81 (s, 1H), 8.57 (s, 1H), 8.15 (s, 1H), 7.953-7.934 (d, J = 5.7 Hz, 1H), 6.324-6.305 (d, J = 5.7 Hz, 1H), 4.675-4.660 (d, J = 4.5 Hz, 1H), 4.55 (m, 1H), 4.34-4.28 (m, 3H), 4.19-4.13 (m, 3H), 4.09-4.05 (m, 1H), 3.35-3.31 (m, 2H), 3.017-2.974 (d, J = 12.9 Hz, 1H), 2.90 (s, 3 H), 2.85 (s, 3H), 1.85-1.65 (m, 1H), 1.60-1.40 (m, 1H), 1.424-1.402 (d, J = 6.6 Hz, 6H), 0.94 (s, 3H), 0.81 (s, 3H). |
| 57 | 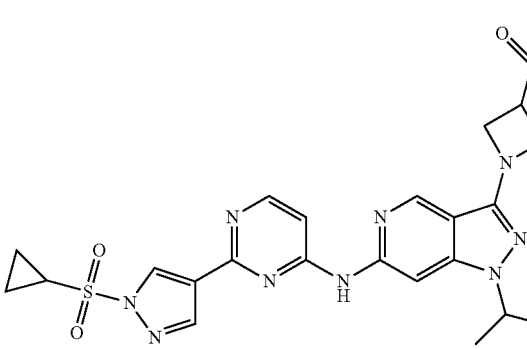<br>1-(6-(2-(1-(cyclopropylsulfonyl)-1H-pyrazol-4-yl)pyrimidin-4-ylamino)-1-isopropyl-1H-pyrazolo[4,3-c]pyridin-3-yl)-N,N-dimethylazetidine-3-carboxamide | 17 | 1.478, 551.15, L | $^1$H NMR (300 MHz, DMSO-d$_6$): □ 10.26 (s, 1H), 8.62 (s, 1H), 8.57 (s, 1H), 8.40 (s, 1H), 8.353-8.334 (d, J = 5.7 Hz, 1H), 8.22 (s, 1H), 7.078-7.059 (d, J = 5.7 Hz, 1H), 4.68-4.60 (m, 1H), 4.28-4.23 (m, 2H), 4.13-4.09 (m, 2H), 3.93-3.85 (m, 1H), 3.3 (m, 1H), 2.84 (s, 3H), 2.78 (s, 3H), 1.407-1.385 (d, J = 6.6 Hz, 6H), 1.27-1.16 (m, 4H). |

TABLE 1-continued

| Example | Structure/Name | Synthesis Method/ Example # | LCMS $R_T$ (min), M + H+, method | 1H NMR (ppm) |
|---|---|---|---|---|
| 58 | 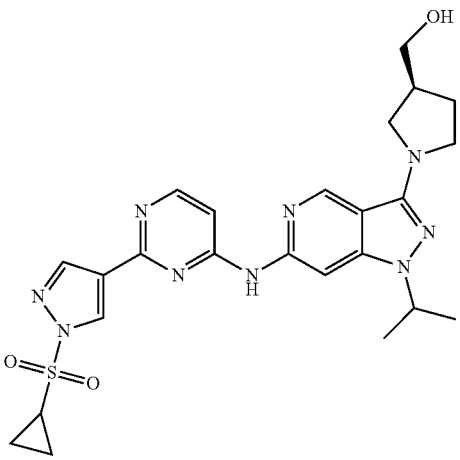 [SMILES: CC(C)n1nc(N2CC[C@H](CO)C2)c2cnc(Nc3ccnc(-c4cnn(S(=O)(=O)C5CC5)c4)n3)cc21]<br>(S)-(1-(6-(2-(1-(cyclopropylsulfonyl)-1H-pyrazol-4-yl)pyrimidin-4-ylamino)-1-isopropyl-1H-pyrazolo[4,3-c]pyridin-3-yl)pyrrolidin-3-yl)methanol | 18 | 1.977, 524.15, L | 1H NMR (400 MHz, DMSO-d6): □ 10.31 (s, 1H), 8.76 (s, 1H), 8.70 (s, 1H), 8.48 (s, 1H), 8.415-8.400 (d, J = 6.0 Hz, 1H), 8.26 (s, 1H), 7.141-7.129 (d, J = 4.8 Hz, 1H), 4.76-4.66 (m, 3H), 3.68-3.42 (m, 5H), 3.32-3.27 (m, 1H), 2.48-2.43 (m, 1H), 2.09-2.02 (m, 1H), 1.81-1.79 (m, 1H), 1.45 (s, 6H), 1.40-1.13 (m, 4H). |
| 59 | 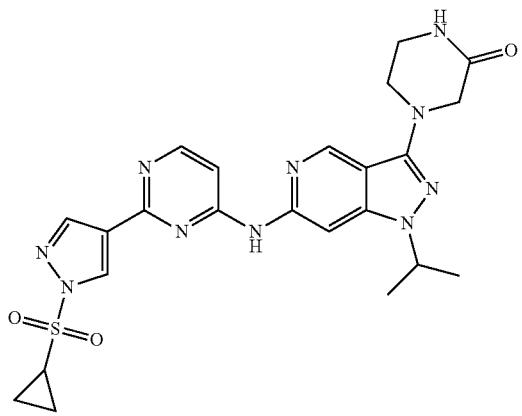 [SMILES: CC(C)n1nc(N2CCNC(=O)C2)c2cnc(Nc3ccnc(-c4cnn(S(=O)(=O)C5CC5)c4)n3)cc21]<br>4-(6-(2-(1-(cyclopropylsulfonyl)-1H-pyrazol-4-yl)pyrimidin-4-ylamino)-1-isopropyl-1H-pyrazolo[4,3-c]pyridin-3-yl)piperazin-2-one | 17 | 1.410, 523.25, L | 1H NMR (300 MHz, DMSO-d6): □ 10.39 (s, 1H), 8.92 (s, 1H), 8.71 (s, 1H), 8.48 (s, 1H), 8.428-8.408 (d, J = 6.0 Hz, 1H), 8.36 (s, 1H), 8.04 (s, 1H), 7.128-7.108 (d, J = 6.0 Hz, 1H), 4.76 (m, 1H), 3.99 (s, 1H), 3.70-3.67 (m, 2H), 3.37 (m, 2H), 3.29 (m, 2H), 1.495-1.473 (d, J = 6.6 Hz, 6H), 1.28-1.27 (m, 2H), 1.26-1.24 (m, 2H). |

TABLE 1-continued

| Example | Structure/Name | Synthesis Method/ Example # | LCMS R$_T$ (min), M + H$^+$, method | $^1$H NMR (ppm) |
|---|---|---|---|---|
| 60 | 1-(6-(2-(1-(cyclopropylsulfonyl)-1H-pyrazol-4-yl)pyrimidin-4-ylamino)-1-isopropyl-1H-pyrazolo[4,3-c]pyridin-3-yl)pyrrolidine-3-carboxamide | 17 | 1.403, 537.20, L | $^1$H NMR (300 MHz, DMSO-d$_6$): ☐ 10.30 (s, 1H), 8.76 (s, 1H), 8.68 (s, 1H), 8.46 (s, 1H), 8.408-8.389 (d, J = 5.7 Hz, 1H), 8.25 (s, 1H), 7.48 (s, 1H), 7.134-7.114 (d, J = 6.0 Hz, 1H), 6.97 (s, 1H), 4.73-4.64 (m, 1H), 3.80-3.53 (m, 4H), 3.31-3.24 (m, 1H), 3.09-3.04 (m, 1H), 2.19-2.07 (m, 2H), 1.474-1.452 (d, J = 6.6 Hz, 6H), 1.376-1.229 (m, 4H). |
| 61 | 1-(6-(2-(1-(cyclopropylsulfonyl)-1H-pyrazol-4-yl)pyrimidin-4-ylamino)-1-isopropyl-1H-pyrazolo[4,3-c]pyridin-3-ylamino)-2-methylpropan-2-ol | 18 | 2.020, 512.15, L | $^1$H NMR (400 MHz, DMSO-d$_6$): ☐ 10.21 (s, 1H), 8.76 (s, 1H), 8.63 (s, 1H), 8.41 (s, 1H), 8.348-8.333 (d, J = 6.0 Hz, 1H), 8.12 (s, 1H), 7.080-7.067 (d, J = 5.2 Hz, 1H), 6.21-6.17 (m, 1H), 4.61-4.56 (m, 1H), 4.53 (s, 1H), 3.26-3.18 (m, 3H), 1.389-1.373 (d, J = 6.4 Hz, 6H), 1.31-1.28 (m, 2H), 1.24-1.18 (m, 2H), 1.13 (s, 6 H). |

TABLE 1-continued

| Example | Structure/Name | Synthesis Method/ Example # | LCMS R$_T$ (min), M + H$^+$, method | $^1$H NMR (ppm) |
|---|---|---|---|---|
| 62 | N-(2-(1-(cyclopropylsulfonyl)-1H-pyrazol-4-yl)pyrimidin-4-yl)-3-isopropoxy-1-isopropyl-1H-pyrazolo[4,3-c]pyridin-6-amine | 19 | 1.856, 483.15, M | 1H NMR (300 MHz, DMSO-d$_6$): ☐ 10.38 (s, 1H), 8.71 (s, 1H), 8.63 (s, 1H), 8.48 (s, 1H), 8.435-8.415 (d, J = 6.0 Hz, 1H), 8.34 (s, 1H), 7.141-7.122 (d, J = 5.7 Hz, 1H), 5.10-5.02 (m, 1H), 4.80-4.71 (m, 1H), 3.3 (m, 1H), 1.490-1.469 (d, J = 6.3 Hz, 6H), 1.415-1.395 (d, J = 6.0 Hz, 6H), 1.348-1.258 (m, 4H). |
| 63 | (1-(6-(2-(1-(cyclopropylsulfonyl)-1H-pyrazol-4-yl)pyrimidin-4-ylamino)-1-isopropyl-1H-pyrazolo[4,3-c]pyridin-3-yl)azetidin-3-yl)methanol | 18 | 2.325, 510.10, R | 1H NMR (300 MHz, DMSO-d$_6$): ☐ 10.30 (s, 1H), 8.69 (s, 1H), 8.59 (s, 1H), 8.47 (s, 1H), 8.418-8.398 (d, J = 6.0 Hz, 1H), 8.26 (s, 1H), 7.147-7.128 (d, J = 5.7 Hz, 1H), 4.77-4.67 (m, 2H), 4.16-4.11 (m, 2H), 3.89-3.84 (m, 2H), 3.63-3.59 (m, 2H), 3.31-3.29 (m, 1H), 2.90 (m, 1H), 1.470-1.448 (d, J = 6.6 Hz, 6 H), 1.337-1.255 (m, 4H). |

Example 64: (3RS,4SR)-3-Fluoro-1-{4-[1-isopropyl-3-(2-oxa-6-azaspiro[3,3]hept-6-yl)-1H-pyrazolo[4,3-c]pyridin-6-ylamino]pyrimidin-2-yl}-4-methylpiperidin-4-ol (mixture of enantiomers)

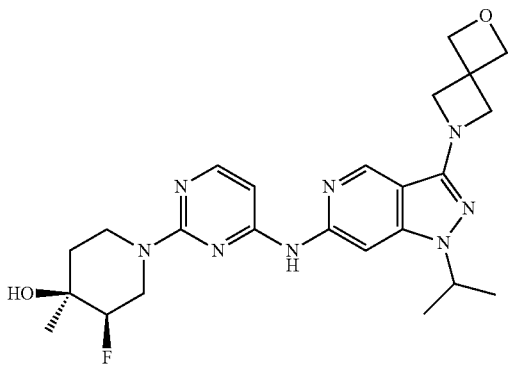 [SMILES: CC(C)n1nc(N2CC3(COC3)C2)c2cnc(Nc3ccnc(N4CC[C@](C)(O)[C@H](F)C4)n3)cc21]

Step 1: (3RS,4SR)-3-Fluoro-4-hydroxy-4-methylpiperidine-1-carboxylic acid benzyl ester (mixture of enantiomers)

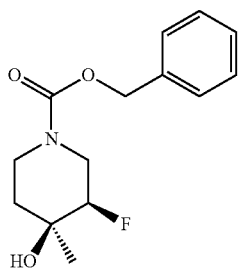 [SMILES: C[C@]1(O)CCN(C(=O)OCc2ccccc2)C[C@H]1F]

Methylmagnesium bromide (1.4 M in tetrahydrofuran:toluene, 1:3) (61 mL, 85.4 mmol) was added over 15 min to a solution of 3-fluoro-4-oxopiperidine-1-carboxylic acid benzyl ester (*J. Med. Chem.*, 2008, 51, 4239) (16.5 g, 65.6 mmol) in tetrahydrofuran (200 mL) at −78° C. The mixture was allowed to warm to −20° C. over 2 h then quenched by addition of saturated ammonium chloride. The aqueous phase was extracted twice with ethyl acetate, and the combined organic extracts were washed with brine, dried over anhydrous sodium sulfate, filtered and concentrated in vacuo. The residue was purified by chromatography on silica (solvent gradient: 50-100% diethyl ether in pentane) to afford the title compound as colorless oil (first eluting isomer, mixture of enantiomers with known relative stereochemistry) (8.0 g, 46%). $^1$H NMR (CDCl$_3$): δ 7.37-7.32 (5H, m), 5.13 (2H, s), 4.28 (1H, br d, J=47 Hz), 4.04-3.88 (1H, m), 3.69-3.64 (1H, m), 3.52-3.33 (2H, m), 2.00 (1H, br s), 1.82-1.77 (1H, m), 1.59-1.51 (1H, m), 1.31 (3H, d, J=0.8 Hz).

Step 2: (3RS,4SR)-3-Fluoro-4-methylpiperidin-4-ol (mixture of enantiomers)

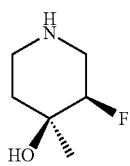

(3RS,4SR)-3-Fluoro-4-hydroxy-4-methylpiperidine-1-carboxylic acid benzyl ester (3.8 g, 14.2 mmol) was dissolved in ethanol (100 mL) and the mixture was purged with nitrogen. Palladium hydroxide on carbon (20%, 0.3 g) was added, the atmosphere was exchanged for hydrogen and the mixture was stirred under an atmosphere of hydrogen for 16 h. The mixture was purged with nitrogen, filtered through a Celite pad and the filtrate was concentrated in vacuo to give the title compound as a colorless gum as a mixture of enantiomers (quantitative). $^1$H NMR (CDCl$_3$): δ 4.29 (1H, ddd, J=48.4, 7.2, 3.5 Hz), 3.13-3.06 (1H, m), 3.00-2.91 (2H, m), 2.71-2.64 (1H, m), 2.18 (2H, br s), 1.80-1.72 (1H, m), 1.60-1.53 (1H, m), 1.28 (3H, d, J=1.3 Hz).

Step 3: (3RS,4SR)-1-(4-Aminopyrimidin-2-yl)-3-fluoro-4-methylpiperidin-4-ol (mixture of enantiomers)

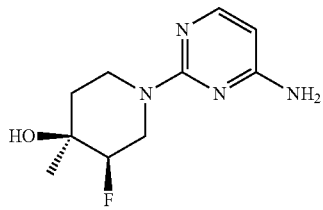 [SMILES: C[C@]1(O)CCN(c2nccc(N)n2)C[C@H]1F]

A mixture of (3RS,4SR)-3-fluoro-4-methylpiperidin-4-ol (1.89 g, 14.2 mmol), 2-chloro-4-aminopyrimidine (1.838 g, 14.2 mmol) and triethylamine (3.9 mL, 28 mmol) in isopropanol (30 mL) was heated under microwave irradiation at 150° C. for 1 h. The reaction mixture was cooled to room temperature and concentrated in vacuo. The residue was dissolved in a mixture of dichloromethane and methanol (30:1, 124 mL), to which potassium carbonate (5.5 g) was added and the mixture stirred for 10 min, filtered and the filtrate concentrated in vacuo. Purification by chromatography on silica (solvent gradient: 50-100% isopropyl acetate in dichloromethane; 50-100% ethyl acetate in isopropyl acetate) gave the product as a mixture of enantiomers as a white solid (2.09 g, 65%). $^1$H NMR (CDCl$_3$): δ 7.92 (1H, d, J=5.6 Hz), 5.76 (1H, d, J=5.6 Hz), 4.56 (2H, br s), 4.48-4.40 (1H, m), 4.33 (1H, ddd, J=47, 9.1, 4.5 Hz), 4.15-4.09 (1H, m), 3.59 (1H, ddd, J=12.6, 8.8, 5.4 Hz), 3.47 (1H, ddd, J=13.4, 10.6, 3.3 Hz), 1.95 (1H, dd, J=2.7, 1.9 Hz), 1.88-1.81 (1H, m), 1.62-1.55 (1H, m), 1.33 (3H, t, J=1.0 Hz).

Step 4: (3RS,4SR)-3-Fluoro-1-{4-[1-isopropyl-3-(2-oxa-6-azaspiro[3,3]hept-6-yl)-1H-pyrazolo[4,3-c]pyridin-6-ylamino]pyrimidin-2-yl}-4-methylpiperidin-4-ol (mixture of enantiomers)

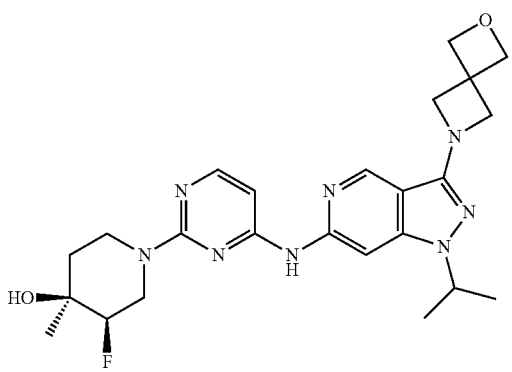 [SMILES: CC(C)n1nc(N2CC3(COC3)C2)c2cnc(Nc3ccnc(N4CC[C@](C)(O)[C@H](F)C4)n3)cc21]

The title compound (0.24 g, 47%) was prepared as an off-white solid from 6-(6-chloro-1-isopropyl-1H-pyrazolo[4,3-c]pyridin-3-yl)-2-oxa-6-azaspiro[3.3]heptane (Example 2, Step 1) (0.312 g, 1.065 mmol) and (3RS,4SR)-1-(4-aminopyrimidin-2-yl)-3-fluoro-4-methylpiperidin-4-ol (0.241 g, 1.065 mmol) by an analogous method to that described in Example 20, Step 3. LCMS (ESI): $R_T$ 2.53 min [M+H]$^+$ 483.2, Method F; $^1$H NMR (400 MHz, DMSO-d$_6$) δ 9.88 (1H, s), 8.56 (1H, d, J=1.0 Hz), 8.13 (1H, s), 7.99 (1H, d, J=5.7 Hz), 6.39 (1H, d, J=5.7 Hz), 4.82 (1H, s), 4.74 (4H, s), 4.54 (1H, septet, J=6.7 Hz), 4.42-4.26 (6H, m), 4.16-4.10 (1H, m), 3.61-3.54 (1H, m), 3.46-3.39 (1H, m), 1.72-1.65 (1H, m), 1.56-1.49 (1H, m), 1.40 (6H, 2d, J=6.6 Hz), 1.24 (3H, s).

Example 65: (3R*,4S*)-1-{4-[1-((S)-sec-Butyl)-3-(2-oxa-6-azaspiro[3.3]hept-6-yl)-1H-pyrazolo[4,3-c]pyridin-6-ylamino]pyrimidin-2-yl}-3-fluoro-4-methylpiperidin-4-ol (Single Diastereoisomer)

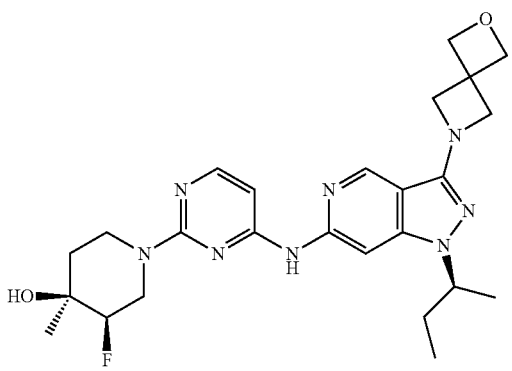 [SMILES: CC[C@H](C)n1nc(N2CC3(COC3)C2)c2cnc(Nc3ccnc(N4CC[C@](C)(O)[C@H](F)C4)n3)cc21]

Step 1: 1-((S)-sec-Butyl)-6-chloro-3-iodo-1H-pyrazolo[4,3-c]pyridine

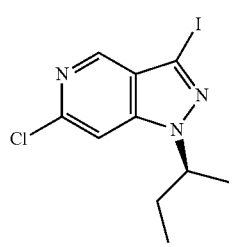

To an ice-cooled solution of triphenylphosphine (1.877 g, 7.156 mmol) in tetrahydrofuran (30 mL) was added a solution of diethyl azodicarboxylate (1.246 g, 7.156 mmol) in tetrahydrofuran (5 mL) over 5 min. The mixture was stirred at 0° C. for 5 min, then a solution of 6-chloro-3-iodo-1H-pyrazolo[4,3-c]pyridine (1.0 g, 3.578 mmol) and (R)-2-butanol (0.318 g, 4.294 mmol) in tetrahydrofuran (5 mL) was added over 5 min. The mixture was stirred at room temperature for 2.5 h and then concentrated in vacuo. Purification by chromatography on silica (solvent gradient: 0-8% ethyl acetate in toluene) gave the product (0.98 g, 82%) as colorless oil. [α]$_D$ +11.2° (c 2.5, methanol); $^1$H NMR (400 MHz, CDCl$_3$) δ 8.57 (1H, s), 7.31 (1H, s), 4.48-4.39 (1H, m), 2.13-2.02 (1H, m), 1.95-1.85 (1H, m), 1.58 (3H, d, J=6.7 Hz), 0.79 (3H, t, J=7.4 Hz).

Step 2: 1-((S)-sec-Butyl)-6-chloro-3-(2-oxa-6-azaspiro[3.3]hept-6-yl)-1H-pyrazolo[4,3-c]pyridine

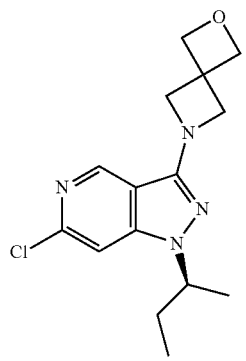 [SMILES: CC[C@H](C)n1nc(N2CC3(COC3)C2)c2cnc(Cl)cc21]

A mixture of 1-((S)-sec-butyl)-6-chloro-3-iodo-1H-pyrazolo[4,3-c]pyridine (0.985 g, 2.935 mmol), 2-oxa-6-azaspiro[3.3]heptane oxalic acid salt (0.555 g, 2.935 mmol), 4,5-bis(diphenylphosphino)-9,9-dimethylxanthene (0.17 g, 0.294 mmol), tris(dibenzylideneacetone)dipalladium(0) (0.0672 g, 0.073 mmol), cesium carbonate (2.87 g, 8.81 mmol), and 1,4-dioxane (19 mL) was heated in a sealed vial at 100° C. After 16 h the cooled reaction mixture was partitioned between ethyl acetate and water. The aqueous phase was extracted with additional ethyl acetate and the combined organic extracts were washed with brine, dried over anhydrous sodium sulfate, filtered and concentrated in vacuo. The residue was purified by chromatography on silica (solvent gradient: 20-70% ethyl acetate in cyclohexane) to afford the title compound (0.657 g, 73%) as a yellow solid. [α]$_D$ +7.0° (c 2.55, methanol). $^1$H NMR (400 MHz, CDCl$_3$) δ 8.53 (1H, d, J=1.0 Hz), 7.11 (1H, d, J=1.0 Hz), 4.88 (4H, s), 4.34 (4H, s), 4.25-4.16 (1H, m), 2.04-1.93 (1H, m), 1.84-1.73 (1H, m), 1.47 (3H, d, J=6.7 Hz), 0.75 (3H, t, J=7.4 Hz).

Step 3: (3R*,4S*)-3-Fluoro-4-hydroxy-4-methylpiperidine-1-carboxylic acid benzyl ester (Enantiomer 2)

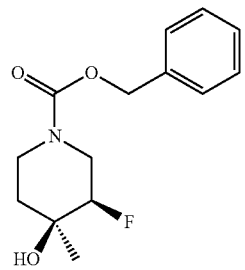 [SMILES: C[C@]1(O)CCN(C(=O)OCc2ccccc2)C[C@H]1F]

The enantiomers of Example 64, Step 1 (7.72 g) were separated by chiral supercritical fluid chromatography. The second eluting enantiomer (2.85 g) (as a single unknown enantiomer with known relative stereochemistry and absolute stereochemistry arbitrarily assigned): (2.84 g) [α]$_D$ 0.0° (c 6.2, methanol) was used in this example.

Step 4: (−)-(3R*,4S*)-3-Fluoro-4-methylpiperidin-4-ol (Absolute Stereochemistry unknown)

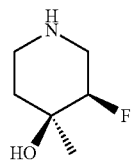

The title compound was prepared with known relative stereochemistry and absolute stereochemistry arbitrarily assigned from the second eluting enantiomer (3R*,4S*)-3-fluoro-4-hydroxy-4-methylpiperidine-1-carboxylic acid benzyl ester (2.85 g, 10.64 mmol) by a procedure analogous to that described in Example 64, Step 2. [α]$_D$ −13.7° (c 3.35, methanol); $^1$H NMR (CDCl$_3$): δ 4.30 (1H, ddd, J=48.4, 7.2, 3.5 Hz), 3.14-3.07 (1H, m), 3.01-2.92 (2H, m), 2.72-2.65 (1H, m), 1.92 (2H, br s), 1.80-1.73 (1H, m), 1.60-1.54 (1H, m), 1.29 (3H, d, J=1.3 Hz).

Step 5: (+)-(3R*,4S*)-1-(4-Aminopyrimidin-2-yl)-3-fluoro-4-methylpiperidin-4-ol (Absolute Stereochemistry Unknown)

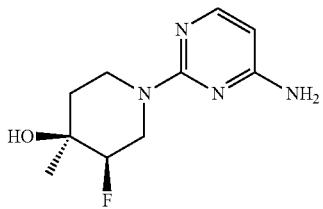 [SMILES: C[C@]1(O)CCN(c2nccc(N)n2)C[C@H]1F]

The title compound (1.68 g, 70%) was prepared as a single unknown stereoisomer with known relative stereochemistry and absolute stereochemistry arbitrarily assigned from (−)-(3R*,4S*)-3-fluoro-4-methylpiperidin-4-ol (1.417 g, 10.64 mmol) by a procedure analogous to that described in Example 64, Step 3. [α]$_D$ +17° (c 1.17, methanol); $^1$H NMR (CDCl$_3$): δ 7.93 (1H, d, J=5.6 Hz), 5.76 (1H, d, J=5.6 Hz), 4.55 (2H, br s), 4.48-4.26 (2H, m), 4.16-4.09 (1H, m), 3.63-3.56 (1H, m), 3.51-3.44 (1H, m), 1.94 (1H, dd, J=2.7, 1.9 Hz), 1.88-1.81 (1H, m), 1.63-1.55 (1H, m), 1.33 (3H, t, J=0.9 Hz).

Step 6: (3R*,4S*)-1-{4-[1-((S)-sec-Butyl)-3-(2-oxa-6-azaspiro[3.3]hept-6-yl)-1H-pyrazolo[4,3-c]pyridin-6-ylamino]pyrimidin-2-yl}-3-fluoro-4-methylpiperidin-4-ol (Single Diastereoisomer)

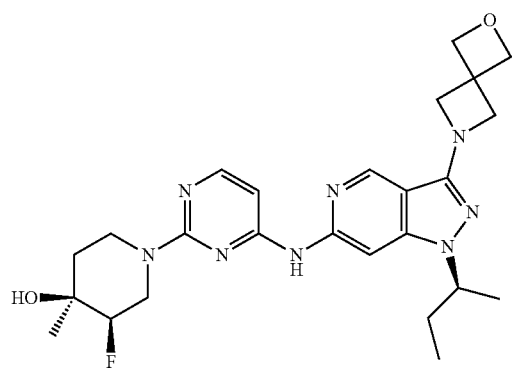 [SMILES: CC[C@H](C)n1nc(N2CC3(COC3)C2)c2cnc(Nc3ccnc(N4CC[C@](C)(O)[C@H](F)C4)n3)cc21]

The title compound (28.9 mg, 12%) was prepared as a white solid from 1-((S)-sec-butyl)-6-chloro-3-(2-oxa-6-azaspiro[3.3]hept-6-yl)-1H-pyrazolo[4,3-c]pyridine (150 mg, 0.489 mmol) and (+)-(3R*,4S*)-1-(4-aminopyrimidin-2-yl)-3-fluoro-4-methylpiperidin-4-ol (111 mg, 0.489 mmol) by an analogous method to that described in Example 20 Step 3. LCMS (ESI): R$_T$ 2.68 min, [M+H]$^+$ 497.3, Method F; $^1$H NMR (400 MHz, DMSO-d$_6$) δ 9.89 (1H, s), 8.55 (1H, s), 8.14 (1H, s), 7.99 (1H, d, J=5.7 Hz), 6.38 (1H, d, J=5.7 Hz), 4.84 (1H, s), 4.74 (4H, s), 4.44-4.20 (7H, m), 4.17-4.11 (1H, m), 3.61-3.54 (1H, m), 3.46-3.39 (1H, m), 1.95-1.83 (1H, m), 1.78-1.63 (2H, m), 1.56-1.49 (1H, m), 1.38 (3H, d, J=6.7 Hz), 1.24 (3H, s), 0.69 (3H, t, J=7.3 Hz).

Example 66: (3R*,4S*)-1-{4-[1-((S)-sec-Butyl)-3-(2-oxa-6-azaspiro[3.3]hept-6-yl)-1H-pyrazolo[4,3-c]pyridin-6-ylamino]pyrimidin-2-yl}-3-fluoro-4-methylpiperidin-4-ol (Single Diastereoisomer)

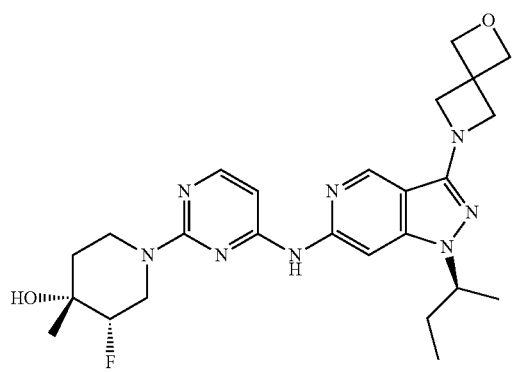 [SMILES: CC[C@H](C)n1nc(N2CC3(COC3)C2)c2cnc(Nc3ccnc(N4CC[C@@](C)(O)[C@@H](F)C4)n3)cc21]

Step 1: (+)-(3R*,4S*)-3-Fluoro-4-hydroxy-4-methylpiperidine-1-carboxylic acid benzyl ester (Enantiomer 1)

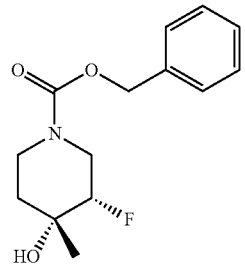 [SMILES: C[C@@]1(O)CCN(C(=O)OCc2ccccc2)C[C@@H]1F]

The enantiomers of Example 64, Step 1 (7.72 g) were separated by chiral supercritical fluid chromatography. The first eluting enantiomer (as a single unknown enantiomer with known relative stereochemistry and absolute stereochemistry arbitrarily assigned): (3.4 g) [α]$_D$ +0.6° (c 3.2, methanol) was used in this example.

Step 2: (+)-(3R*,4S*)-3-Fluoro-4-methylpiperidin-4-ol (Absolute Stereochemistry unknown)

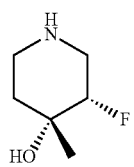

The title compound was prepared with known relative stereochemistry and absolute stereochemistry arbitrarily assigned from the first eluting enantiomer of (3R*,4S*)-3-fluoro-4-hydroxy-4-methylpiperidine-1-carboxylic acid benzyl ester (Example 65, Step 3) (3.4 g, 12.72 mmol) by a procedure analogous to that described in Example 64, Step 2. [α]$_D$ +16.9° (c 2.6, methanol); $^1$H NMR (CDCl$_3$): δ 4.29 (1H, ddd, J=48.4, 7.2, 3.5 Hz), 3.13-3.06 (1H, m), 3.00-2.91 (2H, m), 2.71-2.64 (1H, m), 2.10 (2H, br s), 1.80-1.72 (1H, m), 1.60-1.53 (1H, m), 1.28 (3H, d, J=1.2 Hz).

Step 3: (−)-(3R*,4S*)-1-(4-Aminopyrimidin-2-yl)-3-fluoro-4-methylpiperidin-4-ol (Absolute Stereochemistry Unknown)

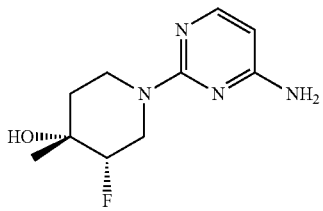 [SMILES: C[C@@]1(O)CCN(c2nccc(N)n2)C[C@@H]1F]

The title compound (2.093 g, 73%) was prepared as a single unknown stereoisomer with known relative stereochemistry and absolute stereochemistry arbitrarily assigned from (+)-(3R*,4S*)-3-fluoro-4-methylpiperidin-4-ol (1.679 g, 12.6 mmol) by a procedure analogous to that described in Example 64, Step 3. [α]$_D$ −16° (c 1.16, methanol); $^1$H NMR (CDCl$_3$): δ 7.93 (1H, d, J=5.6 Hz), 5.76 (1H, d, J=5.6 Hz), 4.55 (2H, br s), 4.48-4.26 (2H, m), 4.16-4.09 (1H, m), 3.63-3.56 (1H, m), 3.51-3.44 (1H, m), 1.94 (1H, dd, J=2.7, 1.9 Hz), 1.88-1.81 (1H, m), 1.63-1.55 (1H, m), 1.33 (3H, t, J=0.9 Hz).

Step 4: (3R*,4S*)-1-{4-[1-((S)-sec-Butyl)-3-(2-oxa-6-azaspiro[3.3]hept-6-yl)-1H-pyrazolo[4,3-c]pyridin-6-ylamino]pyrimidin-2-yl}-3-fluoro-4-methylpiperidin-4-ol (Single Diastereoisomer)

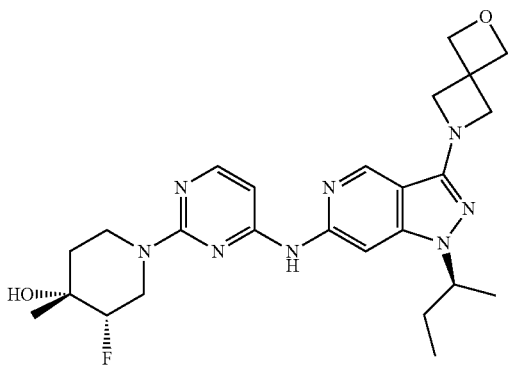 [SMILES: CC[C@H](C)n1nc(N2CC3(COC3)C2)c2cnc(Nc3ccnc(N4CC[C@@](C)(O)[C@@H](F)C4)n3)cc21]

The title compound (89.2 mg, 37%) as a white solid was prepared from 1-((S)-sec-butyl)-6-chloro-3-(2-oxa-6-azaspiro[3.3]hept-6-yl)-1H-pyrazolo[4,3-c]pyridine (Example 65, Step 2) (150 mg, 0.489 mmol) and (−)-(3R*,4S*)-1-(4-aminopyrimidin-2-yl)-3-fluoro-4-methylpiperidin-4-ol (111 mg, 0.489 mmol) by an analogous method to that described in Example 20, Step 3. LCMS (ESI): R$_T$ 2.70 min, [M+H]$^+$ 497.3, Method F; $^1$H NMR (400 MHz, DMSO-d$_6$) δ 9.88 (1H, s), 8.55 (1H, s), 8.13 (1H, s), 7.99 (1H, d, J=5.7 Hz), 6.38 (1H, d, J=5.7 Hz), 4.83 (1H, s), 4.74 (4H, s), 4.43-4.21 (7H, m), 4.18-4.12 (1H, m), 3.61-3.54 (1H, m), 3.45-3.38 (1H, m), 1.95-1.84 (1H, m), 1.78-1.64 (2H, m), 1.57-1.50 (1H, m), 1.37 (3H, d, J=6.6 Hz), 1.24 (3H, s), 0.69 (3H, t, J=7.3 Hz).

Example 67: (3R*,4S*)-1-{4-[1-((R)-sec-Butyl)-3-(2-oxa-6-azaspiro[3.3]hept-6-yl)-1H-pyrazolo[4,3-c]pyridin-6-ylamino]pyrimidin-2-yl}-3-fluoro-4-methylpiperidin-4-ol (Single Diastereoisomer)

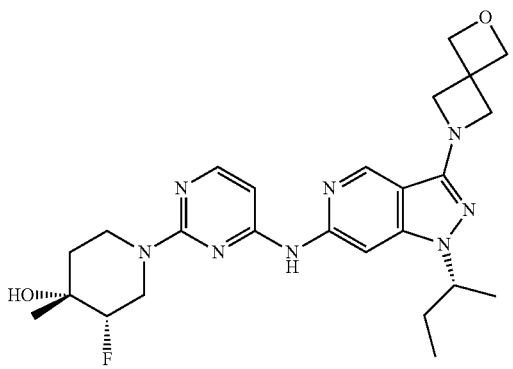 [SMILES: CC[C@@H](C)n1nc(N2CC3(COC3)C2)c2cnc(Nc3ccnc(N4CC[C@@](C)(O)[C@@H](F)C4)n3)cc21]

Step 1: 1-((R)-sec-Butyl)-6-chloro-3-iodo-1H-pyrazolo[4,3-c]pyridine

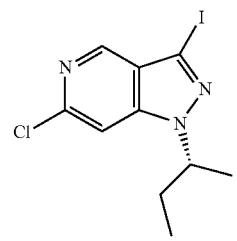

The title compound (0.915 g, 76%) was prepared as a colorless oil from 6-chloro-3-iodo-1H-pyrazolo[4,3-c]pyridine (1.0 g, 3.578 mmol) and (S)-2-butanol (0.318 g, 4.294 mmol) by the method described for Example 65, Step 1. [α]$_D$ −8.5° (c 2.35, methanol). $^1$H NMR (400 MHz, CDCl$_3$) δ 8.57 (1H, s), 7.31 (1H, s), 4.48-4.39 (1H, m), 2.13-2.02 (1H, m), 1.95-1.85 (1H, m), 1.58 (3H, d, J=6.7 Hz), 0.79 (3H, t, J=7.4 Hz).

Step 2: 1-((R)-sec-Butyl)-6-chloro-3-(2-oxa-6-azaspiro[3.3]hept-6-yl)-1H-pyrazolo[4,3-c]pyridine

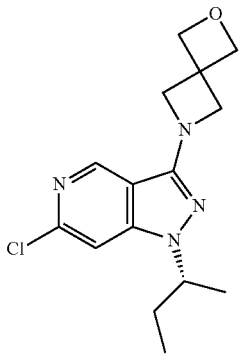 [SMILES: CC[C@@H](C)n1nc(N2CC3(COC3)C2)c2cnc(Cl)cc21]

The title compound (0.60 g, 72%) was prepared as a yellow solid from 1-((R)-sec-butyl)-6-chloro-3-iodo-1H-pyrazolo[4,3-c]pyridine (0.915 g, 2.726 mmol) by the method described for Example 65, Step 2. $[\alpha]_D$ −9.2° (c 1.08, methanol). $^1$H NMR (400 MHz, CDCl$_3$) δ 8.53 (1H, d, J=1.0 Hz), 7.11 (1H, d, J=1.0 Hz), 4.88 (4H, s), 4.34 (4H, s), 4.25-4.15 (1H, m), 2.04-1.93 (1H, m), 1.84-1.73 (1H, m), 1.47 (3H, d, J=6.7 Hz), 0.75 (3H, t, J=7.4 Hz).

Step 3: (3R*,4S*)-1-{4-[1-((R)-sec-Butyl)-3-(2-oxa-6-azaspiro[3.3]hept-6-yl)-1H-pyrazolo[4,3-c]pyridin-6-ylamino]pyrimidin-2-yl}-3-fluoro-4-methylpiperidin-4-ol (Single Diastereoisomer)

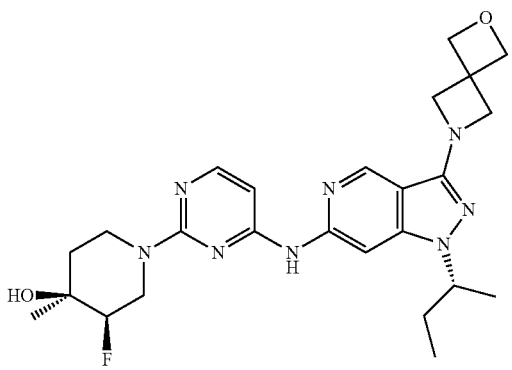 [SMILES: CC[C@@H](C)n1nc(N2CC3(COC3)C2)c2cnc(Nc3ccnc(N4CC[C@](C)(O)[C@H](F)C4)n3)cc21]

The title compound (31 mg, 13%) was prepared as a white solid from 1-((R)-sec-butyl)-6-chloro-3-(2-oxa-6-azaspiro[3.3]hept-6-yl)-1H-pyrazolo[4,3-c]pyridine (150 mg, 0.489 mmol) and (+)-(3R*,4S*)-1-(4-aminopyrimidin-2-yl)-3-fluoro-4-methylpiperidin-4-ol (Example 65, Step 5) (111 mg, 0.489 mmol) by an analogous method to that described in Example 20, Step 3. LCMS (ESI): R$_T$ 2.70 min, [M+H]$^+$ 497.3, Method F; $^1$H NMR (400 MHz, DMSO-d$_6$) δ 9.89 (1H, s), 8.56 (1H, s), 8.13 (1H, s), 7.99 (1H, d, J=5.6 Hz), 6.38 (1H, d, J=5.7 Hz), 4.84 (1H, s), 4.74 (4H, s), 4.43-4.19 (7H, m), 4.17-4.12 (1H, m), 3.61-3.54 (1H, m), 3.45-3.38 (1H, m), 1.95-1.84 (1H, m), 1.78-1.63 (2H, m), 1.57-1.50 (1H, m), 1.37 (3H, d, J=6.6 Hz), 1.24 (3H, s), 0.69 (3H, t, J=7.3 Hz).

Example 68: (3R*,4S*)-1-{4-[1-((R)-sec-Butyl)-3-(2-oxa-6-azaspiro[3.3]hept-6-yl)-1H-pyrazolo[4,3-c]pyridin-6-ylamino]pyrimidin-2-yl}-3-fluoro-4-methylpiperidin-4-ol (Single Diastereoisomer)

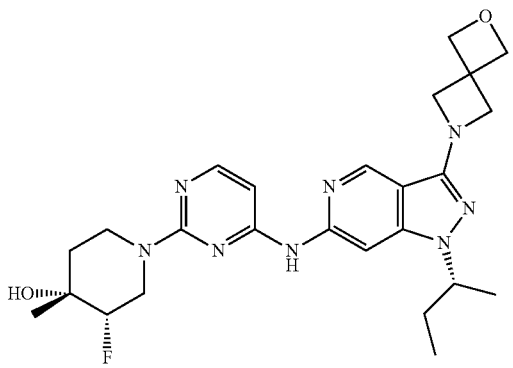 [SMILES: CC[C@@H](C)n1nc(N2CC3(COC3)C2)c2cnc(Nc3ccnc(N4CC[C@@](C)(O)[C@@H](F)C4)n3)cc21]

The title compound (38.3 mg, 16%) was prepared as a white solid from 1-((R)-sec-butyl)-6-chloro-3-(2-oxa-6-azaspiro[3.3]hept-6-yl)-1H-pyrazolo[4,3-c]pyridine (150 mg, 0.489 mmol) and (−)-(3R*,4S*)-1-(4-aminopyrimidin-2-yl)-3-fluoro-4-methylpiperidin-4-ol (Example 66, Step 3) (111 mg, 0.489 mmol) by an analogous method to that described in Example 20, Step 3. LCMS (ESI): R$_T$ 2.68 min, [M+H]$^+$ 497.2, Method F; $^1$H NMR (400 MHz, DMSO-d$_6$) δ 9.88 (1H, s), 8.55 (1H, s), 8.13 (1H, s), 7.99 (1H, d, J=5.7 Hz), 6.38 (1H, d, J=5.6 Hz), 4.83 (1H, s), 4.74 (4H, s), 4.44-4.20 (7H, m), 4.16-4.11 (1H, m), 3.61-3.54 (1H, m), 3.46-3.39 (1H, m), 1.95-1.84 (1H, m), 1.78-1.64 (2H, m), 1.56-1.49 (1H, m), 1.38 (3H, d, J=6.6 Hz), 1.24 (3H, s), 0.69 (3H, t, J=7.3 Hz).

Example 69: (3R*,4S*)-1-{4-[1-((S)-sec-Butyl)-3-((R)-3-hydroxypyrrolidin-1-yl)-1H-pyrazolo[4,3-c]pyridin-6-ylamino]pyrimidin-2-yl}-3-fluoro-4-methylpiperidin-4-ol

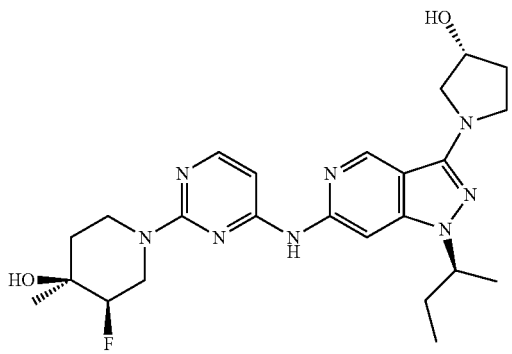 [SMILES: CC[C@H](C)n1nc(N2CC[C@@H](O)C2)c2cnc(Nc3ccnc(N4CC[C@](C)(O)[C@H](F)C4)n3)cc21]

Step 1: (R)-1-[1-((S)-sec-Butyl)-6-chloro-1H-pyrazolo[4,3-c]pyridin-3-yl]pyrrolidin-3-ol

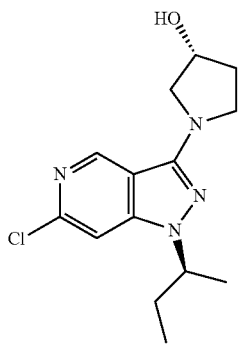 [SMILES: CC[C@H](C)n1nc(N2CC[C@@H](O)C2)c2cnc(Cl)cc21]

The title compound (60.5 mg, 16%) was prepared as a yellow solid from 1-((S)-sec-butyl)-6-chloro-3-iodo-1H-pyrazolo[4,3-c]pyridine (Example 65, Step 1) (433 mg, 1.29 mmol) and (R)-3-pyrrolidinol by an analogous method to that described in Example 65, Step 2. $^1$H NMR (400 MHz, CDCl$_3$) δ 8.70 (1H, s), 7.06 (1H, s), 4.68-4.65 (1H, m), 4.23-4.15 (1H, m), 3.87-3.77 (2H, m), 3.72-3.62 (2H, m), 2.71 (1H, br s), 2.25-2.08 (2H, m), 2.06-1.95 (1H, m), 1.83-1.72 (1H, m), 1.47 (3H, d, J=6.7 Hz), 0.75 (3H, t, J=7.4 Hz).

Step 2: (3R*,4S*)-1-{4-[1-((S)-sec-Butyl)-3-((R)-3-hydroxypyrrolidin-1-yl)-1H-pyrazolo[4,3-c]pyridin-6-ylamino]pyrimidin-2-yl}-3-fluoro-4-methylpiperidin-4-ol

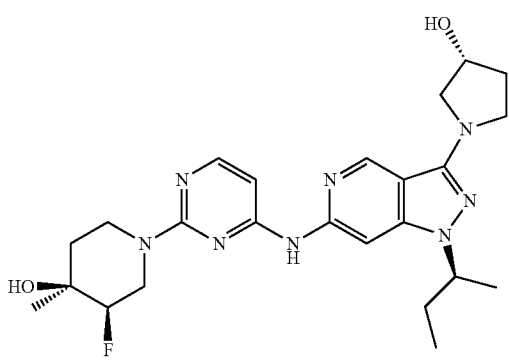 [SMILES: CC[C@H](C)n1nc(N2CC[C@@H](O)C2)c2cnc(Nc3ccnc(N4CC[C@](C)(O)[C@H](F)C4)n3)cc21]

The title compound (42.1 mg, 42%) was prepared as an off-white solid from (R)-1-[1-((S)-sec-butyl)-6-chloro-1H-pyrazolo[4,3-c]pyridin-3-yl]pyrrolidin-3-ol (60.5 mg, 0.205 mmol) and (+)-(3R*,4S*)-1-(4-aminopyrimidin-2-yl)-3-fluoro-4-methylpiperidin-4-ol (Example 65, Step 5) (46.6 mg, 0.205 mmol) by an analogous method to that described in Example 20, Step 3. LCMS (ESI): R$_T$ 2.55 min, [M+H]$^+$ 485.3, Method F; $^1$H NMR (400 MHz, DMSO-d$_6$) δ 9.83 (1H, s), 8.70 (1H, s), 8.10 (1H, s), 7.98 (1H, d, J=5.6 Hz), 6.38 (1H, d, J=5.6 Hz), 4.95 (1H, d, J=3.7 Hz), 4.84 (1H, s), 4.45-4.12 (5H, m), 3.71-3.55 (4H, m), 3.47-3.40 (2H, m), 2.10-2.01 (1H, m), 1.97-1.88 (2H, m), 1.78-1.65 (2H, m), 1.57-1.50 (1H, m), 1.39 (3H, d, J=6.6 Hz), 1.24 (3H, s), 0.72 (3H, t, J=7.3 Hz).

Example 70: (3R*,4S*)-1-{4-[1-((S)-sec-Butyl)-3-((S)-3-hydroxypyrrolidin-1-yl)-1H-pyrazolo[4,3-c]pyridin-6-ylamino]pyrimidin-2-yl}-3-fluoro-4-methylpiperidin-4-ol

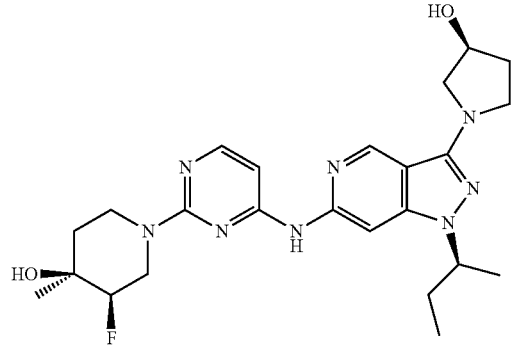 [SMILES: CC[C@H](C)n1nc(N2CC[C@H](O)C2)c2cnc(Nc3ccnc(N4CC[C@](C)(O)[C@H](F)C4)n3)cc21]

Step 1: (S)-1-[1-((S)-sec-Butyl)-6-chloro-1H-pyrazolo[4,3-c]pyridin-3-yl]pyrrolidin-3-ol

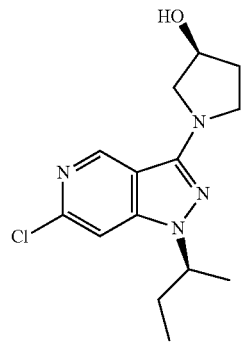 [SMILES: CC[C@H](C)n1nc(N2CC[C@H](O)C2)c2cnc(Cl)cc21]

The title compound (57.7 mg, 22%) as orange gum was prepared from 1-((S)-sec-butyl)-6-chloro-3-iodo-1H-pyrazolo[4,3-c]pyridine (Example 65, Step 1) (300 mg, 0.894 mmol) and (S)-3-pyrrolidinol by an analogous method to that described in Example 65, Step 2. $^1$H NMR (400 MHz, CDCl$_3$) δ 8.70 (1H, s), 7.06 (1H, s), 4.68-4.64 (1H, m), 4.23-4.15 (1H, m), 3.86-3.77 (2H, m), 3.74-3.63 (2H, m), 2.55 (1H, br s), 2.25-2.08 (2H, m), 2.06-1.95 (1H, m), 1.83-1.73 (1H, m), 1.47 (3H, d, J=6.7 Hz), 0.76 (3H, t, J=7.4 Hz).

Step 2: (3R*,4S*)-1-{4-[1-((S)-sec-Butyl)-3-((S)-3-hydroxypyrrolidin-1-yl)-1H-pyrazolo[4,3-c]pyridin-6-ylamino]pyrimidin-2-yl}-3-fluoro-4-methylpiperidin-4-ol

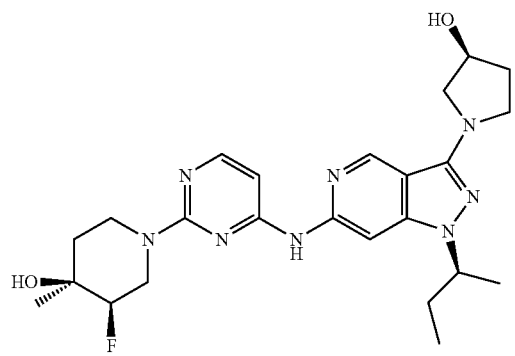 [SMILES: CC[C@H](C)n1nc(N2CC[C@H](O)C2)c2cnc(Nc3ccnc(N4CC[C@](C)(O)[C@H](F)C4)n3)cc21]

The title compound (14 mg, 15%) was prepared as a pale yellow solid from (S)-1-[1-((S)-sec-butyl)-6-chloro-1H-pyrazolo[4,3-c]pyridin-3-yl]pyrrolidin-3-ol (57.7 mg, 0.1957 mmol) and (+)-(3R*,4S*)-1-(4-aminopyrimidin-2-yl)-3-fluoro-4-methylpiperidin-4-ol (Example 65, Step 5) by an analogous method to that described in Example 20, Step 3. LCMS (ESI): $R_T$ 2.53 min, [M+H]$^+$ 485.2, Method F; $^1$H NMR (400 MHz, DMSO-d$_6$) δ 9.83 (1H, s), 8.70 (1H, s), 8.10 (1H, s), 7.98 (1H, d, J=5.7 Hz), 6.38 (1H, d, J=5.7 Hz), 4.94 (1H, d, J=3.7 Hz), 4.84 (1H, s), 4.45-4.12 (5H, m), 3.70-3.55 (4H, m), 3.45-3.36 (2H, m), 2.10-2.01 (1H, m), 1.97-1.87 (2H, m), 1.78-1.65 (2H, m), 1.57-1.50 (1H, m), 1.39 (3H, d, J=6.6 Hz), 1.24 (3H, s), 0.72 (3H, t, J=7.3 Hz).

Example 71: [1-((S)-sec-Butyl)-3-(2-oxa-6-azaspiro [3.3]hept-6-yl)-1H-pyrazolo[4,3-c]pyridin-6-yl]-[2-(2-methanesulfonyl-2-methylpropoxy)pyrimidin-4-yl]amine Step 1: 2-(2-Methanesulfonyl-2-methylpropoxy) pyrimidin-4-ylamine

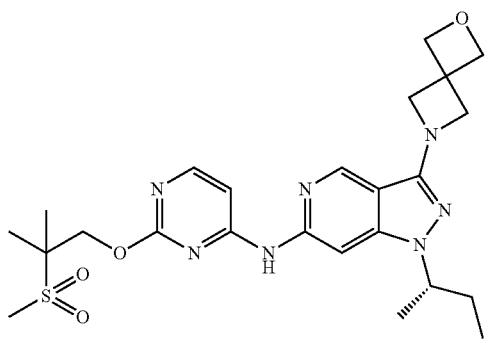 [SMILES: CC[C@H](C)n1nc(N2CC3(COC3)C2)c2cnc(Nc3ccnc(OCC(C)(C)S(C)(=O)=O)n3)cc21]

A microwave reaction vessel was charged with 4-amino-2-chloropyrimidine (100 mg, 0.774 mmol, 1.0 eq), 2-methanesulfonyl-2-methylpropan-1-ol (353 mg, 2.33 mmol, 3.0 eq), and potassium carbonate (160.3 mg, 1.16 mmol, 1.5 eq) in propan-2-ol (1 mL). The reaction was stirred at room temperature for 1 min and heated under microwave irradiation at 200° C. for 2.5 h (Biotage Initiator, maximum pressure set at 22 bar). The reaction mixture was cooled to room temperature and purified by chromatography on silica (solvent gradient: 0-10% 2M methanolic ammonia in ethyl acetate) to afford the title compound (163 mg, 86%). LCMS (ESI): [M+H]$^+$ 246.3.

Step 2: [1-((S)-sec-Butyl)-3-(2-oxa-6-azaspiro[3.3] hept-6-yl)-1H-pyrazolo[4,3-c]pyridin-6-yl]-[2-(2-methanesulfonyl-2-methylpropoxy)pyrimidin-4-yl] amine

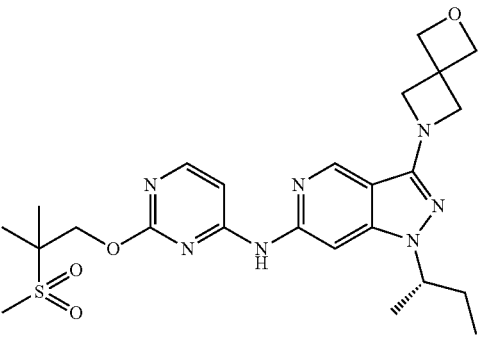 [SMILES: CC[C@H](C)n1nc(N2CC3(COC3)C2)c2cnc(Nc3ccnc(OCC(C)(C)S(C)(=O)=O)n3)cc21]

The title compound (131.9 mg, 42%) was prepared as a white solid from 1-((S)-sec-butyl)-6-chloro-3-(2-oxa-6-azaspiro[3.3]hept-6-yl)-1H-pyrazolo[4,3-c]pyridine (Example 65, Step 2) (188.0 mg, 0.612 mmol) and 2-(2-methanesulfonyl-2-methylpropoxy)pyrimidin-4-ylamine (150.0 mg, 0.612 mmol) by an analogous method to that described in Example 20, Step 3. LCMS (ESI): $R_T$ 3.01 min, [M+H]$^+$ 516, Method F; $^1$H NMR (400 MHz, DMSO-d$_6$) δ 10.32 (1H, s), 8.59 (1H, d, J=0.84 Hz), 8.17 (1H, d, J=5.7 Hz), 8.05 (1H, br s), 6.94 (1H, d, J=5.7 Hz), 4.75 (4H, br s), 4.51 (2H, d d, J=11.0, 14.5 Hz), 4.29-4.21 (5H, m), 3.09 (3H, s), 1.92-1.69 (2H, m), 1.43, 1.42 (6H, 2×s), 1.39 (3H, d, J=6.6 Hz), 0.66 (3H, t, J=7.4 Hz).

Example 72: 3-(6-(2-(1-(Cyclopropylsulfonyl)-1H-pyrazol-4-yl)pyrimidin-4-ylamino)-1-isopropyl-1H-pyrazolo[4,3-c]pyridin-3-yl)oxazolidin-2-one

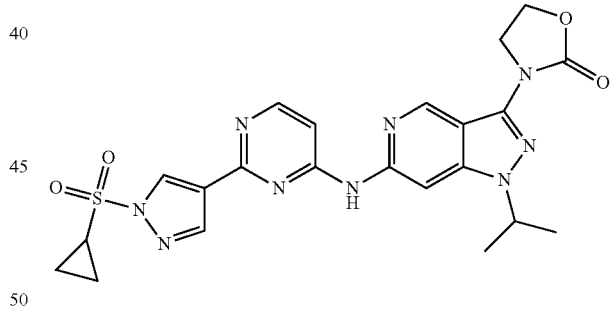

Step 1: 3-(6-Bromo-1-isopropyl-1H-pyrazolo[4,3-c] pyridin-3-yl)oxazolidin-2-one

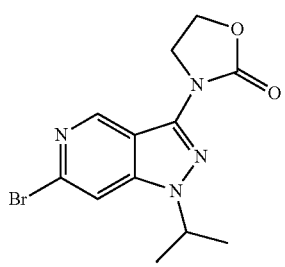 [SMILES: CC(C)n1nc(N2CCOC2=O)c2cnc(Br)cc21]

A mixture of 6-bromo-3-iodo-1-isopropyl-1H-pyrazolo[4,3-c]pyridine (600 mg, 1.64 mmol)(Example 16, step 7), copper (I) iodide (93.7 mg, 0.490 mmol), potassium carbonate (453 mg, 3.28 mmol), 1,3-oxazolidin-2-one (285 mg, 3.28 mmol), (S)-pyrrolidine-2-carboxylic acid (37.8 mg, 0.33 mmol) in N,N-dimethylformamide (8 mL) was stirred for 16 h at 80° C. The reaction mixture was cooled to room temperature and diluted with water (20 mL). The solution was extracted with ethyl acetate (2×), washed with brine, dried over anhydrous sodium sulfate, filtered and concentrated in vacuo. The resulting residue was purified by silica gel chromatography (solvent gradient: 0-50% ethyl acetate in petroleum) to afford the title compound (180 mg, 34%) as a white solid. LCMS (ESI): [M+H]$^+$=325.

Step 2: 3-(6-(2-(1-(Cyclopropylsulfonyl)-1H-pyrazol-4-yl)pyrimidin-4-ylamino)-1-isopropyl-1H-pyrazolo[4,3-c]pyridin-3-yl)oxazolidin-2-one

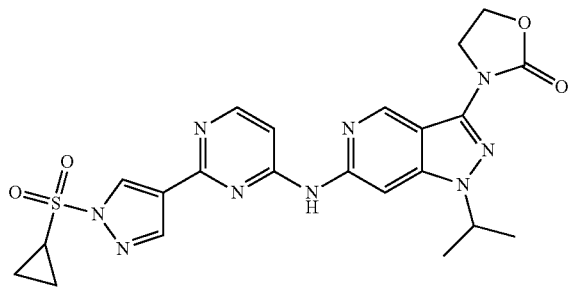 [SMILES: CC(C)n1nc(N2CCOC2=O)c2cnc(Nc3ccnc(-c4cnn(S(=O)(=O)C5CC5)c4)n3)cc21]

A mixture of 3-(6-bromo-1-isopropyl-1H-pyrazolo[4,3-c]pyridin-3-yl) oxazolidin-2-one (140 mg, 0.43 mmol), tris(dibenzylideneacetone)dipalladium(0) (39.2 mg, 0.040 mmol), 4,5-bis(diphenylphosphino)-9,9-dimethylxanthene (49.0 mg, 0.080 mmol), cesium carbonate (280 mg, 0.860 mmol) and 2-[1-(cyclopropanesulfonyl)-1H-pyrazol-4-yl]pyrimidin-4-amine (115 mg, 0.430 mmol)(Example 1, step 2) in dioxane (8 mL) was stirred for 3 h at 100° C. The reaction mixture was cooled to room temperature. The solids were removed by filtration and the solution was concentrated in vacuo. The resulting residue was purified by silica gel chromatography (solvent gradient: 0-10% methanol in dichloromethane) to afford the title compound (23.7 mg, 11%) as a white solid. LCMS (ESI): [M+H]$^+$=510, R$_T$ (min)=1.716, method=R; $^1$H NMR (300 MHz, DMSO-d$_6$): δ 10.48 (s, 1H), 9.28 (s, 1H), 8.73 (s, 1H), 8.49 (s, 1H), 8.43 (d, J=6.0 Hz, 1H), 8.20 (d, J=6.0 Hz, 1H), 4.93-4.86 (m, 1H), 4.61-4.55 (m, 2H), 4.22-4.16 (m, 2H), 3.29-3.26 (m, 1H), 1.52 (d, J=6.6 Hz, 6H), 1.39-1.31 (m, 2H), 1.30-1.23 (m, 3H).

Example 73: 3-(8-Oxa-3-azabicyclo[3.2.1]octan-3-yl)-N-(2-(1-(cyclopropylsulfonyl)-1H-pyrazol-4-yl)pyrimidin-4-yl)-1-isopropyl-1H-pyrazolo[4,3-c]pyridin-6-amine

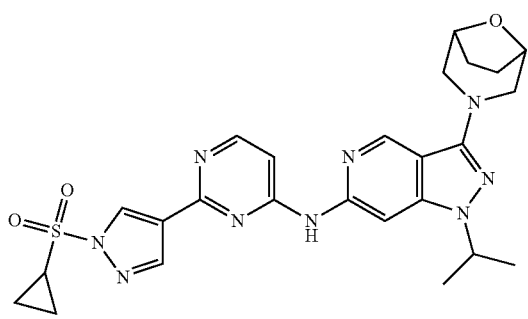 [SMILES: CC(C)n1nc(N2CC3CCC(C2)O3)c2cnc(Nc3ccnc(-c4cnn(S(=O)(=O)C5CC5)c4)n3)cc21]

Step 1: 3-(6-Chloro-1-isopropyl-1H-pyrazolo[4,3-c]pyridin-3-yl)-8-oxa-3-azabicyclo[3.2.1]octane

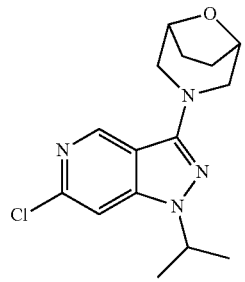 [SMILES: CC(C)n1nc(N2CC3CCC(C2)O3)c2cnc(Cl)cc21]

A mixture of 6-chloro-3-iodo-1-isopropyl-1H-pyrazolo[4,3-c]pyridine (400 mg, 1.24 mmol)(Example 1, step 8), copper (I) iodide (71.1 mg, 0.370 mmol), potassium carbonate (344 mg, 2.49 mmol), 8-oxa-3-azabicyclo [3.2.1] octane (563 mg, 4.98 mmol) and (S)-pyrrolidine-2-carboxylic acid (28.6 mg, 0.250 mmol) in N,N-dimethylformamide (8 mL) was stirred for 16 h at 80° C. The reaction mixture was cooled to room temperature and diluted with water (20 mL), extracted with ethyl acetate, dried over anhydrous sodium sulfate, filtered and concentrated in vacuo. The resulting residue was purified by silica gel chromatography (solvent gradient: 0-10% ethyl acetate in petroleum) to afford the title compound (120 mg, 31%) as a yellow solid. LCMS (ESI): [M+H]$^+$=307.

Step 2: 3-(8-Oxa-3-azabicyclo[3.2.1]octan-3-yl)-N-(2-(1-(cyclopropylsulfonyl)-1H-pyrazol-4-yl)pyrimidin-4-yl)-1-isopropyl-1H-pyrazolo[4,3-c]pyridin-6-amine

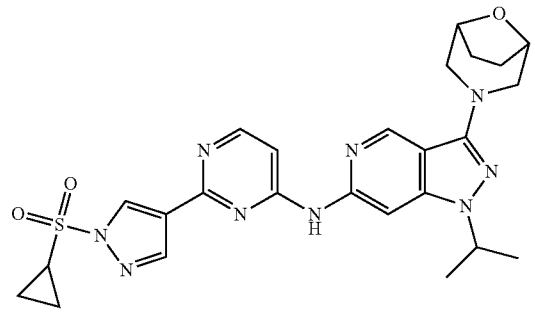 [SMILES: CC(C)n1nc(N2CC3CCC(C2)O3)c2cnc(Nc3ccnc(-c4cnn(S(=O)(=O)C5CC5)c4)n3)cc21]

A mixture of 3-(6-chloro-1-isopropyl-1H-pyrazolo[4,3-c]pyridin-3-yl)-8-oxa-3-aza bicyclo[3.2.1]octane (100 mg, 0.330 mmol), 2-[1-(cyclopropanesulfonyl)-1H-pyrazol-4-yl]pyrimidin-4-amine (86.6 mg, 0.330 mmol)(Example 1, step 2), tris(dibenzylideneacetone)dipalladium(0) (29.8 mg, 0.030 mmol), 4,5-bis(diphenylphosphino)-9,9-dimethylxanthene (37.7 mg, 0.070 mmol) and cesium carbonate (212 mg, 0.650 mmol) in dioxane (10 mL) was heated under microwave irradiation for 45 min at 160° C. The reaction mixture was cooled to room temperature. The solids were removed by filtration and the solution was concentrated in vacuo. The resulting residue was purified by silica gel chromatography (solvent gradient: 0-10% methanol in dichloromethane) to afford the title compound (16.5 mg, 9%) as a white solid. LCMS (ESI): [M+H]$^+$=536, $R_T$ (min)=2.702, method=R; $^1$H NMR (400 MHz, DMSO-$d_6$): δ 10.36 (s, 1H), 8.88 (s, 1H), 8.69 (s, 1H), 8.47 (s, 1H), 8.41 (d, J=6.0 Hz, 1H), 8.32 (s, 1H), 7.10 (d, J=6.0 Hz, 1H), 4.74-4.70 (m, 1H), 4.44 (s, 2H), 3.65 (d, J=11.2 Hz, 2H), 3.29-3.27 (m, 1H), 3.13 (m, 2H), 1.98-1.88 (m, 4H), 1.46 (d, J=6.4 Hz, 6H), 1.37-1.33 (m, 2H), 1.30-1.27 (m, 2H).

Example 74: N$^3$-tert-Butyl-N$^6$-(2-(1-(cyclopropylsulfonyl)-1H-pyrazol-4-yl)pyrimidin-4-yl)-1-isopropyl-1H-pyrazolo[4,3-c]pyridine-3,6-diamine

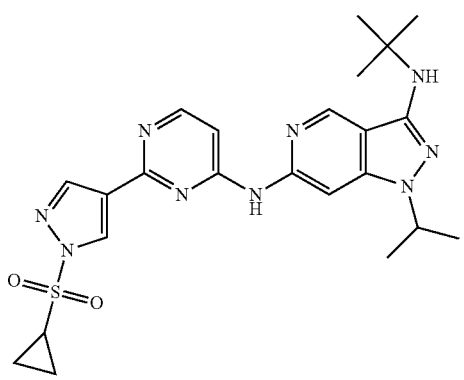 [SMILES: CC(C)n1nc(NC(C)(C)C)c2cnc(Nc3ccnc(-c4cnn(S(=O)(=O)C5CC5)c4)n3)cc21]

Step 1: N-tert-Butyl-6-chloro-1-isopropyl-1H-pyrazolo[4,3-c]pyridin-3-amine

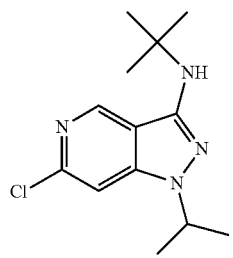 [SMILES: CC(C)n1nc(NC(C)(C)C)c2cnc(Cl)cc21]

A mixture of 6-chloro-3-iodo-1-isopropyl-1H-pyrazolo[4,3-c]pyridine (Example 1, Step 8) (500 mg, 1.55 mmol), copper (I) iodide (30.0 mg, 0.160 mmol), potassium carbonate (440 mg, 3.18 mmol), 2-methylpropan-2-amine (170 mg, 2.32 mmol) and (S)-pyrrolidine-2-carboxylic acid (74.0 mg, 0.640 mmol) in N,N-dimethylformamide (10 mL) was stirred overnight at 90° C. under nitrogen atmosphere. The reaction mixture was diluted with water, extracted with ethyl acetate (2×50 mL), washed with brine, dried over anhydrous sodium sulfate, filtered and concentrated in vacuo. The resultant residue was purified via flash chromatography on silica gel (solvent gradient: 0-20% ethyl acetate in petroleum ether) to afford the title compound (50 mg, 12%) as a white solid. LCMS (ESI): [M+H]$^+$=267.

Step 2: N$^3$-tert-Butyl-N$^6$-(2-(1-(cyclopropylsulfonyl)-1H-pyrazol-4-yl)pyrimidin-4-yl)-1-isopropyl-1H-pyrazolo[4,3-c]pyridine-3,6-diamine

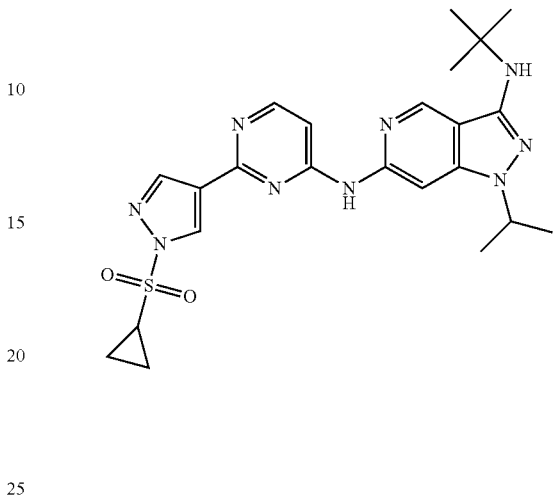

To a mixture of N-tert-butyl-6-chloro-1-isopropyl-1H-pyrazolo[4,3-c]pyridin-3-amine (50.0 mg, 0.190 mmol), 2-(1-(cyclopropylsulfonyl)-1H-pyrazol-4-yl)pyrimidin-4-amine (Example 1, Step 2) (50.0 mg, 0.190 mmol), cesium carbonate (375 mg, 1.15 mmol), 4,5-bis(diphenylphosphino)-9,9-dimethylxanthene (17.5 mg, 0.03 mmol) and tris(dibenzylideneacetone)dipalladium(0) (22.5 mg, 0.02 mmol) in 1,4-dioxane (1 mL) was heated under microwave irradiation for 30 min at 160° C. under nitrogen atmosphere. The solids were removed by filtration, the filtrate was concentrated in vacuo, and the residue was purified via flash chromatography on silica gel (solvent gradient: 0-5% methanol in dichloromethane) to afford the title compound (20.4 mg, 22%) as a white solid. LCMS (ESI): [M+H]$^+$=496.1, $R_T$ (min)=1.918, method=N; $^1$H NMR (300 MHz, DMSO-$d_6$): δ 10.24 (s, 1H), 8.76 (s, 1H), 8.69 (s, 1H), 8.47 (s, 1H), 8.39 (d, J=6.0 Hz, 1H), 8.17 (s, 1H), 7.11 (d, J=6.0 Hz, 1H), 6.01 (s, 1H), 4.66-4.61 (m, 1H), 3.29-3.26 (m, 1H), 1.47-1.43 (m, 15H), 1.38-1.24 (m, 4H).

Example 75: cis-3-Fluoro-1-(4-(3-((R)-2-(hydroxymethyl)morpholino)-1-isopropyl-1H-pyrazolo[4,3-c]pyridin-6-ylamino)pyrimidin-2-yl)piperidin-4-ol (Mixture of Diastereomers)

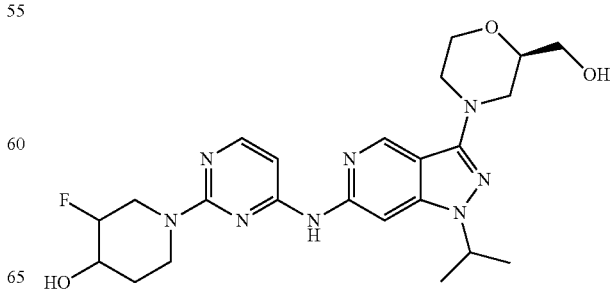

Step 1: (R)-(4-(6-Chloro-1-isopropyl-1H-pyrazolo[4,3-c]pyridin-3-yl)morpholin-2-yl)methanol

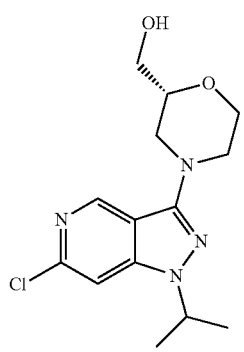 [SMILES: CC(C)n1nc(N2CCO[C@@H](CO)C2)c2cnc(Cl)cc21]

A mixture of 6-chloro-3-iodo-1-isopropyl-1H-pyrazolo[4,3-c]pyridine (500 mg, 1.55 mmol)(Example 1, step 8), (R)-morpholin-2-ylmethanol hydrochloride (950 mg, 6.18 mmol), copper(I) iodide (30.0 mg, 0.160 mmol), (S)-pyrrolidine-2-carboxylic acid (37.0 mg, 0.320 mmol) and potassium carbonate (1.32 g, 9.55 mmol) in N,N-dimethylformamide (10 mL) was stirred overnight at 80° C. under nitrogen atmosphere. The solution was diluted with water (20 mL). The resulting solution was extracted with dichloromethane (3×), washed with brine, dried with anhydrous sodium sulfate, filtered and concentrated in vacuo. The resulting residue was purified by silica gel chromatography (solvent gradient: 0-50% ethyl acetate in petroleum) to afford the title compound (100 mg, 21%) as a white solid. LCMS (ESI): [M+H]$^+$=311.

Step 2: cis-3-Fluoro-1-(4-(3-((R)-2-(hydroxymethyl)morpholino)-1-isopropyl-1H-pyrazolo[4,3-c]pyridin-6-ylamino)pyrimidin-2-0)piperidin-4-ol (Mixture of Diastereomers)

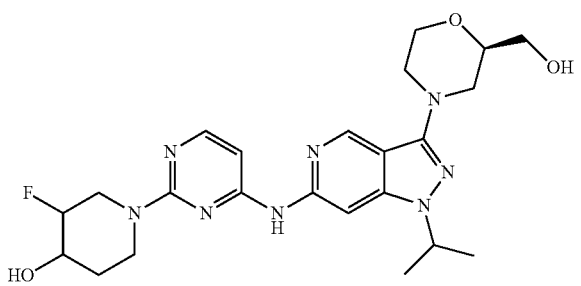 [SMILES: CC(C)n1nc(N2CCO[C@@H](CO)C2)c2cnc(Nc3ccnc(N4CCC(O)C(F)C4)n3)cc21]

A mixture of (R)-(4-(6-chloro-1-isopropyl-1H-pyrazolo[4,3-c]pyridin-3-yl)morpholin-2-yl) methanol (100 mg, 0.320 mmol) and (±)-1-(4-aminopyrimidin-2-yl)-cis-3-fluoropiperidin-4-ol (Example 20, step 2) (68.0 mg, 0.320 mmol), tris(dibenzylideneacetone)dipalladium(0) (30 mg, 0.030 mmol), 4,5-bis(diphenylphosphino)-9,9-dimethylxanthene (37.0 mg, 0.060 mmol) and cesium carbonate (900 mg, 2.76 mmol) in dioxane (4 mL) was heated under microwave irradiation for 40 min at 160° C. under nitrogen atmosphere. The solids were removed by filtration and the filtrate was concentrated in vacuo. The resulting residue was purified by silica gel chromatography (solvent gradient: 0-10% methanol in dichloromethane) to afford the title compound as a mixture of diastereomers (55.8 mg, 36%) as a white solid. LCMS (ESI): [M+H]$^+$=487, R$_T$ (min)=1.219, method=N; $^1$H NMR (300 MHz, DMSO-d$_6$): δ 9.95 (s, 1H), 8.85 (s, 1H), 8.17 (s, 1H), 8.00-7.98 (d, J=5.7 Hz, 1H), 6.39-6.37 (d, J=5.7 Hz, 1H), 5.15-5.13 (m, 1H), 4.83-4.54 (m, 4H), 4.25 (m, 1H), 3.97-3.38 (m, 10H), 2.95 (m, 1H), 2.75 (m, 1H), 1.71 (m, 2H), 1.44 (m, 6H).

Example 76: 1-(6-(2-(cis-3-Fluoro-4-hydroxypiperidin-1-yl)pyrimidin-4-ylamino)-1-isopropyl-1H-pyrazolo[4,3-c]pyridin-3-yl)-3-methylimidazolidin-2-one

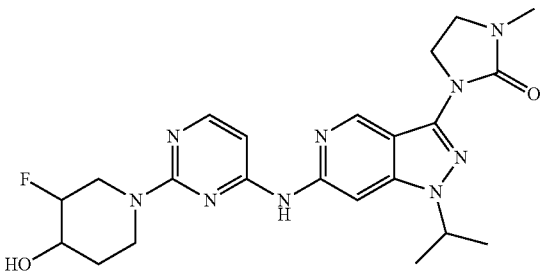 [SMILES: CC(C)n1nc(N2CCN(C)C2=O)c2cnc(Nc3ccnc(N4CCC(O)C(F)C4)n3)cc21]

Step 1: 1-(6-Chloro-1-isopropyl-1H-pyrazolo[4,3-c]pyridin-3-yl)-3-methylimidazolidin-2-one

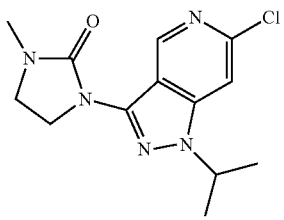 [SMILES: CC(C)n1nc(N2CCN(C)C2=O)c2cnc(Cl)cc21]

A mixture of 1-methylimidazolidin-2-one (300 mg, 3.00 mmol), 6-chloro-3-iodo-1-isopropyl-1H-pyrazolo[4,3-c]pyridine (Example 1, Step 8) (480 mg, 1.49 mmol), tris(dibenzylideneacetone)dipalladium(0) (140 mg, 0.15 mmol), 4,5-bis(diphenylphosphino)-9,9-dimethylxanthene (170 mg, 0.290 mmol) and cesium carbonate (1.96 g, 6.00 mmol) in 1,4-dioxane (10 mL) was stirred for 5 h at 100° C. The solids were removed by filtration and the filtrate was concentrated in vacuo. The resulting residue was purified by silica gel chromatography (solvent gradient: 0-30% ethyl acetate in petroleum ether) to afford the title compound (640 mg, 73%) as a brown solid. LCMS (ESI): [M+H]$^+$=294.

Step 2: 1-(6-(2-(cis-3-Fluoro-4-hydroxypiperidin-1-yl)pyrimidin-4-ylamino)-1-isopropyl-1H-pyrazolo[4,3-c]pyridin-3-yl)-3-methylimidazolidin-2-one

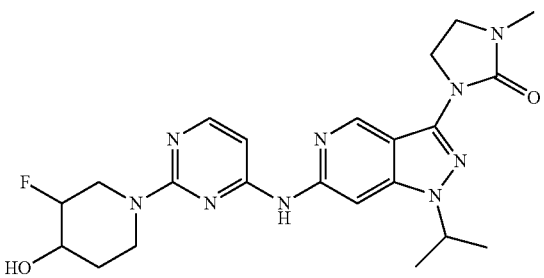 [SMILES: CC(C)n1nc(N2CCN(C)C2=O)c2cnc(Nc3ccnc(N4CCC(O)C(F)C4)n3)cc21]

A mixture of 1-(6-chloro-1-isopropyl-1H-pyrazolo[4,3-c]pyridin-3-yl)-3-methylimidazolidin-2-one (150 mg, 0.510 mmol), 1-(4-aminopyrimidin-2-yl)-cis-3-fluoropiperidin-4-ol (Example 20, Step 2) (108 mg, 0.510 mmol), tris(dibenzylideneacetone)dipalladium(0) (46.9 mg, 0.050 mmol), 4,5-bis(diphenylphosphino)-9,9-dimethylxanthene (59.3 mg, 0.10 mmol) and cesium carbonate (1.00 g, 3.07 mmol) in 1,4-dioxane (8 mL) was heated under microwave irradiation for 1 h at 120° C. under nitrogen atmosphere. The solids were removed by filtration. The filtrate was concentrated in vacuo. The residue was purified by silica gel chromatography (solvent gradient: 0-10% methanol in dichloromethane) to afford the title compound (48.8 mg, 20%) as a white solid. LCMS (ESI): [M+H]+=470, $R_T$ (min)=1.577, Method=N; $^1$H NMR (300 MHz, DMSO-$d_6$): δ 9.99 (s, 1H), 9.34 (s, 1H), 8.23 (s, 1H), 7.98 (d, J=5.7 Hz, 1H), 6.35 (d, J=5.7 Hz, 1H), 5.14-5.13 (m, 1H), 4.68-4.66 (m, 2H), 4.62-4.60 (m, 1H), 4.29-4.21 (m, 1H), 3.94-3.89 (m, 3H), 3.57-3.52 (m, 3H), 3.38-3.32 (m, 1H), 2.83 (s, 3H), 1.72-1.70 (m, 2H), 1.47-1.44 (m, 6H).

Example 77: 4-(6-(2-(4-Hydroxy-4-methylpiperidin-1-yl)pyrimidin-4-ylamino)-1-isopropyl-1H-pyrazolo[4,3-c]pyridin-3-ylamino)pyrrolidin-2-one

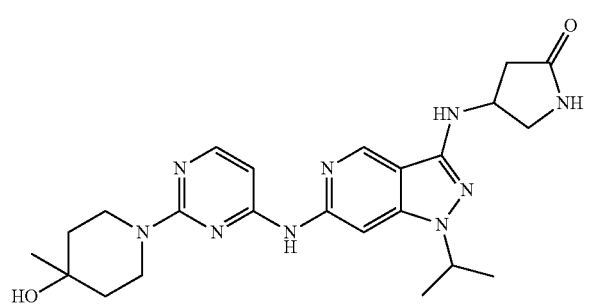 [SMILES: CC(C)n1nc(NC2CNC(=O)C2)c2cnc(Nc3ccnc(N4CCC(C)(O)CC4)n3)cc21]

Step 1: Methyl 1-(4-methoxybenzyl)-5-oxopyrrolidine-3-carboxylate

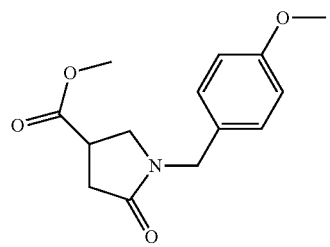 [SMILES: COC(=O)C1CC(=O)N(Cc2ccc(OC)cc2)C1]

A mixture of methyl 5-oxopyrrolidine-3-carboxylate (5.00 g, 34.9 mmol), cesium carbonate (23.0 g, 70.6 mmol), 1-(chloromethyl)-4-methoxybenzene (6.00 g, 38.3 mmol) in N,N-dimethylformamide (50 mL) was stirred for 16 h at room temperature. The resulting mixture was diluted with water (200 mL), extracted with ethyl acetate, washed with brine, dried with anhydrous sodium sulfate, filtered and concentrated in vacuo. The residue was purified by silica gel chromatography (solvent gradient: 0-100% methanol in dichloromethane) to afford the title compound (2.60 g, 28%) as yellow oil. LCMS (ESI): [M+H]+=264.

Step 2: 1-(4-Methoxybenzyl)-5-oxopyrrolidine-3-carboxamide

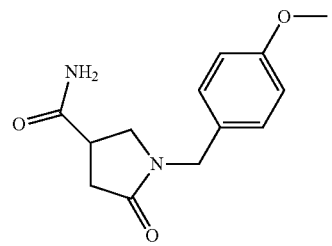 [SMILES: COc1ccc(CN2CC(C(N)=O)CC2=O)cc1]

Methyl 1-(4-methoxybenzyl)-5-oxopyrrolidine-3-carboxylate (2.60 g, 9.88 mmol) was dissolved in a solution of ammonia in methanol (4M, 40 mL). The mixture was stirred for 16 h at room temperature. The resulting mixture was concentrated in vacuo. The residue was dried in an oven under reduced pressure to afford the title compound (1.90 g, 77%) as a white solid. LCMS (ESI): [M+H]+=249

Step 3: 4-Amino-1-(4-methoxybenzyl)pyrrolidin-2-one hydrochloride

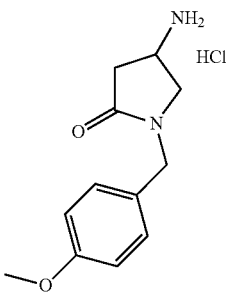 [SMILES: COc1ccc(CN2CC(N)CC2=O)cc1 ; Cl]

A mixture of 1-(4-methoxybenzyl)-5-oxopyrrolidine-3-carboxamide (1.50 g, 6.04 mmol) and iodosobenzene diacetate (2.50 g, 7.76 mmol) in water:acetonitrile (1:1, 30 mL) was stirred for 1 h at room temperature. The resulting mixture was diluted with water (20 mL). The pH value was adjusted to 2-3 with hydrogen chloride (37%). The resulting mixture was extracted with dichloromethane (3×) and the aqueous layer was concentrated in vacuo to afford the title compound (1.40 g, 90%) as brown oil. LCMS (ESI): [M+H]+=221.

Step 4: 4-(6-Chloro-1-isopropyl-1H-pyrazolo[4,3-c]pyridin-3-ylamino)-1-(4-methoxybenzyl)pyrrolidin-2-one

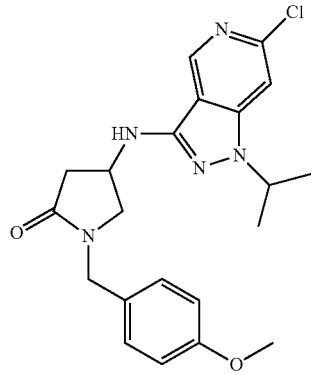 [SMILES: COc1ccc(CN2CC(Nc3nn(C(C)C)c4cc(Cl)ncc34)CC2=O)cc1]

A mixture of 6-chloro-3-iodo-1-isopropyl-1H-pyrazolo[4,3-c]pyridine (300 mg, 0.93 mmol), 4-amino-1-(4-methoxybenzyl)pyrrolidin-2-one hydrochloride (Example 1, Step 8) (600 mg, 2.34 mmol), copper(I) iodide (52.0 mg, 0.270 mmol), L-proline (21.0 mg, 0.180 mmol) and potassium carbonate (380 mg, 2.75 mmol) in dimethyl sulfoxide (10 mL) was stirred for 16 h at 100° C. The reaction mixture was cooled and diluted with water (100 mL), extracted with ethyl acetate, washed with brine, dried with anhydrous sodium sulfate, filtered and concentrated in vacuo. The residue was purified by silica gel chromatography (solvent gradient: 0-80% ethyl acetate in petroleum ether) to afford the title compound (130 mg, 34%) as a yellow solid. LCMS (ESI): $[M+H]^+=414$.

Step 5: 4-(6-Chloro-1-isopropyl-1H-pyrazolo[4,3-c]pyridin-3-ylamino)pyrrolidin-2-one

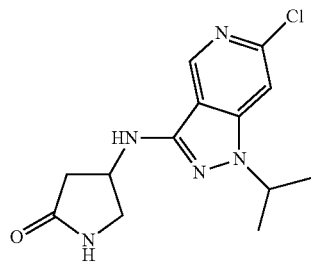 [SMILES: CC(C)n1nc(NC2CNC(=O)C2)c2cnc(Cl)cc21]

4-(6-Chloro-1-isopropyl-1H-pyrazolo[4,3-c]pyridin-3-ylamino)-1-(4-methoxybenzyl)pyrrolidin-2-one (120 mg, 0.290 mmol) was dissolved in 2,2,2-trifluoroacetic acid (10 mL) and stirred for 16 h at 100° C. The resulting mixture was diluted with water (50.0 mL) and the pH value was adjusted to 8-9 with sodium carbonate. The resulting mixture was extracted with ethyl acetate, washed with brine, dried over anhydrous sodium sulfate, filtered and concentrated in vacuo. The residue was purified by silica gel chromatography (solvent gradient: 0-10% methanol in dichloromethane) to afford the title compound (70 mg, 82%)) as a brown solid. LCMS (ESI): $[M+H]^+=294$

Step 6: 4-(6-(2-(4-Hydroxy-4-methylpiperidin-1-yl)pyrimidin-4-ylamino)-1-isopropyl-1H-pyrazolo[4,3-c]pyridin-3-ylamino)pyrrolidin-2-one

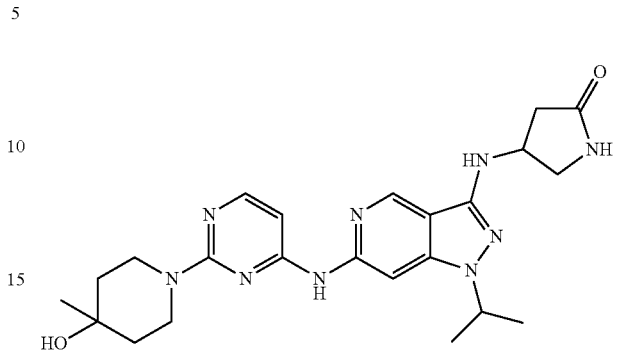

A mixture of 4-(6-chloro-1-isopropyl-1H-pyrazolo[4,3-c]pyridin-3-ylamino)pyrrolidin-2-one (60 mg, 0.20 mmol), 1-(4-aminopyrimidin-2-yl)-4-methylpiperidin-4-ol (50 mg, 0.24 mmol)(Example 86, step 2), 2-(dicyclohexylphosphino)3,6-dimethoxy-2',4',6'-triisopropyl-1,1'-biphenyl (22.0 mg, 0.040 mmol), BrettPhos palladium(II) biphenyl-2-amine mesylate (18.6 mg, 0.020 mmol) and cesium carbonate (200 mg, 0.61 mmol) in 1,4-dioxane (6 mL) was stirred for 1.5 h at 120° C. The reaction mixture was cooled to room temperature and then filtered. The solvent was removed in vacuo and the resulting residue was purified via reverse-phase HPLC and lyophilized to afford the title compound (19.6 mg, 21%) as a white solid. LCMS (ESI): $[M+H]^+=466$, $R_T$ (min)=1.846, method=M. $^1$H NMR (400 MHz, DMSO-$d_6$): δ 9.77 (s, 1H), 8.65 (s, 1H), 8.11 (s, 1H), 7.96 (d, J=5.6 Hz, 1H), 7.64 (s, 1H), 6.77 (d, J=5.6 Hz, 1H), 6.31 (d, J=5.6 Hz, 1H), 4.50-4.45 (m, 1H), 4.39 (s, 1H), 4.34-4.27 (m, 1H), 4.20-4.17 (m, 2H), 3.64-3.60 (m, 1H), 3.49-3.42 (m, 2H), 3.24-3.20 (m, 1H), 2.64-2.57 (m, 1H), 2.21-2.16 (m, 1H), 1.54-1.39 (m, 10H), 1.16 (s, 3H).

Example 78: 2-Hydroxy-1-(4-(6-(2-(4-hydroxy-4-methylpiperidin-1-yl)pyrimidin-4-ylamino)-1-isopropyl-1H-pyrazolo[4,3-c]pyridin-3-yl)piperazin-1-yl)-2-methylpropan-1-one

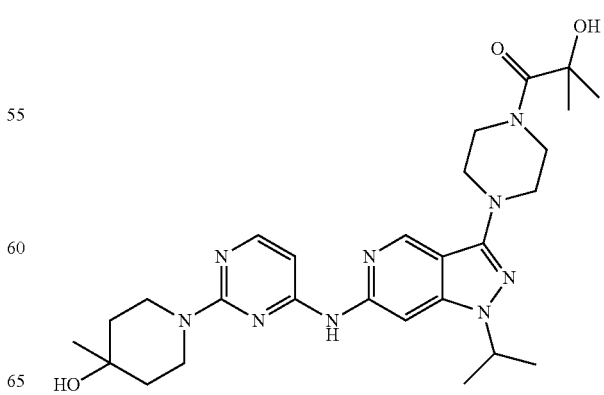

Step 1: 6-Chloro-1-isopropyl-3-(piperazin-1-yl)-1H-pyrazolo[4,3-c]pyridine

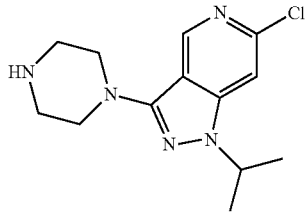 [SMILES: CC(C)n1nc(N2CCNCC2)c2cnc(Cl)cc21]

A mixture of 6-chloro-3-iodo-1-isopropyl-1H-pyrazolo[4,3-c]pyridine (Example 1 Step 8) (1.0 g, 3.11 mmol), piperazine (2.67 g, 31.0 mmol), copper(I) iodide (180 mg, 0.950 mmol), L-proline (110 mg, 0.940 mmol) and potassium carbonate (1.30 g, 9.41 mmol) in N,N-dimethylformamide (17 mL) was irradiated with microwave radiation for 2 h at 80° C. The solution was quenched with water and extracted twice with ethyl acetate. The combined organic washes were washed with brine, dried over sodium sulfate, filtered and concentrated in vacuo. The resulting residue was purified by silica gel chromatography (solvent gradient: 0-10% methanol in dichloromethane) to afford the title compound (500 mg, 57%) as an off-white solid. LCMS (ESI): [M+H]$^+$=280.

Step 2: 1-(4-(6-Chloro-1-isopropyl-1H-pyrazolo[4,3-c]pyridin-3-yl)piperazin-1-yl)-2-hydroxy-2-methylpropan-1-one

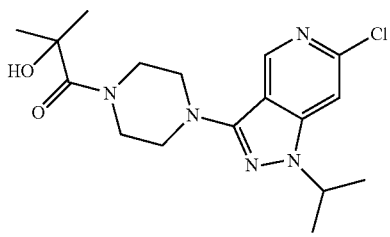 [SMILES: CC(C)n1nc(N2CCN(C(=O)C(C)(C)O)CC2)c2cnc(Cl)cc21]

A mixture of 6-chloro-1-isopropyl-3-(piperazin-1-yl)-1H-pyrazolo[4,3-c]pyridine (200 mg, 0.710 mmol), 2-hydroxy-2-methylpropanoic acid (90.0 mg, 0.860 mmol), O-(7-azabenzotriazol-1-yl)-N,N,N,N-tetramethyluronium hexafluorophosphate (0.330 g, 0.860 mmol) N,N-diisopropylethylamine (0.370 g, 2.86 mmol) in N,N-dimethylformamide (4 mL) was stirred for 16 h at room temperature. The reaction was quenched with water, extracted twice with ethyl acetate, washed with brine, dried over sodium sulfate, filtered and concentrated in vacuo to afford the title compound (260 mg, 99%) as a brown solid. LCMS (ESI): [M+H]$^+$=366.

Step 3: 2-Hydroxy-1-(4-(6-(2-(4-hydroxy-4-methylpiperidin-1-yl)pyrimidin-4-ylamino)-1-isopropyl-1H-pyrazolo[4,3-c]pyridin-3-yl)piperazin-1-yl)-2-methylpropan-1-one

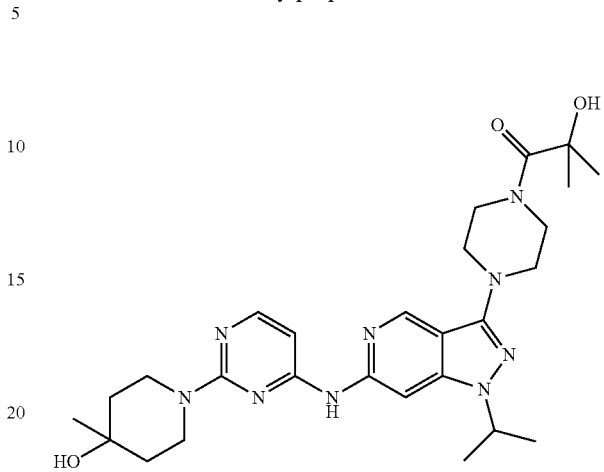

A mixture of 1-(4-(6-chloro-1-isopropyl-1H-pyrazolo[4,3-c]pyridin-3-yl)piperazin-1-yl)-2-hydroxy-2-methylpropan-1-one (250 mg, 0.680 mmol), 1-(4-aminopyrimidin-2-yl)-4-methylpiperidin-4-ol (Example 86, Step 2) (140 mg, 0.690 mmol), BrettPhos palladium(II) biphenyl-2-amine mesylate (60.0 mg, 0.070 mmol), 2-(dicyclohexylphosphino)-3,6-dimethoxy-2',4',6'-triisopropyl-1,1'-biphenyl (70.0 mg, 0.140 mmol) and cesium carbonate (670 mg, 2.05 mmol) in 1,4-dioxane (6 mL) was stirred for 3 h at 120° C. The mixture was filtered and concentrated in vacuo. The resulting residue was purified via reverse-phase HPLC and lyophilized to afford the title compound (80 mg, 20%) as a white solid. LCMS (ESI): [M+1]$^+$=563, R$_T$ (min)=1.71, method=M; $^1$H NMR (400 MHz, DMSO-d$_6$): δ 9.87 (s, 1H), 8.87 (s, 1H), 8.21 (s, 1H), 7.98-7.96 (d, J=5.6 Hz, 1H), 6.33-6.32 (d, J=5.6 Hz, 1H), 5.47 (s, 1H), 4.56-4.53 (m, 1H), 4.39 (s, 1H), 4.21-3.58 (m, 6H), 3.50-3.40 (m, 6H), 1.55-1.47 (m, 4H), 1.44-1.42 (d, J=6.8 Hz, 6H), 1.35 (s, 6H), 1.17 (s, 3H).

Example 79: (3RS,4SR)-3-Fluoro-1-(4-(3-((R)-3-hydroxypyrrolidin-1-yl)-1-((S*)-1,1,1-trifluoropropan-2-yl)-1H-pyrazolo[4,3-c]pyridin-6-ylamino)pyrimidin-2-yl)-4-methylpiperidin-4-ol (Mixture of Diastereomers)

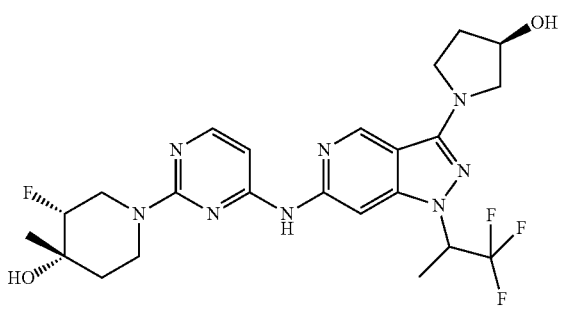 [SMILES: CC(n1nc(N2CC[C@@H](O)C2)c2cnc(Nc3ccnc(N4CC[C@](C)(O)[C@H](F)C4)n3)cc21)C(F)(F)F]

Step 1: (3RS,4SR)-tert-Butyl 3-fluoro-4-hydroxy-4-methylpiperidine-1-carboxylate

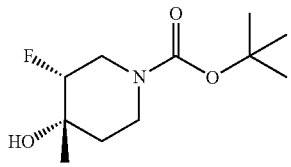 [SMILES: CC(C)(C)OC(=O)N1CC[C@](C)(O)[C@H](F)C1]

A solution of methylmagnesium bromide (3 M, 691 mmol) in tetrahydrofuran (230 mL) was added dropwise to a solution of tert-butyl 3-fluoro-4-oxopiperidine-1-carboxylate (100 g, 460 mmol) in tetrahydrofuran (1 L) at 5° C. under nitrogen atmosphere. The resulting mixture was stirred for 2 h at 5° C. then cooled to 0° C. and quenched with saturated ammonium chloride, extracted twice with ethyl acetate, washed with brine, dried over sodium sulfate, filtered and concentrated in vacuo. The resulting residue was purified by silica gel chromatography (solvent gradient: 0-10% ethyl acetate in petroleum) to afford the title compound as a mixture of diastereomers with known relative stereochemistry (19 g, 18%) as a yellow solid. LCMS (ESI): [M+H]$^+$=234

Step 2: (3RS,4SR)-3-Fluoro-4-methylpiperidin-4-ol hydrochloride

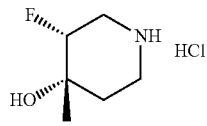

A mixture of (3RS,4SR)-tert-butyl 3-fluoro-4-hydroxy-4-methylpiperidine-1-carboxylate (15 g, 64.3 mmol) and hydrogen chloride in ether (1 M, 130 mL) was stirred for 16 h at room temperature. The solids were collected by filtration to afford the title compound (6.75 g, 62%) as a white solid (mixture of diastereomers with known relative stereochemistry). LCMS (ESI): [M+H]$^+$=134.

Step 3: (3RS, 4SR)-1-(4-Aminopyrimidin-2-yl)-3-fluoro-4-methylpiperidin-4-ol

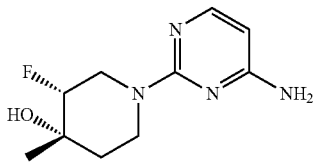 [SMILES: C[C@]1(O)CCN(c2nccc(N)n2)C[C@H]1F]

A mixture of (3RS,4SR)-3-fluoro-4-methylpiperidin-4-ol hydrochloride (400 mg, 2.36 mmol), 2-chloro-4-aminopyrimidine (255 mg, 1.97 mmol) and potassium carbonate (812 mg, 5.88 mmol) in acetonitrile (5 mL) was stirred for 16 h at 100° C. The solids were removed by filtration and the filtrate was concentrated in vacuo. The resulting residue was purified by silica gel chromatography (solvent gradient: 0-10% methanol in dichloromethane) to afford the title compound (200 mg, 45%) as a yellow solid (mixture of diastereomers with known relative stereochemistry). LCMS (ESI): [M+H]$^+$=227

Step 4: (R)-1-(6-Chloro-1-((S*)-1,1,1-trifluoropropan-2-yl)-1H-pyrazolo[4,3-c]pyridin-3-yl)pyrrolidin-3-ol

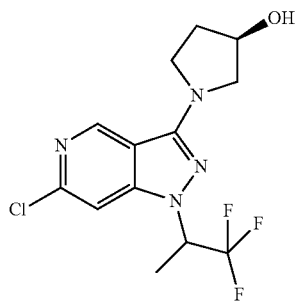 [SMILES: CC(n1nc(N2CC[C@@H](O)C2)c2cnc(Cl)cc21)C(F)(F)F]

A mixture of 6-chloro-3-iodo-1-(1,1,1-trifluoropropan-2-yl)-1H-pyrazolo[4,3-c]pyridine (Example 87, step 2) (350 mg, 0.930 mmol), (R)-pyrrolidin-3-ol hydrochloride (574 mg, 4.64 mmol), copper (I) iodide (35.0 mg, 0.190 mmol), (S)-pyrrolidine-2-carboxylic acid (22.0 mg, 0.190 mmol) and potassium carbonate (1.16 g, 8.39 mmol) in dimethyl sulfoxide (8 mL) was stirred for 12 h at 80° C. under a nitrogen atmosphere. After the reaction was cooled to room temperature the reaction mixture was concentrated in vacuo. The resulting residue was purified by silica gel chromatography (solvent gradient: 0-50% ethyl acetate in petroleum) and chiral HPLC (conditions: Chiralpak IA column, 2*25 cm, 5 um; mobile phase, hexanes and ethanol (hold 15.0% ethanol in 13 min); Detector, uv 254/220 nm, collection of the first peak, elutes at 7.1 min) to afford the title compound as a single unknown stereoisomer (64 mg, 19%) as a white solid. LCMS (ESI): [M+H]$^+$=335.

Step 5: (3RS,4SR)-3-Fluoro-1-(4-(3-((R)-3-hydroxypyrrolidin-1-yl)-1-((S*)-1,1,1-trifluoropropan-2-yl)-1H-pyrazolo[4,3-c]pyridin-6-ylamino)pyrimidin-2-yl)-4-methylpiperidin-4-ol

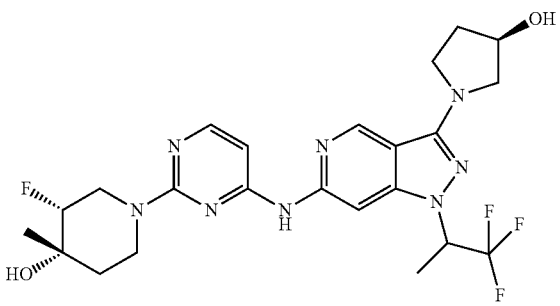 [SMILES: CC(n1nc(N2CC[C@@H](O)C2)c2cnc(Nc3ccnc(N4CC[C@](C)(O)[C@H](F)C4)n3)cc21)C(F)(F)F]

A mixture of (R)-1-(6-chloro-1-((S*)-1,1,1-trifluoropropan-2-yl)-1H-pyrazolo[4,3-c]pyridin-3-yl)pyrrolidin-3-ol (63.6 mg, 0.190 mmol), (3RS,4SR)-1-(4-aminopyrimidin-2-yl)-3-fluoro-4-methylpiperidin-4-ol (43.0 mg, 0.190 mmol), cesium carbonate (124 mg, 0.380 mmol), 2-(dicyclohexylphosphino)3,6-dimethoxy-2',4',6'-triisopropyl-1,1'-biphenyl (20.5 mg, 0.0380 mmol) and BrettPhos palladium (II) biphenyl-2-amine mesylate (17.2 mg, 0.0190 mmol) in 1,4-dioxane (4 mL) was stirred for 1 h at 120° C. under a nitrogen atmosphere. After the reaction was cooled to room temperature, the solution was concentrated in vacuo. The resulting residue was purified by silica gel chromatography (solvent gradient: 0-10% methanol in dichloromethane) to afford the title compound (35.5 mg, 36%) as a white solid as a mixture of diastereomers. LCMS (ESI): [M+H]$^+$=525, R$_T$ (min)=1.920, method=M; $^1$H NMR (300 MHz, DMSO-d$_6$): δ 9.95-9.93 (m, 1H), 8.77 (s, 1H), 8.19-8.12 (m, 1H), 8.01-7.99 (d, J=5.7 Hz, 1H), 6.40-6.39 (d, J=5.7 Hz, 1H), 5.23-5.19 (m, 1H), 4.99-4.98 (m, 1H), 4.83-4.82 (m, 1H), 4.42-4.21 (m, 3H), 4.09 (m, 1H), 3.71-3.62 (m, 4H), 3.45-3.41 (m, 2H), 2.08-2.03 (m, 1H), 1.94-1.92 (m, 1H), 1.71-1.69 (m, 4H), 1.66 (m, 1H), 1.20 (d, J=6.6 Hz, 3H).

Example 80: (±)-1-(4-(1-sec-Butyl-3-(3-hydroxy-3-(hydroxymethyl)azetidin-1-yl)-1H-pyrazolo[4,3-c]pyridin-6-ylamino)pyrimidin-2-yl)-4-methylpiperidin-4-ol

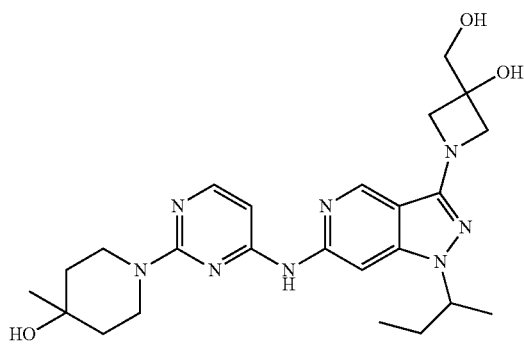 [SMILES: CCC(C)n1nc(N2CC(O)(CO)C2)c2cnc(Nc3ccnc(N4CCC(C)(O)CC4)n3)cc21]

Step 1: tert-Butyl 3-methyleneazetidine-1-carboxylate

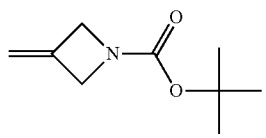

A mixture of methyltriphenylphosphonium bromide (49 g, 137 mmol), potassium 2-methylpropan-2-olate (15.5 g, 138 mmol) in tetrahydrofuran (400 mL) was stirred for 1 h at room temperature. This was followed by the addition of a solution of tert-butyl 3-oxoazetidine-1-carboxylate (10 g, 58.4 mmol) in tetrahydrofuran (100 mL) dropwise with stirring. Then the reaction system was stirred for additional 2 h while the temperature was maintained at 35° C. The solution was diluted with water, extracted with ethyl acetate, washed with brine and concentrated in vacuo. The resulting residue was purified by silica gel chromatography (solvent gradient: 0-10% ethyl acetate in petroleum ether) to afford the title compound (8.0 g, 81%) as a yellow oil. LCMS (ESI): [M+H]$^+$=170.

Step 2: tert-Butyl 3-hydroxy-3-(hydroxymethyl)azetidine-1-carboxylate

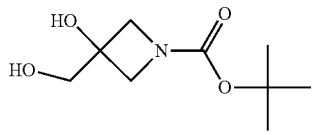

A mixture of potassium dioxidodioxoosmium (21.8 mg, 0.060 mmol), 4-methylmorpholin-4-ium-4-olate (761 mg, 6.50 mmol) and tert-butyl 3-methylideneazetidine-1-carboxylate (1 g, 5.91 mmol) in acetone (12 mL) and water (7 mL) was stirred for 12 h at room temperature. The solution was quenched with a saturated aqueous solution of sodium hydrogen sulfite, extracted twice with ethyl acetate, washed with brine, dried over sodium sulfate, filtered and concentrated in vacuo. The resulting residue was purified by silica gel chromatography (solvent gradient: 0-50% ethyl acetate in petroleum) to afford the title compound (500 mg, 42%) as a white solid. LCMS (ESI): [M+H]$^+$=204.

Step 3: 3-(Hydroxymethyl)azetidin-3-ol 2,2,2-trifluoroacetate

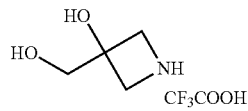

To a reaction vessel was added tert-butyl 3-hydroxy-3-(hydroxymethyl)azetidine-1-carboxylate (230 mg, 1.13 mmol), dichloromethane (20 mL) and trifluoroacetic acid (4 mL, 53.9 mmol). The reaction mixture was stirred for 2 h at room temperature. The resulting solution was concentrated in vacuo to afford the title compound (250 mg, 99%) as a brown oil. LCMS (ESI): [M+H]$^+$=218.

Step 4: 1-[1-(Butan-2-yl)-6-chloro-1H-pyrazolo[4,3-c]pyridin-3-yl]-3-(hydroxymethyl)azetidin-3-ol

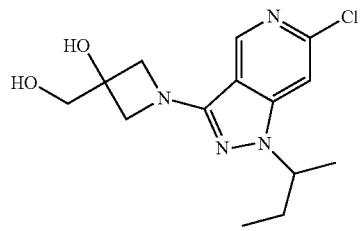 [SMILES: CCC(C)n1nc(N2CC(O)(CO)C2)c2cnc(Cl)cc21]

A mixture of 3-(hydroxymethyl)azetidin-3-ol 2,2,2-trifluoroacetate (200 mg, 0.920 mmol), 1-(butan-2-yl)-6-chloro-3-iodo-1H-pyrazolo[4,3-c]pyridine (Example 12, step 1) (309 mg, 0.920 mmol), copper (I) iodide (17.5 mg, 0.090 mmol), (S)-pyrrolidine-2-carboxylic acid (21.2 mg, 0.180 mmol) and potassium carbonate (763 mg, 5.52 mmol) in N,N-dimethylformamide (10 mL) was stirred for 16 h at 80° C. under nitrogen atmosphere. The resulting solution was filtered and the filtrate was concentrated in vacuo. The resulting residue was purified by silica gel chromatography (solvent gradient: 0-50% ethyl acetate in petroleum) to afford the title compound (100 mg, 35%) as a light yellow solid. LCMS (ESI): [M+H]$^+$=311.

Step 5: (±)-1-(4-(1-sec-Butyl-3-(3-hydroxy-3-(hydroxymethyl)azetidin-1-yl)-1H-pyrazolo[4,3-c]pyridin-6-ylamino)pyrimidin-2-yl)-4-methylpiperidin-4-ol

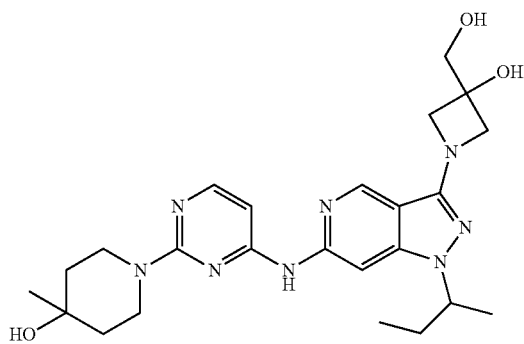 [SMILES: CCC(C)n1nc(N2CC(O)(CO)C2)c2cnc(Nc3ccnc(N4CCC(C)(O)CC4)n3)cc21]

A mixture of 1-[1-(butan-2-yl)-6-chloro-1H-pyrazolo[4,3-c]pyridin-3-yl]-3-(hydroxymethyl)azetidin-3-ol (40.0 mg, 0.130 mmol), 1-(4-aminopyrimidin-2-yl)-4-methylpiperidin-4-ol (Example 86, Step 2) (26.8 mg, 0.13 mmol), BrettPhos palladium(II) biphenyl-2-amine mesylate (9.20 mg, 0.010 mmol), 2-(dicyclohexylphosphino)3,6-dimethoxy-2',4',6'-triisopropyl-1,1'-biphenyl (14.0 mg, 0.030 mmol) and cesium carbonate (212 mg, 0.650 mmol) in 1,4-dioxane (2 mL) was stirred for 1.5 h at 120° C. under nitrogen atmosphere. The resulting solution was filtered, concentrated in vacuo and purified via reverse-phase HPLC and lyophilized to afford the title compound (100 mg, 35%) as a light yellow solid. LCMS (ESI): [M+H]$^+$=483, R$_T$ (min)=2.342, method=R; $^1$H NMR (400 MHz, DMSO-d$_6$): δ 9.80 (s, 1H), 8.53 (s, 1H), 8.15 (s, 1H), 7.96 (d, J=5.6 Hz, 1H), 6.31 (d, J=5.6 Hz, 1H), 5.63 (s, 1H), 4.92-4.89 (m, 1H), 4.40 (s, 1H), 4.20-4.11 (m, 5H), 3.84-3.82 (m, 2H), 3.52-3.33 (m, 4H), 1.95-1.84 (m, 1H), 1.80-1.70 (m, 1H), 1.60-1.41 (m, 4H), 1.41-1.31 (m, 3H), 1.16 (s, 3H), 0.73-0.69 (m, 3H).

Example 81: 2-(1-(4-(1-sec-Butyl-3-((R)-3-hydroxypyrrolidin-1-yl)-1H-pyrazolo[4,3-c]pyridin-6-ylamino)pyrimidin-2-yl)-4-methoxypiperidin-4-yl)acetonitrile

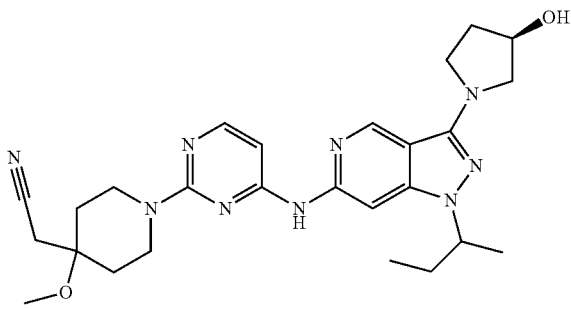 [SMILES: CCC(C)n1nc(N2CC[C@@H](O)C2)c2cnc(Nc3ccnc(N4CCC(CC#N)(OC)CC4)n3)cc21]

Step 1: tert-Butyl 4-(cyanomethyl)-4-hydroxypiperidine-1-carboxylate

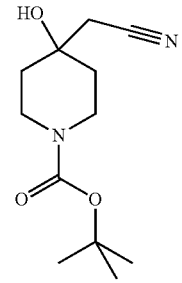 [SMILES: CC(C)(C)OC(=O)N1CCC(O)(CC#N)CC1]

A solution of n-butyl lithium (2.5 M in hexanes, 12 mL, 30.1 mmol) was added dropwise to a pre-cooled solution at 0° C. of diisopropylamine (3.05 g, 30.1 mmol) in tetrahydrofuran (25 mL) under nitrogen atmosphere. The resulting mixture was stirred for 0.5 h at room temperature then cooled to −78° C. To the reaction mixture was added dropwise a solution of acetonitrile (1.24 g, 30.2 mmol) in tetrahydrofuran at −78° C. The mixture was stirred for 1 h at −78° C. then a solution of tert-butyl 4-oxopiperidine-1-carboxylate (3.0 g, 15.1 mmol) in tetrahydrofuran (12 mL) was added. The resulting solution was stirred for 1 h at room temperature. The reaction was quenched by ammonium chloride (aq. 100 mL), extracted with ethyl acetate, and the organic wash was washed with brine, dried over anhydrous sodium sulfate, filtered and concentrated in vacuo. The residue was purified by silica gel chromatography (solvent gradient: 0-20% ethyl acetate in petroleum ether) to afford the title compound (1.5 g, 41%) as a white solid. LCMS (ESI): [M+H]$^+$=241.

Step 2: tert-Butyl 4-(cyanomethyl)-4-methoxypiperidine-1-carboxylate

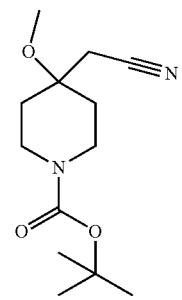 [SMILES: COC1(CC#N)CCN(C(=O)OC(C)(C)C)CC1]

Sodium hydride (100 mg, 2.5 mmol) was added to a precooled solution at 0° C. of tert-butyl 4-(cyanomethyl)-4-hydroxypiperidine-1-carboxylate (400 mg, 1.66 mmol), iodomethane (470 mg, 3.33 mmol) in N,N-dimethylformamide (5 mL). The resulting mixture was stirred for 2 h at room temperature, and quenched by water (30 mL), extracted with ethyl acetate (3×), washed with brine, dried over anhydrous sodium sulfate, filtered and concentrated in vacuo. The resulting residue was purified by silica gel chromatography (solvent gradient: 0-25% ethyl acetate in petroleum ether) to afford the title compound (350 mg, 83%) as a colorless oil. LCMS (ESI): [M+H]$^+$=255.

Step 3: 2-(4-Methoxypiperidin-4-yl)acetonitrile hydrochloride

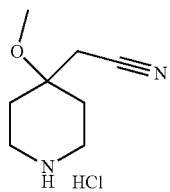

A solution of hydrogen chloride in 1,4-dioxane (4 M, 4 mL) was added to a solution of tert-butyl 4-(cyanomethyl)-4-methoxypiperidine-1-carboxylate (350 mg, 1.38 mmol) in 1,4-dioxane (2.5 mL). The resulting mixture was stirred for 2 h at room temperature, and concentrated in vacuo to afford the title compound (240 mg, 91%) as a white solid. LCMS (ESI): [M+H]$^+$=155.

Step 4: 2-(1-(4-Aminopyrimidin-2-yl)-4-methoxypiperidin-4-yl)acetonitrile

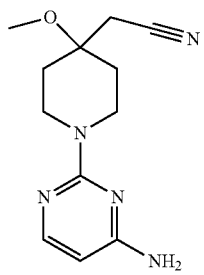 [SMILES: COC1(CC#N)CCN(c2nccc(N)n2)CC1]

A mixture of 2-(4-methoxypiperidin-4-yl)acetonitrile hydrochloride (200 mg, 1.05 mmol), 2-chloropyrimidin-4-amine (90 mg, 0.70 mmol) and N-ethyl-N-isopropylpropan-2-amine (360 mg, 2.79 mmol) in N,N-dimethylformamide (7 mL) was stirred overnight at 100° C. The solution was quenched with water, extracted with ethyl acetate (3×), washed with brine, dried over anhydrous sodium sulfate, filtered and concentrated in vacuo. The resulting residue was purified by silica gel chromatography (solvent gradient: 0-10% methanol in dichloromethane) to afford the title compound (120 mg, 69%) as a brown solid. LCMS (ESI): [M+H]$^+$=248.

Step 5: (3R)-1-(1-sec-Butyl-6-chloro-1H-pyrazolo[4,3-c]pyridin-3-yl)pyrrolidin-3-ol

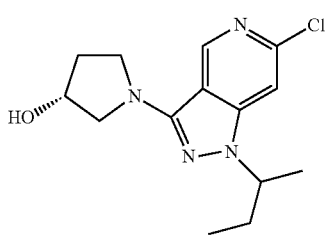 [SMILES: CCC(C)n1nc(N2CC[C@@H](O)C2)c2cnc(Cl)cc21]

A mixture of 1-sec-butyl-6-chloro-3-iodo-1H-pyrazolo[4,3-c]pyridine (400 mg, 1.19 mmol)(Example 12, Step 1), (R)-pyrrolidin-3-ol hydrochloride (400 mg, 3.24 mmol), copper(I) iodide (70.0 mg, 0.360 mmol), L-proline (30 mg, 0.230 mmol) and potassium carbonate (1 g, 7.24 mmol) in dimethyl sulfoxide (15 mL) was stirred for 16 h at 100° C. The solution was quenched with water, extracted with ethyl acetate, washed with brine, dried over anhydrous sodium sulfate, filtered and concentrated in vacuo. The resulting residue was purified by silica gel chromatography (solvent gradient: 0-50% ethyl acetate in petroleum ether) to afford the title compound (300 mg, 85%) as a yellow oil. LCMS (ESI): [M+H]$^+$=295.

Step 6: 2-(1-(4-(1-sec-Butyl-3-((R)-3-hydroxypyrrolidin-1-yl)-1H-pyrazolo[4,3-c]pyridin-6-ylamino)pyrimidin-2-yl)-4-methoxypiperidin-4-yl)acetonitrile

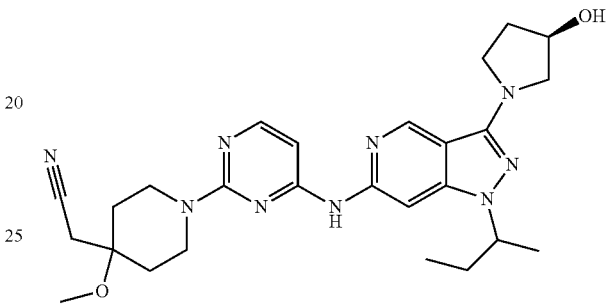

A mixture of 2-[1-(4-aminopyrimidin-2-yl)-4-methoxypiperidin-4-yl]acetonitrile (80 mg, 0.320 mmol), (3R)-1-(1-sec-butyl-6-chloro-1H-pyrazolo[4,3-c]pyridin-3-yl)pyrrolidin-3-ol (100 mg, 0.330 mmol), BrettPhos palladium(II) biphenyl-2-amine mesylate (30 mg, 0.040 mmol), 2-(dicyclohexylphosphino)3,6-dimethoxy-2',4',6'-triisopropyl-1,1'-biphenyl (40 mg, 0.070 mmol) and cesium carbonate (260 mg, 0.790 mmol) in 1,4-dioxane (5 mL) was stirred for 1.5 h at 120° C. The solids were removed by filtration and the filtrate was concentrated in vacuo. The resulting residue was purified via reverse-phase HPLC and lyophilized to afford the title compound (10 mg, 6%) as a white solid as a mixture of diastereoisomers. LCMS (ESI): [M+1]$^+$=506, R$_T$ (min)=2.64, method=M; $^1$H NMR (400 MHz, DMSO-d$_6$): δ 9.82 (s, 1H), 8.71 (s, 1H), 8.09 (s, 1H), 7.99-7.98 (d, J=5.6 Hz, 1H), 6.38-6.36 (d, J=5.6 Hz, 1H), 4.96-4.96 (m, 1H), 4.42-4.33 (m, 3H), 4.21-4.19 (m, 1H), 3.70-3.59 (m, 3H), 3.43-3.40 (m, 1H), 3.33-3.23 (m, 5H), 2.93 (s, 2H), 2.06-2.03 (m, 1H), 1.95-1.84 (m, 4H), 1.81-1.71 (m, 1H), 1.63-1.57 (m, 2H), 1.40-1.39 (d, J=6.4 Hz, 3H), 0.75-0.71 (m, 3H).

Example 82: 1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-3-methylazetidin-3-ol

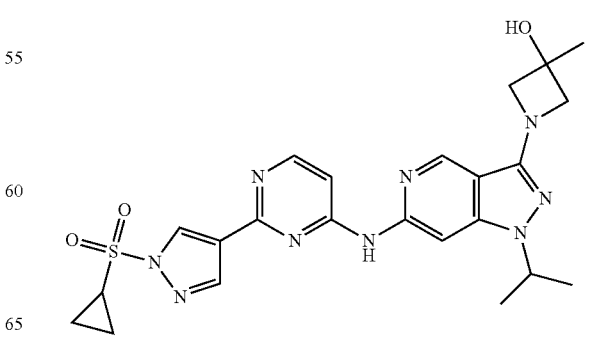

Step 1: 1-(6-Chloro-1-isopropyl-1H-pyrazolo[4,3-c]pyridin-3-yl)-3-methylazetidin-3-ol

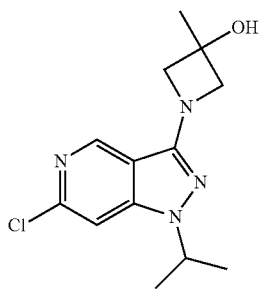 [SMILES: CC(C)n1nc(N2CC(C)(O)C2)c2cnc(Cl)cc21]

A mixture of 6-chloro-3-iodo-1-isopropyl-1H-pyrazolo[4,3-c]pyridine (300 mg, 0.930 mmol)(Example 1, step 8), 4,5-bis(diphenylphosphino)-9,9-dimethylxanthene (108 mg, 0.190 mmol), tris(dibenzylideneacetone)dipalladium(0) (85.4 mg, 0.100 mmol), cesium carbonate (760 mg, 2.33 mmol) and 3-methylazetidin-3-ol hydrochloride (115 mg, 0.930 mmol) in 1,4-dioxane (8 mL) was stirred for 6 h at 100° C. The reaction mixture was cooled to room temperature. The solids were removed by filtration and the solution was concentrated in vacuo. The resulting residue was purified by silica gel chromatography (solvent gradient: 0-50% ethyl acetate in petroleum) to afford the title compound (120 mg, 46%) as a white solid. LCMS (ESI): [M+H]$^+$=281.

Step 2: 1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-3-methylazetidin-3-ol

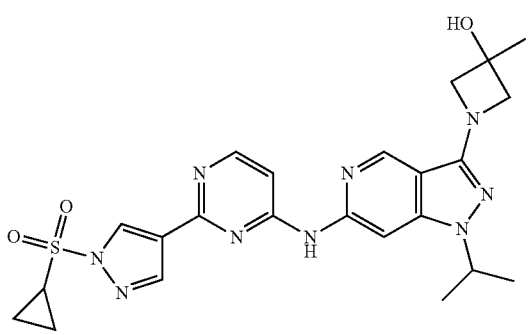 [SMILES: CC(C)n1nc(N2CC(C)(O)C2)c2cnc(Nc3ccnc(-c4cnn(S(=O)(=O)C5CC5)c4)n3)cc21]

A mixture of 1-(6-chloro-1-isopropyl-1H-pyrazolo[4,3-c]pyridin-3-yl)-3-methylazetidin-3-ol (120 mg, 0.430 mmol), tris(dibenzylideneacetone)dipalladium(0) (39.4 mg, 0.040 mmol), 4,5-bis(diphenylphosphino)-9,9-dimethylxanthene (49.8 mg, 0.080 mmol), cesium carbonate (278 mg, 0.850 mmol) and 2-[1-(cyclopropanesulfonyl)-1H-pyrazol-4-yl]pyrimidin-4-amine (114 mg, 0.430 mmol)(Example 1, step 2) in dioxane (8 mL) was heated under microwave irradiation for 45 min at 160° C. The reaction mixture was cooled to room temperature. The solids were removed by filtration and the solution was concentrated in vacuo. The resulting residue was purified by silica gel chromatography (solvent gradient: 0-10% methanol in dichloromethane) to afford the title compound (12.9 mg, 6%) as a light yellow solid. LCMS (ESI): [M+H]$^+$=510, $R_T$ (min)=2.472, Method=R; $^1$H NMR (300 MHz, DMSO-d$_6$): δ 10.30 (s, 1H), 8.69 (s, 1H), 8.59 (s, 1H), 8.47 (s, 1H), 8.41 (d, J=6.0 Hz, 1H), 8.26 (s, 1H), 7.14 (d, J=6.0 Hz, 1H), 5.57 (s, 1H), 4.72-4.67 (m, 1H), 4.03-3.93 (m, 4H), 3.28-3.25 (m, 1H), 1.50 (s, 3H), 1.46 (d, J=6.6 Hz, 6H), 1.38-1.32 (m, 2H), 1.31-1.23 (m, 2H).

Example 83: 1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-3-methylimidazolidin-2-one

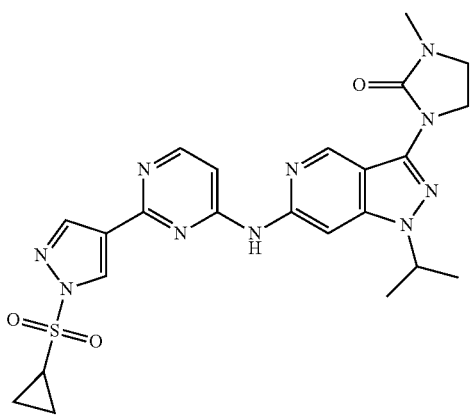 [SMILES: CC(C)n1nc(N2CCN(C)C2=O)c2cnc(Nc3ccnc(-c4cnn(S(=O)(=O)C5CC5)c4)n3)cc21]

Step 1: 1-(6-Bromo-1-isopropyl-1H-pyrazolo[4,3-c]pyridin-3-yl)-3-methylimidazolidin-2-one

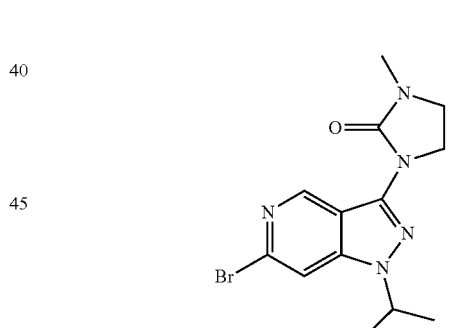

A mixture of 6-bromo-3-iodo-1-(propan-2-yl)-1H-pyrazolo[4,3-c]pyridine (Example 16, Step 7) (300 mg, 0.820 mmol), 1-methylimidazolidin-2-one (84.0 mg, 0.840 mmol), tris(dibenzylideneacetone)dipalladium(0) (78.0 mg, 0.090 mmol), 4,5-bis(diphenylphosphino)-9,9-dimethylxanthene (96.0 mg, 0.170 mmol) and cesium carbonate (822 mg, 2.52 mmol) in 1,4-dioxane (9 mL) was stirred for 30 min at 100° C. under nitrogen atmosphere. After cooling to room temperature, the solids were removed by filtration. The filtrate was concentrated in vacuo. The resulting residue was purified by silica gel chromatography (solvent gradient: 0-5% methanol in dichloromethane) to afford the title compound (100 mg, 36%) as a white solid. LCMS (ESI): [M+H]$^+$=338.

Step 2: 1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-3-methylimidazolidin-2-one

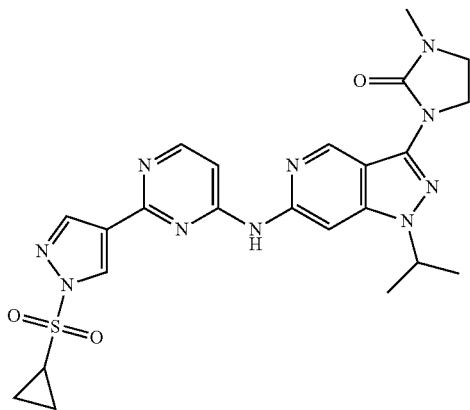 [SMILES: CC(C)n1nc(N2CCN(C)C2=O)c2cnc(Nc3ccnc(-c4cnn(S(=O)(=O)C5CC5)c4)n3)cc21]

A mixture of 1-(6-bromo-1-isopropyl-1H-pyrazolo[4,3-c]pyridin-3-yl)-3-methylimidazolidin-2-one (90.0 mg, 0.270 mmol), 2-[1-(cyclopropanesulfonyl)-1H-pyrazol-4-yl]pyrimidin-4-amine (Example 1, Step 2) (70.0 mg, 0.260 mmol), tris(dibenzylideneacetone)dipalladium(0) (25 mg, 0.030 mmol), 4,5-bis(diphenylphosphino)-9,9-dimethylxanthene (30.0 mg, 0.050 mmol) and cesium carbonate (265 mg, 0.810 mmol) in 1,4-dioxane (6 mL) was stirred for 1 h at 100° C. under nitrogen atmosphere. After cooling to room temperature, the solids were removed by filtration. The filtrate was concentrated in vacuo. The resulting residue was purified by silica gel chromatography (solvent gradient: 0-10% methanol in dichloromethane) to afford the title compound (11 mg, 8%) as a white solid. LCMS (ESI): [M+H]$^+$=523.1, $R_T$ (min)=1.661, Method=N; $^1$H NMR (300 MHz, DMSO-d$_6$) δ 10.45 (s, 1H), 9.40 (s, 1H), 8.73 (s, 1H), 8.49-8.41 (m, 3H), 7.09 (m, 1H), 4.92-4.81 (m, 1H), 3.96-3.94 (m, 2H), 3.59-3.54 (m, 2H), 3.31-3.25 (m, 1H), 2.84 (s, 3H), 1.51 (d, J=6.6 Hz, 6H), 1.36-1.26 (m, 4H).

Example 84: 2-(1-(6-(2-(4-Hydroxy-4-methylpiperidin-1-yl)pyrimidin-4-ylamino)-1-isopropyl-1H-pyrazolo[4,3-c]pyridin-3-yl)azetidin-3-yl)-2-methylpropanamide

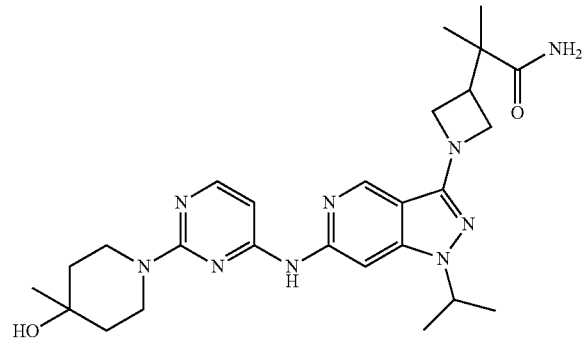 [SMILES: CC(C)n1nc(N2CC(C(C)(C)C(N)=O)C2)c2cnc(Nc3ccnc(N4CCC(C)(O)CC4)n3)cc21]

Step 1: Benzyl 3-hydroxy-3-(1-methoxy-2-methyl-1-oxopropan-2-yl)azetidine-1-carboxylate

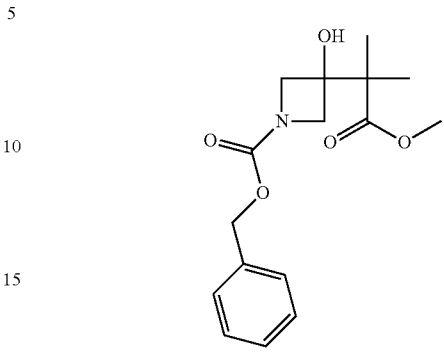

To a solution of benzyl 3-oxoazetidine-1-carboxylate (10 g, 48.7 mmol) in dichloromethane (200 mL) was added titanium tetrachloride (9.31 g, 49.1 mmol) dropwise with stirring at −20° C. under a nitrogen atmosphere. After stirring for 40 min, to this was added (1-methoxy-2-methylprop-1-enyloxy) trimethylsilane (17.0 g, 97.5 mmol) dropwise. The reaction mixture was stirred for 40 min at −20° C., then quenched by the addition of saturated aqueous sodium hydrogen carbonate (100 mL), extracted with dichloromethane, dried over anhydrous sodium sulfate, filtered and concentrated in vacuo. The resulting residue was purified by silica gel chromatography (solvent gradient: 0-30% ethyl acetate in petroleum ether) to afford the title compound (12 g, 80%) as yellow oil. $^1$H NMR (300 MHz, CDCl$_3$): δ 7.36-7.28 (m, 5H), 5.10 (s, 2H), 4.08 (d, J=9.6 Hz, 2H), 3.87 (d, J=9.6 Hz, 2H), 3.72 (s, 3H), 3.51 (bs, 1H), 1.28 (s, 6H).

Step 2: Benzyl 3-(1-methoxy-2-methyl-1-oxopropan-2-yl)-3-(methylthiocarbonothioyloxy)azetidine-1-carboxylate

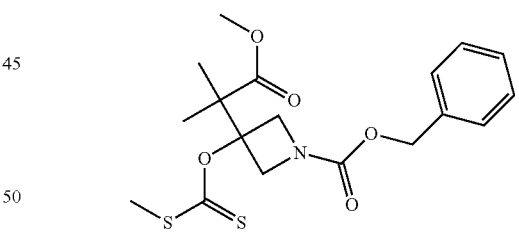

To a suspension of sodium hydride (1.08 g, 45.0 mmol) in tetrahydrofuran (100 mL) was added a solution of benzyl 3-hydroxy-3-(1-methoxy-2-methyl-1-oxopropan-2-yl)azetidine-1-carboxylate (5 g, 16.3 mmol) in tetrahydrofuran (2 mL) with stirring at 0° C. under nitrogen atmosphere. The reaction mixture was stirred for 1 hour at room temperature. After cooling to 0° C., carbon disulfide (2.05 g, 26.9 mmol) was added dropwise. After stirring for 20 min, iodomethane (5.11 g, 36.0 mmol) was added dropwise and stirred for additional 20 min. The reaction was then quenched by the addition of saturated aqueous ammonium chloride (100 mL), extracted with ethyl acetate, dried over anhydrous sodium sulfate, filtered and concentrated in vacuo to give a residue, which was purified via flash chromatography on silica gel (solvent gradient: 0-20% ethyl acetate in petroleum ether) to afford the title compound as yellow oil (2 g, 31%). LCMS (ESI): [M+H]$^+$=398.

Step 3: Benzyl 3-(1-methoxy-2-methyl-1-oxopropan-2-yl)azetidine-1-carboxylate

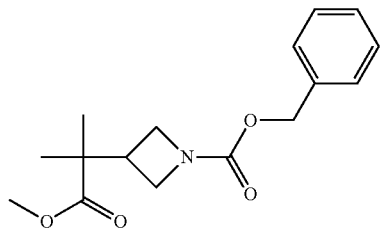 [SMILES: COC(=O)C(C)(C)C1CN(C(=O)OCc2ccccc2)C1]

To a solution of benzyl 3-(1-methoxy-2-methyl-1-oxopropan-2-yl)-3-(methylthiocarbonothioyloxy)azetidine-1-carboxylate (1 g, 2.52 mmol) in toluene (20 mL) was added tributylstannane (2.90 g, 10.0 mmol) and (E)-2,2'-(diazene-1,2-diyl)bis(2-methylpropanenitrile)(50.0 mg, 0.30 mmol). The reaction mixture was stirred for 1 h at 100° C., then quenched by the addition of water (50 mL), extracted with ethyl acetate (3×). The organic layers combined, washed with brine (30 mL), dried over anhydrous sodium sulfate, filtered and concentrated in vacuo. The residue was purified via flash chromatography on silica gel (solvent gradient: 0-20% ethyl acetate in petroleum ether) to afford the title compound (500 mg, 68%) as colorless oil. LCMS (ESI): [M+H]$^+$=292.

Step 4: Methyl 2-(azetidin-3-yl)-2-methylpropanoate hydrochloride

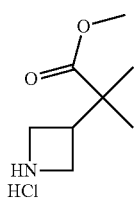

To a solution of benzyl 3-(1-methoxy-2-methyl-1-oxopropan-2-yl)azetidine-1-carboxylate (500 mg, 1.72 mmol) in methanol (5 mL) was added palladium hydroxide on C (50 mg, 20%). The reaction mixture was stirred overnight at room temperature under hydrogen atmosphere. The solids were removed by filtration and the filtrate was concentrated in vacuo, then treated with ether saturated with hydrogen chloride, stirred for 10 min at room temperature. The solids collected by filtration to afford the title compound (250 mg, 75%) as a white solid. LCMS (ESI): [M+H]$^+$=158.

Step 5: Methyl 2-(1-(6-chloro-1-isopropyl-1H-pyrazolo[4,3-c]pyridin-3-yl)azetidin-3-yl)-2-methylpropanoate

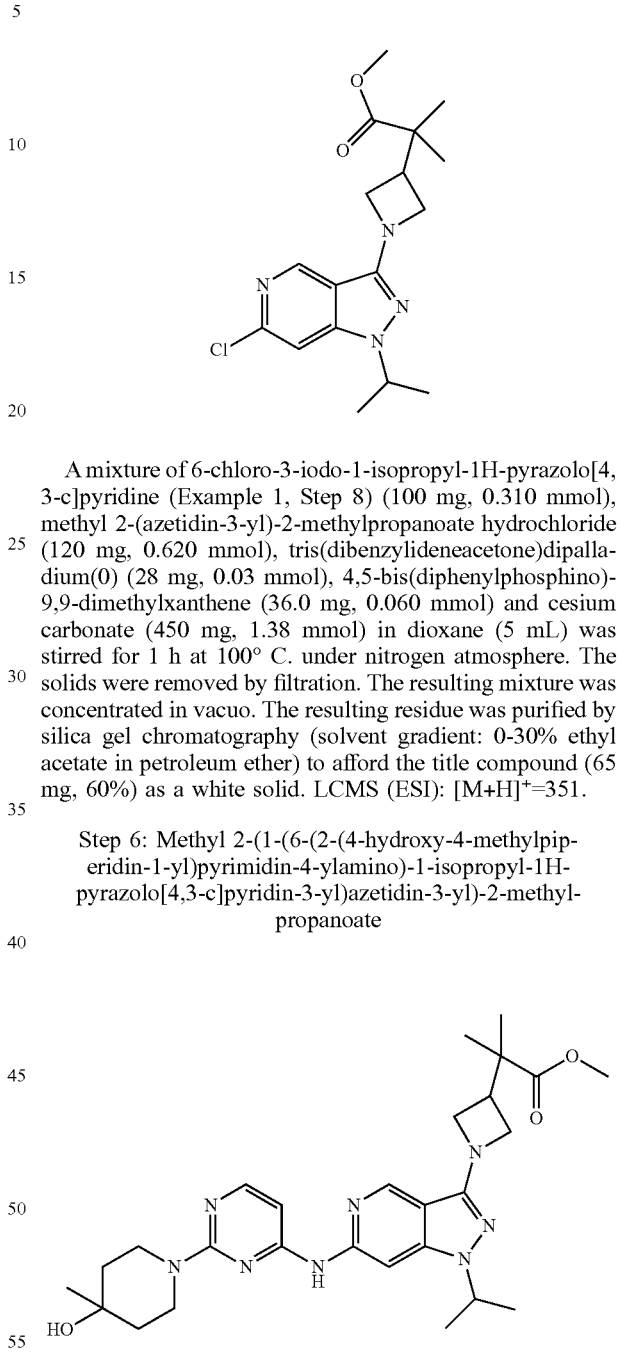

A mixture of 6-chloro-3-iodo-1-isopropyl-1H-pyrazolo[4,3-c]pyridine (Example 1, Step 8) (100 mg, 0.310 mmol), methyl 2-(azetidin-3-yl)-2-methylpropanoate hydrochloride (120 mg, 0.620 mmol), tris(dibenzylideneacetone)dipalladium(0) (28 mg, 0.03 mmol), 4,5-bis(diphenylphosphino)-9,9-dimethylxanthene (36.0 mg, 0.060 mmol) and cesium carbonate (450 mg, 1.38 mmol) in dioxane (5 mL) was stirred for 1 h at 100° C. under nitrogen atmosphere. The solids were removed by filtration. The resulting mixture was concentrated in vacuo. The resulting residue was purified by silica gel chromatography (solvent gradient: 0-30% ethyl acetate in petroleum ether) to afford the title compound (65 mg, 60%) as a white solid. LCMS (ESI): [M+H]$^+$=351.

Step 6: Methyl 2-(1-(6-(2-(4-hydroxy-4-methylpiperidin-1-yl)pyrimidin-4-ylamino)-1-isopropyl-1H-pyrazolo[4,3-c]pyridin-3-yl)azetidin-3-yl)-2-methylpropanoate A mixture of methyl 2-(1-(6-chloro-1-isopropyl-1H-pyrazolo[4,3-c]pyridin-3-yl)azetidin-3-yl)-2-methylpropanoate (130 mg, 0.37 mmol), 1-(4-aminopyrimidin-2-yl)-4-methylpiperidin-4-ol (Example 86, Step 2) (77.0 mg, 0.370 mmol), BrettPhos palladium(II) biphenyl-2-amine mesylate (34.0 mg, 0.0370 mmol), 2-(dicyclohexylphosphino)3,6-dimethoxy-2',4',6'-triisopropyl-1,1'-biphenyl (40.0 mg, 0.070 mmol) and cesium carbonate (302 mg, 0.930 mmol) in dioxane (7.5 mL) was stirred for 2 h at 120° C. under nitrogen atmosphere. The solids were removed by filtration. The resulting mixture was concentrated in vacuo. The residue was purified via flash chromatography on silica gel (solvent gradient: 0-5% methanol in dichloromethane) to afford the title compound (130 mg, 67%) as a white solid. LCMS (ESI): [M+H]⁺=523.

Step 7: 2-(1-(6-(2-(4-Hydroxy-4-methylpiperidin-1-yl)pyrimidin-4-ylamino)-1-isopropyl-1H-pyrazolo[4,3-c]pyridin-3-yl)azetidin-3-yl)-2-methylpropanamide

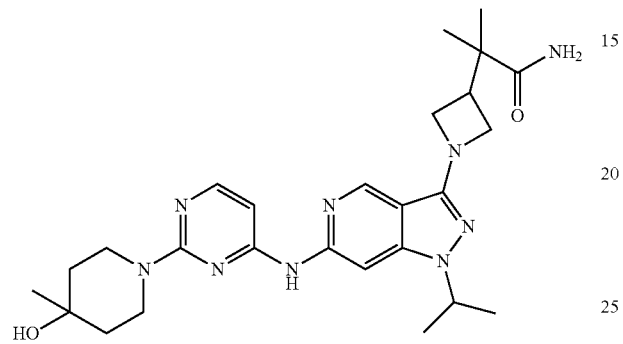

A mixture of 2-(1-(6-(2-(4-hydroxy-4-methylpiperidin-1-yl)pyrimidin-4-ylamino)-1-isopropyl-1H-pyrazolo[4,3-c]pyridin-3-yl)azetidin-3-yl)-2-methylpropanoate (100 mg, 0.19 mmol), sodium methanolate (200 mg, 3.70 mmol) and formamide (1 mL) in N,N-dimethylformamide (1 mL) was heated under microwave irradiation for 2 h at 120° C. The solids were removed by filtration and concentrated under vacuum. The residue was purified via reverse-phase HPLC and lyophilized to afford the title compound (38.6 mg, 40%) as a white solid. LCMS (ESI): [M+H]⁺=508.2, $R_T$(min)=2.91, method=R; ¹H NMR (300 MHz, DMSO-d₆): δ 9.82 (s, 1H), 8.54 (s, 1H), 8.15 (s, 1H), 7.96 (d, J=5.7 Hz, 1H), 7.10 (s, 1H), 6.88 (s, 1H), 6.32 (d, J=5.7 Hz, 1H), 4.52-4.47 (m, 1H), 4.38 (s, 1H), 4.21-4.16 (m, 2H), 4.10-4.05 (m, 2H), 3.93-3.89 (m, 2H), 3.51-3.41 (m, 2H), 3.11-2.98 (m, 1H), 1.55-1.47 (m, 4H), 1.41 (d, J=6.6 Hz, 6H), 1.16 (s, 3H), 1.13 (s, 9H).

Example 85: 1-(4-(3-(3,3-Difluoro-4-hydroxypyrrolidin-1-yl)-1-isopropyl-1H-pyrazolo[4,3-c]pyridin-6-ylamino)pyrimidin-2-yl)-4-methylpiperidin-4-ol

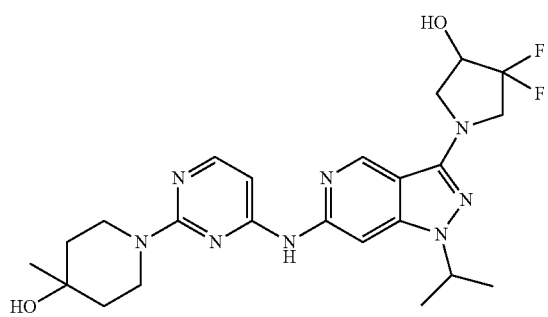 [SMILES: CC(C)n1nc(N2CC(O)C(F)(F)C2)c2cnc(Nc3ccnc(N4CCC(C)(O)CC4)n3)cc21]

Step 1: tert-Butyl 3-(benzyloxy)-4-hydroxypyrrolidine-1-carboxylate

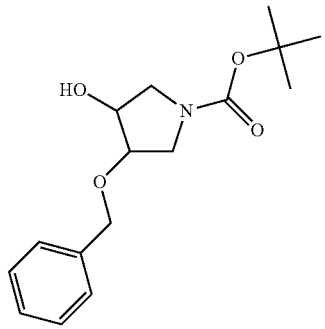 [SMILES: CC(C)(C)OC(=O)N1CC(O)C(OCc2ccccc2)C1]

A mixture of sodium (62.0 mg, 2.70 mmol) in phenylmethanol (6 g) was stirred for 40 min at 60° C., then treated with tert-butyl 6-oxa-3-azabicyclo[3.1.0]hexane-3-carboxylate (500 mg, 2.70 mmol). The solution was stirred for 12 h at 60° C., diluted with water, extracted with dichloromethane (3×) and the combined organic washes were dried over anhydrous sodium sulfate, filtered and concentrated in vacuo. The resulting residue was purified by silica gel chromatography (solvent gradient: 0-25% ethyl acetate in petroleum ether) to afford the title compound (300 mg, 38%) as a light yellow oil. LCMS (ESI): [M+H]⁺=293.

Step 2: tert-Butyl 3-(benzyloxy)-4-oxopyrrolidine-1-carboxylate

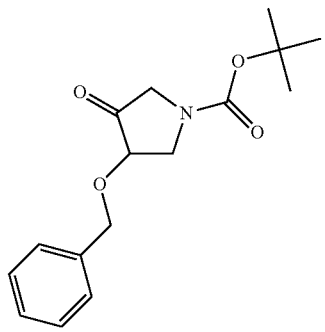 [SMILES: CC(C)(C)OC(=O)N1CC(=O)C(OCc2ccccc2)C1]

A mixture of tert-butyl 3-(benzyloxy)-4-hydroxypyrrolidine-1-carboxylate (4 g, 13.6 mmol) and (1,1,1-triacetoxy)-1,1-dihydro-1,2-benziodoxol-3(1H)-one (8.68 g, 20.5 mmol) in dichloromethane (15 mL) was stirred for 4 h at 25° C. The solution was diluted with saturated aqueous of sodium bisulfite (15 mL), extracted with dichloromethane (2×), dried over anhydrous sodium sulfate, filtered and concentrated in vacuo. The resulting residue was purified by silica gel chromatography (solvent gradient: 0-20% ethyl acetate in petroleum ether) to afford the title compound (3.5 g, 88%) as a yellow oil. LCMS (ESI): [M+H]⁺=291.

Step 3: tert-Butyl 4-(benzyloxy)-3,3-difluoropyrrolidine-1-carboxylate

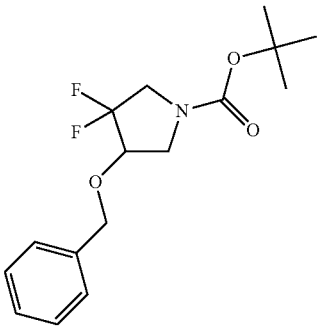 [SMILES: CC(C)(C)OC(=O)N1CC(OCc2ccccc2)C(F)(F)C1]

A solution of tert-butyl 3-(benzyloxy)-4-oxopyrrolidine-1-carboxylate (1.50 g, 5.15 mmol) and diethylaminosulfur trifluoride (3.30 g, 14.4 mmol) in 1,2-dichloroethane (20 mL) was stirred for 4 h at 70° C. The solution was diluted with saturated aqueous sodium bicarbonate (50 mL), extracted with dichloromethane (2×), dried over anhydrous sodium sulfate, filtered and concentrated in vacuo. The resulting residue was purified by silica gel chromatography (solvent gradient: 0-20% ethyl acetate in petroleum ether) to afford the title compound (1.2 g, 74%) as a yellow oil. LCMS (ESI): [M+H]$^+$=313.

Step 4: 4-(Benzyloxy)-3,3-difluoropyrrolidine Hydrochloride

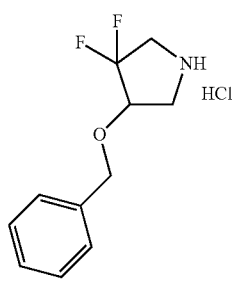 [SMILES: FC1(F)CNCC1OCc1ccccc1 ; Cl]

A solution of tert-butyl 4-(benzyloxy)-3,3-difluoropyrrolidine-1-carboxylate (200 mg, 0.640 mmol) in hydrogen chloride/ether (4 M, 0.8 mL) was stirred for 12 h at 25° C. The solution was concentrated in vacuo to afford the title compound (300 mg, 74%) as a black oil. LCMS (ESI): [M+H]$^+$=250.

Step 5: 3-(4-(Benzyloxy)-3,3-difluoropyrrolidin-1-yl)-6-chloro-1-isopropyl-1H-pyrazolo[4,3-c]pyridine

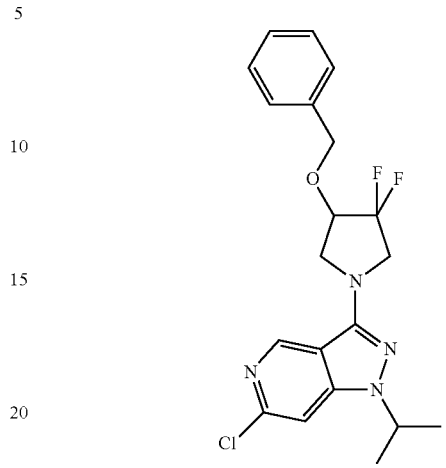

A mixture of 4-(benzyloxy)-3,3-difluoropyrrolidine hydrochloride (291 mg, 1.17 mmol), 6-chloro-3-iodo-1-isopropyl-1H-pyrazolo[4,3-c] pyridine (Example 1, Step 8) (150 mg, 0.460 mmol), tris(dibenzylideneacetone)dipalladium(0) (43.0 mg, 0.050 mmol), 4,5-bis(diphenylphosphino)-9,9-dimethylxanthene (54.0 mg, 0.090 mmol) and cesium carbonate (914 mg, 2.80 mmol) in 1,4-dioxane (7 mL) was stirred for 2 h at 100° C. under an atmosphere of nitrogen. The solution was filtered and the resulting solution was concentrated in vacuo. The resulting residue was purified by silica gel chromatography (solvent gradient: 0-20% ethyl acetate in petroleum ether) to afford the title compound (120 mg, 63%) as a brown solid. LCMS (ESI): [M+H]$^+$=407.

Step 6: 1-(4-(3-(4-(Benzyloxy)-3,3-difluoropyrrolidin-1-yl)-1-isopropyl-1H-pyrazolo[4,3-c]pyridin-6-ylamino)pyrimidin-2-yl)-4-methylpiperidin-4-ol

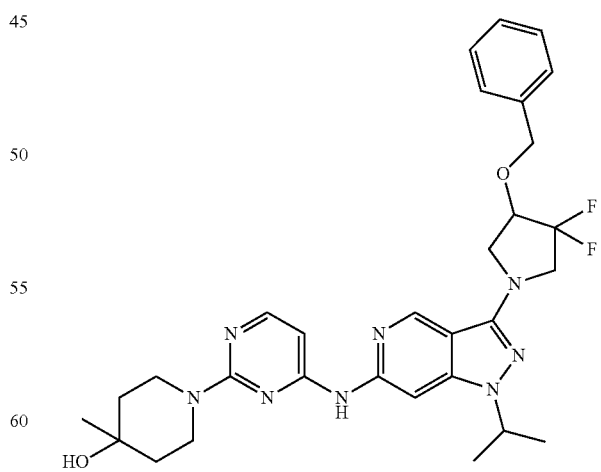

A mixture of 3-(4-(benzyloxy)-3,3-difluoropyrrolidin-1-yl)-6-chloro-1-isopropyl-1H-pyrazolo[4,3-c]pyridine (150 mg, 0.370 mmol), 1-(4-aminopyrimidin-2-yl)-4-methylpiperidin-4-ol (Example 86, Step 2) (77.0 mg, 0.370 mmol), BrettPhos palladium(II) biphenyl-2-amine mesylate (33.0 mg, 0.04 mmol), 2-(dicyclohexylphosphino)3,6-dimethoxy-2',4',6'-triisopropyl-1,1'-biphenyl (40.0 mg, 0.07 mmol) and cesium carbonate (240 mg, 0.740 mmol) in 1,4-dioxane (5 mL) was stirred for 1.5 h at 120° C. under an atmosphere of nitrogen. The solids were removed by filtration and the filtrate was concentrated in vacuo. The resulting residue was purified by silica gel chromatography (solvent gradient: 0-10% methanol in dichloromethane) to afford the title compound (120 mg, 56%) as a yellow solid. LCMS (ESI): [M+H]$^+$=579.

Step 7: 1-(4-(3-(3,3-Difluoro-4-hydroxypyrrolidin-1-yl)-1-isopropyl-1H-pyrazolo[4,3-c]pyridin-6-ylamino)pyrimidin-2-yl)-4-methylpiperidin-4-ol

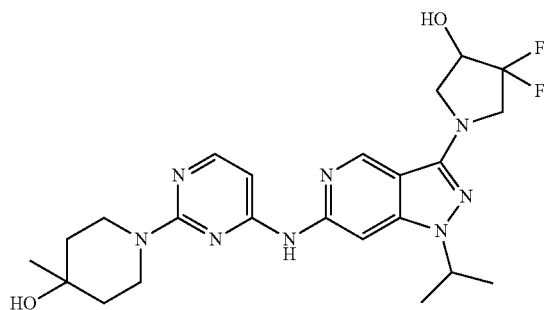 [SMILES: CC(C)n1nc(N2CC(O)C(F)(F)C2)c2cnc(Nc3ccnc(N4CCC(C)(O)CC4)n3)cc21]

A mixture of 1-(4-(3-(4-(benzyloxy)-3,3-difluoropyrrolidin-1-yl)-1-isopropyl-1H-pyrazolo[4,3-c]pyridin-6-ylamino)pyrimidin-2-yl)-4-methylpiperidin-4-ol (100 mg, 0.170 mmol) and dihydroxypalladium (50 mg) in methanol (3 mL) maintained with an inert atmosphere of hydrogen was stirred for 20 h at 25° C. The solids were removed by filtration and the filtrate was concentrated in vacuo. The resulting residue was purified via reverse-phase HPLC and lyophilized to afford the title compound (30 mg, 36%) as a white solid. LCMS (ESI): [M+H]$^+$=489. R$_T$ (min)=1.285, method=L; $^1$HNMR (300 MHz, DMSO-d$_6$): δ 9.83 (s, 1H), 8.76 (s, 1H), 8.16 (s, 1H), 7.96 (d, J=6.0 Hz, 1H), 6.33 (d, J=6.0 Hz, 1H), 6.10 (s, 1H), 4.54 (m, 1H), 4.38 (m, 2H), 4.21-4.16 (m, 2H), 4.02-3.94 (m, 3H), 3.47-3.46 (m, 3H), 1.51-1.41 (m, 10H), 1.16 (s, 3H).

Example 86: 4-Amino-1-(6-(2-(4-hydroxy-4-methylpiperidin-1-yl)pyrimidin-4-ylamino)-1-isopropyl-1H-pyrazolo[4,3-c]pyridin-3-yl)pyrrolidin-2-one

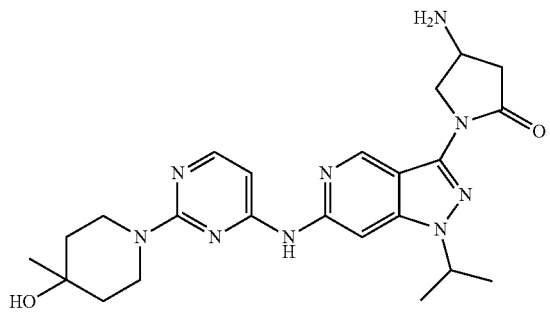 [SMILES: CC(C)n1nc(N2CC(N)CC2=O)c2cnc(Nc3ccnc(N4CCC(C)(O)CC4)n3)cc21]

Step 1: 4-Amino-1-(6-chloro-1-isopropyl-1H-pyrazolo[4,3-c]pyridin-3-yl)pyrrolidin-2-one

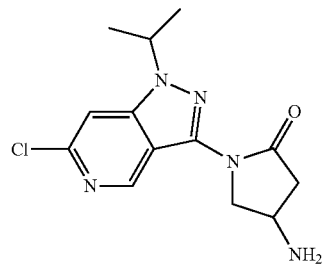 [SMILES: CC(C)n1nc(N2CC(N)CC2=O)c2cnc(Cl)cc21]

A mixture of 6-chloro-3-iodo-1-isopropyl-1H-pyrazolo[4,3-c]pyridine (100 mg, 0.310 mmol), 4-aminopyrrolidin-2-one hydrochloride (85.0 mg, 0.620 mmol), tris(dibenzylideneacetone)dipalladium(0) (28.5 mg, 0.030 mmol), 4,5-bis(diphenylphosphino)-9,9-dimethylxanthene (36.0 mg, 0.06 mmol) and cesium carbonate (304 mg, 0.930 mmol) in 1,4-dioxane (5 mL) was stirred for 5 h at 100° C. The solids were removed by filtration and the filtrate was concentrated in vacuo. The resulting residue was purified by silica gel chromatography (solvent gradient: 0-10% methanol in dichloromethane) to afford the title compound (48 mg, 53%) as a yellow solid. LCMS (ESI): [M+H]$^+$=294.

Step 2: 1-(4-Aminopyrimidin-2-yl)-4-methylpiperidin-4-ol

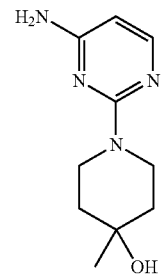

A mixture of 2-chloropyrimidin-4-amine (2 g, 15.4 mmol) and 4-methylpiperidin-4-ol (1.94 g, 16.8 mmol) in DMSO (20 mL) was stirred overnight at 100° C. The solution was diluted with water (100 mL), extracted with ethyl acetate (10×), dried over anhydrous sodium sulfate, filtered and concentrated in vacuo. The resulting residue was purified by silica gel chromatography (solvent gradient: 0-10% methanol in dichloromethane) to afford the title compound (1.9 g, 59%) as a yellow solid. LCMS (ESI): [M+H]$^+$=209.

Step 3: 4-Amino-1-(6-(2-(4-hydroxy-4-methylpiperidin-1-yl)pyrimidin-4-ylamino)-1-isopropyl-1H-pyrazolo[4,3-c]pyridin-3-yl)pyrrolidin-2-one

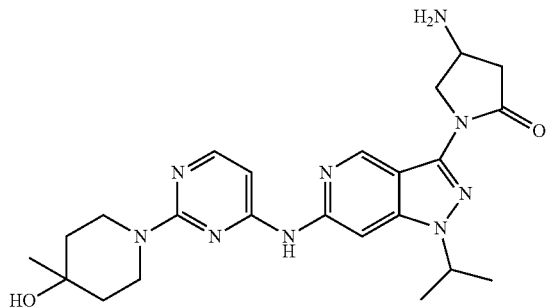 [SMILES: CC(C)n1nc(N2CC(N)CC2=O)c2cnc(Nc3ccnc(N4CCC(C)(O)CC4)n3)cc21]

A mixture of 4-amino-1-(6-chloro-1-isopropyl-1H-pyrazolo[4,3-c]pyridin-3-yl)pyrrolidin-2-one (40 mg, 0.140 mmol), 1-(4-aminopyrimidin-2-yl)-4-methylpiperidin-4-ol (28.3 mg, 0.140 mmol), BrettPhos palladium(II) biphenyl-2-amine mesylate (10.9 mg, 0.01 mmol), 2-(dicyclohexylphosphino)3,6-dimethoxy-2',4',6'-triisopropyl-1,1'-biphenyl (14.6 mg, 0.03 mmol) and cesium carbonate (113 mg, 0.410 mmol) in 1,4-dioxane (3 mL) was stirred for 1.5 h at 120° C. The solids were removed by filtration and the filtrate concentrated in vacuo. The resulting residue was purified by reverse-phase HPLC and lyophilized to afford the title compound (13.8 mg, 22%) as a off-white solid. LCMS (ESI): [M+H]$^+$=465.6, R$_T$ (min)=1.336, Method=R; $^1$H NMR (300 MHz, DMSO-d$_6$): δ 9.97 (s, 1H), 9.28 (s, 1H), 8.31 (s, 1H), 7.98 (d, J=5.7 Hz, 1H), 6.32 (d, J=5.7 Hz, 1H), 4.72-4.63 (m, 1H), 4.40 (s, 1H), 4.21 (d, J=13.2 Hz, 2H), 4.08-4.02 (m, 1H), 3.75-3.69 (m, 1H), 3.66-3.61 (m, 1H), 3.52-3.43 (m, 2H), 2.82-2.76 (m, 1H), 2.28-2.21 (m, 1H), 1.96 (s, 2H), 1.57-1.46 (m, 10H), 1.17 (s, 3H).

Example 87: 4-Methyl-1-[4-[(3-[2-oxa-6-azaspiro[3.3]heptan-6-yl]-1-(1,1,1-trifluoropropan-2-yl)-1H-pyrazolo[4,3-c]pyridin-6-yl)amino]pyrimidin-2-yl]piperidin-4-ol

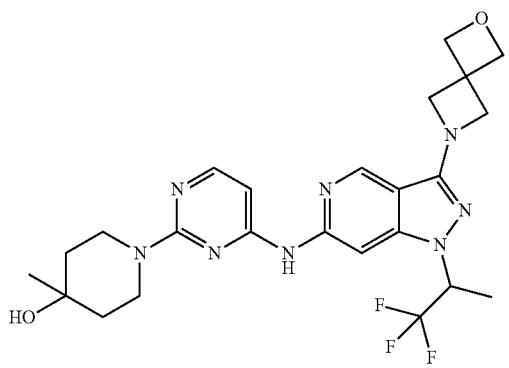 [SMILES: CC(n1nc(N2CC3(COC3)C2)c2cnc(Nc3ccnc(N4CCC(C)(O)CC4)n3)cc21)C(F)(F)F]

Step 1: 1,1,1-Trifluoropropan-2-yl 1,1,2,2,3,3,4,4,4-nonafluorobutane-1-sulfonate

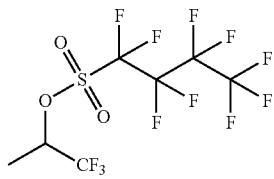 [SMILES: CC(OS(=O)(=O)C(F)(F)C(F)(F)C(F)(F)C(F)(F)F)C(F)(F)F]

1,1,2,2,3,3,4,4,4-Nonafluorobutane-1-sulfonyl fluoride (72.7 g, 241 mmol) was added dropwise to a pre-cooled solution at −40° C. of 1,1,1-trifluoropropan-2-ol (20 g, 175 mmol) and triethylamine (17.7 g, 175 mmol) in dichloromethane (200 mL). The resulting mixture was stirred overnight at room temperature. The solution was washed with water (300 mL) and the combined organic layers were dried over anhydrous sodium sulfate, filtered and concentrated in vacuo. The crude product was purified by distillation under reduced pressure (collected fraction at 35° C.) to afford the title compound (42 g, 60%) as a colorless liquid. $^1$H NMR (300 MHz, DMSO-d$_6$) δ 5.22-5.09 (m, 1H), 1.69-1.67 (m, 3H).

Step 2: 6-Chloro-3-iodo-1-(1,1,1-trifluoropropan-2-yl)-1H-pyrazolo[4,3-c]pyridine

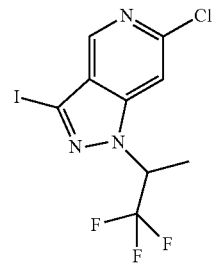 [SMILES: CC(n1nc(I)c2cnc(Cl)cc21)C(F)(F)F]

A mixture of 6-chloro-3-iodo-1H-pyrazolo[4,3-c]pyridine (Example 1, Step 7) (1.2 g, 4.29 mmol), 1,1,1-trifluoropropan-2-yl 1,1,2,2,3,3,4,4,4-nonafluorobutane-1-sulfonate (3.41 g, 8.61 mmol) and cesium carbonate (3.51 g, 10.8 mmol) in N,N-dimethylformamide (20 mL) was stirred 12 h at room temperature. The solution was diluted with water (100 mL) and extracted with ethyl acetate, dried over anhydrous sodium sulfate, filtered and concentrated in vacuo. The resulting residue was purified by silica gel chromatography (solvent gradient: 0-20% ethyl acetate in petroleum ether) to afford the title compound (1.1 g, 68%) as a white solid. LCMS (ESI): [M+H]$^+$=376.

Step 3: 6-[6-Chloro-1-(1,1,1-trifluoropropan-2-yl)-1H-pyrazolo[4,3-c]pyridin-3-yl]-2-oxa-6-azaspiro[3.3]heptanes

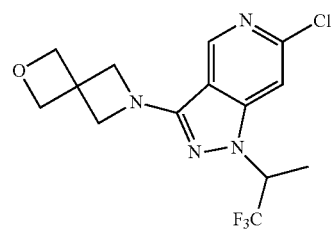 [SMILES: CC(n1nc(N2CC3(COC3)C2)c2cnc(Cl)cc21)C(F)(F)F]

A mixture of 6-chloro-3-iodo-1-(1,1,1-trifluoropropan-2-yl)-1H-pyrazolo[4,3-c]pyridine (400 mg, 1.07 mmol), 2-oxa-6-azaspiro[3.3]heptane (302 mg, 3.1 mmol), tris(dibenzylideneacetone)dipalladium(0) (97.5 mg, 0.11 mmol), 4,5-bis(diphenylphosphino)-9,9-dimethylxanthene (36.0 mg, 0.06 mmol) and cesium carbonate (123 mg, 0.21 mmol) in 1,4-dioxane (20 mL) was stirred for 5 h at 100° C. The solids were removed by filtration and the filtrate was Step 4: 4-Methyl-1-[4-[(3-[2-oxa-6-azaspiro[3.3] heptan-6-yl]-1-(1,1,1-trifluoropropan-2-yl)-1H-pyrazolo[4,3-c]pyridin-6-yl)amino]pyrimidin-2-yl]piperidin-4-ol

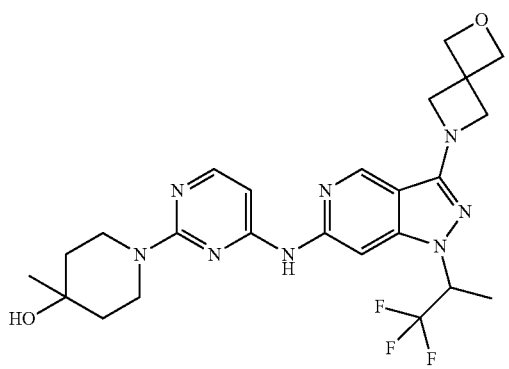 [SMILES: CC(n1nc(N2CC3(COC3)C2)c2cnc(Nc3ccnc(N4CCC(C)(O)CC4)n3)cc21)C(F)(F)F]

A mixture of 6-[6-chloro-1-(1,1,1-trifluoropropan-2-yl)-1H-pyrazolo[4,3-c]pyridin-3-yl]-2-oxa-6-azaspiro[3.3]heptanes (70.0 mg, 0.20 mmol), 1-(4-aminopyrimidin-2-yl)-4-methylpiperidin-4-ol (Example 86, step 2) (42.3 mg, 0.20 mmol), BrettPhos palladium(II) biphenyl-2-amine mesylate (18.3 mg, 0.02 mmol), 2-(dicyclohexylphosphino)3,6-dimethoxy-2',4',6'-triisopropyl-1,1'-biphenyl (21.7 mg, 0.04 mmol) and cesium carbonate (198 mg, 0.61 mmol) in 1,4-dioxane (5 mL) was stirred for 1.5 h at 120° C. The solids were removed by filtration and the filtrate was concentrated in vacuo. The resulting residue was purified by reverse-phase HPLC and lyophilized to afford the title compound (38.6 mg, 37%) as a off-white solid. LCMS (ESI): [M+H]$^+$=519, $R_T$ (min)=1.625, method=R; $^1$H NMR (300 MHz, DMSO-$d_6$): δ 9.90 (s, 1H), 8.60 (s, 1H), 8.23 (s, 1H), 7.97 (d, J=5.7 Hz, 1H), 6.31 (d, J=5.7 Hz, 1H), 5.32-5.18 (m, 1H), 4.74 (s, 4H), 4.36 (s, 1H), 4.30 (s, 4H), 4.18-4.12 (m, 2H), 3.46-3.42 (m, 2H), 1.68 (d, J=6.9 Hz, 3H), 1.49-1.42 (m, 4H), 1.14 (s, 3H).

Example 88: (±)-1-(6-(2-(cis-3-Fluoro-4-hydroxypiperidin-1-yl)pyrimidin-4-ylamino)-1-isopropyl-1H-pyrazolo[4,3-c]pyridin-3-yl)-4,4-dimethylimidazolidin-2-one

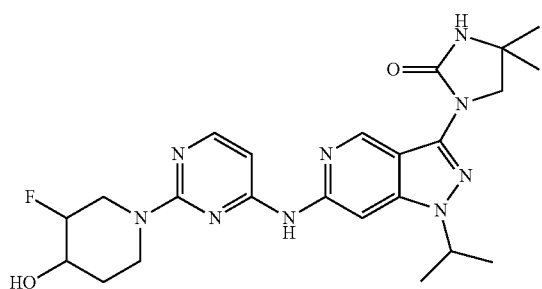 [SMILES: CC(C)n1nc(N2CC(C)(C)NC2=O)c2cnc(Nc3ccnc(N4CCC(O)C(F)C4)n3)cc21]

Step 1: 4,4-Dimethylimidazolidin-2-one

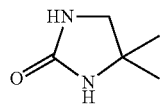

A mixture of 4,4-dimethylimidazolidin-2-one (5.70 g, 35.2 mmol) and 2-methylpropane-1,2-diamine (3.0 g, 34.0 mmol) in tetrahydrofuran (100 mL) was stirred overnight at 60° C. The reaction mixture was concentrated in vacuo to give a residue, which was purified by silica gel chromatography (solvent gradient: 0-10% methanol in dichloromethane) to afford the title compound (2 g, 51%) as a white solid. LCMS (ESI): [M+H]$^+$=115.

Step 2: 1-(6-Chloro-1-isopropyl-1H-pyrazolo[4,3-c]pyridin-3-yl)-4,4-dimethylimidazolidin-2-one

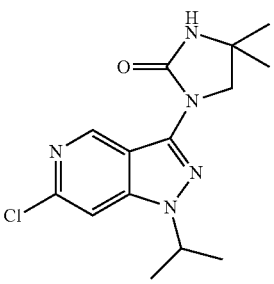 [SMILES: CC(C)n1nc(N2CC(C)(C)NC2=O)c2cnc(Cl)cc21]

A mixture of 6-chloro-3-iodo-1-isopropyl-1H-pyrazolo[4,3-c]pyridine (Example 1, Step 8) (300 mg, 0.930 mmol), 4,4-dimethylimidazolidin-2-one (324 mg, 2.84 mmol), tris(dibenzylideneacetone)dipalladium(0) (84 mg, 0.09 mmol), 4,5-bis(diphenylphosphino)-9,9-dimethylxanthene (108 mg, 0.190 mmol) and cesium carbonate (936 mg, 2.87 mmol) in dioxane (10 mL) was stirred for 40 min at 100° C. under nitrogen atmosphere. The solids were removed by filtration. The filtrate was concentrated in vacuo to give a residue, which was purified by silica gel chromatography (solvent gradient: 0-30% ethyl acetate in petroleum ether) to afford the title compound (150 mg, 52%) as a white solid. LCMS (ESI): [M+H]$^+$=308.

Step 3: (±)-1-(6-(2-(cis-3-Fluoro-4-hydroxypiperidin-1-yl)pyrimidin-4-ylamino)-1-isopropyl-1H-pyrazolo[4,3-c]pyridin-3-yl)-4,4-dimethylimidazolidin-2-one

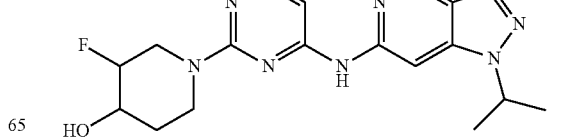

A mixture of 1-(6-chloro-1-isopropyl-1H-pyrazolo[4,3-c]pyridin-3-yl)-4,4-dimethylimidazolidin-2-one (100 mg, 0.320 mmol), (±)-1-(4-aminopyrimidin-2-yl)-cis-3-fluoropiperidin-4-ol (Example 20, Step 2) (67.0 mg, 0.320 mmol), chloro[2-(dicyclohexylphosphino)-3,6-dimethoxy-2'-4'-6'-tri-1-propyl-1,1'-biphenyl][2-(2-aminoethyl)phenyl]palladium(II)(26.0 mg, 0.032 mmol), 2-(dicyclohexylphosphino)3,6-dimethoxy-2',4',6'-triisopropyl-1,1'-biphenyl (35 mg, 0.06 mmol) and cesium carbonate (21.0 mg, 0.640 mmol) in 1,4-dioxane (8 mL) was stirred for 1 h at 120° C. under nitrogen atmosphere. The solids were removed by filtration and the filtrate was concentrated in vacuo. The residue was purified by silica gel chromatography (solvent gradient: 0-10% methanol in dichloromethane) to afford the title compound (77 mg, 49%) as a white solid. LCMS (ESI): [M+H]$^+$=484.2, R$_T$ (min)=1.598, method=R; $^1$H NMR (300 MHz, DMSO-d$_6$): δ 9.96 (s, 1H), 9.33 (s, 1H), 8.22 (s, 1H), 7.99 (d, J=5.7 Hz, 1H), 7.42 (s, 1H), 6.37 (d, J=5.7 Hz, 1H), 5.13 (d, J=5.7 Hz, 1H), 4.80-4.76 (m, 2H), 4.56-4.45 (m, 1H), 4.35-4.21 (m, 1H), 4.01-3.78 (m, 1H), 3.75-3.50 (m, 3H), 3.46-3.34 (m, 1H), 1.81-1.64 (m, 2H), 1.48-1.45 (m, 6H), 1.34 (s, 6H).

Example 89: 4-[1-(sec-Butyl)-6-[[2-(4-hydroxy-4-methylpiperidin-1-yl)pyrimidin-4-yl]amino]-1H-pyrazolo[4,3-c]pyridin-3-yl]-1-imino-4-thiomorpholin-1-one

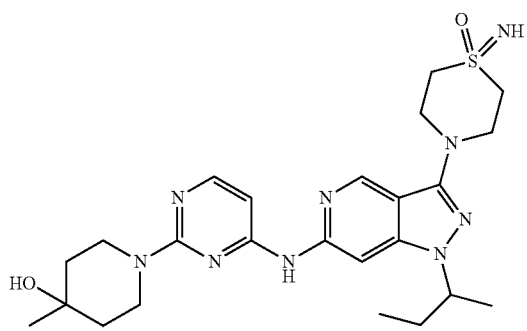 [SMILES: CCC(C)n1nc(N2CCS(=N)(=O)CC2)c2cnc(Nc3ccnc(N4CCC(C)(O)CC4)n3)cc21]

Step 1: 4-(1-sec-Butyl-6-chloro-1H-pyrazolo[4,3-c]pyridin-3-yl)thiomorpholine

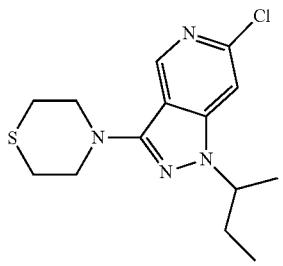 [SMILES: CCC(C)n1nc(N2CCSCC2)c2cnc(Cl)cc21]

A mixture of 1-sec-butyl-6-chloro-3-iodo-1H-pyrazolo[4,3-c]pyridine (Example 12, Step 1) (600 mg, 1.79 mmol), thiomorpholine (368 mg, 3.57 mmol), tris(dibenzylideneacetone)dipalladium(0) (163 mg, 0.180 mmol), 4,5-bis(diphenylphosphino)-9,9-dimethylxanthene (207 mg, 0.360 mmol) and cesium carbonate (1.75 g, 5.37 mmol) in 1,4-dioxane (15 mL) was stirred for 5 h at 100° C. The solids were removed by filtration and the filtrate was concentrated in vacuo. The resulting residue was purified by silica gel chromatography (solvent gradient: 0-20% ethyl acetate in petroleum ether) to afford the title compound (190 mg, 34%) as a yellow oil. LCMS (ESI): [M+H]$^+$=311.

Step 2: 4-(1-(sec-Butyl)-6-chloro-1H-pyrazolo[4,3-c]pyridin-3-yl)thiomorpholine-1-oxide

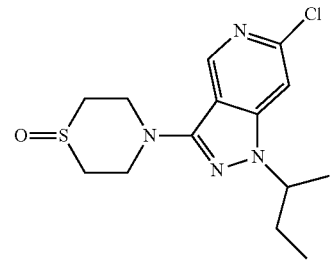 [SMILES: CCC(C)n1nc(N2CCS(=O)CC2)c2cnc(Cl)cc21]

A mixture of 4-(1-sec-butyl-6-chloro-1H-pyrazolo[4,3-c]pyridin-3-yl)thiomorpholine (180 mg, 0.58 mmol) and 3-chlorobenzoperoxoic acid (70.1 mg, 0.410 mmol) in dichloromethane (5 mL) was stirred for 1 h at 0° C. The solution was quenched with sodium hydrogencarbonate (10 mL), extracted with ethyl acetate, dried over anhydrous sodium sulfate, filtered and concentrated in vacuo. The resulting residue was purified by silica gel chromatography (solvent gradient: 0-10% methanol in dichloromethane) to afford the title compound (120 mg, 23%) as a yellow solid. LCMS (ESI): [M+H]$^+$=327.

Step 3: 4-[1-(sec-Butyl)-6-chloro-1H-pyrazolo[4,3-c]pyridin-3-yl]-1-imino-4-thiomorpholin-1-one

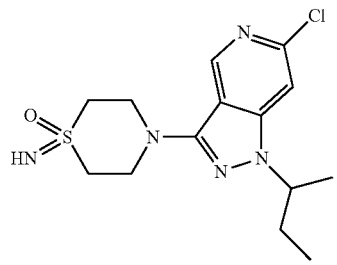 [SMILES: CCC(C)n1nc(N2CCS(=N)(=O)CC2)c2cnc(Cl)cc21]

A mixture of 4-(1-(sec-butyl)-6-chloro-1H-pyrazolo[4,3-c]pyridin-3-yl)thiomorpholine 1-oxide (120 mg, 0.370 mmol) and sodium azide (71.6 mg, 1.10 mmol) in polyphosphoric acid (2 mL) was stirred for 6 h at 60° C. The solution was quenched with sodium hydrogencarbonate (10 mL), extracted with ethyl acetate, dried over anhydrous sodium sulfate, filtered and concentrated in vacuo to afford the title compound (105 mg, 84%) as a yellow solid. LCMS (ESI): [M+H]$^+$=342.

Step 4: 4-[1-(sec-Butyl)-6-[[2-(4-hydroxy-4-methyl-piperidin-1-yl)pyrimidin-4-yl]amino]-1H-pyrazolo[4,3-c]pyridin-3-yl]-1-imino-4-thiomorpholin-1-one

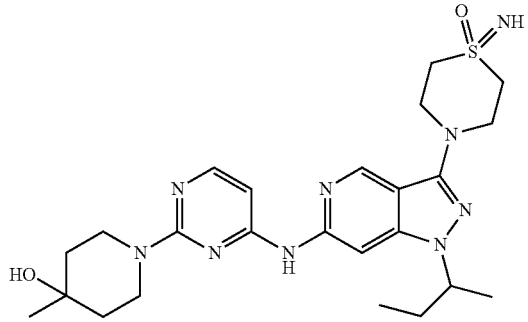 [SMILES: CCC(C)n1nc(N2CCS(=N)(=O)CC2)c2cnc(Nc3ccnc(N4CCC(C)(O)CC4)n3)cc21]

A mixture of 4-[1-(sec-Butyl)-6-chloro-1H-pyrazolo[4,3-c]pyridin-3-yl]-1-imino-4-thiomorpholin-1-one (100 mg, 0.290 mmol), 1-(4-aminopyrimidin-2-yl)-4-methylpiperidin-4-ol (Example 86, step 2) (61.1 mg, 0.290 mmol), BrettPhos palladium(II) biphenyl-2-amine mesylate (26.5 mg, 0.030 mmol), 2-(dicyclohexylphosphino)3,6-dimethoxy-2',4',6'-triisopropyl-1,1'-biphenyl (31.4 mg, 0.06 mmol) and cesium carbonate (286 mg, 0.880 mmol) in 1,4-dioxane (5 mL) was stirred for 1.5 h at 120° C. The solids were removed by filtration and the filtrate was concentrated in vacuo. The resulting residue was purified by reverse-phase HPLC and lyophilized to afford the title compound (12 mg, 8%) as a white solid. LCMS (ESI): [M+H]$^+$=513.7, R$_T$(min)=2.672, method=R; $^1$H NMR (300 MHz, DMSO-d$_6$): δ 9.89 (s, 1H), 9.85 (s, 1H), 8.23 (s, 1H), 7.97 (d, J=5.4 Hz, 1H), 6.32 (d, J=5.4 Hz, 1H), 4.41 (s, 1H), 4.27-4.18 (m, 3H) 4.03-3.98 (m, 2H), 3.83-3.75 (m, 3H), 3.50-3.44 (m, 2H), 3.22-3.12 (m, 4H), 2.02-1.89 (m, 1H), 1.88-1.71 (m, 1H), 1.51-1.41 (m, 7H), 1.16 (s, 3H), 0.73 (m, 3H).

Example 90: 1-(1-sec-Butyl-6-(2-(cis-5-fluoro-4-hydroxy-3,3-dimethylpiperidin-1-yl)pyrimidin-4-ylamino)-1H-pyrazolo[4,3-c]pyridin-3-yl)imidazolidin-2-one (Mixture of Diastereomers)

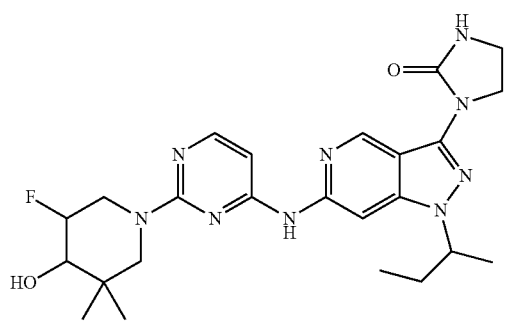 [SMILES: CCC(C)n1nc(N2CCNC2=O)c2cnc(Nc3ccnc(N4CC(F)C(O)C(C)(C)C4)n3)cc21]

Step 1: tert-Butyl 5,5-dimethyl-4-(trimethylsilyloxy)-5,6-dihydropyridine-1(2H)-carboxylate

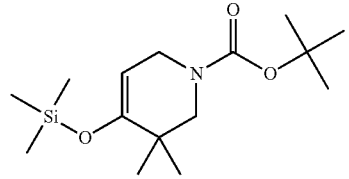 [SMILES: CC(C)(C)OC(=O)N1CC=C(O[Si](C)(C)C)C(C)(C)C1]

A solution of tert-butyl 3,3-dimethyl-4-oxopiperidine-1-carboxylate (7.35 g, 32.1 mmol) in toluene (150 mL) was cooled to 0° C. Triethylamine (13.1 g, 129 mmol) and trimethylsilyl trifluoromethanesulfonate (14.4 g, 64.6 mmol) were added and the reaction mixture stirred for 1 h at 0° C. under an atmosphere of nitrogen. The solution was diluted with water, extracted with ethyl acetate, washed with brine, dried over anhydrous sodium sulfate and concentrated in vacuo to afford the title compound (7.5 g, 77%) as a colorless oil. LCMS (ESI): [M+H]$^+$=300

Step 2: tert-Butyl 5-fluoro-3,3-dimethyl-4-oxopiperidine-1-carboxylate

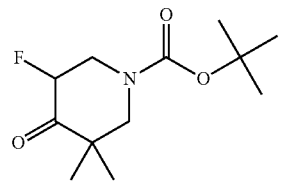 [SMILES: CC(C)(C)OC(=O)N1CC(F)C(=O)C(C)(C)C1]

A solution of tert-butyl 5,5-dimethyl-4-(trimethylsilyloxy)-5,6-dihydropyridine-1(2H)-carboxylate (7.50 g, 25.0 mmol) in acetonitrile (150 mL) was cooled to 0° C. and added 1-chloromethyl-4-fluoro-1,4-diazoniabicyclo[2,2,2]octane bis(tetrafluoroborate)(9.70 g, 27.4 mmol) and stirred for 1 h at 0° C. under an atmosphere of nitrogen. The solution was diluted with brine, extracted with ethyl acetate, washed with brine, dried over anhydrous sodium sulfate and concentrated in vacuo. The resulting residue was purified by silica gel chromatography (solvent gradient: 0-20% ethyl acetate in petroleum ether) to afford the title compound (1.4 g, 23%) as a white solid. LCMS (ESI): [M+H]$^+$=246.

Step 3: (±)-tert-Butyl-cis-5-fluoro-4-hydroxy-3,3-dimethylpiperidine-1-carboxylate

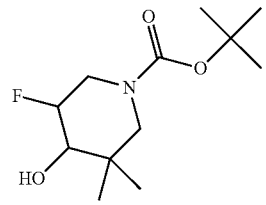 [SMILES: CC(C)(C)OC(=O)N1CC(F)C(O)C(C)(C)C1]

A solution of tert-butyl 5-fluoro-3,3-dimethyl-4-oxopiperidine-1-carboxylate (2.0 g, 8.15 mmol) in tetrahydrofuran (50 mL) was treated with L-selectride (17 mL, 1 M in THF) and stirred for 2 h at 0° C. The solution was quenched with NaOH (6M aqueous solution, 17 mL), extracted with ethyl acetate, washed with brine, dried over anhydrous sodium sulfate and concentrated in vacuo to afford the title compound (1.5 g, 75%) as a light yellow oil. LCMS (ESI): [M+H]$^+$=248.

Step 4: (±)-cis-5-Fluoro-3,3-dimethylpiperidin-4-ol hydrochloride

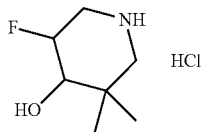

A solution of (±)-tert-butyl-cis-5-fluoro-4-hydroxy-3,3-dimethylpiperidine-1-carboxylate (3.2 g, 12.9 mmol) in ether (60 mL) was treated with hydrogen chloride in 1,4-dioxane (4 M, 20 mL) and stirred 15 h at room temperature. The solution was concentrated in vacuo to afford the title compound (1.36 g, 57%) as a white solid. LCMS (ESI): [M+H]$^+$=148.

Step 5: (±)-1-(4-Aminopyrimidin-2-yl)-cis-5-fluoro-3,3-dimethylpiperidin-4-ol

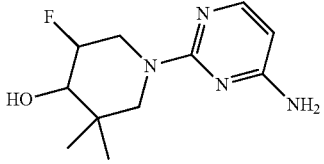 [SMILES: CC1(C)CN(c2nccc(N)n2)CC(F)C1O]

A mixture of (±)-cis-5-fluoro-3,3-dimethylpiperidin-4-ol hydrochloride (1.36 g, 7.39 mmol), 2-chloropyrimidin-4-amine (880 mg, 6.79 mmol) and potassium carbonate (2.81 g, 20.3 mmol) in DMSO (10 mL) was stirred for 48 h at 100° C. The solution was diluted with water (50 mL), extracted with ethyl acetate, washed with brine, dried over anhydrous sodium sulfate and concentrated in vacuo. The resulting residue was purified by silica gel chromatography (solvent gradient: 0-20% methanol in dichloromethane) to afford the title compound (700 mg, 43%) as a light yellow solid. LCMS (ESI): [M+H]$^+$=241.

Step 6: 1-(1-sec-Butyl-6-chloro-1H-pyrazolo[4,3-c]pyridin-3-yl)imidazolidin-2-one

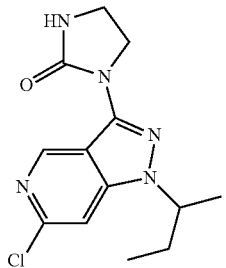 [SMILES: CCC(C)n1nc(N2CCNC2=O)c2cnc(Cl)cc21]

A mixture of imidazolidin-2-one (77.0 mg, 0.890 mmol), 1-(sec-butyl)-6-chloro-3-iodo-1H-pyrazolo[4,3-c]pyridine (Example 12, Step 1) (100 mg, 0.30 mmol), tris(dibenzylideneacetone)dipalladium(0) (27.5 mg, 0.030 mmol), 4,5-bis(diphenylphosphino)-9,9-dimethylxanthene (34.0 mg, 0.060 mmol) and cesium carbonate (194.5 mg, 0.60 mmol) in 1,4-dioxane (5 mL) was stirred for 14 h at 60° C. under an atmosphere of nitrogen. The solid was removed by filtration and the filtrate was concentrated in vacuo. The resulting residue was purified by silica gel chromatography (solvent gradient: 0-60% acetate in petroleum ether) to afford the title compound (50 mg, 57%) as a brown solid. LCMS (ESI): [M+H]$^+$=294.

Step 7: 1-(1-sec-Butyl-6-(2-(cis-5-fluoro-4-hydroxy-3,3-dimethylpiperidin-1-yl)pyrimidin-4-ylamino)-1H-pyrazolo[4,3-c]pyridin-3-yl)imidazolidin-2-one (Mixture of Diastereomers)

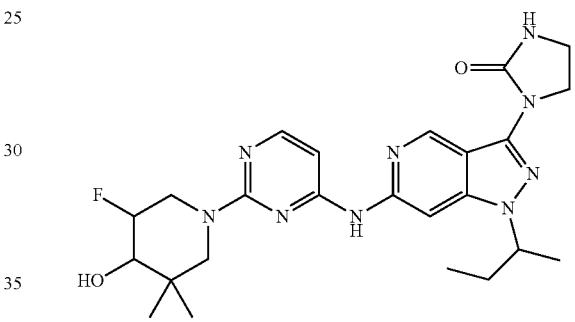

A mixture of 1-(1-sec-butyl-6-chloro-1H-pyrazolo[4,3-c]pyridin-3-yl)imidazolidin-2-one (62.7 mg, 0.210 mmol), (±)-1-(4-aminopyrimidin-2-yl)-cis-5-fluoro-3,3-dimethylpiperidin-4-ol (42.8 mg, 0.180 mmol), BrettPhos palladium (II) biphenyl-2-amine mesylate (16.0 mg, 0.180 mmol), 2-(dicyclohexylphosphino)3,6-dimethoxy-2',4',6'-triisopropyl-1,1'-biphenyl (19.0 mg, 0.04 mmol) and cesium carbonate (116 mg, 0.360 mmol) in 1,4-dioxane (3 mL) was stirred for 1.5 h at 120° C. under an atmosphere of nitrogen. The solids were removed by filtration and the filtrate was concentrated in vacuo. T The resulting residue was purified by reverse-phase HPLC and lyophilized to afford the title compound (22 mg, 21%) as a white solid as a mixture of diastereoisomers. LCMS (ESI): [M+H]$^+$=498, $R_T$ (min)=2.137, method=L; $^1$H NMR (300 MHz, DMSO-d$_6$): δ 9.98 (s, 1H), 9.32 (s, 1H), 8.22-8.21 (m, 1H), 7.97 (d, J=6 Hz, 1H), 7.21 (s, 1H), 6.36 (d, J=6 Hz, 1H), 5.28-5.08 (m, 1H), 4.92-4.61 (m, 1H), 4.50-4.31 (m, 1H), 4.30-4.09 (m, 1H), 4.08-3.88 (m, 3H), 3.85-3.66 (m, 1H), 3.58-3.47 (m, 4H), 2.10-1.90 (m, 1H), 1.90-1.71 (m, 1H), 1.49-1.38 (m, 3H), 0.95 (d, J=6 Hz, 6H), 0.73-0.68 (m, 3H).

Example 91: N-(2-(1-(Cyclopropylsulfonyl)-1H-pyrazol-4-yl)pyrimidin-4-yl)-3-(2,5-dimethylpyrrolidin-1-yl)-1-isopropyl-1H-pyrazolo[4,3-c]pyridin-6-amine

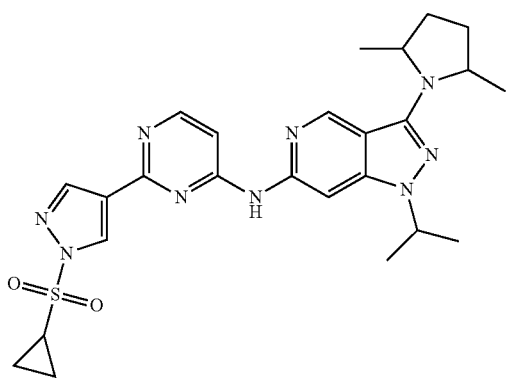 [SMILES: CC1CCC(C)N1c1nn(C(C)C)c2cc(Nc3ccnc(-c4cnn(S(=O)(=O)C5CC5)c4)n3)ncc12]

Step 1: 4,6-Dichloronicotinoyl Chloride

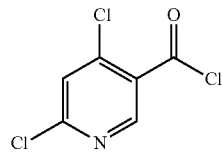 [SMILES: O=C(Cl)c1cnc(Cl)cc1Cl]

Oxalic dichloride (2.8 g, 22.1 mmol) was added dropwise to a pre-cooled mixture at 0° C. of 4,6-dichloronicotinic acid (1.40 g, 7.29 mmol) and N,N-dimethylformamide (0.10 mL, 1.29 mmol) in dichloromethane (20 mL). The resulting mixture was stirred for 3 h at room temperature. After the reaction was completed, the resulting mixture was concentrated in vacuo to afford the title compound (1.8 g) as a yellow solid, which was carried forward without purification.

Step 2: (4,6-Dichloropyridin-3-yl)(2,5-dimethylpyrrolidin-1-yl)methanone

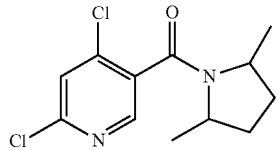 [SMILES: CC1CCC(C)N1C(=O)c1cnc(Cl)cc1Cl]

A solution of 4,6-dichloronicotinoyl chloride (1.8 g, crude) in dichloromethane (10 mL) was added dropwise to a mixture of 2,5-dimethylpyrrolidine hydrochloride (1.0 g, 7.37 mmol) and triethylamine (3.0 g, 29.6 mmol) in dichloromethane (30 mL) at 0° C. under a nitrogen atmosphere. The reaction mixture was stirred for 16 h at room temperature. The reaction was quenched with water (30 mL), extracted with dichloromethane, washed with brine, dried over anhydrous sodium sulfate and concentrated in vacuo. The resulting residue was purified by silica gel chromatography (solvent gradient: 0-20% ethyl acetate in petroleum ether) to afford the title compound (1.38 g, 69%) as a white solid. LCMS (ESI): [M+H]$^+$=273.

Step 3: (6-Chloro-4-hydrazinylpyridin-3-yl)(2,5-dimethylpyrrolidin-1-yl)methanone

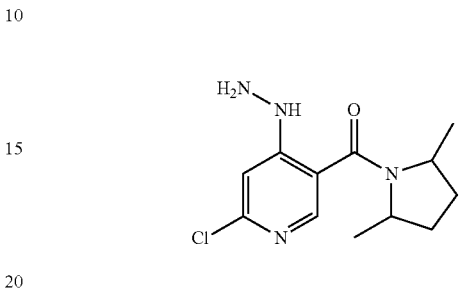

A mixture of (4,6-dichloropyridin-3-yl)(2,5-dimethylpyrrolidin-1-yl)methanone (1.38 g, 5.05 mmol) and hydrazine (4 g, 99.9 mmol, 80%) in methanol (15.0 mL) was stirred for 8 h at room temperature. The resulting mixture was diluted with water (40 mL), extracted with ethyl acetate, washed with brine, dried over anhydrous sodium sulfate, and concentrated in vacuo. The resulting residue was purified by silica gel chromatography (solvent gradient: 0-80% ethyl acetate in petroleum ether) to afford the title compound (400 mg, 29%) as a light yellow solid. LCMS (ESI): [M+H]$^+$=269.

Step 4: 6-Chloro-3-(2,5-dimethylpyrrolidin-1-yl)-1H-pyrazolo[4,3-c]pyridine

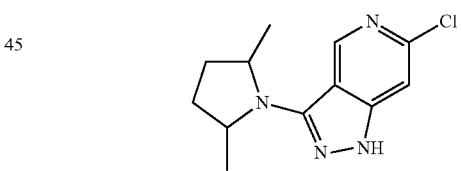

A mixture of (6-chloro-4-hydrazinylpyridin-3-yl)(2,5-dimethylpyrrolidin-1-yl)methanone (380 mg, 1.41 mmol) and phosphorus pentachloride (600 mg, 2.88 mmol) in toluene (10 mL) was stirred for 3 h at 120° C. The reaction mixture was cooled to room temperature and poured into water (50 mL). The mixture was filtered and the solids were dissolved in methanol:water (1:1, 20 mL). The pH value was adjusted to 7-8 with saturated sodium bicarbonate and extracted with dichloromethane (3×). The combined dichloromethane extracts were washed with brine, dried over anhydrous sodium sulfate and concentrated in vacuo. The residue was purified by silica gel chromatography (solvent gradient: 0-10% methanol in dichloromethane) to afford the title compound (130 mg, 37%) as a brown solid. LCMS (ESI): [M+H]$^+$=251.

Step 5: 6-Chloro-3-(2,5-dimethylpyrrolidin-1-yl)-1-isopropyl-1H-pyrazolo[4,3-c]pyridine

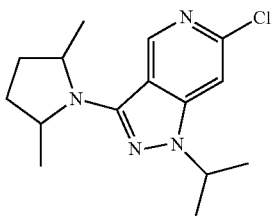 [SMILES: CC1CCC(C)N1c1nn(C(C)C)c2cc(Cl)ncc12]

A mixture of 6-chloro-3-(2,5-dimethylpyrrolidin-1-yl)-1H-pyrazolo[4,3-c]pyridine (120 mg, 0.480 mmol) and sodium hydride (30.0 mg, 0.75 mmol, 60% mineral oil) in N,N-dimethylformamide (5 mL) was stirred for 10 min at room temperature. 2-Iodopropane (177 mg, 1.04 mmol) was then added to the mixture and stirred for 4 h at room temperature. The reaction mixture was quenched with water (20 mL) and extracted with ethyl acetate, washed with brine, dried over anhydrous sodium sulfate and concentrated in vacuo. The residue was purified by silica gel chromatography (solvent gradient: 0-25% ethyl acetate in petroleum ether) to afford the title compound (70 mg, 50%) as a yellow oil. LCMS (ESI): $[M+H]^+=293$.

Step 6: N-(2-(1-(Cyclopropylsulfonyl)-1H-pyrazol-4-yl)pyrimidin-4-yl)-3-(2,5-dimethylpyrrolidin-1-yl)-1-isopropyl-1H-pyrazolo[4,3-c]pyridin-6-amine

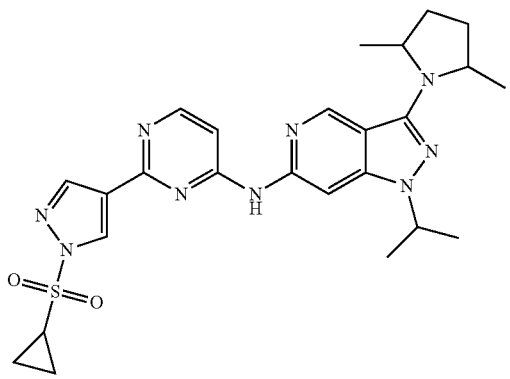 [SMILES: CC1CCC(C)N1c1nn(C(C)C)c2cc(Nc3ccnc(-c4cnn(S(=O)(=O)C5CC5)c4)n3)ncc12]

A mixture of 6-chloro-3-(2,5-dimethylpyrrolidin-1-yl)-1-isopropyl-1H-pyrazolo[4,3-c]pyridine (50.0 mg, 0.170 mmol), 2-(1-(cyclopropylsulfonyl)-1H-pyrazol-4-yl)pyrimidin-4-amine (Example 1, step 2) (45.0 mg, 0.170 mmol), tris(dibenzylideneacetone)dipalladium(0) (16.5 mg, 0.02 mmol), 4,5-bis(diphenylphosphino)-9,9-dimethylxanthene (20.0 mg, 0.0300 mmol) and cesium carbonate (165 mg, 0.510 mmol) in 1,4-dioxane (5 mL) was heated under microwave irradiation for 30 min at 160° C. The reaction mixture was cooled to room temperature and concentrated in vacuo. The residue was purified by silica gel chromatography (solvent gradient: 0-6% methanol in dichloromethane) to afford the title compound (12.2 mg, 14%) as a light yellow solid. LCMS (ESI): $[M+H]^+=522.1$, $R_T$ (min)=6.389, method=N; $^1$H NMR (400 MHz, DMSO-$d_6$): δ 10.26 (s, 1H), 8.69 (s, 1H), 8.63 (s, 1H), 8.48 (s, 1H), 8.41 (d, J=6.0 Hz, 1H), 8.23 (s, 1H), 7.17 (d, J=6.0 Hz, 1H), 4.72-4.65 (m, 1H), 4.08-4.07 (m, 2H), 3.33-3.27 (m, 1H), 2.08-2.06 (m, 2H), 1.74-1.73 (m, 2H), 1.46 (d, J=6.4 Hz, 6H), 1.37-1.36 (m, 8H), 1.28-1.26 (m, 2H).

Example 92: 4-(1-sec-Butyl-6-(2-(4-hydroxy-4-methylpiperidin-1-yl)pyrimidin-4-ylamino)-1H-pyrazolo[4,3-c]pyridin-3-yl)piperazin-2-one

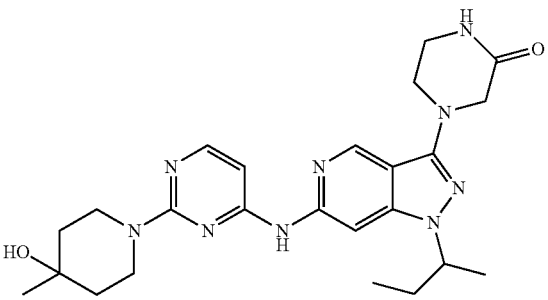 [SMILES: CCC(C)n1nc(N2CCNC(=O)C2)c2cnc(Nc3ccnc(N4CCC(C)(O)CC4)n3)cc21]

Step 1: $N^1$-(1-sec-Butyl-6-chloro-1H-pyrazolo[4,3-c]pyridin-3-yl)ethane-1,2-diamine

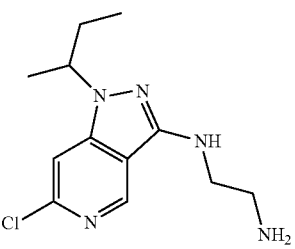 [SMILES: CCC(C)n1nc(NCCN)c2cnc(Cl)cc21]

A mixture of 1-sec-butyl-6-chloro-3-iodo-1H-pyrazolo[4,3-c]pyridine (Example 12, step 1) (300 mg, 0.890 mmol), ethane-1,2-diamine (540 mg, 8.99 mmol), copper (I) iodide (35.0 mg, 0.180 mmol), L-proline (21.0 mg, 0.180 mmol) and potassium carbonate (375 mg, 2.71 mmol) in dimethyl sulfoxide (10 mL) was heated under microwave irradiation for 90 min at 100° C. The reaction mixture was cooled to room temperature and diluted with water (50 mL). The resulting mixture was extracted with ethyl acetate, washed with brine, dried over anhydrous sodium sulfate and concentrated in vacuo to afford the title compound (200 mg, 86%) as yellow oil. LCMS (ESI): $[M+H]^+=268$.

Step 2: N-(2-(1-sec-Butyl-6-chloro-1H-pyrazolo[4,3-c]pyridin-3-ylamino)ethyl)-2-chloroacetamide

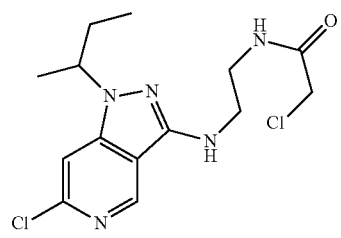 [SMILES: CCC(C)n1nc(NCCNC(=O)CCl)c2cnc(Cl)cc21]

2-Chloroacetyl chloride (110 mg, 0.970 mmol) was added dropwise to a mixture of N¹-(1-sec-butyl-6-chloro-1H-pyrazolo[4,3-c]pyridin-3-yl)ethane-1,2-diamine (250 mg, 0.930 mmol) and triethylamine (280 mg, 2.77 mmol) in dichloromethane (10 mL) at 0° C. under a nitrogen atmosphere. The resulting mixture was stirred for 2 h at room temperature and then concentrated in vacuo. The residue was purified by silica gel chromatography (solvent gradient: 0-30% ethyl acetate in petroleum ether) to afford the title compound (200 mg, 62%) as a yellow solid. LCMS (ESI): [M+H]⁺=344.

Step 3: 4-(1-sec-Butyl-6-chloro-1H-pyrazolo[4,3-c]pyridin-3-yl)piperazin-2-one

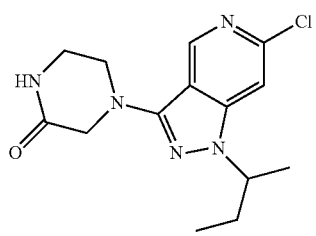 [SMILES: CCC(C)n1nc(N2CCNC(=O)C2)c2cnc(Cl)cc21]

A mixture of N-(2-(1-sec-butyl-6-chloro-1H-pyrazolo[4,3-c]pyridin-3-ylamino)ethyl)-2-chloroacetamide (300 mg, 0.870 mmol), sodium bicarbonate (300 mg, 3.57 mmol) and potassium iodide (150 mg, 0.90 mmol) in acetone (20 mL) was stirred for 48 h at 70° C. The reaction mixture was cooled to room temperature concentrated in vacuo. The residue was purified by silica gel chromatography (solvent gradient: 0-100% ethyl acetate in petroleum ether) to afford the title compound (55 mg, 21%) as a yellow solid. LCMS (ESI): [M+H]⁺=308.

Step 4: 4-(1-sec-Butyl-6-(2-(4-hydroxy-4-methylpiperidin-1-yl)pyrimidin-4-ylamino)-1H-pyrazolo[4,3-c]pyridin-3-yl)piperazin-2-one

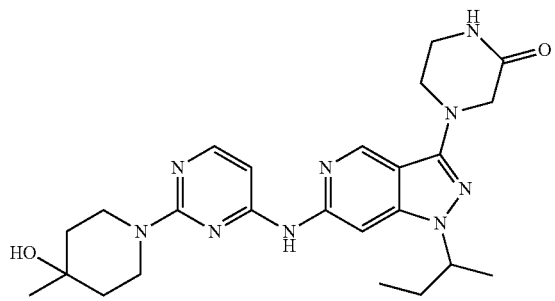 [SMILES: CCC(C)n1nc(N2CCNC(=O)C2)c2cnc(Nc3ccnc(N4CCC(C)(O)CC4)n3)cc21]

A mixture of 4-(1-sec-butyl-6-chloro-1H-pyrazolo[4,3-c]pyridin-3-yl)piperazin-2-one (45.0 mg, 0.150 mmol), 1-(4-aminopyrimidin-2-yl)-4-methylpiperidin-4-ol (Example 86, step 2) (30.4 mg, 0.150 mmol), 2-(dicyclohexylphosphino)3,6-dimethoxy-2',4',6'-triisopropyl-1,1'-biphenyl (15.7 mg, 0.030 mmol), BrettPhos palladium(II) biphenyl-2-amine mesylate (13.2 mg, 0.010 mmol) and cesium carbonate (95.3 mg, 0.290 mmol) in dioxane (3 mL) was stirred for 1.5 h at 120° C. The reaction mixture was cooled to room temperature and concentrated in vacuo. The residue was purified via reverse-phase HPLC and lyophilized to afford the title compound (16.2 mg, 23%) as a white solid. LCMS (ESI): [M+H]⁺=480, R_T (min)=1.470, method=R; ¹H NMR (300 MHz, DMSO-d₆): δ 9.89 (s, 1H), 8.85 (s, 1H), 8.21 (s, 1H), 8.03 (s, 1H), 7.96 (d, J=5.7 Hz, 1H), 6.31 (d, J=5.7 Hz, 1H), 4.40 (s, 1H), 4.22-4.17 (m, 3H), 3.95 (s, 2H), 3.67-3.64 (m, 2H), 3.48-3.44 (m, 2H), 3.36-3.32 (m, 2H), 1.93-1.91 (m, 2H), 1.51-1.40 (m, 7H), 1.16 (s, 3H), 0.74-0.70 (m, 3H).

Example 93: 6-(2-(1-(Cyclopropylsulfonyl)-1H-pyrazol-4-yl)pyrimidin-4-ylamino)-1-isopropyl-1H-pyrazolo[4,3-c]pyridine-3-carbonitrile

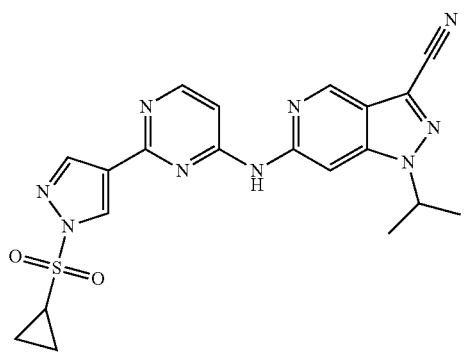 [SMILES: CC(C)n1nc(C#N)c2cnc(Nc3ccnc(-c4cnn(S(=O)(=O)C5CC5)c4)n3)cc21]

Step 1: 6-Chloro-1-isopropyl-1H-pyrazolo[4,3-c]pyridine-3-carbonitrile

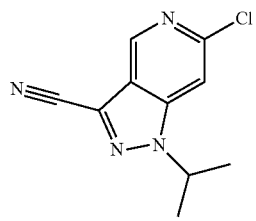

A mixture of 6-chloro-3-iodo-1-isopropyl-1H-pyrazolo[4,3-c]pyridine (Example 1, Step 8) (300 mg, 0.930 mmol), zinc cyanide (164 mg, 1.40 mmol) and tetrakis(triphenylphosphine)palladium (108 mg, 0.09 mmol) in N,N-dimethylformamide (4 mL) was stirred for 16 h at 100° C. under nitrogen atmosphere. The solids were removed by filtration and the filtrate was concentrated in vacuo. The residue was purified by silica gel chromatography (solvent gradient: 0-10% ethyl acetate in petroleum ether) to afford the title compound (62 mg, 30%) as a white solid. LCMS (ESI): [M+H]⁺=221.

Step 2: 6-(2-(1-(Cyclopropylsulfonyl)-1H-pyrazol-4-yl)pyrimidin-4-ylamino)-1-isopropyl-1H-pyrazolo[4,3-c]pyridine-3-carbonitrile

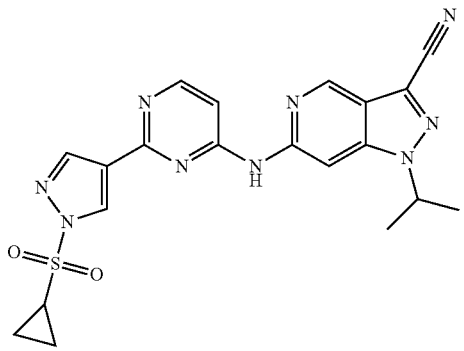 [SMILES: CC(C)n1nc(C#N)c2cnc(Nc3ccnc(-c4cnn(S(=O)(=O)C5CC5)c4)n3)cc21]

A mixture of 6-chloro-1-isopropyl-1H-pyrazolo[4,3-c]pyridine-3-carbonitrile (40 mg, 0.18 mmol), 2-[1-(cyclopropanesulfonyl)-1H-pyrazol-4-yl]pyrimidin-4-amine (Example 1, Step 2) (48 mg, 0.18 mmol), tris(dibenzylideneacetone)dipalladium(0) (16.6 mg, 0.020 mmol), 4,5-bis(diphenylphosphino)-9,9-dimethylxanthene (21 mg, 0.04 mmol) and cesium carbonate (356 mg, 1.09 mmol) in 1,4-dioxane (3 mL) was heated under microwave irradiation for 0.5 h at 160° C. The solids were removed by filtration. The filtrate was concentrated in vacuo. The resulting residue was purified by silica gel chromatography (solvent gradient: 0-10% methanol in dichloromethane) to afford the title compound (9.9 mg, 12%) as a white solid. LCMS (ESI): [M+H]$^+$=450, R$_T$(min)=2.091, method=N; $^1$H NMR (400 MHz, DMSO-d$_6$): δ 10.71 (s, 1H), 9.09 (s, 1H), 8.77 (s, 2H), 8.51 (s, 1H), 8.47 (d, J=6.0 Hz, 1H), 7.12 (d, J=6.0 Hz, 1H), 5.18-5.15 (m, 1H), 3.35 (m, 1H), 1.59 (d, J=6.4 Hz, 6H), 1.36-1.23 (m, 4H).

Example 94: 1-(4-(1-Isopropyl-3-(2-methyltetrahydrofuran-2-yl)-1H-pyrazolo[4,3-c]pyridin-6-ylamino)pyrimidin-2-yl)-4-methylpiperidin-4-ol

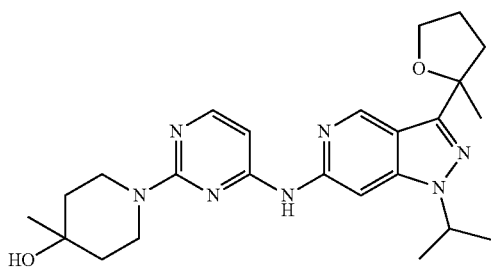 [SMILES: CC(C)n1nc(C2(C)CCCO2)c2cnc(Nc3ccnc(N4CCC(C)(O)CC4)n3)cc21]

Step 1: Ethyl 4-bromopent-4-enoate

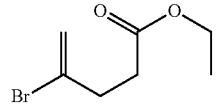

To a solution of ethyl acetate (3.52 g, 40.0 mmol) in tetrahydrofuran (100 mL) was added copper (I) iodide (15.2 g, 79.8 mmol). A solution of lithium diisopropylamide in tetrahydrofuran (1M. 40 mL) was then added dropwise with stirring at −80° C. under nitrogen atmosphere. The reaction mixture was warmed to −30° C. and a solution of 2,3-dibromoprop-1-ene (3.28 g, 16.4 mmol) in tetrahydrofuran (20 mL) was added dropwise. The reaction mixture was stirred for 1 h at −30° C. under nitrogen atmosphere, and then quenched by addition of saturated aqueous ammonia chloride (200 mL), extracted with ethyl acetate, dried over anhydrous sodium sulfate, filtered and concentrated in vacuo. The resultant residue was purified via flash chromatography on silica gel (solvent gradient: 0-10% ethyl acetate in petroleum ether) to afford the title compound (900 mg, 26%) as orange oil. $^1$H NMR (400 MHz, CDCl$_3$): δ 5.64 (s, 1H), 5.44 (s, 1H), 4.18-4.12 (m, 2H), 2.78-2.74 (m, 2H), 2.60-2.56 (m, 2H), 1.28-1.25 (m, 3H).

Step 2: Ethyl 4-(4,4,5,5-tetramethyl-1,3,2-dioxaborolan-2-yl)pent-4-enoate

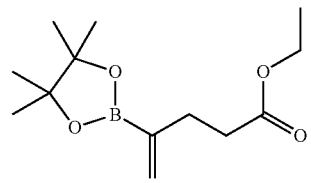 [SMILES: C=C(CCC(=O)OCC)B1OC(C)(C)C(C)(C)O1]

A mixture of ethyl 4-bromopent-4-enoate (500 mg, 2.41 mmol), 4,4,5,5-tetramethyl-2-(tetramethyl-1,3,2-dioxaborolan-2-yl)-1,3,2-dioxaborolane (740 mg, 2.91 mmol), dichlorobis(triphenyl-phosphine)palladium(II)(170 mg, 0.24 mmol) and triphenylphosphine (130 mg, 0.50 mmol) in toluene (10 mL) was stirred for 5 h at 50° C. under nitrogen atmosphere. The reaction mixture was concentrated in vacuo to give a residue, which was purified via flash chromatography on silica gel (solvent gradient: 0-10% ethyl acetate in petroleum ether) to afford the title compound as yellow oil (200 mg, 33%). $^1$H NMR (400 MHz, CDCl$_3$) δ 5.80 (s, 1H), 5.65 (s, 1H), 4.14-4.09 (m, 2H), 2.46 (s, 4H), 1.27-1.23 (m, 15H).

Step 3: Ethyl 4-(6-chloro-1-isopropyl-1H-pyrazolo[4,3-c]pyridin-3-yl)pent-4-enoate

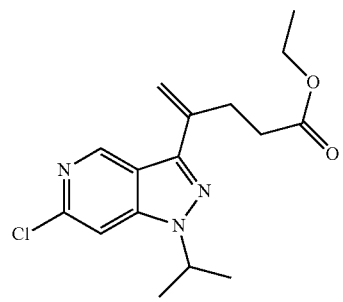 [SMILES: C=C(CCC(=O)OCC)c1nn(C(C)C)c2cc(Cl)ncc12]

A mixture of 6-chloro-3-iodo-1-isopropyl-1H-pyrazolo[4,3-c]pyridine (300 mg, 0.930 mmol), ethyl 4-(4,4,5,5-tetramethyl-1,3,2-dioxaborolan-2-yl)pent-4-enoate (300 mg, 1.18 mmol), [1,1'-bis(diphenylphosphino)ferrocene]dichloropalladium(II)(78.0 mg, 0.110 mmol) and potassium carbonate (400 mg, 2.89 mmol) in 1,4-dioxane (6 mL) and water (0.4 mL) was stirred for 2 h at 90° C. under nitrogen atmosphere. The solids were removed by filtration and the filtrate was concentrated in vacuo. The residue was purified via flash chromatography on silica gel (solvent gradient: 0-10% ethyl acetate in petroleum ether) to afford the title compound (80 mg, 27%) as a white solid. LCMS (ESI): [M+H]$^+$=322.

Step 4: Ethyl 4-(6-chloro-1-isopropyl-1H-pyrazolo[4,3-c]pyridin-3-yl)pent-4-enoate

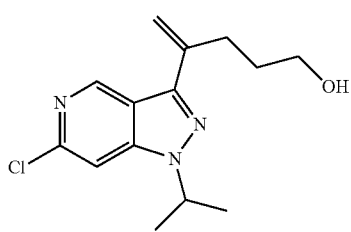 [SMILES: C=C(CCCO)c1nn(C(C)C)c2cc(Cl)ncc12]

To a suspension of aluminum(III) lithium hydride (29.0 mg, 0.760 mmol) in tetrahydrofuran (5 mL) was added a solution of ethyl 4-[6-chloro-1-isopropyl-1H-pyrazolo[4,3-c]pyridin-3-yl]pent-4-enoate (120 mg, 0.370 mmol) in tetrahydrofuran (0.5 mL) dropwise with stirring at 0° C. under nitrogen atmosphere. The reaction mixture was stirred for 5 min at 0° C., then quenched by the addition of water (90 mg), dried over anhydrous sodium sulfate, filtered and concentrated in vacuo. The residue was purified via flash chromatography on silica gel (solvent gradient: 0-50% ethyl acetate in petroleum ether) to afford the title compound (90 mg, 86%) as a white solid. LCMS (ESI): [M+H]$^+$=280.

Step 5: 6-Chloro-1-isopropyl-3-(2-methyl-tetrahydrofuran-2-yl)-1H-pyrazolo[4,3-c]pyridine

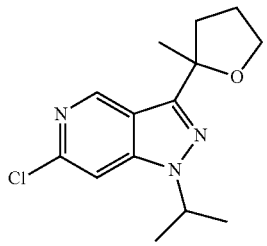 [SMILES: CC(C)n1nc(C2(C)CCCO2)c2cnc(Cl)cc21]

A mixture of 4-[6-chloro-1-isopropyl-1H-pyrazolo[4,3-c]pyridin-3-yl]pent-4-en-1-ol (100 mg, 0.360 mmol), tetrabutylammonium hexafluorophosphate(V)(14.0 mg, 0.04 mmol) and calcium bis(trifluoromethylsulfonyl)amide (22.4 mg, 0.036 mmol) in 1,2-dichloroethane (5 mL) was stirred 12 h at 80° C. The solids were removed by filtration. The filtrate was concentrated in vacuo. The residue was purified via flash chromatography on silica gel (solvent gradient: 0-25% ethyl acetate in petroleum ether) to afford the title compound as a white solid (40 mg, 40%). LCMS (ESI): [M+H]$^+$=280.

Step 5: 1-(4-(1-Isopropyl-3-(2-methyltetrahydrofuran-2-yl)-1H-pyrazolo[4,3-c]pyridin-6-ylamino)pyrimidin-2-yl)-4-methylpiperidin-4-ol

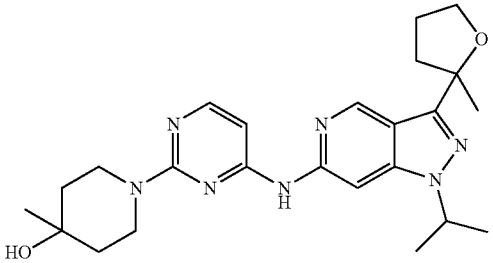 [SMILES: CC(C)n1nc(C2(C)CCCO2)c2cnc(Nc3ccnc(N4CCC(C)(O)CC4)n3)cc21]

A mixture of 6-chloro-1-isopropyl-3-(2-methyl-tetrahydrofuran-2-yl)-1H-pyrazolo[4,3-c]pyridine (60.0 mg, 0.210 mmol), 1-(4-aminopyrimidin-2-yl)-4-methylpiperidin-4-ol (Example 86, step 2) (44.4 mg, 0.210 mmol), BrettPhos palladium(II) biphenyl-2-amine mesylate (20.0 mg, 0.022 mmol), 2-(dicyclohexylphosphino)3,6-dimethoxy-2',4',6'-triisopropyl-1,1'-biphenyl (23.4 mg, 0.04 mmol) and cesium carbonate (174 mg, 0.530 mmol) in 1,4-dioxane (3 mL) was stirred for 1 h at 110° C. under nitrogen atmosphere. The solids were removed by filtration. The filtrate was concentrated in vacuo. The residue was purified via flash chromatography on silica gel (solvent gradient: 0-5% methanol in dichloromethane) to afford the title compound (33.7 mg, 35%) as a white solid. LCMS (ESI): [M+H]$^+$=452.2, R$_T$ (min)=1.954, Method=R; $^1$H NMR (300 MHz, DMSO-d$_6$): δ9.92 (s, 1H), 8.84 (s, 1H), 8.33 (s, 1H), 7.97 (d, J=5.7 Hz, 1H), 6.33 (d, J=5.7 Hz, 1H), 4.71-4.66 (m, 1H), 4.39 (s, 1H), 4.23-4.18 (m, 2H), 3.98-3.95 (m, 1H), 3.80-3.77 (m, 1H), 3.50-3.44 (m, 2H), 2.57-2.56 (m, 1H), 2.02-1.85 (m, 3H), 1.61 (s 3H), 1.58-1.45 (m, 10H), 1.18 (s, 3H).

Example 95: 4-(6-(2-(4-Hydroxy-4-methylpiperidin-1-yl)pyrimidin-4-ylamino)-1-isopropyl-1H-pyrazolo[4,3-c]pyridin-3-yl)-2,2-dimethyl-1,2-dihydroimidazol-5-one

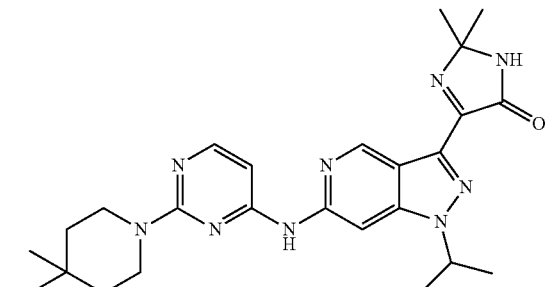

Step 1: Methyl 2-(6-chloro-1-isopropyl-1H-pyrazolo[4,3-c]pyridin-3-yl)-2-oxoacetate

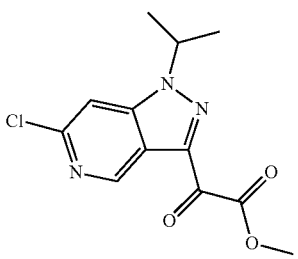 [SMILES: COC(=O)C(=O)c1nn(C(C)C)c2cc(Cl)ncc12]

A solution of isopropylmagnesium bromide (1 M in tetrahydrofuran, 1.9 mL) was added dropwise to a solution of 6-chloro-3-iodo-1-isopropyl-1H-pyrazolo[4,3-c]pyridine (400 mg, 1.24 mmol) in tetrahydrofuran (5 mL) at −30° C. under a nitrogen atmosphere, followed by addition of methyl 2-chloro-2-oxoacetate (1.04 g, 8.49 mmol) at −30° C. in 0.5 min. The resulting solution was stirred for 5 min at −30° C. then quenched by the addition of ammonium hydrochloride (aq. 20 mL). The resulting solution was extracted with ethyl acetate (4×) and dried over anhydrous sodium sulfate and concentrated in vacuo. The resulting residue was purified by silica gel chromatography (solvent gradient: 0-30% ethyl acetate in petroleum ether) to afford the title compound (270 mg, 77%) as a white solid. LCMS (ESI): [M+H]⁺=282.

Step 2: 4-(6-Chloro-1-isopropyl-1H-pyrazolo[4,3-c]pyridin-3-yl)-2,2-dimethyl-1,2-dihydroimidazol-5-one

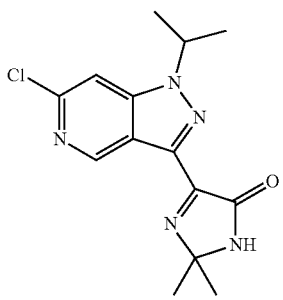 [SMILES: CC(C)n1nc(C2=NC(C)(C)NC2=O)c2cnc(Cl)cc21]

To a reaction vial was added methyl 2-(6-chloro-1-isopropyl-1H-pyrazolo[4,3-c]pyridin-3-yl)-2-oxoacetate (160 mg, 0.570 mmol), propan-2-one (1 mL, 13.6 mmol) and a solution of ammonia in methanol (7 M, 3 mL). The reaction was heated under microwave radiation for 1 h at 120° C. The reaction mixture was cooled to room temperature and concentrated in vacuo. The resulting residue was purified by silica gel chromatography (solvent gradient: 0-50% ethyl acetate in petroleum ether) to afford the title compound (67 mg, 39%) as a yellow solid. LCMS (ESI): [M+H]⁺=306.

Step 3: 4-(6-(2-(4-Hydroxy-4-methylpiperidin-1-yl)pyrimidin-4-ylamino)-1-isopropyl-1H-pyrazolo[4,3-c]pyridin-3-yl)-2,2-dimethyl-1,2-dihydroimidazol-5-one

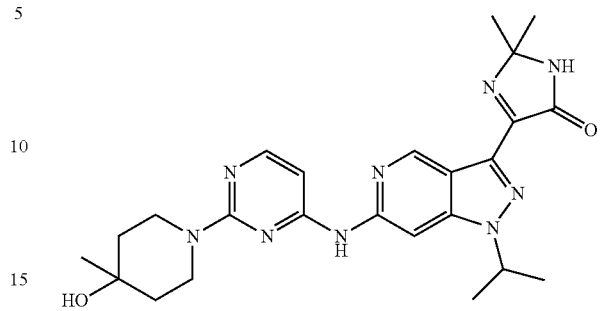

To a reaction vial was added 4-(6-chloro-1-isopropyl-1H-pyrazolo[4,3-c]pyridin-3-yl)-2,2-dimethyl-1,2-dihydroimidazol-5-one (60.0 mg, 0.20 mmol), 2-(dicyclohexylphosphino)3,6-dimethoxy-2',4',6'-triisopropyl-1,1'-biphenyl (21.1 mg, 0.0400 mmol), BrettPhos palladium(II) biphenyl-2-amine mesylate (17.8 mg, 0.02 mmol), cesium carbonate (192 mg, 0.590 mmol), 1-(4-aminopyrimidin-2-yl)-4-methylpiperidin-4-ol (Example 86, step 2) (49.2 mg, 0.240 mmol) and 1,4-dioxane (5 mL). The resulting solution was stirred for 1.5 h at 110° C. then cooled to room temperature and concentrated in vacuo. The resulting residue was purified by silica gel chromatography (solvent gradient: 0-50% methanol in dichloromethane) to afford the title compound (29.6 mg, 32%) as a white solid. LCMS (ESI): [M+H]⁺=478, $R_T$ (min)=2.216, Method=N; ¹H NMR (300 MHz, DMSO-d₆): δ 10.09 (s, 1H), 9.99 (s, 1H), 9.24 (s, 1H), 8.51 (s, 1H), 8.01-7.99 (d, J=5.7 Hz, 1H), 6.36-6.34 (d, J=5.7 Hz, 1H), 4.91-4.82 (m, 1H), 4.41 (s, 1H), 4.24-4.20 (m, 2H), 3.52-3.44 (m, 2H), 1.57-1.46 (m, 16H), 1.17 (s, 3H).

Each compound in Table 6 below was prepared following a similar experimental procedure (using appropriately substituted reagents) as described in another Example herein, such with the Example being referenced in the Synthesis Method column.

| Example | Structure/Name | Synthesis Method | LCMS $R_T$ (min), M + H⁺, method | ¹H NMR (ppm) |
|---|---|---|---|---|
| 96 | ![structure] [1-((R)-sec-Butyl)-3-(2-oxa-6-azaspiro[3.3]hept-6-yl)-1H-pyrazolo[4,3-c]pyridin-6-yl]-[2-(2-methanesulfonyl-2-methylpropoxy)pyrimidin-4-yl]amine (Mixture of enantiomers) | 71 | 3.01, 516.2, F | ¹H NMR (400 MHz, DMSO-d₆) δ 10.32 (1H, s), 8.59 (1H, d, J = 0.84 Hz), 8.17 (1H, d, J = 5.7 Hz), 8.05 (1H, br s), 6.94 (1H, d, J = 5.7 Hz), 4.75 (4H, br s), 4.51 (2H, dd, J = 11.0, 14.5 Hz), 4.29-4.21 (5H, m), 3.09 (3H, s), 1.92-1.69 (2H, m), 1.43, 1.42 (6H, 2 × s), 1.39 (3H, d, J = 6.6 Hz), 0.66 (3H, t, J = 7.4 Hz). |

| Example | Structure/Name | Synthesis Method | LCMS R$_T$ (min), M + H$^+$, method | $^1$H NMR (ppm) |
|---|---|---|---|---|
| 97 | [1-(sec-Butyl)-3-(2-oxa-6-azaspiro[3.3]hept-6-yl)-1H-pyrazolo[4,3-c]pyridin-6-yl]-[2-(2-methanesulfonyl-2-methylpropoxy)pyrimidin-4-yl]amine (Mixture of enantiomers) | 71 | 3.01, 516.2, F | $^1$H NMR (400 MHz, DMSO-d$_6$) δ 10.32 (1H, s), 8.59 (1H, d, J = 0.84 Hz), 8.17 (1H, d, J = 5.7 Hz), 8.05 (1H, br s), 6.94 (1H, d, J = 5.7 Hz), 4.75 (4H, br s), 4.51 (2H, dd, J = 11.0, 14.5 Hz), 4.29-4.21 (5H, m), 3.09 (3H, s), 1.92-1.69 (2H, m), 1.43, 1.42 (6H, 2 x s), 1.39 (3H, d, J = 6.6 Hz), 0.66 (3H, t, J = 7.4 Hz). |
| 98 | 1-{1-(sec-Butyl)-6-[2-((3R,4S)-3-fluoro-4-methoxypiperidin-1-yl)pyrimidin-4-ylamino]-1H-pyrazolo[4,3-c]pyridin-3-yl}imidazolidin-2-one (Mixture of diastereoisomers) | 26 | 2.94, 484.2, F | $^1$H NMR (400 MHz, DMSO-d$_6$) δ 9.95 (1H, s), 9.31 (1H, d, J = 0.88 Hz), 8.19 (1H, d, J = 2.2 Hz), 7.99 (1H, d, J = 5.7 Hz), 7.20 (1H, br s), 6.39 (1H, d, J = 5.7 Hz), 4.94 (1H, d, J = 49.0 Hz), 4.67-4.60 (1H, m), 4.41-4.33 (2H, m), 3.98-3.95 (2H, m), 3.65-3.47 (4H, m), 3.36 (3H, s), 2.02-1.89 (1H, m), 1.87-1.70 (4H, m), 1.45, 1.43 (3H, 2 x d, J = 6.6 Hz), 0.74, 0.73 (3H, 2 x t, J = 7.4 Hz). |
| 99 | 1-{1-sec-Butyl-6-[2-(2-methanesulfonyl-2-methylpropoxy)pyrimidin-4-ylamino]-1H-pyrazolo[4,3-c]pyridin-3-yl}imidazolidin-2-one (Mixture of enantiomers) | 22 71 | 3.07, 503.2, F | $^1$H NMR (400 MHz, DMSO-d$_6$) δ 10.36 (1H, s), 9.30 (1H, d, J = 0.87 Hz), 8.13 (1H, d, J = 5.7 Hz), 8.12 (1H, br s), 7.17 (1H, br s), 6.88 (1H, d, J = 5.7 Hz), 4.49 (2H, dd, J = 11.0, 14.5 Hz), 4.36-4.31 (1H, m), 3.92 (2H, t, J = 7.9 Hz), 3.47 (2H, t, J = 7.9 Hz), 3.06 (3H, s), 1.91-1.72 (2H, m), 1.39-1.38 (9H, m), 0.64 (3H, t, J = 7.2 Hz). |

-continued

| Example | Structure/Name | Synthesis Method | LCMS R$_T$ (min), M + H$^+$, method | $^1$H NMR (ppm) |
|---|---|---|---|---|
| 100 | N$^4$-(1-Isopropyl-3-morpholin-4-yl-1H-pyrazolo[4,3-c]pyridin-6-yl)-N$^2$-(2-methanesulfonyl-2-methylpropyl)pyrimidine-2,4-diamine | 20 | 2.81, 489.2, F | $^1$H NMR (400 MHz, DMSO-d$_6$) δ 9.81 (1H, s), 8.83 (1H, d, J = 0.87 Hz), 8.12 (1H, br s), 7.93 (1H, d, J = 5.7 Hz), 6.80 (1H, t, J = 6.6 Hz), 6.45 (1H, d, J = 5.7 Hz), 4.78-4.72 (1H, m), 3.82-3.77 (6H, m), 3.40-3.37 (4H, m), 2.98 (3H, s), 1.40 (6H, d, J = 6.6 Hz), 1.34 (6H, s). |
| 101 | 1-{1-sec-Butyl-6-[2-(2-methanesulfonyl-2-methylpropylamino)pyrimidin-4-ylamino]-1H-pyrazolo[4,3-c]pyridin-3-yl}imidazolidin-2-one (Mixture of enantiomers) | 22 | 2.74, 502.2, F | $^1$H NMR (400 MHz, DMSO-d$_6$) δ 9.84 (1H, s), 9.23 (1H, s), 8.20 (1H, br s), 7.94 (1H, d, J = 5.7 Hz), 7.18 (1H, br s), 6.80 (1H, t, J = 6.5 Hz), 6.46 (1H, d, J = 5.7 Hz), 4.60-4.55 (1H, m), 3.96 (2H, t, J = 7.9 Hz), 3.90-3.73 (2H, m), 3.52 (2H, t, J = 7.9 Hz), 2.98 (3H, s), 1.94-1.74 (2H, m), 1.44 (3H, d, J = 6.6 Hz), 1.36, 1.34 (6H, 2 x s), 0.70 (3H, t, J = 7.2 Hz). |
| 102 | 1-{1-sec-Butyl-6-[2-(4-methanesulfonylpiperidin-1-yl)pyrimidin-4-ylamino]-1H-pyrazolo[4,3-c]pyridin-3-yl}imidazolidin-2-one (Mixture of enantiomers) | 22 | 2.68, 514.3, F | $^1$H NMR (400 MHz, DMSO-d$_6$) δ 9.96 (1H, s), 9.32 (1H, d, J = 0.87 Hz), 8.17 (1H, br s), 8.02 (1H, d, J = 5.7 Hz), 7.20 (1H, br s), 6.42 (1H, d, J = 5.7 Hz), 4.86-4.82 (2H, m), 4.41-4.32 (1H, m), 3.97 (2H, t, J = 7.9 Hz), 3.52 (2H, t, J = 7.9 Hz), 3.48-3.40 (1H, m), 3.04-2.98 (2H, m), 2.95 (3H, s), 2.10-2.07 (2H, m), 2.02-1.77 (2H, m), 1.66-1.56 (2H,m), 1.44 (3H, d, J = 6.6 Hz), 0.74 (3H, t, J = 7.2 Hz). |

-continued

| Example | Structure/Name | Synthesis Method | LCMS R$_T$ (min), M + H$^+$, method | $^1$H NMR (ppm) |
|---|---|---|---|---|
| 103 | [2-((cis)-(±)-3-Fluoro-4-methoxypiperidin-1-yl)pyrimidin-4-yl]-[1-isopropyl-3-(2-oxa-6-azaspiro[3.3]hept-6-yl)-1H-pyrazolo[4,3-c]pyridin-6-yl]amine (mixture of enantiomers) | 23 | 2.70, 483.2, F | $^1$H NMR (400 MHz, DMSO-d$_6$) δ 8.46 (1H, d, J = 0.84 Hz), 8.05 (1H, d, J = 5.7 Hz), 7.40 (1H, br s), 7.26 (1H, s), 6.08 (1H, d, J = 5.7 Hz), 4.88 (4H, s), 4.86-4.72 (1H, m), 4.59-4.52 (1H, m), 4.46-4.40 (1H, m), 4.34 (4H, s), 4.15-4.10 (1H, m), 3.93-3.85 (1H, m), 3.71-3.61 (2H, m), 3.51 (3H, s), 2.07-1.77 (2H, m), 1.51 (6H, d, J = 6.7 Hz). |
| 104 | (3S*,4R*)-3-fluoro-1-(4-((3-(3-hydroxy-3-methylpyrrolidin-1-yl)-1-isopropyl-1H-pyrazolo[4,3-c]pyridin-6-yl)amino)pyrimidin-2-yl)piperidin-4-ol (mixture of diastereomers) | 8 | 3.256, 471.2, B | $^1$H NMR (400 MHz, DMSO-d$_6$) δ 9.90 (s, 1H), 8.70 (d, J = 1.0 Hz, 1H), 8.07 (s, 1H), 7.97 (d, J = 5.8 Hz, 1H), 6.38 (d, J = 5.7 Hz, 1H), 5.15 (d, J = 5.0 Hz, 1H), 4.80 (s, 1H), 4.77-4.61 (m, 1H), 4.56-4.42 (m, 2H), 4.26 (d, J = 13.4 Hz, 1H), 3.86 (d, J = 24.5 Hz, 1H), 3.73-3.53 (m, 3H), 3.52-3.42 (m, 2H), 3.42-3.37 (m, 1H), 1.97-1.86 (m, 2H), 1.77-1.65 (m, 2H), 1.41 (dd, J = 6.6, 3.0 Hz, 6H), 1.38 (s, 3H). |
| 105 | (3S*,4R*)-3-fluoro-1-(4-((3-((R)-3-hydroxypyrrolidin-1-yl)-1-isopropyl-1H-pyrazolo[4,3-c]pyridin-6-yl)amino)pyrimidin-2-yl)piperidin-4-ol (single diastereoisomer with absolute piperidine stereochemistry arbitrariliy assigned) | 8 | 3.099, 457.2, B | $^1$H NMR (400 MHz, DMSO-d$_6$) δ 9.87-9.79 (m, 1H), 8.71 (d, J = 0.9 Hz, 1H), 8.08 (s, 1H), 7.97 (d, J = 5.6 Hz, 1H), 6.38 (d, J = 5.7 Hz, 1H), 5.14 (d, J = 5.0 Hz, 1H), 4.96 (d, J = 3.7 Hz, 1H), 4.77-4.59 (m, 1H), 4.57-4.47 (m, 2H), 4.41 (s, 1H), 4.26 (d, J = 13.3 Hz, 1H), 3.94-3.77 (m, 1H), 3.72-3.50 (m, 5H), 3.46-3.39 (m, 1H), 2.09-1.99 (m, 1H), 1.95-1.85 (m, 1H), 1.77-1.63 (m, 2H), 1.46-1.39 (m, 6H). |

| Example | Structure/Name | Synthesis Method | LCMS R$_T$ (min), M + H$^+$, method | $^1$H NMR (ppm) |
|---|---|---|---|---|
| 106 | 1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)pyrrolidin-2-one | 72 | 2.189 508.3 S | $^1$H NMR (300 MHz, DMSO-d$_6$): δ 10.46 (s, 1H), 9.31 (s, 1H), 8.73 (s, 1H), 8.49 (s, 1H), 8.48 (s, 1H), 8.43 (d, J = 6.0 Hz, 1H), 7.10 (d, J = 6.0 Hz, 1H), 4.92-4.88 (m, 1H), 4.01-3.96 (m, 2H), 3.29-3.26 (m, 1H), 2.61-2.56 (m, 2H), 2.20-2.15 (m, 2H), 1.52 (d, J = 6.6 Hz, 6H), 1.36-1.33 (m, 2H), 1.30-1.25 (m, 2H). |
| 107 | 3-((6-((2-(1-(Cyclopropylsulfonyl)-1H-pyrazol-4-yl)pyrimidin-4-yl)amino)-1-isopropyl-1H-pyrazolo[4,3-c]pyridin-3-yl)amino)tetrahydrothiophene 1,1-dioxide | 74 | 1.828 558.30 S | $^1$H NMR (400 MHz, DMSO-d$_6$): δ 10.32 (s, 1H), 8.70 (d, J = 8.8 Hz, 2H), 8.47 (s, 1H), 8.41 (d, J = 6.0 Hz, 1H), 8.24 (s, 1H), 7.12 (d, J = 6.0 Hz, 1H), 6.92 (d, J = 6.0 Hz, 1H), 4.70-4.66 (m, 1H), 4.48-4.42 (m, 1H), 3.63-3.58 (m, 1H), 3.38-3.31 (m, 1H), 3.29-3.27 (m, 2H), 3.25-3.22 (m, 1H), 2.56-2.50 (m, 1H), 2.30-2.28 (m, 1H), 1.46 (d, J = 6.0 Hz, 6H), 1.36-1.33 (m, 2H), 1.29-1.25 (m, 2H). |

| Example | Structure/Name | Synthesis Method | LCMS R$_T$ (min), M + H$^+$, method | $^1$H NMR (ppm) |
|---|---|---|---|---|
| 108 | 1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-4-methylimidazolidin-2-one | 72 | 1.906 523.15 R | $^1$H NMR (400 MHz, DMSO-d$_6$): δ 10.42 (s, 1H), 9.37 (s, 1H), 8.72 (s, 1H), 8.49 (s, 1H), 8.42 (d, J = 5.6 Hz, 2H), 7.40 (s, 1H), 7.11 (d, J = 5.6 Hz, 1H), 4.91-4.79 (m, 1H), 4.15-4.10 (m, 1H), 3.97-3.85 (m, 1H), 3.59-3.51 (m, 1H), 3.27-3.23 (m, 1H), 1.50 (d, J = 6.4 Hz, 6H), 1.36-1.34 (m, 2H), 1.28-1.25 (m, 5H). |
| 109 | 2-(6-(2-(1-(Cyclopropylsulfonyl)-1H-pyrazol-4-yl)pyrimidin-4-ylamino)-1-isopropyl-1H-pyrazolo[4,3-c]pyridin-3-ylamino)propanamide | 74 | 1.364 511.25 L | $^1$H NMR (300 MHz, DMSO-d$_6$): δ 10.25 (s, 1H), 8.81 (s, 1H), 8.68 (s, 1H), 8.47 (s, 1H), 8.41-8.39 (m, 1H), 8.18 (s, 1H), 7.36 (s, 1H), 7.14-7.12 (m, 1H), 6.95 (s, 1H), 6.55-6.53 (m, 1H), 4.66-4.61 (m, 1H), 4.23-4.18 (m, 1H), 3.29-3.26 (m, 1H), 1.45-1.42 (m, 6H), 1.40-1.30 (m, 5H), 1.30-1.25 (m, 2H). |
| 110 | 4-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)thiomorpholine 1-oxide | 73 | 2.647 542.15 L | $^1$H NMR (300 MHz, DMSO-d$_6$): δ 10.39 (s, 1H), 8.93 (s, 1H), 8.71 (s, 1H), 8.48 (s, 1H), 8.42 (d, J = 6.0 Hz, 1H), 8.36 (s, 1H), 7.12 (d, J = 6.0 Hz, 1H), 4.81-4.72 (m, 1H), 3.97-3.84 (m, 4H), 3.31-3.25 (m, 1H), 3.11-3.03 (m, 2H), 2.85-2.75 (m, 2H), 1.49 (d, J = 6.6 Hz, 6H), 1.39-1.32 (m, 4H). |

-continued

| Example | Structure/Name | Synthesis Method | LCMS R_T (min), M + H+, method | 1H NMR (ppm) |
|---|---|---|---|---|
| 111 | 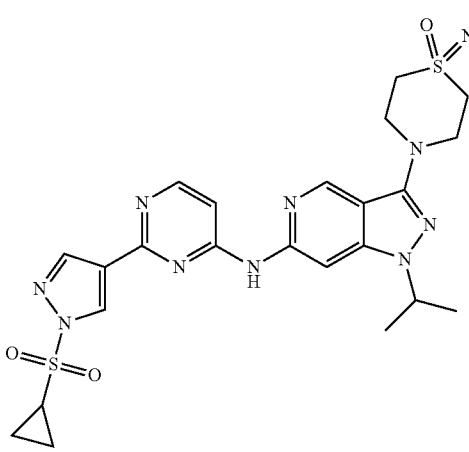<br>4-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)-1-iminothiomorpholine 1-oxide | 73 | 1.595 557.15 R | 1H NMR (300 MHz, DMSO-d6): δ 10.40 (s, 1H), 8.91 (s, 1H), 8.71 (s, 1H), 8.48 (s, 1H), 8.42 (d, J = 6.0 Hz, 1H), 8.37 (s, 1H), 7.13 (d, J = 6.0 Hz, 1H), 4.81-4.72 (m, 1H), 4.05-4.00 (m, 2H), 3.84-3.75 (m, 3H), 3.29-3.27 (m, 1H), 3.20-3.10 (m, 4H), 1.49 (d, J = 6.6 Hz, 6H), 1.39-1.30 (m, 4H). |
| 112 | 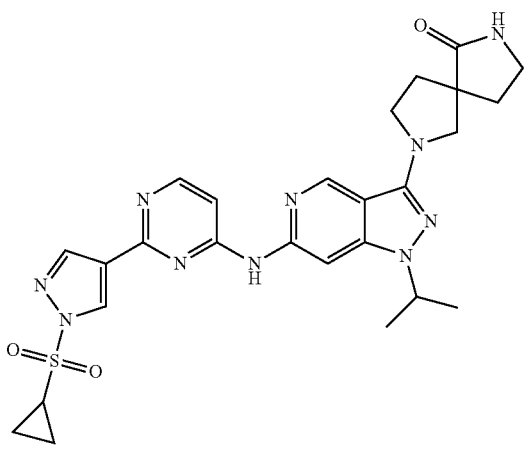 [SMILES: CC(C)n1nc(N2CCC3(CCNC3=O)C2)c2cnc(Nc3ccnc(-c4cnn(S(=O)(=O)C5CC5)c4)n3)cc21]<br>7-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)-2,7-diazaspiro[4.4]nonan-1-one | 73 | 2.635 563.15 R | 1H NMR (300 MHz, DMSO-d6): δ 10.31 (s, 1H), 8.78 (s, 1H), 8.70 (s, 1H), 8.48 (s, 1H), 8.41 (m, 1H), 8.26 (s, 7.80 (s, 1H), 7.14 (s, 1H), 4.79-4.60 (m, 1H), 3.89-3.58 (m, 4H), 3.29-3.24 (m, 3H), 2.21-1.89 (m, 4H), 1.47 (d, J = 6.6 Hz, 6H), 1.35-1.25 (m, 4H). |

-continued

| Example | Structure/Name | Synthesis Method | LCMS R_T (min), M + H+, method | 1H NMR (ppm) |
|---|---|---|---|---|
| 113 | 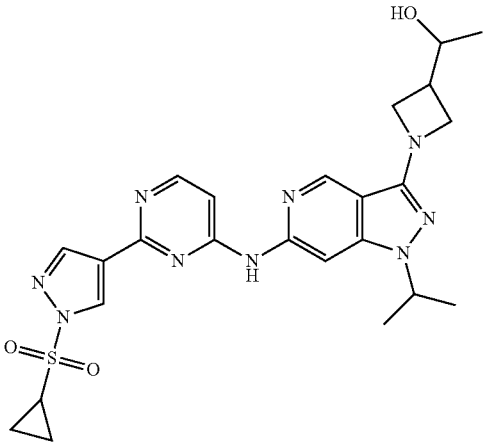 [SMILES: CC(O)C1CN(c2nn(C(C)C)c3cc(Nc4ccnc(-c5cnn(S(=O)(=O)C6CC6)c5)n4)ncc23)C1]<br>1-(1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)azetidin-3-yl)ethanol | 73 | 1.474<br>524.15<br>L | $^1$H NMR (300 MHz, DMSO-d$_6$): δ 10.30 (s, 1H), 8.69 (s, 1H), 8.60 (s, 1H), 8.48 (s, 1H), 8.41 (d, J = 6.0 Hz, 1H), 8.27 (s, 1H), 7.14 (d, J = 6.0 Hz, 1H), 4.74-4.67 (m, 2H), 4.14-4.08 (m, 2H), 4.01-3.97 (m, 1H), 3.88-3.78 (m, 2H), 3.30-3.26 (m, 1H), 2.76-2.71 (m, 1H), 1.47 (d, J = 6.6 Hz, 6H), 1.39-1.30 (m, 2H), 1.30-1.23 (m, 2H), 1.06 (d, J = 6.0 Hz, 3H). |
| 114 | 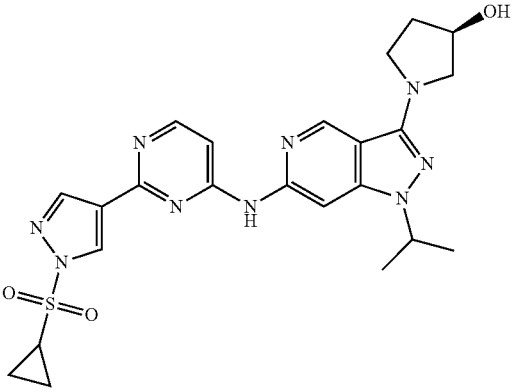 [SMILES: CC(C)n1nc(N2CC[C@@H](O)C2)c2cnc(Nc3ccnc(-c4cnn(S(=O)(=O)C5CC5)c4)n3)cc21]<br>(R)-1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)pyrrolidin-3-ol | 73 | 1.504<br>510.20<br>M | $^1$H NMR (400 MHz, DMSO-d$_6$): δ 10.30 (s, 1H), 8.76 (s, 1H), 8.70 (s, 1H), 8.47 (s, 1H), 8.41 (d, J = 5.6 Hz, 1H), 8.24 (s, 1H), 7.14 (d, J = 5.6 Hz, 1H), 4.96 (s, 1H), 4.72-4.67 (m, 1H), 4.46-4.40 (m, 1H), 3.72-3.62 (m, 3H), 3.45-3.43 (m, 1H), 3.29-3.27 (m, 1H), 2.08-2.04 (m, 1H), 1.94-1.90 (m, 1H), 1.47 (d, J = 6.0 Hz, 6H), 1.38-1.33 (m, 2H), 1.31-1.24 (m, 2H). |

| Example | Structure/Name | Synthesis Method | LCMS R_T (min), M + H+, method | ¹H NMR (ppm) |
|---|---|---|---|---|
| 115 | 7-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)-2,7-diazaspiro[4.4]nonan-3-one | 73 | 2.175 563.25 M | ¹H NMR (400 MHz, DMSO-d₆): δ 10.32 (s, 1H), 8.77 (s, 1H), 8.70 (s, 1H), 8.48 (s, 1H), 8.41 (d, J = 6.0 Hz, 1H), 8.25 (s, 1H), 7.68 (s, 1H), 7.13 (d, J = 6.0 Hz, 1H), 4.75-4.65 (m, 1H), 3.71-3.68 (m, 2H), 3.59-3.54 (m, 2H), 3.30-3.20 (m, 3H), 2.38-2.22 (m, 2H), 2.08-1.97 (m, 2H), 1.46 (d, J = 6.8 Hz, 6H), 1.35-1.34 (m, 2H), 1.28-1.26 (m, 2H). |
| 116 | N-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-2-hydroxy-2-methylpropanamide | 72 | 2.240 526.15 M | ¹H NMR (400 MHz, DMSO-d₆): δ 10.50 (s, 1H), 9.96 (s, 1H), 9.07 (s, 1H), 8.74 (s, 1H), 8.51-8.42 (m, 3H), 7.10-7.08 (m, 1H), 5.83 (s, 1H), 4.93-4.89 (m, 1H), 3.32-3.26 (m, 1H), 1.52 (d, J = 6.4 Hz, 6H), 1.43 (s, 6H), 1.37-1.35 (m, 2H), 1.28-1.26 (m, 2H). |

| Example | Structure/Name | Synthesis Method | LCMS R$_T$ (min), M + H$^+$, method | $^1$H NMR (ppm) |
|---|---|---|---|---|
| 117 | 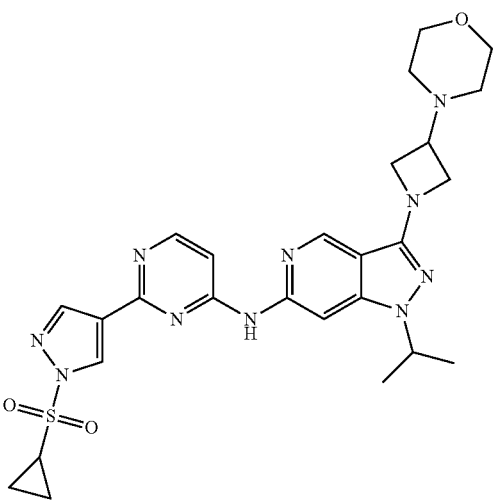 [SMILES: CC(C)n1nc(N2CC(N3CCOCC3)C2)c2cnc(Nc3ccnc(-c4cnn(S(=O)(=O)C5CC5)c4)n3)cc21]<br>N-(2-(1-(Cyclopropylsulfonyl)-1H-pyrazol-4-yl)pyrimidin-4-yl)-1-isopropyl-3-(3-morpholinoazetidin-1-yl)-1H-pyrazolo[4,3-c]pyridin-6-amine | 73 | 1.818<br>565.20<br>N | $^1$H NMR (300 MHz, DMSO-d$_6$): δ 10.33 (s, 1H), 8.69 (s, 1H), 8.62 (s, 1H), 8.45 (s, 1H), 8.41 (d, J = 6.0 Hz, 1H), 8.29 (s, 1H), 7.13 (d, J = 6.0 Hz, 1H), 4.73-4.68 (m, 1H), 4.21-4.17 (m, 2H), 3.96-3.92 (m, 2H), 3.60 (m, 4H), 3.36-3.30 (m, 1H), 3.27-3.24 (m, 1H), 2.36 (s, 4H), 1.46 (d, J = 6.6 Hz, 6H), 1.38-1.28 (m, 4H). |
| 118 | 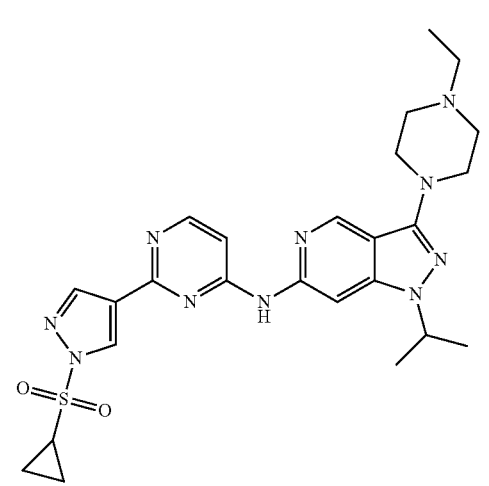 [SMILES: CCN1CCN(c2nn(C(C)C)c3cc(Nc4ccnc(-c5cnn(S(=O)(=O)C6CC6)c5)n4)ncc23)CC1]<br>N-(2-(1-(Cyclopropylsulfonyl)-1H-pyrazol-4-yl)pyrimidin-4-yl)-3-(4-ethylpiperazin-1-yl)-1-isopropyl-1H-pyrazolo[4,3-c]pyridin-6-amine | 73 | 1.331<br>537.25<br>M | $^1$H NMR (300 MHz, DMSO-d$_6$): δ 10.37 (s, 1H), 8.90 (s, 1H), 8.70 (s, 1H), 8.48 (s, 1H), 8.42 (d, J = 5.7 Hz, 1H), 8.34 (s, 1H), 7.12 (d, J = 5.7 Hz, 1H), 4.78-4.68 (m, 1H), 3.45 (s, 4H), 3.34-3.26 (m, 1H), 2.64 (s, 4H), 2.51-2.49 (m, 2H), 1.48 (d, J = 6.6 Hz, 6H), 1.35-1.23 (m, 4H), 1.10-1.06 (m, 3H). |

-continued

| Example | Structure/Name | Synthesis Method | LCMS R_T (min), M + H+, method | ¹H NMR (ppm) |
|---|---|---|---|---|
| 119 | 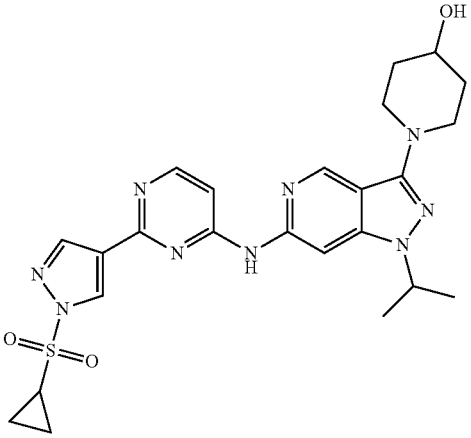 [SMILES: CC(C)n1nc(N2CCC(O)CC2)c2cnc(Nc3ccnc(-c4cnn(S(=O)(=O)C5CC5)c4)n3)cc21]<br>1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)piperidin-4-ol | 73 | 2.271 524.20 M | ¹H NMR (300 MHz, DMSO-d₆): δ 10.36 (s, 1H), 8.86 (s, 1H), 8.70 (s, 1H), 8.47 (s, 1H), 8.41 (d, J = 5.7 Hz, 1H), 8.31 (s, 1H), 7.11 (d, J = 5.7 Hz, 1H), 4.73-4.70 (m, 2H), 3.84-3.80 (m, 2H), 3.67-3.66 (m, 1H), 3.32-3.26 (m, 1H), 3.10-3.03 (m, 2H), 1.90-1.87 (m, 2H), 1.59-1.53 (m, 2H), 1.47 (d, J = 6.3 Hz, 6H), 1.34-1.23 (m, 4H). |
| 120 | 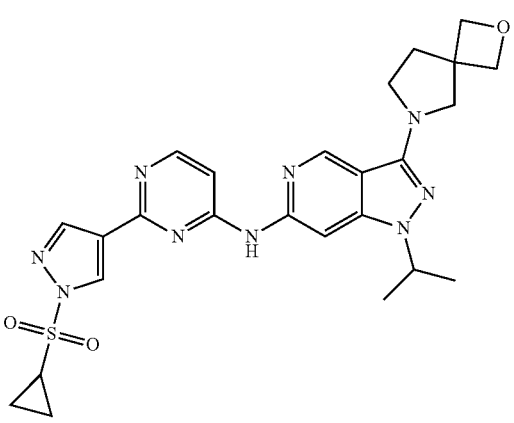 [SMILES: CC(C)n1nc(N2CCC3(COC3)C2)c2cnc(Nc3ccnc(-c4cnn(S(=O)(=O)C5CC5)c4)n3)cc21]<br>N-(2-(1-(Cyclopropylsulfonyl)-1H-pyrazol-4-yl)pyrimidin-4-yl)-1-isopropyl-3-(2-oxa-6-azaspiro[3.4]octan-6-yl)-1H-pyrazolo[4,3-c]pyridin-6-amine | 73 | 1.616 536.10 N | ¹H NMR (300 MHz, DMSO-d₆): δ 10.32 (s, 1H), 8.80 (s, 1H), 8.69 (s, 1H), 8.47 (s, 1H), 8.41 (d, J = 5.7 Hz, 1H), 8.26 (s, 1H), 7.12 (d, J = 5.7 Hz, 1H), 4.71-4.65 (m, 3H), 4.56-4.54 (m, 2H), 3.81 (s, 2H), 3.60-3.56 (m, 2H), 3.32-3.26 (m, 1H), 2.30-2.26 (m, 2H), 1.47 (d, J = 6.6 Hz, 6H), 1.35-1.25 (m, 4H). |

| Example | Structure/Name | Synthesis Method | LCMS $R_T$ (min), M + H+, method | 1H NMR (ppm) |
|---|---|---|---|---|
| 121 | 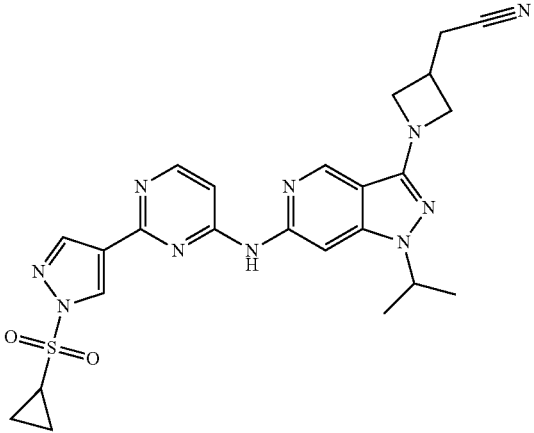 [SMILES: CC(C)n1nc(N2CC(CC#N)C2)c2cnc(Nc3ccnc(-c4cnn(S(=O)(=O)C5CC5)c4)n3)cc21]<br>2-(1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)azetidin-3-yl)acetonitrile | 73 | 2.807 519.00 N | 1H NMR (300 MHz, DMSO-d6): δ 10.34 (s, 1H), 8.70 (s, 1H), 8.63 (s, 1H), 8.48 (s, 1H), 8.41 (d, J = 6.0 Hz, 1H), 8.29 (s, 1H), 7.13 (d, J = 6.0 Hz, 1H), 4.74-4.69 (m, 1H), 4.31-4.25 (m, 2H), 3.90-3.86 (m, 2H), 3.33-3.26 (m, 1H), 3.16-3.12 (m, 1H), 2.95-2.93 (m, 2H), 1.46 (d, J = 6.6 Hz, 6H), 1.38-1.27 (m, 4H). |
| 122 | (1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-3-methylazetidin-3-yl)methanol | 73 | 1.785 524.10 N | 1H NMR (400 MHz, DMSO-d6): δ 10.32 (s, 1H), 8.69 (s, 1H), 8.59 (s, 1H), 8.47 (s, 1H), 8.41 (d, J = 5.6 Hz, 1H), 8.26 (s, 1H), 7.13 (d, J = 5.6 Hz, 1H), 4.92-4.89 (m, 1H), 4.71-4.68 (m, 1H), 3.97 (m, 2H), 3.71 (m, 2H), 3.47 (m, 2H), 3.33-3.28 (m, 1H), 1.46 (d, J = 6.4 Hz, 6H), 1.36-1.33 (m, 2H), 1.29 (s, 3H), 1.28-1.26 (m, 2H). |

| Example | Structure/Name | Synthesis Method | LCMS R$_T$ (min), M + H$^+$, method | $^1$H NMR (ppm) |
|---|---|---|---|---|
| 123 | (S)-1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)pyrrolidin-3-ol | 73 | 2.179 510.20 L | $^1$H NMR (300 MHz, DMSO-d$_6$): δ 10.27 (s, 1H), 8.76 (s, 1H), 8.70 (s, 1H), 8.47 (s, 1H), 8.40 (d, J = 5.7 Hz, 1H), 8.24 (s, 1H), 7.14 (d, J = 5.7 Hz, 1H), 4.95 (s, 1H), 4.70-4.66 (m, 1H), 4.43 (s, 1H), 3.72-3.62 (m, 3H), 3.46-3.42 (m, 1H), 3.31-3.26 (m, 1H), 2.08-2.03 (m, 1H), 1.95-1.92 (m, 1H), 1.48-1.46 (d, J = 6.6 Hz, 6H), 1.38-1.23 (m, 4H). |
| 124 | 1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-3-(hydroxymethyl)azetidin-3-ol | 73 | 1.499 526.15 R | $^1$H NMR (300 MHz, DMSO-d$_6$): δ 10.32 (s, 1H), 8.70 (s, 1H), 8.60 (s, 1H), 8.48 (s, 1H), 8.41 (d, J = 6 Hz, 1H), 8.27 (s, 1H), 7.14 (d, J = 6 Hz, 1H), 5.64 (s, 1H), 4.94-4.92 (m, 1H), 4.77-4.71 (m, 1H), 4.16-4.13 (m, 2H), 3.87-3.85 (m, 2H), 3.53-3.51 (m, 2H), 3.33-3.21 (m, 1H), 1.46 (d, J = 6.6 Hz, 6H), 1.36-1.26 (m, 4H). |

| Example | Structure/Name | Synthesis Method | LCMS R$_T$(min), M + H$^+$, method | $^1$H NMR (ppm) |
|---|---|---|---|---|
| 125 | 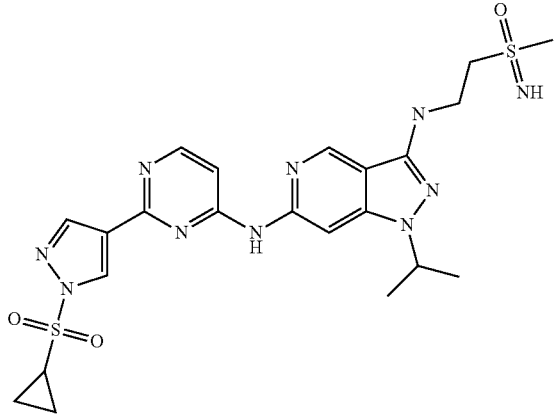 [SMILES: CC(C)n1nc(NCCS(C)(=N)=O)c2cnc(Nc3ccnc(-c4cnn(S(=O)(=O)C5CC5)c4)n3)cc21]<br>N$^6$-(2-(1-(Cyclopropylsulfonyl)-1H-pyrazol-4-yl)pyrimidin-4-yl)-1-isopropyl-N$^3$-(2-(S-methylsulfonimidoyl)ethyl)-1H-pyrazolo[4,3-c]pyridine-3,6-diamine | 74 | 1.497<br>545.15<br>R | $^1$H NMR (300 MHz, DMSO-d$_6$): δ 10.29 (s, 1H), 8.70 (s, 2H), 8.47 (s, 1H), 8.41 (d, J = 5.7 Hz, 1H), 8.22 (s, 1H), 7.14 (d, J = 5.7 Hz, 1H), 6.76-6.72 (m, 1H), 4.70-4.65 (m, 1H), 3.81 (s, 1H), 3.72-3.66 (m, 2H), 3.44-3.37 (m, 2H), 3.29-3.27 (m, 1H), 2.97 (s, 3H), 1.47 (d, J = 6.6 Hz, 6H), 1.38-1.26 (m, 4H). |
| 126 | 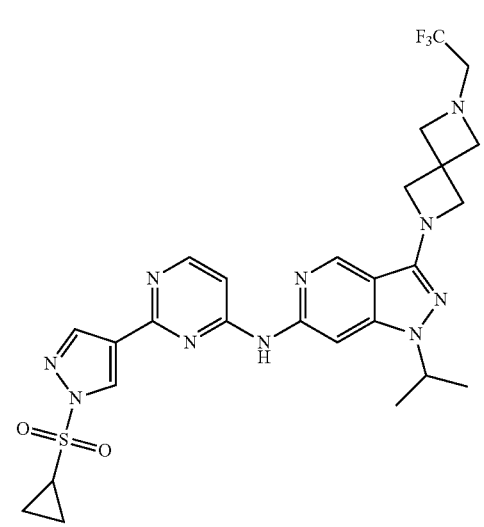 [SMILES: CC(C)n1nc(N2CC3(CN(CC(F)(F)F)C3)C2)c2cnc(Nc3ccnc(-c4cnn(S(=O)(=O)C5CC5)c4)n3)cc21]<br>N-(2-(1-(Cyclopropylsulfonyl)-1H-pyrazol-4-yl)pyrimidin-4-yl)-1-isopropyl-3-(6-(2,2,2-trifluoroethyl)-2,6-diazaspiro[3.3]heptan-2-yl)-1H-pyrazolo[4,3-c]pyridin-6-amine | 73 | 2.932<br>603.15<br>R | $^1$H NMR (300 MHz, DMSO-d$_6$): δ 10.31 (s, 1H), 8.69 (s, 1H), 8.60 (s, 1H), 8.47 (s, 1H), 8.41 (d, J = 5.7 Hz, 1H), 8.27 (s, 1H), 7.14 (d, J = 5.1 Hz, 1H), 4.72-4.67 (m, 1H), 4.21 (s, 4H), 3.56 (s, 4H), 3.32-3.20 (m, 3H), 1.45 (d, J = 6.6 Hz, 6H), 1.35-1.15 (m, 4H). |

| Example | Structure/Name | Synthesis Method | LCMS R$_T$ (min), M + H$^+$, method | $^1$H NMR (ppm) |
|---|---|---|---|---|
| 127 | 1-(6-(2-(cis-3-Fluoro-4-hydroxypiperidin-1-yl)pyrimidin-4-ylamino)-1-isopropyl-1H-pyrazolo[4,3-c]pyridin-3-yl)-4-methylimidazolidin-2-one(mixture of diastereoisomers) | 76 | 1.503 470.15 R | $^1$H NMR (300 MHz, DMSO-d$_6$): δ 9.96 (s, 1H), 9.31 (s, 1H), 8.22 (s, 1H), 7.99 (d, J = 5.6 Hz, 1H), 7.37 (s, 1H), 6.37 (d, J = 5.6 Hz, 1H), 5.14 (m, 1H), 4.72-4.62 (m, 2H), 4.64-4.54 (m, 1H), 4.29-4.25 (m, 1H), 4.11-4.06 (m, 1H), 3.93-3.83 (m, 2H), 3.54-3.50 (m, 2H), 3.36-3.33 (m, 1H), 1.71(m, 2H), 1.47-1.44 (m, 6H), 1.25 (m, 3H). |
| 128 | 1-(6-(2-(cis-3-Fluoro-4-hydroxypiperidin-1-yl)pyrimidin-4-ylamino)-1-isopropyl-1H-pyrazolo[4,3-c]pyridin-3-yl)-5-methylimidazolidin-2-one(mixture of diastereoisomers) | 76 | 1.858 470.15 R | $^1$H NMR (300 MHz, DMSO-d$_6$): δ 9.95 (s, 1H), 9.12 (s, 1H), 8.23 (s, 1H), 7.99 (d, J = 5.6 Hz, 1H), 7.16 (s, 1H), 6.37 (d, J = 5.6 Hz, 1H), 5.15 (m, 1H), 4.75-4.62 (m, 2H), 4.56-4.51 (m, 2H), 4.29-4.26 (m, 1H), 3.90-3.89 (m, 1H), 3.84-3.54 (m, 3H), 3.12-3.08 (m, 1H), 1.71 (m, 2H), 1.47-1.46 (m, 6H), 1.35 (m, 3H). |
| 129 | (±)-cis-3-Fluoro-1-(4-(3-(3-hydroxy-3-(trifluoromethyl)azetidin-1-yl)-1-isopropyl-1H-pyrazolo[4,3-c]pyridin-6-ylamino)pyrimidin-2-yl)piperidin-4-ol | 75 | 1.894 511.25 L | $^1$H NMR (300 MHz, DMSO-d$_6$): δ 9.89 (s, 1H), 8.64 (s, 1H), 8.15 (s, 1H), 7.99 (d, J = 5.7 Hz, 1H), 7.33 (s, 1H), 6.38 (d, J = 5.7 Hz, 1H), 5.12 (d, J = 5.1 Hz, 1H), 4.80-4.41 (m, 5H), 4.30-4.20 (m, 1H), 4.14-4.11 (m, 2H), 3.95-3.80 (m, 1H), 3.70-3.50 (m, 1H), 3.45-3.31 (m, 1H), 1.75-1.65 (m, 2H), 1.50-1.35 (m, 6H) |

| Example | Structure/Name | Synthesis Method | LCMS $R_T$ (min), M + H+, method | 1H NMR (ppm) |
|---|---|---|---|---|
| 130 | (±)-cis-3-Fluoro-1-(4-(3-(3-fluoro-3-(hydroxymethyl)azetidin-1-yl)-1-isopropyl-1H-pyrazolo[4,3-c]pyridin-6-ylamino)pyrimidin-2-yl)piperidin-4-ol | 75 | 1.238 475.20 L | 1H NMR (300 MHz, DMSO-d$_6$): δ 9.89 (s, 1H), 8.59 (s, 1H), 8.14 (s, 1H), 7.98 (d, J = 5.7 Hz, 1H), 6.38 (d, J = 5.7 Hz, 1H), 5.34-5.30 (m, 1H), 5.13 (m, 1H), 4.77-4.48 (m, 3H), 4.31-4.09 (m, 5H), 3.91-3.51 (m, 4H), 3.45-3.31 (m, 1H), 1.75-1.65 (m, 2H), 1.45-1.35 (m, 6H). |
| 131 | cis-3-Fluoro-1-(4-(3-(trans-3-fluoro-4-hydroxypyrrolidin-1-yl)-1-isopropyl-1H-pyrazolo[4,3-c]pyridin-6-ylamino)pyrimidin-2-yl)piperidin-4-ol(mixture of diastereoisomers) | 75 | 1.261 475.20 L | 1H NMR (400 MHz, DMSO-d$_6$): δ 9.86 (s, 1H), 8.76 (s, 1H), 8.11 (s, 1H), 7.98 (d, J = 5.6 Hz, 1H), 6.38 (d, J = 5.6 Hz, 1H), 5.57 (m, 1H), 5.16-5.02 (m, 2H), 4.75-4.62 (m, 1H), 4.56-4.49 (m, 2H), 4.38-4.26 (m, 2H), 3.94-3.81 (m, 4H), 3.76-3.36 (m, 3H), 1.85-1.63 (m, 2H), 1.50-1.36 (m, 6H). |
| 132 | cis-3-Fluoro-1-(4-(3-((S)-2-(hydroxymethyl)morpholino)-1-isopropyl-1H-pyrazolo[4,3-c]pyridin-6-ylamino)pyrimidin-2-yl)piperidin-4-ol(mixture of diastereoisomers) | 75 | 1.366 487.15 R | 1H NMR (300 MHz, DMSO-d$_6$): δ 9.91 (s, 1H), 8.84 (s, 1H), 8.18 (s, 1H), 7.99-7.97 (d, J = 6.0 Hz, 1H), 6.38-6.36 (d, J = 6.0 Hz, 1H), 5.14-5.12 (m, 1H), 4.82-4.59 (m, 4H), 4.35-4.17 (m, 1H), 4.06-3.70 (m, 5H), 3.68-3.31 (m, 5H), 2.96-2.95 (m, 1H), 2.75-2.71 (m, 1H), 1.71-1.69 (m, 2H), 1.44-1.42 (d, J = 6.0 Hz, 6H). |

| Example | Structure/Name | Synthesis Method | LCMS R_T (min), M + H+, method | 1H NMR (ppm) |
|---|---|---|---|---|
| 133 | (±)-1-(6-(2-(cis-3-Fluoro-4-hydroxypiperidin-1-yl)pyrimidin-4-ylamino)-1-isopropyl-1H-pyrazolo[4,3-c]pyridin-3-yl)pyrrolidin-2-one | 76 | 1.714 455.30 S | 1H NMR (300 MHz, DMSO-d6): δ 10.03 (s, 1H), 9.26 (s, 1H), 8.28 (s, 1H), 8.00 (d, J = 5.7 Hz, 1H), 6.37 (d, J = 5.7 Hz, 1H), 5.15 (m, 1H), 4.78-4.47 (m, 3H), 4.28 (m, 1H), 3.99-3.83 (m, 3H), 3.68-3.53 (m, 1H), 3.44-3.37 (m, 1H), 2.60-2.50 (m, 2H), 2.22-2.12 (m, 2H), 1.84-1.62 (m, 2H), 1.59-1.41 (m, 6H). |
| 134 | 1-(4-(6-(2-(4-Hydroxy-4-methylpiperidin-1-yl)pyrimidin-4-ylamino)-1-isopropyl-1H-pyrazolo[4,3-c]pyridin-3-yl)piperazin-1-yl)propan-1-one | 78 | 2.894 508.20 R | 1H NMR (400 MHz, DMSO-d6): δ 9.86 (s, 1H), 8.86 (s, 1H), 8.21 (s, 1H), 7.97 (d, J = 5.6 Hz, 1H), 6.32 (d, J = 5.6 Hz, 1H), 4.57-4.51 (m, 1H), 4.39 (s, 1H), 4.20-4.17 (m, 2H), 3.65-3.62 (m, 4H), 3.50-3.37 (m, 6H), 2.40-2.34 (m, 2H), 1.59-1.47 (m, 4H), 1.43 (d, J = 6.0 Hz, 6H), 1.15 (s, 3H), 1.08-0.95 (m, 3H). |
| 135 | 2-Hydroxy-1-(4-(6-(2-(4-hydroxy-4-methylpiperidin-1-yl)pyrimidin-4-ylamino)-1-isopropyl-1H-pyrazolo[4,3-c]pyridin-3-yl)piperazin-1-yl)ethanone | 78 | 1.631 510.05 H | 1H NMR (400 MHz, DMSO-d6): δ 9.87 (s, 1 H), 8.86 (s, 1 H), 8.21 (s, 1 H), 7.97 (d, J = 5.6 Hz, 1 H), 6.32 (d, J = 5.6 Hz, 1 H), 4.68-4.62 (m, 1 H), 4.59-4.47 (m, 1 H), 4.41 (s, 1 H), 4.21-4.15 (m, 4 H), 3.73-3.62 (m, 2 H), 3.57-3.50 (m, 2 H), 3.40-3.30 (m, 6 H), 1.55-1.42 (m, 10 H), 1.17 (s, 3 H). |

-continued

| Example | Structure/Name | Synthesis Method | LCMS R$_T$ (min), M + H$^+$, method | $^1$H NMR (ppm) |
|---|---|---|---|---|
| 136 | 2-Hydroxy-1-(4-(6-(2-(4-hydroxy-4-methylpiperidin-1-yl)pyrimidin-4-ylamino)-1-isopropyl-1H-pyrazolo[4,3-c]pyridin-3-yl)piperazin-1-yl)propan-1-one | 78 | 2.134 524.25 M | $^1$H NMR (400 MHz, DMSO-d$_6$): δ 9.88 (s, 1H), 8.87 (s, 1H), 8.22 (s, 1H), 7.99-7.97 (d, J = 5.6 Hz, 1H), 6.34-6.33 (d, J = 5.6 Hz, 1H), 4.99-4.98 (m, 1H), 4.59-4.46 (m, 2H), 4.40 (s, 1H), 4.22-4.18 (m, 2H), 3.73-3.62 (m, 4H), 3.51-3.35 (m, 6H), 1.56-1.48 (m, 10H), 1.44-1.43 (d, J = 6.4 Hz, 3H), 1.39 (s, 3H). |
| 137 | 1-(6-(2-(4-Hydroxy-4-methylpiperidin-1-yl)pyrimidin-4-ylamino)-1-isopropyl-1H-pyrazolo[4,3-c]pyridin-3-yl)-5-oxopyrrolidine-3-carbonitrile | 72 | 2.171 476.20 M | $^1$H NMR (300 MHz, DMSO-d$_6$): δ 9.99 (s, 1H), 9.20 (s, 1H), 8.34 (s, 1H), 7.99 (d, J = 5.4 Hz, 1H), 6.32 (d, J = 5.4 Hz, 1H), 4.76-4.63 (m, 1H), 4.39 (s, 1H), 4.37-4.27 (m, 1H), 4.26-4.10 (m, 3H), 3.97-3.83 (m, 1H), 3.55-3.41 (m, 2H), 3.02-2.96 (m, 2H), 1.52-1.46 (m, 10H), 1.16 (s, 3H). |
| 138 | 6-(6-((2-(4-Hydroxy-4-methylpiperidin-1-yl)pyrimidin-4-yl)amino)-1-isopropyl-1H-pyrazolo[4,3-c]pyridin-3-yl)-2-thia-6-azaspiro[3.3]heptane 2-oxide | 73 | 1.768 497.20 M | $^1$H NMR (300 MHz, DMSO-d$_6$): δ 9.82 (s, 1H), 8.51 (s, 1H), 8.16 (s, 1H), 7.96 (d, J = 5.7 Hz, 1H), 6.31 (d, J = 5.7 Hz, 1H), 4.55-4.40 (m, 1H), 4.37 (s, 1H), 4.22-4.12 (m, 6H), 4.04-3.96 (m, 2H), 3.45-3.41 (m, 4H), 1.50-1.39 (m, 10H), 1.15 (s, 3H). |

| Example | Structure/Name | Synthesis Method | LCMS R<sub>T</sub> (min), M + H+, method | $^1$H NMR (ppm) |
|---|---|---|---|---|
| 139 | 1-(4-(3-(2-(5-Amino-1,3-dioxan-2-yl)ethylamino)-1-isopropyl-1H-pyrazol[4,3-c]pyridin-6-ylamino)pyrimidin-2-yl)-4-methylpiperidin-4-ol | 74 | 1.404 512.20 N | $^1$H NMR (300 MHz, DMSO-d$_6$): δ 9.72 (s, 1H), 8.63 (s, 1H), 8.08 (s, 1H), 7.95 (m, 1H), 6.32-6.30 (m, 2H), 4.72-4.69 (m, 1H), 4.47-4.43 (m, 1H), 4.37 (s, 1H), 4.20-4.16 (m, 2H), 3.88-3.84 (m, 2H), 3.74-3.70 (m, 2H), 3.50-3.41 (m, 2H), 3.31-3.27 (m, 2H), 2.57 (s, 1H), 2.51-2.49 (m, 2H), 1.92-1.85 (m, 2H), 1.55-1.43 (m, 10H), 1.16 (s, 3H). |
| 140 | (3RS,4SR)-3-Fluoro-1-(4-(3-((R)-3-hydroxypyrrolidin-1-yl)-1-((R*)-1,1,1-trifluoropropan-2-yl)-1H-pyrazolo[4,3-c]pyridin-6-ylamino)pyrimidin-2-yl)-4-methylpiperidin-4-ol(mixture of diastereomers) | 79 | 1.650 525.25 M | $^1$H NMR (400 MHz, DMSO-d$_6$): δ 9.95-9.93 (d, J = 9.6 Hz, 1H), 8.77 (s, 1H), 8.19-8.12 (d, J = 28.4 Hz, 1H), 8.01-7.99 (d, J = 5.6 Hz, 1H), 6.40-6.39 (d, J = 5.6 Hz, 1H), 5.21-5.19 (m, 1H), 4.99-4.98 (m, 1H), 4.84-4.83 (m, 1H), 4.42-4.23 (m, 3H), 4.09 (m, 1H), 3.71-3.58 (m, 4H), 3.50-3.42 (m, 2H), 2.07-2.03 (m, 1H), 1.93-1.90 (m, 1H), 1.71-1.69 (m, 4H), 1.60-1.45 (m, 1H), 1.20 (d, J = 6.4 Hz, 3H) |
| 141 | (±)-cis-3-Fluoro-1-(4-(3-((R)-3-hydroxypyrrolidin-1-yl)-1-((S*)-1,1,1-trifluoropropan-2-yl)-1H-pyrazolo[4,3-c]pyridin-6-ylamino)pyrimidin-2-yl)piperidin-4-ol(mixture of diastereomers) | 79 | 1.697 511.10 N | $^1$H NMR (400 MHz, DMSO-d$_6$): δ 9.93 (s, 1H), 8.77 (s, 1H), 8.16 (m, 1H), 7.99 (d, J = 5.6 Hz, 1H), 6.37 (d, J = 5.6 Hz, 1H), 5.26-5.13 (m, 1H), 5.12 (m, 1H), 4.98 (m, 1H), 4.70-4.60 (m, 1H), 4.60-4.53 (m, 1H), 4.42 (s, 1H), 4.38-4.25 (m, 1H), 3.90-3.76 (m, 1H), 3.76-3.61 (m, 3H), 3.59-3.41 (m, 2H), 3.33-3.22 (m, 1H), 2.07-2.03 (m, 1H), 1.94-1.90 (m, 1H), 1.71-1.65 (m, 5H). |

| Example | Structure/Name | Synthesis Method | LCMS R$_T$ (min), M + H$^+$, method | $^1$H NMR (ppm) |
|---|---|---|---|---|
| 142 | (±)-cis-3-Fluoro-1-(4-(3-((R)-3-hydroxypyrrolidin-1-yl)-1-((R*)-1,1,1-trifluoropropan-2-yl)-1H-pyrazolo[4,3-c]pyridin-6-ylamino)pyrimidin-2-yl)piperidin-4-ol(mixture of diastereomers) | 79 | 1.334 511.15 M | $^1$H NMR (400 MHz, DMSO-d$_6$): δ 9.93 (s, 1H), 8.77 (s, 1H), 8.16 (m, 1H), 7.99 (d, J = 5.6 Hz, 1H), 6.37 (d, J = 5.6 Hz, 1H), 5.26-5.13 (m, 1H), 5.12 (m, 1H), 4.98 (m, 1H), 4.70-4.60 (m, 1H), 4.60-4.53 (m, 1H), 4.42 (s, 1H), 4.38-4.25 (m, 1H), 3.90-3.76 (m, 1H), 3.76-3.61 (m, 3H), 3.59-3.41 (m, 2H), 3.33-3.22 (m, 1H), 2.07-2.03 (m, 1H), 1.94-1.90 (m, 1H), 1.71-1.65 (m, 5H). |
| 143 | 1-(4-(3-((R)-3-Hydroxypyrrolidin-1-yl)-1-(1,1,1-trifluoropropan-2-yl)-1H-pyrazolo[4,3-c]pyridin-6-ylamino)pyrimidin-2-yl)-4-methylpiperidin-4-ol | 79 | 1.801 507.05 R | $^1$H NMR (300 MHz, DMSO-d$_6$): δ 9.86 (s, 1H), 8.76 (s, 1H), 8.20 (s, 1H), 7.98 (d, J = 5.4 Hz, 1H), 6.32 (d, J = 5.4 Hz, 1H), 5.24-5.15 (m, 1H), 4.97 (m, 1H), 4.42 (s, 2H), 4.19-4.14 (m, 2H), 3.70-3.62 (m, 3H), 3.51-3.42 (m, 3H), 2.07-2.04 (m, 1H), 2.03-1.93 (m, 1H), 1.70 (m, 3H), 1.55-1.40 (m, 4H), 1.15 (s, 3H). |
| 144 | (3S)-1-(1-sec-Butyl-6-(2-(4-hydroxy-4-methylpiperidin-1-yl)pyrimidin-4-ylamino)-1H-pyrazolo[4,3-c]pyridin-3-yl)pyrrolidine-3-carboxamide | 80 | 2.185 494.20 R | $^1$H NMR (400 MHz, DMSO-d$_6$): δ 9.80 (s, 1H), 8.70 (s, 1H), 8.14 (s, 1H), 7.96 (d, J = 5.6 Hz, 1H), 7.48 (s, 1H), 6.97 (s, 1H), 6.31 (d, J = 5.6 Hz, 1H), 4.40 (s, 1H), 4.21-4.17 (m, 3H), 3.75-3.70 (m, 1H), 3.67-3.40 (m, 5H), 3.08-3.04 (m, 1H), 2.18-2.11 (m, 2H), 2.01-1.87 (m, 1H), 1.85-1.68 (m, 1H), 1.60-1.43 (m, 4H), 1.43-1.33 (m, 3H), 1.15 (s, 3H), 0.78-0.68 (m, 3H). |

| Example | Structure/Name | Synthesis Method | LCMS R$_T$ (min), M + H$^+$, method | $^1$H NMR (ppm) |
|---|---|---|---|---|
| 145 | (3R)-1-(1-sec-Butyl-6-(2-(4-hydroxy-4-methylpiperidin-1-yl)pyrimidin-4-ylamino)-1H-pyrazolo[4,3-c]pyridin-3-yl)pyrrolidine-3-carboxamide | 80 | 1.262 494.20 M | $^1$H NMR (400 MHz, DMSO-d$_6$): δ 9.79 (s, 1H), 8.70 (s, 1H), 8.14 (s, 1H), 7.96-7.94 (d, J = 6 Hz, 1H), 7.48 (s, 1H), 6.97 (s, 1H). 6.32-6.30 (d, J = 6 Hz, 1H), 4.40 (s, 1H), 4.27-4.03 (m, 3H), 3.83-3.70 (m, 1H), 3.70-3.40 (m, 5H), 3.16-2.99 (m, 1H), 2.49-2.16 (m, 2H), 1.98-1.81 (m, 1H), 1.74-1.51 (m, 1H), 1.47-1.40 (m, 7H), 1.38-1.16 (m, 3H), 0.80-0.65 (m, 3H). |
| 146 | 1-(4-(1-sec-Butyl-3-(3,3-difluoroazetidin-1-yl)-1H-pyrazolo[4,3-c]pyridin-6-ylamino)pyrimidin-2-yl)-4-methylpiperidin-4-ol | 80 | 1.981 473.15 R | $^1$H NMR (400 MHz, DMSO-d$_6$): δ 9.87 (s, 1H), 8.62 (s, 1H), 8.21 (s, 1H), 7.97 (d, J = 5.6 Hz, 1H), 6.33 (d, J = 5.6 Hz, 1H), 4.60-4.54 (m, 4H), 4.40 (s, 1H), 4.27-4.18 (m, 3H), 3.49-3.44 (m, 2H), 1.96-1.88 (m, 1H), 1.80-1.73 (m, 1H), 1.54-1.45 (m, 7H), 1.18 (s, 3H), 1.75-1.71 (m, 3H). |
| 147 | (4SR,5RS)-1-(4-((1-(sec-Butyl)-3-(2-oxa-6-azaspiro[3.3]heptan-6-yl)-1H-pyrazolo[4,3-c]pyridin-6-yl)amino)pyrimidin-2-yl)-5-fluoro-3,3-dimethylpiperidin-4-ol(mixture of diastereomers) | 80 | 1.966 511.20 R | $^1$H NMR (300 MHz, DMSO-d$_6$): δ 9.88 (s, 1H), 8.56 (s, 1H), 8.13 (m, 1H), 7.96 (d, J = 5.7 Hz, 1H), 6.35 (d, J = 5.7 Hz, 1H), 5.17-5.15 (m, 1H), 4.83-4.67 (m, 5H), 4.27-4.02 (m, 6H), 3.97-3.70 (m, 2H), 3.51-3.41 (m, 2H), 1.93-1.70 (m, 2H), 1.40-1.37 (m, 3H), 0.95 (m, 6H), 0.75-0.60 (m, 3H). |

| Example | Structure/Name | Synthesis Method | LCMS R_T (min), M + H+, method | ¹H NMR (ppm) |
|---|---|---|---|---|
| 148 | cis-5-Fluoro-1-(4-(3-((R)-3-hydroxypyrrolidin-1-yl)-1-isopropyl-1H-pyrazolo[4,3-c]pyridin-6-ylamino)pyrimidin-2-yl)-3,3-dimethylpiperidin-4-ol(mixture of diastereomers) | 80 | 1.489 485.20 M | ¹H NMR (300 MHz, DMSO-d₆): δ 9.83 (s, 1H), 8.70 (s, 1H), 8.09 (s, 1H), 7.96 (d, J = 5.7 Hz, 1H), 6.36 (d, J = 5.7 Hz, 1H), 5.16-5.14 (m, 1H), 4.96-4.95 (m, 1H), 4.84-4.68 (m, 1H), 4.59-4.50 (m, 1H), 4.41 (m, 1H), 4.20-4.09 (m, 1H), 3.99-3.88 (m, 1H), 3.81-3.63 (m, 4H), 3.44-3.40 (m, 3H), 2.07-1.92 (m, 2H), 1.42 (d, J = 6.4 Hz, 6H), 0.97-0.92 (m, 6H). |
| 149 | 2-(1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)azetidin-3-yl)propan-2-ol | 82 | 2.047 538.10 Q | ¹H NMR (300 MHz, DMSO-d₆): δ 10.32 (s, 1H), 8.69 (s, 1H), 8.61 (s, 1H), 8.47 (s, 1H), 8.40 (d, J = 5.6 Hz, 1H), 8.27 (s, 1H), 7.13 (d, J = 5.6 Hz, 1H), 4.71-4.67 (m, 1H), 4.44 (s, 1H), 4.07-4.01 (m, 4H), 3.29-3.27 (m, 1H), 2.84-2.81 (m, 1H), 1.46 (d, J = 6.8 Hz, 6H), 1.34 (m, 2H), 1.30-1.23 (m, 2H), 1.08 (s, 6H). |
| 150 | 3-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-tetrahydropyrimidin-2(1H)-one | 83 | 2.610 523.20 M | ¹H NMR (400 MHz, DMSO-d₆): δ 10.41 (s, 1 H), 8.88 (s, 1 H), 8.73 (s, 1 H), 8.49 (s, 1 H), 8.42 (m, 2 H), 7.10 (m, 1 H), 6.97 (s, 1 H), 4.90-4.83 (m, 1 H), 3.88-3.85 (m, 2 H), 3.32-3.26 (m, 3 H), 2.03-1.97 (m, 2 H), 1.52 (d, J = 6.4 Hz, 6 H), 1.38-1.33 (m, 2 H), 1.31-1.28 (m, 2 H). |

-continued

| Example | Structure/Name | Synthesis Method | LCMS R$_T$ (min), M + H$^+$, method | $^1$H NMR (ppm) |
|---|---|---|---|---|
| 151 | 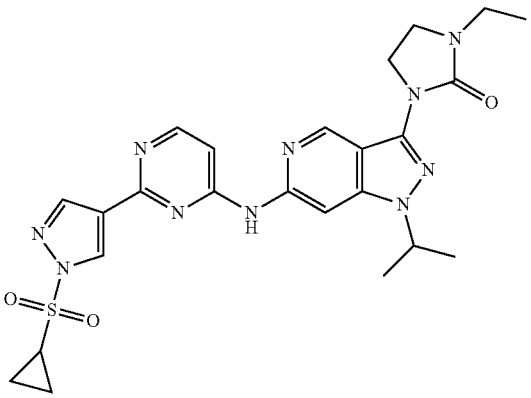 [SMILES: CCN1CCN(c2nn(C(C)C)c3cc(Nc4ccnc(-c5cnn(S(=O)(=O)C6CC6)c5)n4)ncc23)C1=O]  1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-3-ethylimidazolidin-2-one | 83 | 1.602 537.10 N | $^1$H NMR (400 MHz, DMSO-d$_6$): δ 10.39 (s, 1H), 9.59 (s, 1H), 8.73 (s, 1H), 8.49 (s, 1H), 8.43-8.40 (m, 2H), 7.09 (m, 1H), 4.87-4.84 (m, 1H), 4.52-4.49 (m, 2H), 4.06-4.02 (m, 2H), 3.31-3.27 (m, 3H), 1.54-1.51 (m, 6H), 1.38-1.24 (m, 4H), 1.15-1.11 (m, 3H). |
| 152 | 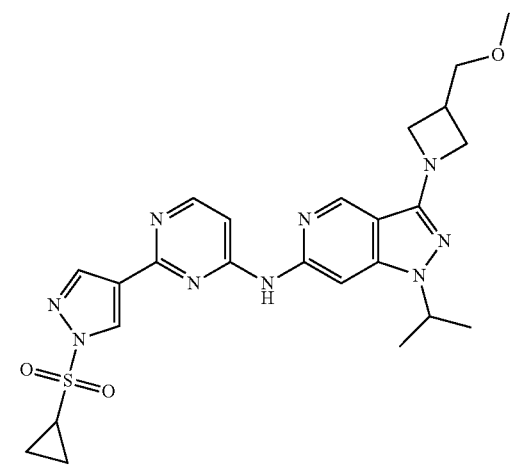 [SMILES: COCC1CN(c2nn(C(C)C)c3cc(Nc4ccnc(-c5cnn(S(=O)(=O)C6CC6)c5)n4)ncc23)C1]  N-(2-(1-(Cyclopropylsulfonyl)-1H-pyrazol-4-yl)pyrimidin-4-yl)-1-isopropyl-3-(3-(methoxymethyl)azetidin-1-yl)-1H-pyrazolo[4,3-c]pyridin-6-amine | 82 | 1.913 324.10 R | $^1$H NMR (400 MHz, DMSO-d$_6$): δ 10.32 (s, 1H), 8.69 (s, 1H), 8.61 (s, 1H), 8.47 (s, 1H), 8.41 (d, J = 5.7 Hz, 1H), 8.27 (s, 1H), 7.14 (d, J = 5.7 Hz, 1H), 4.74-4.65 (m, 1H), 4.20-4.15 (m, 2H), 3.88-3.83 (m, 2H), 3.57 (m, 2H), 3.32-3.25 (m, 4H), 3.07-2.98 (m, 1H), 1.46 (d, J = 6.6 Hz, 6H), 1.38-1.30 (m, 4H). |

-continued

| Example | Structure/Name | Synthesis Method | LCMS R$_T$ (min), M + H$^+$, method | $^1$H NMR (ppm) |
|---|---|---|---|---|
| 153 | 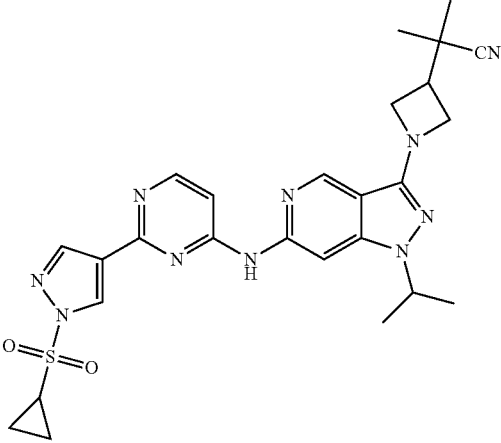 [SMILES: CC(C)n1nc(N2CC(C(C)(C)C#N)C2)c2cnc(Nc3ccnc(-c4cnn(S(=O)(=O)C5CC5)c4)n3)cc21]<br>2-(1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)azetidin-3-yl)-2-methylpropanenitrile | 82 | 1.733 547.10 N | $^1$H NMR (300 MHz, DMSO-d$_6$): δ 10.36 (s, 1H), 8.70 (s, 1H), 8.66 (s, 1H), 8.48 (s, 1H), 8.41 (d, J = 5.7 Hz, 1H), 8.30 (s, 1H), 7.13 (d, J = 5.7 Hz, 1H), 4.74-4.70 (m, 1H), 4.29-4.24 (m, 2H), 4.03-3.98 (m, 2H), 3.31-3.26 (m, 1H), 3.00-2.96 (m, 1H), 1.47 (d, J = 6.6 Hz, 6H), 1.33-1.24 (m, 10H). |
| 154 | 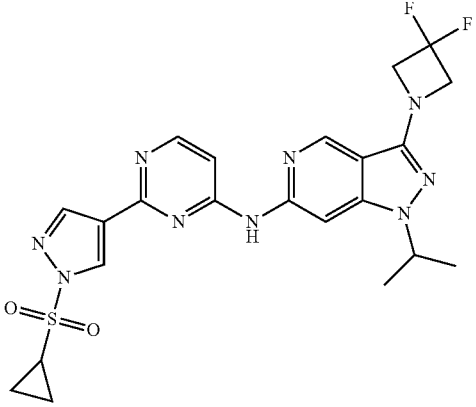 [SMILES: CC(C)n1nc(N2CC(F)(F)C2)c2cnc(Nc3ccnc(-c4cnn(S(=O)(=O)C5CC5)c4)n3)cc21]<br>N-(2-(1-(Cyclopropylsulfonyl)-1H-pyrazol-4-yl)pyrimidin-4-yl)-3-(3,3-difluoroazetidin-1-yl)-1-isopropyl-1H-pyrazolo[4,3-c]pyridin-6-amine | 82 | 1.770 516.00 N | $^1$H NMR (300 MHz, DMSO-d$_6$): δ 10.38 (s, 1H), 8.70-8.69 (m, 2H), 8.48 (s, 1H), 8.42 (d, J = 6.0 Hz, 1H), 8.35 (s, 1H), 7.14 (d, J = 6.0 Hz, 1H), 4.78-4.74 (m, 1H), 4.60 (m, 4H), 3.30-3.26 (m, 1H), 1.48 (d, J = 6.6 Hz, 6H), 1.35-1.23 (m, 4H). |

| Example | Structure/Name | Synthesis Method | LCMS $R_T$ (min), M + H$^+$, method | $^1$H NMR (ppm) |
|---|---|---|---|---|
| 155 | 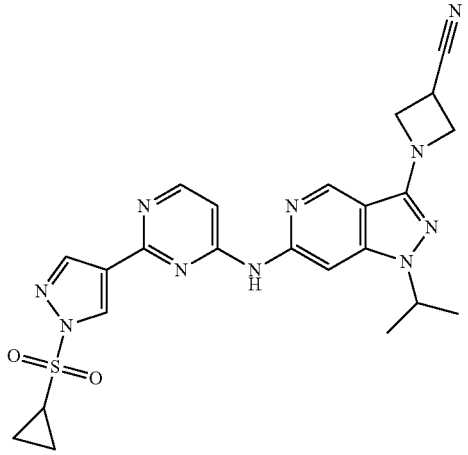 [SMILES: CC(C)n1nc(N2CC(C#N)C2)c2cnc(Nc3ccnc(-c4cnn(S(=O)(=O)C5CC5)c4)n3)cc21]<br>1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)azetidine-3-carbonitrile | 82 | 1.285<br>505.20<br>N | $^1$H NMR (300 MHz, DMSO-d$_6$): δ 10.36 (s, 1H), 8.70 (s, 1H), 8.66 (s, 1H), 8.48 (s, 1H), 8.42 (d, J = 6.0 Hz, 1H), 8.32 (s, 1H), 7.14 (d, J = 6.0 Hz, 1H), 4.77-4.71 (m, 1H), 4.42-4.38 (m, 2H), 4.30-4.27 (m, 2H), 4.93-4.00 (m, 1H), 3.31-3.26 (m, 1H), 1.47 (d, J = 6.8 Hz, 6H), 1.37-1.27 (m, 4H). |
| 156 | 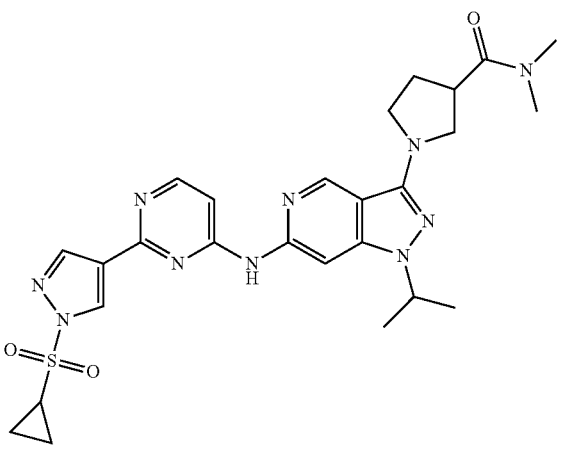 [SMILES: CC(C)n1nc(N2CCC(C(=O)N(C)C)C2)c2cnc(Nc3ccnc(-c4cnn(S(=O)(=O)C5CC5)c4)n3)cc21]<br>1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)N,N-dimethylpyrrolidine-3-carboxamide | 82 | 2.335<br>565.25<br>M | $^1$H NMR (300 MHz, DMSO-d$_6$): δ 10.30 (s, 1H), 8.78-8.69 (m, 2H), 8.47-8.39 (m, 2H), 8.25 (s, 1H), 7.13 (m, 1H), 4.73-4.64 (m, 1H), 3.88-3.71 (m, 1H), 3.70-3.52 (m, 4H), 3.30-3.24 (m, 1H), 3.09 (s, 3H), 2.86 (s, 3H), 2.25-2.07 (m, 2H), 1.46 (d, J = 6.6 Hz, 6H), 1.38-1.22 (m, 4H). |

| Example | Structure/Name | Synthesis Method | LCMS R$_T$ (min), M + H$^+$, method | $^1$H NMR (ppm) |
|---|---|---|---|---|
| 157 | 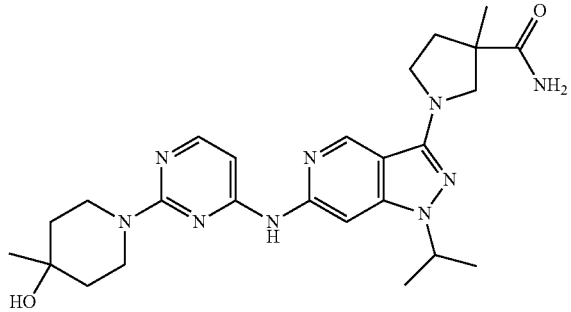 [SMILES: CC(C)n1nc(N2CCC(C)(C(N)=O)C2)c2cnc(Nc3ccnc(N4CCC(C)(O)CC4)n3)cc21]<br>1-(6-(2-(4-Hydroxy-4-methylpiperidin-1-yl)pyrimidin-4-ylamino)-1-isopropyl-1H-pyrazolo[4,3-c]pyridin-3-yl)-3-methylpyrrolidine-3-carboxamide | 85 | 1.475<br>494.15<br>Q | $^1$H NMR (400 MHz, DMSO-d$_6$): δ 9.80 (s, 1H), 8.70 (s, 1H), 8.13 (s, 1H), 7.96 (d, J = 5.6 Hz, 1H), 7.37 (s, 1H), 6.99 (s, 1H), 6.32 (d, J = 5.6 Hz, 1H), 4.50-4.45 (m, 1H), 4.39 (s, 1H), 4.20-4.17 (m, 2H), 3.90-3.88 (m, 1H), 3.63-3.58 (m, 2H), 3.49-3.43 (m, 2H), 3.39-3.33 (m, 1H), 2.50-2.34 (m, 1H), 1.86-1.79 (m, 1H), 1.58-1.49 (m, 4H), 1.42 (d, J = 6.0 Hz, 6H), 1.36 (s, 3H), 1.24 (s, 3H). |
| 158 | 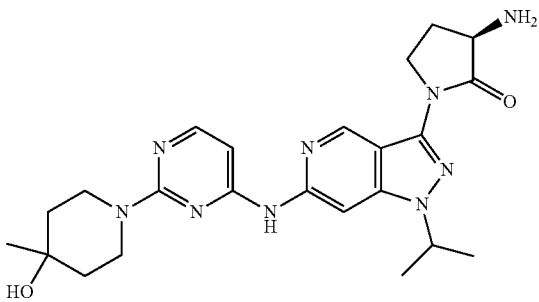 [SMILES: CC(C)n1nc(N2CC[C@@H](N)C2=O)c2cnc(Nc3ccnc(N4CCC(C)(O)CC4)n3)cc21]<br>(R)-3-Amino-1-(6-(2-(4-hydroxy-4-methylpiperidin-1-yl)pyrimidin-4-ylamino)-1-isopropyl-1H-pyrazolo[4,3-c]pyridin-3-yl)pyrrolidin-2-one | 86 | 1.316<br>466.00<br>H | $^1$H NMR (300 MHz, DMSO-d$_6$): δ 9.98 (s, 1H), 9.32 (s, 1H), 8.31 (s, 1H), 7.97 (d, J = 5.7 Hz, 1H), 6.30 (d, J = 5.7 Hz, 1H), 4.69-4.65 (m, 1H), 4.38 (s, 1H), 4.22-4.17 (m, 2H), 3.95-3.89 (m, 1H), 3.79-3.76 (m, 2H), 3.67-3.64 (m, 1H), 3.51-3.47 (m, 2H), 2.49-2.40 (m, 1H), 2.07 (s, 1H), 1.90-1.83 (m, 1H), 1.56-1.45 (m, 10H), 1.16 (s, 3H). |
| 159 | 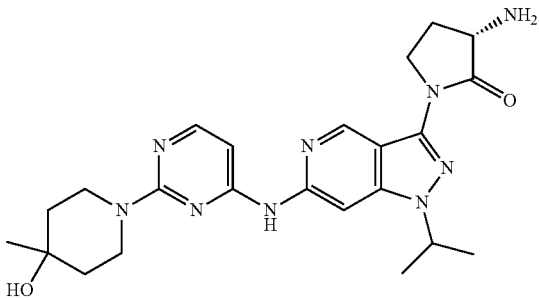 [SMILES: CC(C)n1nc(N2CC[C@H](N)C2=O)c2cnc(Nc3ccnc(N4CCC(C)(O)CC4)n3)cc21]<br>(S)-3-Amino-1-(6-(2-(4-hydroxy-4-methylpiperidin-1-yl)pyrimidin-4-ylamino)-1-isopropyl-1H-pyrazolo[4,3-c]pyridin-3-yl)pyrrolidin-2-one | 86 | 1.318<br>466.00<br>H | $^1$H NMR (300 MHz, DMSO-d$_6$): δ 9.98 (s, 1H), 9.32 (s, 1H), 8.31 (s, 1H), 7.97 (d, J = 5.7 Hz, 1H), 6.30 (d, J = 5.4 Hz, 1H), 4.69-4.65 (m, 1H), 4.38 (s, 1H), 4.22-4.17 (m, 2H), 3.95-3.89 (m, 1H), 3.79-3.76 (m, 2H), 3.67-3.64 (m, 1H), 3.51-3.47 (m, 2H), 2.49-2.40 (m, 1H), 1.98 (s, 1H), 1.90-1.82 (m, 1H), 1.56-1.45 (m, 10H), 1.16 (s, 3H). |

| Example | Structure/Name | Synthesis Method | LCMS R$_T$ (min), M + H$^+$, method | $^1$H NMR (ppm) |
|---|---|---|---|---|
| 160 | 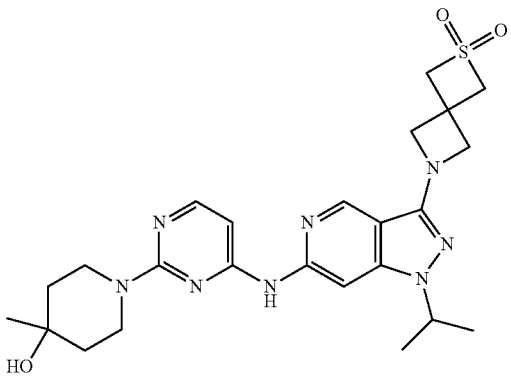 [SMILES: CC(C)n1nc(N2CC3(C2)CS(=O)(=O)C3)c2cnc(Nc3ccnc(N4CCC(C)(O)CC4)n3)cc21]<br>6-(6-((2-(4-Hydroxy-4-methylpiperidin-1-yl)pyrimidin-4-yl)amino)-1-isopropyl-1H-pyrazolo[4,3-c]pyridin-3-yl)-2-thia-6-azaspiro[3.3]heptane 2,2-dioxide | 85 | 1.526<br>513.10<br>R | $^1$H NMR (300 MHz, DMSO-d$_6$): δ 9.84 (s, 1H), 8.55 (s, 1H), 8.18 (s, 1H), 7.96 (d, J = 5.7 Hz, 1H), 6.32 (d, J = 5.7 Hz, 1H), 4.56-4.50 (m, 5H), 4.38-4.30 (m, 5H), 4.20-4.16 (m, 2H), 3.50-3.41 (m, 2H), 1.55-1.40 (m, 10H), 1.16 (s, 3H). |
| 161 | 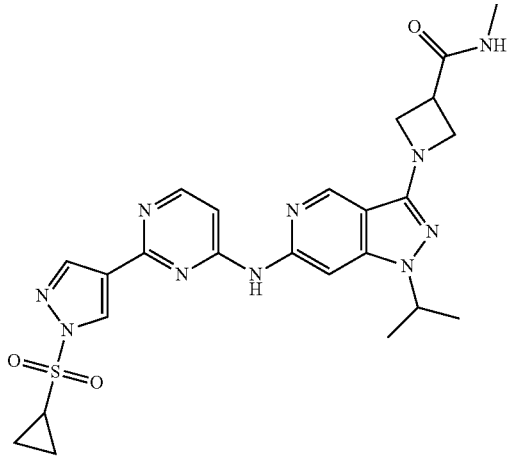 [SMILES: CNC(=O)C1CN(c2nn(C(C)C)c3cc(Nc4ccnc(-c5cnn(S(=O)(=O)C6CC6)c5)n4)ncc23)C1]<br>1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-N-methylazetidine-3-carboxamide | 30 | 2.085<br>537.20<br>M | $^1$H NMR (300 MHz, DMSO-d$_6$): δ 10.32 (s, 1H), 8.69 (s, 1H), 8.61 (s, 1H), 8.47 (s, 1H), 8.41 (d, J = 5.7 Hz, 1H), 8.28 (s, 1H), 7.97 (m, 1H), 7.14 (d, J = 5.7 Hz, 1H), 4.73-4.69 (m, 1H), 4.26-4.21 (m, 2H), 4.14-4.10 (m, 2H), 3.58-3.53 (m, 1H), 3.29-3.26 (m, 1H), 2.61 (d, J = 4.5 Hz, 3H), 1.46 (d, J = 6.6 Hz, 6H), 1.38-1.28 (m, 4H). |

| Example | Structure/Name | Synthesis Method | LCMS $R_T$ (min), M + H⁺, method | ¹H NMR (ppm) |
| --- | --- | --- | --- | --- |
| 162 | 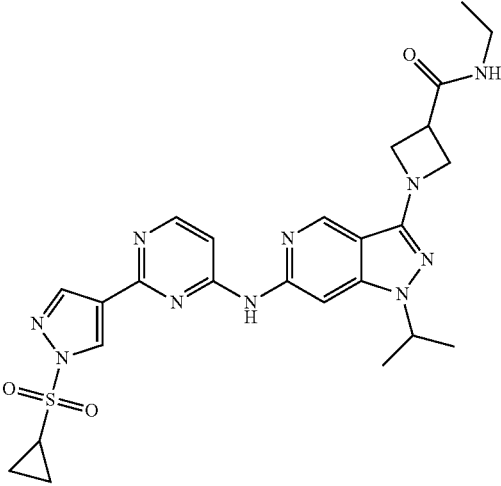 [SMILES: CCNC(=O)C1CN(c2nn(C(C)C)c3cc(Nc4ccnc(-c5cnn(S(=O)(=O)C6CC6)c5)n4)ncc23)C1]<br>1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-N-ethylazetidine-3-carboxamide | 30 | 1.166<br>551.35<br>S | ¹H NMR (300 MHz, DMSO-d₆): δ 10.31 (s, 1H), 8.69 (s, 1H), 8.61 (s, 1H), 8.47 (s, 1H), 8.41 (d, J = 6.0 Hz, 1H), 8.27 (s, 1H), 8.02-7.98 (m, 1H), 7.14 (d, J = 6.0 Hz, 1H), 4.73-4.68 (m, 1H), 4.24-4.14 (m, 2H), 4.12-4.10 (m, 2H), 3.57-3.52 (m, 2H), 3.29-3.26 (m, 1H), 3.15-3.06 (m, 1H), 1.46 (d, J = 6.6 Hz, 6H), 1.35-1.32 (m, 2H), 1.31-1.27 (m, 2H), 1.08-0.99 (m, 3H). |
| 163 | 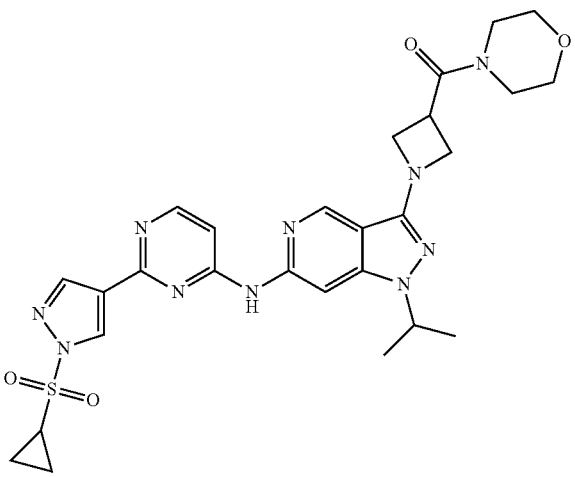 [SMILES: CC(C)n1nc(N2CC(C(=O)N3CCOCC3)C2)c2cnc(Nc3ccnc(-c4cnn(S(=O)(=O)C5CC5)c4)n3)cc21]<br>(1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)azetidin-3-yl)(morpholino)methanone | 30 | 1.481<br>593.20<br>L | ¹H NMR (300 MHz, DMSO-d₆): δ 10.34 (s, 1H), 8.70 (s, 1H), 8.64 (s, 1H), 8.47 (s, 1H), 8.41 (d, J = 6.0 Hz, 1H), 8.30 (s, 1H), 7.14 (d, J = 6.0 Hz, 1H), 4.78-4.70 (m, 1H), 4.32-4.30 (m, 2H), 4.24-4.19 (m, 2H), 4.00-3.90 (m, 1H), 3.61-3.58 (m, 4H), 3.50-3.48 (m, 2H), 3.40-3.36 (m, 2H), 3.32-3.29 (m, 1H), 1.47 (d, J = 6.6 Hz, 6H), 1.35-1.26 (m, 4H). |

| Example | Structure/Name | Synthesis Method | LCMS $R_T$ (min), M + H+, method | $^1$H NMR (ppm) |
|---|---|---|---|---|
| 164 | 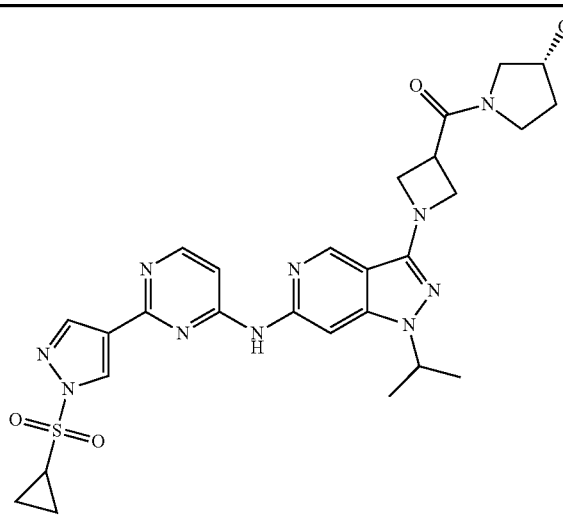<br>(R)-(1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)azetidin-3-yl)(3-hydroxypyrrolidin-1-yl)methanone | 30 | 2.246<br>593.15<br>R | $^1$H NMR (300 MHz, DMSO-d$_6$): δ 10.32 (s, 1H), 8.69 (s, 1H), 8.64 (s, 1H), 8.47 (s, 1H), 8.41 (d, J = 5.7 Hz, 1H), 8.28 (s, 1H), 7.14 (d, J = 5.7 Hz, 1H), 5.02-4.92 (m, 1H), 4.75-4.65 (m, 1H), 4.40-4.15 (m, 5H), 3.95-3.75 (m, 1H), 3.50-3.30 (m, 3H), 3.29-3.15 (m, 2H), 2.00-1.70 (m, 2H), 1.47 (d, J = 6.6 Hz, 6H), 1.40-1.20 (m, 4H). |
| 165 | 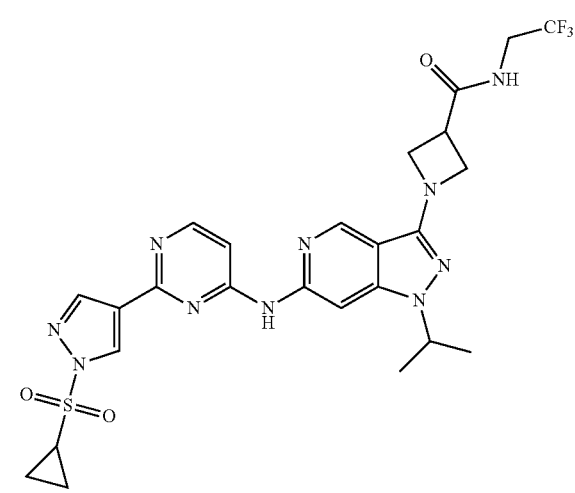 [SMILES: CC(C)n1nc(N2CC(C(=O)NCC(F)(F)F)C2)c2cnc(Nc3ccnc(-c4cnn(S(=O)(=O)C5CC5)c4)n3)cc21]<br>1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-N-(2,2,2-trifluoroethyl)azetidine-3-carboxamide | 30 | 1.576<br>605.10<br>L | $^1$H NMR (300 MHz, DMSO-d$_6$): δ 10.32 (s, 1H), 8.74-8.63 (m, 3H), 8.47 (s, 1H), 8.40 (d, J = 6.0 Hz, 1H), 8.29 (s, 1H), 7.14 (d, J = 6.0 Hz, 1H), 4.74-4.69 (m, 1H), 4.32-4.27 (m, 2H), 4.16-4.12 (m, 2H), 4.02-3.90 (m, 2H), 3.72-3.66 (m, 1H), 3.30-3.26 (m, 1H), 1.47 (d, J = 6.6 Hz, 6H), 1.48-1.33 (m, 4H). |

-continued

| Example | Structure/Name | Synthesis Method | LCMS R$_T$ (min), M + H$^+$, method | $^1$H NMR (ppm) |
|---|---|---|---|---|
| 166 | 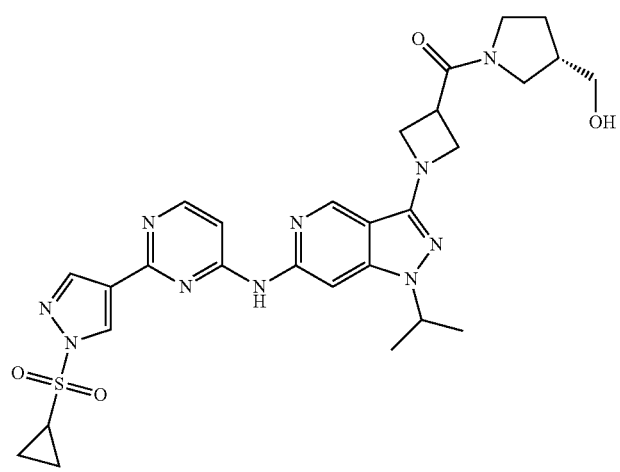 [SMILES: CC(C)n1nc(N2CC(C(=O)N3CC[C@H](CO)C3)C2)c2cnc(Nc3ccnc(-c4cnn(S(=O)(=O)C5CC5)c4)n3)cc21]<br>(S)-(1-(6-(2-(1-(cyclopropylsulfonyl)-1H-pyrazol-4-yl)pyrimidin-4-ylamino)-1-isopropyl-1H-pyrazolo[4,3-c]pyridin-3-yl)azetidin-3-yl)(3-(hydroxymethyl)pyrrolidin-1-yl)methanone | 30 | 2.077<br>607.30<br>M | $^1$H NMR (400 MHz, DMSO-d$_6$): δ 10.33 (s, 1H), 8.70 (s, 1H), 8.64 (s, 1H), 8.47 (s, 1H), 8.42-8.40 (d, J = 6.0 Hz, 1H), 8.29 (s, 1H), 7.15-7.13 (d, J = 6.0 Hz, 1H), 4.74-4.66 (m, 2H), 4.33-4.29 (m, 2H), 4.22-4.16 (m, 2H), 3.86-3.82 (m, 1H), 3.48-3.27 (m, 6H), 3.13-3.11 (m, 1H), 2.39-2.21 (m, 1H), 1.99-1.82 (m, 1H), 1.74-1.53 (m, 1H), 1.47-1.46 (d, J = 6.8 Hz, 6H), 1.35-1.33 (m, 2H), 1.29-1.24 (m, 2H). |
| 167 | 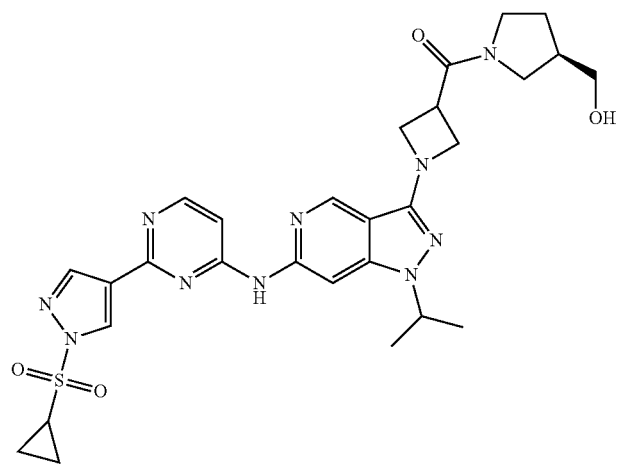 [SMILES: CC(C)n1nc(N2CC(C(=O)N3CC[C@@H](CO)C3)C2)c2cnc(Nc3ccnc(-c4cnn(S(=O)(=O)C5CC5)c4)n3)cc21]<br>(R)-(1-(6-(2-(1-(cyclopropylsulfonyl)-1H-pyrazol-4-yl)pyrimidin-4-ylamino)-1-isopropyl-1H-pyrazolo[4,3-c]pyridin-3-yl)azetidin-3-yl)(3-(hydroxymethyl)pyrrolidin-1-yl)methanone | 30 | 2.114<br>607.30<br>M | $^1$H NMR (400 MHz, DMSO-d$_6$): δ 10.34 (s, 1H), 8.70 (s, 1H), 8.64 (s, 1H), 8.48 (s, 1H), 8.42-8.41 (d, J = 6.0 Hz, 1H), 8.30 (s, 1H), 7.15-7.13 (d, J = 6.0 Hz, 1H), 4.76-4.67 (m, 2H), 4.33-4.30 (m, 2H), 4.22-4.17 (m, 2H), 3.86-3.84 (m, 1H), 3.48-3.26 (m, 6H), 3.14-3.11 (m, 1H), 2.40-2.22 (m, 1H), 1.99-1.83 (m, 1H), 1.74-1.53 (m, 1H), 1.48-1.46 (d, J = 6.4 Hz, 6H), 1.38-1.35 (m, 2H), 1.34-1.26 (m, 2H). |

| Example | Structure/Name | Synthesis Method | LCMS R$_T$ (min), M + H$^+$, method | $^1$H NMR (ppm) |
|---|---|---|---|---|
| 168 | 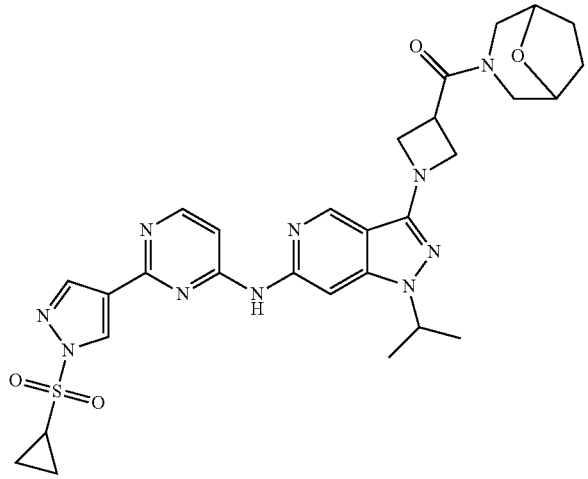 [SMILES: CC(C)n1nc(N2CC(C(=O)N3CC4CCC(C3)O4)C2)c2cnc(Nc3ccnc(-c4cnn(S(=O)(=O)C5CC5)c4)n3)cc21]<br>8-Oxa-3-azabicyclo[3.2.1]octan-3-yl(1-(6-(2-(1-(cyclopropylsulfonyl)-1H-pyrazol-4-yl)pyrimidin-4-ylamino)-1-isopropyl-1H-pyrazolo[4,3-c]pyridin-3-yl)azetidin-3-yl)methanone | 30 | 2.282<br>619.30<br>M | $^1$H NMR (400 MHz, DMSO-d$_6$): δ 10.33 (s, 1H), 8.70 (s, 1H), 8.64 (s, 1H), 8.47 (s, 1H), 8.42-8.41 (d, J = 5.6 Hz, 1H), 8.30 (s, 1H), 7.14-7.13 (d, J = 5.6 Hz, 1H), 4.73-4.70 (m, 1H), 4.35-4.14 (m, 6H), 3.97-3.94 (m, 2H), 3.33-3.25 (m, 3H), 2.84-2.81 (m, 1H), 1.81-1.57 (m, 4H), 1.47-1.46 (d, J = 6.4 Hz, 6H), 1.35-1.33 (m, 2H), 1.29-1.23 (m, 2H). |
| 169 | 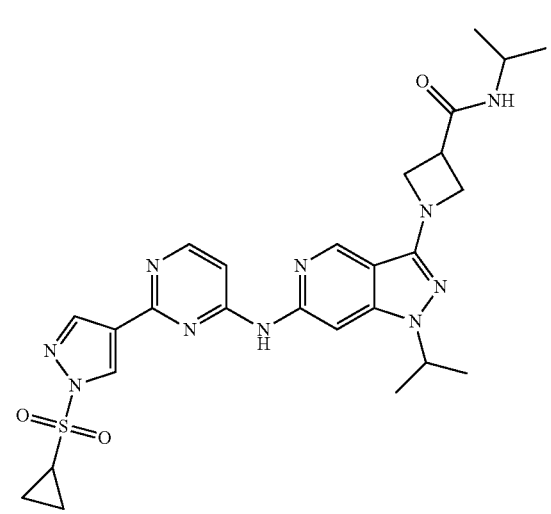 [SMILES: CC(C)NC(=O)C1CN(c2nn(C(C)C)c3cc(Nc4ccnc(-c5cnn(S(=O)(=O)C6CC6)c5)n4)ncc23)C1]<br>1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-N-isopropylazetidine-3-carboxamide | 30 | 1.821<br>565.20<br>R | $^1$H NMR (300 MHz, DMSO-d$_6$): δ 10.33 (s, 1H), 8.70 (s, 1H), 8.62 (s, 1H), 8.48 (s, 1H), 8.41 (d, J = 6.0 Hz, 1H), 8.29 (s, 1H), 7.89 (m, 1H), 7.14 (d, J = 6.0 Hz, 1H), 4.74-4.69 (m, 1H), 4.26-4.21 (m, 2H), 4.14-4.09 (m, 2H), 3.90-3.83 (m, 1H), 3.57-3.52 (m, 1H), 3.31-3.27 (m, 1H), 1.47 (d, J = 6.6 Hz, 6H), 1..38-1.33 (m, 4H), 1.11-1.05 (m, 6H). |

| Example | Structure/Name | Synthesis Method | LCMS $R_T$ (min), M + H+, method | ¹H NMR (ppm) |
|---|---|---|---|---|
| 170 | 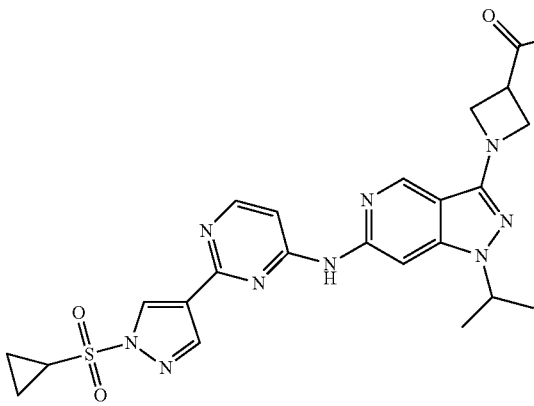<br>1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-N-(3-hydroxycyclobutyl)azetidine-3-carboxamide | 30 | 2.483<br>593.20<br>R | ¹H NMR (300 MHz, DMSO-d₆): δ 10.30 (s, 1H), 8.70 (s, 1H), 8.61 (s, 1H), 8.47 (s, 1H), 8.41 (d, J = 5.6 Hz, 1H), 8.28-8.20 (m, 2H), 7.14 (d, J = 5.6 Hz, 1H), 5.08-5.01 (m, 1H), 4.73-4.69 (m, 1H), 4.25-4.21 (m, 2H), 4.13-4.08 (m, 2H), 3.85-3.62 (m, 2H), 3.60-3.45 (m, 1H), 3.31-3.27 (m, 1H), 2.47 (s, 1H), 2.11-2.01 (m, 1H). 1.73-1.70 (m, 1H), 1.46 (d, J = 6.8 Hz, 6H), 1.29-1.23 (m, 5H). |
| 171 | 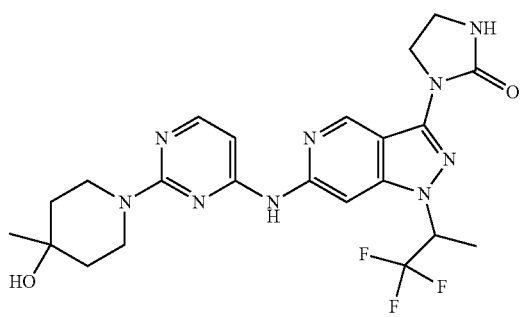 [SMILES: CC(n1nc(N2CCNC2=O)c2cnc(Nc3ccnc(N4CCC(C)(O)CC4)n3)cc21)C(F)(F)F]<br>1-(6-(2-(4-Hydroxy-4-methylpiperidin-1-yl)pyrimidin-4-ylamino)-1-(1,1,1-trifluoropropan-2-yl)-1H-pyrazolo[4,3-c]pyridin-3-yl)imidazolidin-2-one | 87 | 1.466<br>506.20<br>M | ¹H NMR (300 MHz, DMSO-d₆): δ 9.97 (s, 1H), 9.34 (s, 1H), 8.32 (s, 1H), 7.98 (d, J = 5.7 Hz, 1H), 7.31 (s, 1H), 6.31 (d, J = 5.7 Hz, 1H), 5.50-5.32 (m, 1H), 4.37 (s, 1H), 4.23-4.11 (m, 2H), 3.96-3.90 (m, 2H), 3.52-3.32 (m, 4H), 1.74 (d, J = 6.9 Hz, 3H), 1.59-1.39 (m, 4H), 1.15 (s, 3H). |
| 172 | 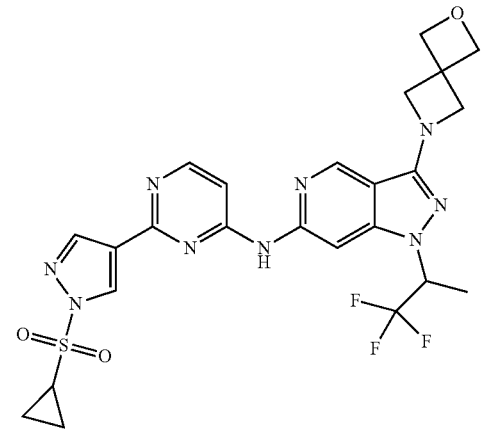 [SMILES: CC(n1nc(N2CC3(COC3)C2)c2cnc(Nc3ccnc(-c4cnn(S(=O)(=O)C5CC5)c4)n3)cc21)C(F)(F)F]<br>N-(2-(1-(Cyclopropylsulfonyl)-1H-pyrazol-4-yl)pyrimidin-4-yl)-3-(2-oxa-6-azaspiro[3.3]heptan-6-yl)-1-(1,1,1-trifluoropropan-2-yl)-1H-pyrazolo[4,3-c]pyridin-6-amine | 87 | 1.812<br>576.05<br>R | ¹H NMR (300 MHz, DMSO-d₆): δ 10.39 (s, 1H), 8.70-8.66 (m, 2H), 8.46 (s, 1H), 8.43 (d, J = 6.0 Hz, 1H), 8.23 (s, 1H), 7.15 (d, J = 6.0 Hz, 1H), 5.68-5.49 (m, 1H), 4.75 (s, 4H), 4.32 (s, 4H), 3.32-3.18 (m, 1H), 1.71 (d, J = 6.9 Hz, 3H), 1.40-1.15 (m, 4H) |

| Example | Structure/Name | Synthesis Method | LCMS R$_T$ (min), M + H$^+$, method | $^1$H NMR (ppm) |
|---|---|---|---|---|
| 173 | (±)-1-(6-(2-(cis-3-Fluoro-4-hydroxypiperidin-1-yl)pyrimidin-4-ylamino)-1-isopropyl-1H-pyrazolo[4,3-c]pyridin-3-yl)-4-hydroxypyrrolidin-2-one(mixture of diastereomers) | 75 | 1.267 471.20 M | $^1$H NMR (400 MHz, DMSO-d$_6$): δ 10.03 (s, 1H), 9.30 (s, 1H), 8.29 (s, 1H), 8.01-8.00 (d, J = 5.6 Hz, 1H), 6.38-6.36 (d, J = 5.6 Hz, 1H), 5.41-5.40 (m, 1H), 5.15-5.14 (m, 1H), 4.77-4.63 (m, 2H), 4.53-4.49 (m, 2H), 4.30-4.26 (d, J = 13.2 Hz, 1H), 4.15-4.11 (m, 1H), 3.91-3.81 (m, 2H), 3.77-3.65 (m, 1H), 3.43-3.34 (m, 1H), 2.96-2.90 (m, 1H), 2.38-2.34 (d, J = 17.6 Hz, 1H), 1.78-1.68 (m, 2H), 1.49-1.47 (m, 6H). |
| 174 | (±)-cis-1-(4-(3-(3,3-Difluoroazetidin-1-yl)-1-isopropyl-1H-pyrazolo[4,3-c]pyridin-6-ylamino)pyrimidin-2-yl)-3-fluoropiperidin-4-ol | 20 | 1.394 463.25 L | $^1$H NMR (400 MHz, DMSO-d$_6$): δ 9.92 (s, 1H), 8.63 (s, 1H), 8.17 (s, 1H), 7.80-7.98 (d, J = 5.7 Hz, 1H), 6.39-6.37 (d, J = 5.7 Hz, 1H), 5.15-5.13 (m, 1H), 4.62 (m, 7H), 4.29-4.25 (m, 1H), 3.91-3.82 (m, 1H), 3.65-3.51 (m, 2H), 1.71 (m, 2H), 1.45-1.42 (m, 6H). |
| 175 | (±)-2-(6-((2-((cis)-3-Fluoro-4-hydroxypiperidin-1-yl)pyrimidin-4-yl)amino)-1-isopropyl-1H-pyrazolo[4,3-c]pyridin-3-yl)-2-azaspiro[3.3]heptan-6-ol | 20 | 1.349 483.15 R | $^1$H NMR (400 MHz, DMSO-d$_6$): δ 9.86 (s, 1H), 8.52 (s, 1H), 8.10 (s, 1H), 7.97 (d, J = 5.7 Hz, 1H), 6.37 (d, J = 5.7 Hz, 1H), 5.14-5.05 (m, 2H), 4.50-4.82 (m, 3H), 4.31-4.19 (m, 1H), 4.07-4.00 (m, 5H), 3.95-3.79 (m, 1H), 3.69-3.46 (m, 1H), 3.36 (s, 1H), 2.51-2.46 (m, 2H), 2.05-1.98 (m, 2H), 1.69 (m, 2H), 1.42-1.39 (m, 6H). |

| Example | Structure/Name | Synthesis Method | LCMS R$_T$ (min), M + H$^+$, method | $^1$H NMR (ppm) |
|---|---|---|---|---|
| 176 | (4S)-1-(1-sec-Butyl-6-(2-(4-hydroxy-4-methylpiperidin-1-yl)pyrimidin-4-ylamino)-1H-pyrazolo[4,3-c]pyridin-3-yl)-4-(hydroxymethyl)imidazolidin-2-one(mixture of diastereoisomers) | 90 | 1.465 496.20 R | $^1$H NMR (300 MHz, DMSO-d$_6$): δ 9.95 (s, 1H), 9.34 (s, 1H), 8.26 (s, 1H), 7.98 (d, J = 5.7 Hz, 1H), 7.35 (s, 1H), 6.32 (d, J = 5.7 Hz, 1H), 5.03-5.00 (m, 1H), 4.42 (s, 1H) 4.36-4.29 (m, 1H), 4.21 (d, J = 12.9 Hz, 2H), 4.05-3.99 (m, 1H), 3.85-3.73 (m, 2H), 3.49-3.46 (m, 4H), 1.99-1.91 (m, 1H), 1.85-1.76 (m, 1H), 1.57-1.43 (m, 7H), 1.17 (s, 3H), 0.77-0.73 (m, 3H). |
| 177 | 1-(4-(3-(cis-3-Amino-4-fluoropyrrolidin-1-yl)-1-sec-butyl-1H-pyrazolo[4,3-c]pyridin-6-ylamino)pyrimidin-2-yl)-4-methylpiperidin-4-ol(mixture of diastereoisomers) | 89 | 1.497 484.20 R | $^1$H NMR (300 MHz, DMSO-d$_6$): δ 9.85 (s, 1H), 8.70 (s, 1H), 8.15 (s, 1H), 7.96 (d, J = 5.7 Hz, 1H), 6.31 (d, J = 5.7 Hz, 1H), 5.11-4.91 (m, 1H), 4.41 (s, 1H), 4.22-4.17 (m, 3H), 3.91-3.78 (m, 3H), 3.75-3.44 (m, 3H), 3.25-3.19 (m, 1H), 1.96-1.72 (m, 4H), 1.55-1.38 (m, 7H), 1.16 (s, 3H), 0.75-0.70 (m, 3H). |
| 178 | 1-(4-(1-sec-Butyl-3-(trans-3-fluoro-4-hydroxypyrrolidin-1-yl)-1H-pyrazolo[4,3-c]pyridin-6-ylamino)pyrimidin-2-yl)-4-methylpiperidin-4-ol(mixture of diastereoisomers) | 89 | 1.612 485.20 N | $^1$H NMR (300 MHz, DMSO-d$_6$): δ 9.80 (s, 1H), 8.75 (s, 1H), 8.15 (s, 1H), 7.97 (d, J = 5.7 Hz, 1H), 6.33 (d, J = 5.7 Hz, 1H), 5.56 (m, 1H), 5.09 (d, J = 51.6 Hz, 1H), 4.41-4.36 (m, 2H), 4.23-4.18 (m, 3H), 3.93-3.74 (m, 3H), 3.59-3.48 (m, 3H), 1.97-1.90 (m, 1H), 1.80-1.73 (m, 1H), 1.59-1.39 (m, 7H), 1.15 (s, 3H), 0.79-0.69 (m, 3H). |

-continued

| Example | Structure/Name | Synthesis Method | LCMS R_T (min), M + H+, method | $^1$H NMR (ppm) |
|---|---|---|---|---|
| 179 | 2-(6-(2-(cis-3-Fluoro-4-hydroxypiperidin-1-yl)pyrimidin-4-ylamino)-1-isopropyl-1H-pyrazolo[4,3-c]pyridin-3-ylamino)propanenitrile(mixture of diastereoisomers) | 91 | 1.573 440.15 R | $^1$H NMR (400 MHz, DMSO-d$_6$): δ 9.87 (s, 1H), 8.67 (s, 1H), 8.12 (s, 1H), 7.98 (d, J = 5.6 Hz, 1H), 7.20 (m, 1H), 6.37 (d, J = 5.6 Hz, 1H), 5.13 (m, 1H), 4.71-4.69 (m, 2H), 4.56-4.42 (m, 2H), 4.38-4.29 (m, 1H), 3.97-3.85 (m, 1H), 3.65-3.43 (m, 1H), 3.38-3.34 (m, 1H), 1.70 (m, 2H), 1.61 (m, 3H), 1.44-1.42 (m, 6H). |
| 180 | N-(2-(1-(Cyclopropylsulfonyl)-1H-pyrazol-4-yl)pyrimidin-4-yl)-3-(3,5-dimethylmorpholino)-1-isopropyl-1H-pyrazolo[4,3-c]pyridin-6-amine | 91 | 2.397 538.25 L | $^1$H NMR (300 MHz, DMSO-d$_6$): δ 10.40 (s, 1H), 8.79 (s, 1H), 8.72 (s, 1H), 8.49 (s, 1H), 8.42 (d, J = 6.0 Hz, 1H), 8.39 (s, 1H), 7.11 (d, J = 6.0 Hz, 1H), 4.84-4.75 (m, 1H), 3.92-3.87 (m, 2H), 3.79-3.74 (m, 2H), 3.51-3.45 (m, 2H), 3.31-3.26 (m, 1H), 1.53-1.46 (m, 6H), 1.36-1.29 (m, 4H), 1.05-0.95 (m, 6H). |
| 181 | N$^6$-(2-(1-(cyclopropylsulfonyl)-1H-pyrazol-4-yl)pyrimidin-4-yl)-1-isopropyl-N$^3$-(2,2,2-trifluoroethyl)-1H-pyrazolo[4,3-c]pyridine-3,6-diamine | 91 | 1.722 522.15 L | $^1$H NMR (400 MHz, DMSO-d$_6$): δ 10.31 (s, 1H), 8.77 (s, 1H), 8.70 (s, 1H), 8.48 (s, 1H), 8.42 (d, J = 6.0 Hz, 1H), 8.24 (s, 1H), 7.19-7.14 (m, 2 H), 4.69-4.50 (m, 1H), 4.14-4.10 (m, 2H), 3.35-3.28 (m, 1H), 1.46 (d, J = 6.4 Hz, 6H), 1.36-1.35 (m, 2H), 1.28-1.26 (m, 2H). |

| Example | Structure/Name | Synthesis Method | LCMS R$_T$ (min), M + H$^+$, method | $^1$H NMR (ppm) |
|---|---|---|---|---|
| 182 | 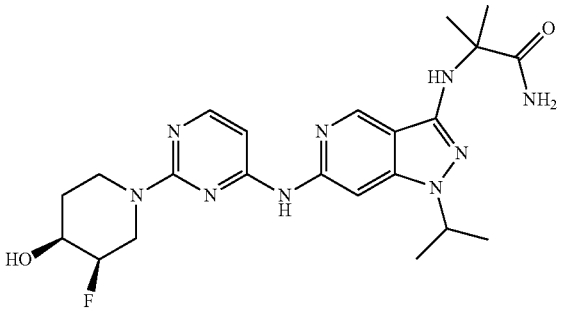 [SMILES: CC(C)n1nc(NC(C)(C)C(N)=O)c2cnc(Nc3ccnc(N4CC[C@H](O)[C@H](F)C4)n3)cc21]<br>(±)-2-(6-(2-(cis-3-Fluoro-4-hydroxypiperidin-1-yl)pyrimidin-4-ylamino)-1-isopropyl-1H-pyrazolo[4,3-c]pyridin-3-ylamino)-2-methylpropanamide | 91 | 1.070<br>472.25<br>R | $^1$H NMR (400 MHz, DMSO-d$_6$): δ 9.80 (s, 1 H), 8.72 (s, 1 H), 8.04 (s, 1 H), 7.97 (d, J = 5.6 Hz, 1 H), 7.06 (s, 1 H), 6.82 (s, 1 H), 6.40 (s, 1 H), 6.35 (d, J = 5.6 Hz, 1 H), 5.12 (m, 1 H), 4.73-4.60 (m, 1 H), 4.51-4.46 (m, 2 H), 4.27-4.24 (m, 1 H), 3.95-3.75 (m, 1 H), 3.65-3.45 (m, 1 H), 3.40-3.30 (m, 1 H), 1.70-1.68 (m, 2 H), 1.51 (s, 6 H), 1.39-1.37 (m, 6 H). |
| 183 | 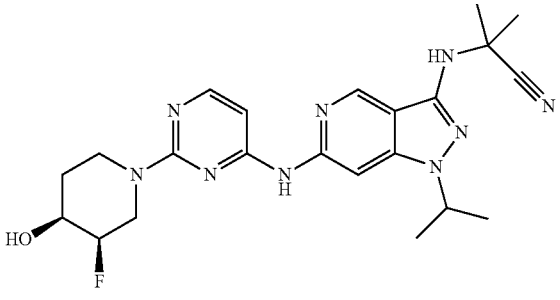 [SMILES: CC(C)n1nc(NC(C)(C)C#N)c2cnc(Nc3ccnc(N4CC[C@H](O)[C@H](F)C4)n3)cc21]<br>(±)-2-(6-(2-(cis-3-Fluoro-4-hydroxypiperidin-1-yl)pyrimidin-4-ylamino)-1-isopropyl-1H-pyrazolo[4,3-c]pyridin-3-ylamino)-2-methylpropanenitrile | 91 | 1.700<br>454.15<br>R | $^1$H NMR (300 MHz, DMSO-d$_6$): δ 9.86 (s, 1H), 8.70 (s, 1H), 8.18 (s, 1H), 7.98 (d, J = 5.7 Hz, 1H), 7.01 (s, 1H), 6.36 (d, J = 5.7 Hz, 1H), 5.16 (m, 1H), 4.77 (s, 1H), 4.60-4.49 (m, 3H), 4.30-4.25 (m, 1H), 3.91-3.81 (m, 1H), 3.63-3.43 (m, 1H), 1.71-1.70 (m, 8H), 1.45-1.42 (m, 6H). |
| 184 | 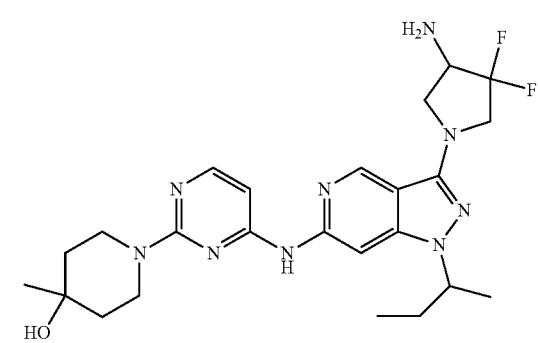 [SMILES: CCC(C)n1nc(N2CC(N)C(F)(F)C2)c2cnc(Nc3ccnc(N4CCC(C)(O)CC4)n3)cc21]<br>1-(4-(3-(4-Amino-3,3-difluoropyrrolidin-1-yl)-1-sec-butyl-1H-pyrazolo[4,3-c]pyridin-6-ylamino)pyrimidin-2-yl)-4-methylpiperidin-4-ol | 85 | 0.723<br>502.30<br>R | $^1$H NMR (400 MHz, DMSO-d$_6$): δ 9.86 (s, 1H), 8.74 (s, 1H), 8.18 (s, 1H), 7.97 (d, J = 5.6 Hz, 1H), 6.32 (d, J = 5.6 Hz, 1H), 4.41 (s, 1H), 4.22-4.18 (m, 3H), 4.02-3.96 (m, 3H), 3.70 (bs, 1H), 3.49-3.46 (m, 2H), 3.45-3.36 (m, 1H), 1.99-1.89 (m, 3H), 1.79-1.72 (m, 1H), 1.55-1.39 (m, 7H), 1.17 (s, 3H), 1.76-1.70 (m, 3H). |

| Example | Structure/Name | Synthesis Method | LCMS R$_T$ (min), M + H$^+$, method | $^1$H NMR (ppm) |
|---|---|---|---|---|
| 185 | (3S)-(1-sec-Butyl-6-(2-(1-(cyclopropylsulfonyl)-1H-pyrazol-4-yl)pyrimidin-4-ylamino)-1H-pyrazolo[4,3-c]pyridin-3-yl)-3-hydroxypyrrolidin-2-one | 86 | 1.615 538.25 M | $^1$H NMR (300 MHz, DMSO-d$_6$): δ 10.49 (s, 1H), 9.40 (s, 1H), 8.73 (s, 1H), 8.50-8.43 (m, 3H), 7.10 (m, 1H), 5.88-5.86 (m, 1H), 4.80-4.56 (m, 1H), 4.51-4.39 (m, 1H), 3.94-3.89 (m, 1H), 3.82-3.79 (m, 1H), 3.31-3.27 (m, 1H), 2.41-2.42 (m, 1H), 2.02-1.88 (m, 3H), 1.51 (d, J = 6.3 Hz, 3H), 1.36-1.30 (m, 4H), 0.83-0.71 (m, 3H). |
| 186 | (3R)-1-(1-sec-Butyl-6-(2-(1-(cyclopropylsulfonyl)-1H-pyrazol-4-yl)pyrimidin-4-ylamino)-1H-pyrazolo[4,3-c]pyridin-3-yl)-3-hydroxypyrrolidin-2-one | 86 | 2.510 538.25 M | $^1$H NMR (300 MHz, DMSO-d$_6$): δ 10.50 (s, 1H), 9.40 (s, 1H), 8.74 (s, 1H), 8.50-8.43 (m, 3H), 7.10 m, 1H), 5.89-5.87 (m, 1H), 4.67-4.60 (m, 1H), 4.49-4.40 (m, 1H), 3.98-3.91 (m, 1H), 3.90-3.79 (m, 1H), 3.33-3.24 (m, 1H), 2.51-2.43 (m, 1H), 2.10-1.82 (m, 3H), 1.52 (d, J = 8.0 Hz, 3H), 1.39-1.20 (m, 4H), 0.83-0.65 (m, 3H). |
| 187 | (2S)-1-(4-(1-sec-Butyl-6-(2-(1-(cyclopropylsulfonyl)-1H-pyrazol-4-yl)pyrimidin-4-ylamino)-1H-pyrazolo[4,3-c]pyridin-3-yl)piperazin-1-yl)-2-hydroxypropan-1-one | 78 | 2.410 595.25 M | $^1$H NMR (400 MHz, DMSO-d$_6$): δ 10.40 (s, 1H), 8.94 (s, 1H), 8.71 (s, 1H), 8.49 (s, 1H), 8.43-8.41 (d, J = 6.0 Hz, 1H), 8.34 (s, 1H), 7.12-7.11 (d, J = 6.0 Hz, 1H), 5.01-4.99 (m, 1H), 4.52-4.44 (m, 2H), 3.78-3.62 (m, 4H), 3.44 (s, 4H), 3.34-3.26 (m, 1H), 2.02-1.79 (m, 2H), 1.48-1.46 (m, 3H), 1.35-1.26 (m, 4H), 1.24-1.22 (d, J = 6.8 Hz, 3H), 0.75-0.71 (m, 3H). |

| Example | Structure/Name | Synthesis Method | LCMS R$_T$ (min), M + H$^+$, method | $^1$H NMR (ppm) |
|---|---|---|---|---|
| 188 | (2R)-1-(4-(1-sec-Butyl-6-(2-(1-(cyclopropylsulfonyl)-1H-pyrazol-4-yl)pyrimidin-4-ylamino)-1H-pyrazolo[4,3-c]pyridin-3-yl)piperazin-1-yl)-2-hydroxypropan-1-one | 78 | 1.632 595.30 M | $^1$H NMR (400 MHz, DMSO-d$_6$): δ 10.40 (s, 1H), 8.94 (s, 1H), 8.71 (s, 1H), 8.49 (s, 1H), 8.43-8.41 (d, J = 6.0 Hz, 1H), 8.34 (s, 1H), 7.12-7.11 (d, J = 6.0 Hz, 1H), 5.01-4.99 (m, 1H), 4.52-4.44 (m, 2H), 3.78-3.62 (m, 4H), 3.44 (s, 4H), 3.34-3.26 (m, 1H), 2.02-1.79 (m, 2H), 1.48-1.46 (m, 3H), 1.35-1.26 (m, 4H), 1.24-1.22 (d, J = 6.8 Hz, 3H), 0.75-0.71 (m, 3H) |
| 189 | (4S)-1-(1-sec-Butyl-6-(2-(1-(cyclopropylsulfonyl)-1H-pyrazol-4-yl)pyrimidin-4-ylamino)-1H-pyrazolo[4,3-c]pyridin-3-yl)-4-(hydroxymethyl)imidazolidin-2-one | 90 | 2.968 553.10 R | $^1$H NMR (300 MHz, DMSO-d$_6$): δ 10.41 (s, 1H), 9.40 (s, 1H), 8.72 (s, 1H), 8.49 (s, 1H), 8.43-8.39 (m, 2H), 7.37 (s, 1H), 7.11 (m, 1H), 5.02-4.99 (m, 1H) 4.65-4.48 (m, 1H), 4.11-3.96 (m, 1H), 3.84-3.76 (m, 2H), 3.49-3.46 (m, 2H), 3.3.31-3.27 (m, 1H), 2.12-1.79 (m, 2H), 1.50 (d, J = 6.6 Hz, 3H), 1.36-1.24 (m, 4H), 0.83-0.69 (m, 3H). |
| 190 | 1-(1-(1-sec-Butyl-6-(2-(1-(cyclopropylsulfonyl)-1H-pyrazol-4-yl)pyrimidin-4-ylamino)-1H-pyrazolo[4,3-c]pyridin-3-yl)azetidin-3-yl)ethanol | 73 | 2.646 538.25 M | $^1$H NMR (300 MHz, DMSO-d$_6$): δ 10.32 (s, 1H), 8.69 (s, 1H), 8.69 (s, 1H), 8.60 (s, 1H), 8.42-8.40 (d, J = 6.0 Hz, 1H), 8.25 (s, 1H), 7.14-7.12 (d, J = 6.0 Hz, 1H), 4.74-4.73 (m, 1H), 4.45-4.30 (m, 1H), 4.13-4.09 (m, 2H), 4.08-3.98 (m, 1H), 3.88-3.79 (m, 2H), 3.25-3.31 (m, 1H), 2.73-2.70 (m, 1H), 1.91-1.80 (m, 2H), 1.46-1.44 (d, J = 6.6 Hz, 3H), 1.35-1.25 (m, 4H), 1.06-1.04 (d, J = 6.3 Hz, 3H), 0.73 (m, 3H). |

| Example | Structure/Name | Synthesis Method | LCMS R$_T$(min), M + H$^+$, method | $^1$H NMR (ppm) |
|---|---|---|---|---|
| 191 | (±)-1-(6-(2-(4-Hydroxy-4-methylpiperidin-1-yl)pyrimidin-4-ylamino)-1-isopropyl-1H-pyrazolo[4,3-c]pyridin-3-yl)pyrrolidine-cis-3,4-diol | 85 | 1.022 469.10 N | $^1$H NMR (300 MHz, DMSO-d$_6$): δ 9.79 (s, 1 H), 8.68 (s, 1 H), 8.13 (s, 1 H), 7.96 (d, J = 5.4 Hz, 1 H), 6.32 (d, J = 5.4 Hz, 1 H), 4.92 (m, 2 H), 4.53-4.44 (m, 1 H), 4.39 (s, 1 H), 4.21-4.16 (m, 4 H), 3.75-3.70 (m, 2 H), 3.49-3.34 (m, 4 H), 1.55-1.40 (m, 10 H), 1.16 (s, 3 H). |
| 192 | (3S,4S)-1-(6-(2-(4-Hydroxy-4-methylpiperidin-1-yl)pyrimidin-4-ylamino)-1-isopropyl-1H-pyrazolo[4,3-c]pyridin-3-yl)pyrrolidine-3,4-diol | 85 | 2.307 469.20 R | $^1$H NMR (400 MHz, DMSO-d$_6$): δ 9.76 (s, 1H), 8.70 (s, 1H), 8.12 (s, 1H), 7.96 (d, J = 5.6 Hz, 1H), 6.31 (d, J = 5.6 Hz, 1H), 5.11 (m, 2H), 4.50-4.47 (m, 1H), 4.39 (s, 1H), 4.20-4.17 (m, 2H), 4.06 (s, 2H), 3.77-3.74 (m, 2H), 3.49-3.42 (m, 4H), 1.54-1.45 (m, 4H), 1.41 (d, J = 6.4 Hz, 6H), 1.16 (s, 3H) |
| 193 | (3S,4R)-1-(4-((1-((R*)-sec-Butyl)-3-(3-(2-hydroxypropan-2-yl)azetidin-1-yl)-1H-pyrazolo[4,3-c]pyridin-6-yl)amino)pyrimidin-2-yl)-3-fluoropiperidin-4-ol | 65 | 3.58 499.3 B | $^1$H NMR (400 MHz, DMSO) δ 9.82 (s, 1H), 8.55 (s, 1H), 8.10 (s, 1H), 7.97 (d, J = 5.6 Hz, 1H), 6.37 (d, J = 5.7 Hz, 1H), 5.11 (d, J = 5.0 Hz, 1H), 4.66 (d, J = 48.9 Hz, 1H), 4.55-4.43 (m, 1H), 4.40 (s, 1H), 4.23 (m, 2H), 4.08-3.97 (m, 4H), 3.86 (m, 1H), 3.59 (m, 1H), 3.39 (s, 1H), 2.86-2.77 (m, 1H), 1.98-1.85 (m, 1H), 1.81-1.64 (m, 3H), 1.39 (d, J = 6.6 Hz, 3H), 1.08 (s, 6H), 0.72 (t, J = 7.3 Hz, 3H). |

| Example | Structure/Name | Synthesis Method | LCMS R$_T$ (min), M + H$^+$, method | $^1$H NMR (ppm) |
|---|---|---|---|---|
| 194 | (3S,4R)-1-(4-((1-((S*)-sec-Butyl)-3-(3-(2-hydroxypropan-2-yl)azetidin-1-yl)-1H-pyrazolo[4,3-c]pyridin-6-yl)amino)pyrimidin-2-yl)-3-fluoropiperidin-4-ol | 65 | 3.58 499.3 B | $^1$H NMR (400 MHz, DMSO) δ 9.82 (s, 1H), 8.55 (s, 1H), 8.10 (s, 1H), 7.97 (d, J = 5.6 Hz, 1H), 6.37 (d, J = 5.7 Hz, 1H), 5.11 (d, J = 5.0 Hz, 1H), 4.66 (d, J = 48.9 Hz, 1H), 4.55-4.43 (m, 1H), 4.40 (s, 1H), 4.23 (m, 2H), 4.08-3.97 (m, 4H), 3.86 (m, 1H), 3.59 (m, 1H), 3.39 (s, 1H), 2.86-2.77 (m, 1H), 1.98-1.85 (m, 1H), 1.81-1.64 (m, 3H), 1.39 (d, J = 6.6 Hz, 3H), 1.08 (s, 6H), 0.72 (t, J = 7.3 Hz, 3H). |
| 195 | 1-(1-(sec-Butyl)-6-((2-((3R,4S)-3-fluoro-4-hydroxypiperidin-1-yl)pyrimidin-4-yl)amino)-1H-pyrazolo[4,3-c]pyridin-3-yl)imidazolidin-2-one | 76 | 3.43 470.2 B | $^1$H NMR (400 MHz, DMSO) δ 9.82 (s, 1H), 8.55 (s, 1H), 8.10 (s, 1H), 7.97 (d, J = 5.6 Hz, 1H), 6.37 (d, J = 5.7 Hz, 1H), 5.10 (d, J = 5.0 Hz, 1H), 4.66 (d, J = 48.7 Hz, 1H), 4.50 (m, 1H), 4.40 (s, 1H), 4.24 (m, 2H), 4.10-3.94 (m, 4H), 3.87 (m, 1H), 3.60 (m, 1H), 3.38 (s, 1H), 2.83 (m, 1H), 2.00-1.83 (m, 1H), 1.83-1.62 (m, 3H), 1.40 (d, J = 6.6 Hz, 3H), 1.08 (s, 6H), 0.71 (t, J = 7.3 Hz, 3H). |
| 196 | (3R,4S)-1-(4-((1-(sec-Butyl)-3-((R)-3-hydroxypyrrolidin-1-yl)-1H-pyrazolo[4,3-c]pyridin-6-yl)amino)pyrimidin-2-yl)-3-fluoropiperidin-4-ol | 69 | 3.27 471.3 B | $^1$H NMR (400 MHz, DMSO) δ 9.79 (s, 1H), 8.70 (s, 1H), 8.08 (d, J = 3.6 Hz, 1H), 7.97 (d, J = 5.7 Hz, 1H), 6.37 (d, J = 5.0 Hz, 1H), 5.11 (d, J = 5.0 Hz, 1H), 4.93 (d, J = 3.7 Hz, 1H), 4.67 (d, J = 49.2 Hz, 1H), 4.50 (m, 1H), 4.42 (s, 1H), 4.24 (m, 2H), 3.87 (m, 1H), 3.75-3.52 (m, 4H), 3.42 (m, 2H), 2.12-1.99 (m, 1H), 1.92 (s, 2H), 1.85-1.62 (m, 3H), 1.39 (m, 3H), 0.73 (m, 3H). |

| Example | Structure/Name | Synthesis Method | LCMS R$_T$ (min), M + H$^+$, method | $^1$H NMR (ppm) |
|---|---|---|---|---|
| 197 | (3S,4R)-1-(4-((1-((R*)-sec-Butyl)-3-(2-oxa-6-azaspiro[3.3]heptan-6-yl)-1H-pyrazolo[4,3-c]pyridin-6-yl)amino)pyrimidin-2-yl)-3-fluoropiperidin-4-ol | 64 | 3.34 483.3 B | $^1$H NMR (400 MHz, DMSO) δ 9.84 (s, 1H), 8.55 (d, J = 0.8 Hz, 1H), 8.11 (s, 1H), 7.98 (d, J = 5.7 Hz, 1H), 6.37 (d, J = 5.7 Hz, 1H), 5.11 (d, J = 5.1 Hz, 1H), 4.74 (s, 4H), 4.60 (s, 1H), 4.48 (m, 1H), 4.34-4.16 (m, 5H), 3.86 (m, 1H), 3.59 (m, 1H), 3.38 (m, 2H), 1.90 (m, 1H), 1.82-1.60 (m, 3H), 1.38 (d, J = 6.6 Hz, 3H), 0.71 (t, J = 7.3 Hz, 3H). |
| 198 | (3S,4R)-1-(4-((1-((S*)-sec-Butyl)-3-(2-oxa-6-azaspiro[3.3]heptan-6-yl)-1H-pyrazolo[4,3-c]pyridin-6-yl)amino)pyrimidin-2-yl)-3-fluoropiperidin-4-ol | 64 | 3.33 483.2 B | $^1$H NMR (400 MHz, DMSO) δ 9.84 (s, 1H), 8.55 (s, 1H), 8.12 (s, 1H), 7.98 (d, J = 5.7 Hz, 1H), 6.37 (d, J = 5.7 Hz, 1H), 5.11 (d, J = 5.0 Hz, 1H), 4.74 (s, 4H), 4.60 (s, 1H), 4.50 (m, 1H), 4.26 (m, 5H), 3.87 (m, 1H), 3.59 (m, 1H), 3.37 (s, 2H), 1.89 (m, 1H), 1.83-1.62 (m, 3H), 1.39 (d, J = 6.6 Hz, 3H), 0.70 (t, J = 7.3 Hz, 3H). |
| 199 | (S)-1-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)-3-hydroxypyrrolidin-2-one | 83 | 3.69 524.2 B | n/a |

| Example | Structure/Name | Synthesis Method | LCMS R$_T$ (min), M + H$^+$, method | $^1$H NMR (ppm) |
|---|---|---|---|---|
| 200 | 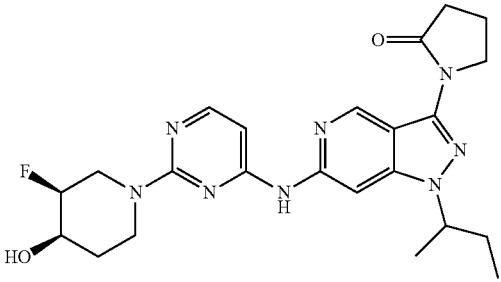 [SMILES: CCC(C)n1nc(N2CCCC2=O)c2cnc(Nc3ccnc(N4CC[C@@H](O)[C@@H](F)C4)n3)cc21]<br>1-(1-(sec-Butyl)-6-((2-((3S,4R)-3-fluoro-4-hydroxypiperidin-1-yl)pyrimidin-4-yl)amino)-1H-pyrazolo[4,3-c]pyridin-3-yl)pyrrolidin-2-one | 86 | 3.64<br>469.2<br>B | $^1$H NMR (400 MHz, DMSO) δ 9.99 (s, 1H), 9.27 (d, J = 0.8 Hz, 1H), 8.27 (d, J = 2.5 Hz, 1H), 8.00 (d, J = 5.6 Hz, 1H), 6.37 (d, J = 5.5 Hz, 1H), 5.13 (s, 1H), 4.68 (d, J = 49.0 Hz, 1H), 4.58-4.37 (m, 2H), 4.26 (s, 1H), 3.96 (t, J = 7.1 Hz, 2H), 3.88 (d, J = 24.2 Hz, 1H), 3.62 (m, 1H), 3.40 (s, 1H), 2.58 (t, J = 8.0 Hz, 2H), 2.25-2.09 (m, 2H), 2.06-1.89 (m, 1H), 1.89-1.64 (m, 3H), 1.45 (m, 3H), 0.73 (m, 3H). |
| 201 | 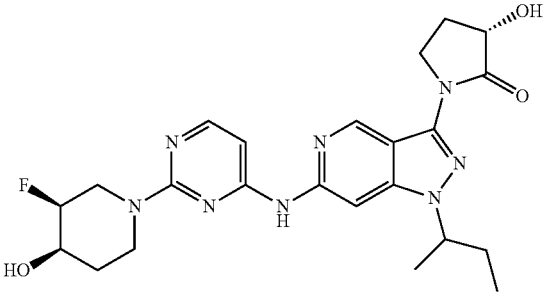 [SMILES: CCC(C)n1nc(N2CC[C@H](O)C2=O)c2cnc(Nc3ccnc(N4CC[C@@H](O)[C@@H](F)C4)n3)cc21]<br>(3S)-1-(1-(sec-Butyl)-6-((2-((3S,4R)-3-fluoro-4-hydroxypiperidin-1-yl)pyrimidin-4-yl)amino)-1H-pyrazolo[4,3-c]pyridin-3-yl)-3-hydroxypyrrolidin-2-one | 86 | 2.57<br>485.3<br>B | n/a |
| 202 | 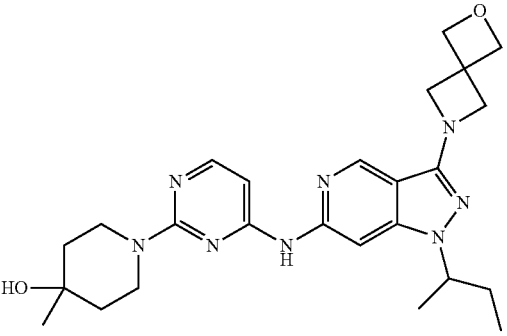 [SMILES: CCC(C)n1nc(N2CC3(COC3)C2)c2cnc(Nc3ccnc(N4CCC(C)(O)CC4)n3)cc21]<br>1-(4-((1-(sec-Butyl)-3-(2-oxa-6-azaspiro[3.3]heptan-6-yl)-1H-pyrazolo[4,3-c]pyridin-6-yl)amino)pyrimidin-2-yl)-4-methylpiperidin-4-ol | 68 | 3.72<br>479.3<br>B | $^1$H NMR (400 MHz, DMSO) δ 9.77 (s, 1H), 8.54 (s, 1H), 8.15 (s, 1H), 7.96 (d, J = 5.6 Hz, 1H), 6.32 (d, J = 5.7 Hz, 1H), 4.74 (s, 4H), 4.36 (s, 1H), 4.26 (s, 4H), 4.19 (m, 3H), 3.48 (m, 2H), 1.97-1.84 (m, 1H), 1.84-1.63 (m, 1H), 1.51 (m, 4H), 1.38 (d, J = 6.7 Hz, 3H), 1.16 (s, 3H), 0.71 (t, J = 7.3 Hz, 3H). |

| Example | Structure/Name | Synthesis Method | LCMS R$_T$ (min), M + H$^+$, method | $^1$H NMR (ppm) |
|---|---|---|---|---|
| 203 | 1-(4-((1-(sec-Butyl)-3-((R)-3-hydroxypyrrolidin-1-yl)-1H-pyrazolo[4,3-c]pyridin-6-yl)amino)pyrimidin-2-yl)-4-methylpiperidin-4-ol | 69 | 3.48 467.4 B | $^1$H NMR (400 MHz, DMSO) δ 9.72 (s, 1H), 8.69 (s, 1H), 8.12 (s, 1H), 7.96 (d, J = 5.6 Hz, 1H), 6.33 (d, J = 5.7 Hz, 1H), 4.92 (d, J = 3.6 Hz, 1H), 4.42 (s, 1H), 4.37 (s, 1H), 4.18 (m, 3H), 3.75-3.56 (m, 3H), 3.55-3.37 (m, 3H), 2.15-1.99 (m, 1H), 1.93 (m, 2H), 1.83-1.66 (m, 1H), 1.51 (m, 4H), 1.39 (d, J = 6.6 Hz, 3H), 1.17 (s, 3H), 0.73 (t, J = 7.3 Hz, 3H). |
| 204 | 1-(1-(sec-Butyl)-6-((2-(4-hydroxy-4-methylpiperidin-1-yl)pyrimidin-4-yl)amino)-1H-pyrazolo[4,3-c]pyridin-3-yl)pyrrolidin-2-one | 69 | 3.93 465.3 B | $^1$H NMR (400 MHz, DMSO) δ 9.96 (s, 1H), 9.26 (s, 1H), 8.30 (s, 1H), 7.98 (d, J = 5.6 Hz, 1H), 6.33 (d, J = 5.6 Hz, 1H), 4.45-4.29 (m, 2H), 4.20 (d, J = 13.2 Hz, 2H), 3.96 (t, J = 7.1 Hz, 2H), 3.51 (d, J = 10.2 Hz, 2H), 2.58 (t, J = 8.0 Hz, 2H), 2.25-2.10 (m, 2H), 1.89 (m, 2H), 1.63-1.39 (m, 7H), 1.17 (s, 3H), 0.74 (t, J = 7.4 Hz, 3H). |
| 205 | (R)-1-(4-((3-(3-Hydroxypyrrolidin-1-yl)-1-isopropyl-1H-pyrazolo[4,3-c]pyridin-6-yl)amino)pyrimidin-2-yl)-4-methylpiperidin-4-ol | 69 | 3.17 453.2 B | $^1$H NMR (400 MHz, DMSO) δ 9.74 (s, 1H), 8.70 (d, J = 0.8 Hz, 1H), 8.12 (s, 1H), 7.96 (d, J = 5.6 Hz, 1H), 6.33 (d, J = 5.7 Hz, 1H), 4.93 (d, J = 3.7 Hz, 1H), 4.56-4.43 (m, 1H), 4.41 (s, 1H), 4.36 (s, 1H), 4.18 (d, J = 13.1 Hz, 2H), 3.73-3.56 (m, 3H), 3.56-3.38 (m, 3H), 2.12-1.97 (m, 1H), 1.92 (s, 1H), 1.51 (t, J = 14.4 Hz, 4H), 1.42 (d, J = 6.7 Hz, 6H), 1.16 (s, 3H). |

| Example | Structure/Name | Synthesis Method | LCMS R$_T$ (min), M + H$^+$, method | $^1$H NMR (ppm) |
|---|---|---|---|---|
| 206 | (3R)-1-(1-(sec-Butyl)-6-((2-(4-(methylsulfonyl)piperidin-1-yl)pyrimidin-4-yl)amino)-1H-pyrazolo[4,3-c]pyridin-3-yl)pyrrolidin-3-ol | 69 | 3.34 515.3 B | $^1$H NMR (400 MHz, DMSO) δ 9.82 (s, 1H), 8.71 (d, J = 0.7 Hz, 1H), 8.06-7.94 (m, 2H), 6.43 (d, J = 5.7 Hz, 1H), 4.93 (d, J = 3.7 Hz, 1H), 4.83 (d, J = 12.2 Hz, 2H), 4.42 (s, 1H), 4.33-4.15 (m, 1H), 3.80-3.57 (m, 3H), 3.42 (d, J = 12.0 Hz, 2H), 3.00 (t, J = 13.0 Hz, 2H), 2.94 (s, 3H), 2.13-1.99 (m, 3H), 1.93 (m, 2H), 1.85-1.68 (m, 1H), 1.68-1.52 (m, 2H), 1.40 (d, J = 6.6 Hz, 3H), 0.73 (t, J = 7.3 Hz, 3H). |
| 207 | 9-(4-((1-((S*)-sec-Butyl)-3-((R)-3-hydroxypyrrolidin-1-yl)-1H-pyrazolo[4,3-c]pyridin-6-yl)amino)pyrimidin-2-yl)-1-oxa-4,9-diazaspiro[5.5]undecan-3-one | 69 | 2.87 522.3 B | $^1$H NMR (400 MHz, DMSO) δ 8.84 (s, 1H), 7.78 (s, 1H), 7.73 (s, 1H), 6.36 (s, 2H), 5.71 (d, J = 5.7 Hz, 1H), 4.95 (d, J = 3.7 Hz, 1H), 4.50-4.32 (m, 2H), 4.30 (s, 2H), 4.24 (m, 2H), 3.93 (m, 2H), 3.65 (m, 3H), 3.42 (m, 1H), 3.28-3.20 (m, 2H), 2.16-1.98 (m, 1H), 1.88 (m, 4H), 1.82-1.69 (m, 1H), 1.63 (m, 2H), 1.38 (d, J = 6.6 Hz, 3H), 0.69 (t, J = 7.3 Hz, 3H). |
| 208 | 9-(4-((1-((R*)-sec-Butyl)-3-((R)-3-hydroxypyrrolidin-1-yl)-1H-pyrazolo[4,3-c]pyridin-6-yl)amino)pyrimidin-2-yl)-1-oxa-4,9-diazaspiro[5.5]undecan-3-one | 69 | 2.86 522.3 B | $^1$H NMR (400 MHz, DMSO) δ 9.78 (s, 1H), 8.70 (s, 1H), 5.07 (s, 1H), 7.99 (m, 2H), 6.39 (m, 1H), 4.94 (m, 1H), 4.30-4.42 (m, 3H), 4.24 (m, 1H), 3.60-3.67 (m, 3H), 3.42 (m, 1H), 3.15 (s, 2H), 1.56-2.07 (m, 8H), 1.38 (d, J = 6.6 Hz, 3H), 0.69 (t, J = 7.3 Hz, 2H). |

| Example | Structure/Name | Synthesis Method | LCMS $R_T$ (min), M + H[+], method | $^1$H NMR (ppm) |
|---|---|---|---|---|
| 209 | 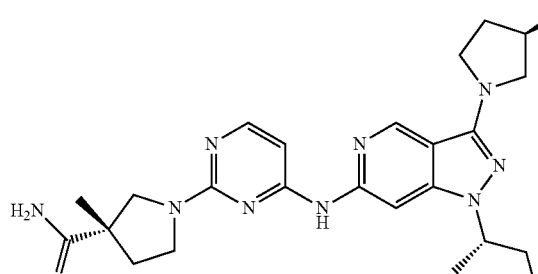<br>(S*)-1-(4-((1-((S*)-sec-Butyl)-3-((R)-3-hydroxypyrrolidin-1-yl)-1H-pyrazolo[4,3-c]pyridin-6-yl)amino)pyrimidin-2-yl)-3-methylpyrrolidine-3-carboxamide | 69 | 3.76, 480.28 B | n/a |
| 210 | 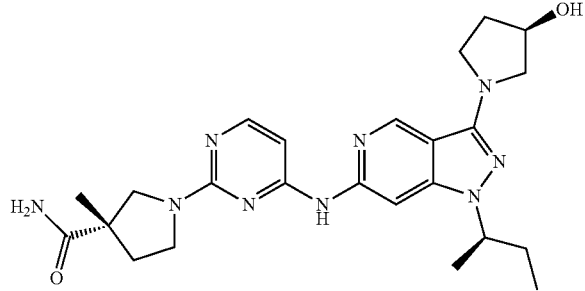 [SMILES: CC[C@@H](C)n1nc(N2CC[C@@H](O)C2)c2cnc(Nc3ccnc(N4CC[C@](C)(C(N)=O)C4)n3)cc21]<br>(S*)-1-(4-((1-((R*)-sec-Butyl)-3-((R)-3-hydroxypyrrolidin-1-yl)-1H-pyrazolo[4,3-c]pyridin-6-yl)amino)pyrimidin-2-yl)-3-methylpyrrolidine-3-carboxamide | 69 | 3.87 480.28 B | n/a |

BIOCHEMICAL ASSAYS

The exemplified compounds described herein were tested according to the assay below. The enzyme data reported in Tables 4-5 is generally a representative of multiple experiments.

EGFR T790M L858R:

Ten nM EGFR T790M L858R enzyme (Life Technologies, PV4879) phosphorylates 1 µM 5-FAM-EEPLYWSF-PAKKK-CONH$_2$ peptide substrate (FL-Peptide 22, Caliper Life Sciences, 760366) in the presence of 5 µM adenosine-5'-triphosphate (ATP) and varying concentrations of test compound in 50 mM 2-[4-(2-hydroxyethyl)piperazin-1-yl]ethanesulfonic acid (HEPES), pH 7.5, 10 mM MgCl$_2$, 4 mM MnCl$_2$, 0.01% Brij-35, 1 mM dithiothreitol (DTT), 0.5% dimehylsulfoxide (DMSO). Reactions proceed for 30 minutes at room temperature (22° C.) and are terminated with 80 mM 2,2',2",2'''-(ethane-1,2-diyldinitrilo)tetraacetic acid (EDTA). Product is detected using the Caliper mobility shift detection method where product and substrate are electrophoretically separated and measured. Percent activity is plotted against log concentration of compound and points are fit to the Morrison equation (shown below) to generate an apparent $K_i$. This apparent $K_i$ is further converted to $K_i$ using a Cheng-Prusoff conversion for competitive inhibitors: $K_i$=apparent $K_i/(1+[ATP]/K_m$ of ATP) where [ATP]=5 µM and $K_m$ of ATP=1.3 µM.

Morrison equation: $v = v_0 \dfrac{[E] - [I] - K + \sqrt{([E] - [I] - K)^2 + 4[E]K}}{2[E]}$ EGFR del746-750 T790M Five nM EGFR del746-750 T790M enzyme (Carna Biosciences, 08-528) phosphorylates 1 µM 5-FAM-EEPLYWS-FPAKKK-CONH$_2$ peptide substrate (FL-Peptide 22, Caliper Life Sciences, 760366) in the presence of 5 µM adenosine-5'-triphosphate (ATP) and varying concentrations of test compound in 50 mM 2-[4-(2-hydroxyethyl)piperazin-1-yl]ethanesulfonic acid (HEPES), pH 7.5, 10 mM MgCl$_2$, 4 mM MnCl$_2$, 0.01% Brij-35, 1 mM dithiothreitol (DTT), 0.5% dimehylsulfoxide (DMSO). Reactions proceed for 30 minutes at room temperature (22° C.) and are terminated with 80 mM 2,2',2",2'''-(ethane-1,2-diyldinitrilo)tetraacetic acid (EDTA). Product is detected using the Caliper mobility shift detection method where product and substrate are electrophoretically separated and measured. Percent activity is plotted against log concentration of compound and points are fit to the Morrison equation (shown below) to generate an apparent $K_i$. This apparent $K_i$ is further converted to $K_i$ using a Cheng-Prusoff conversion for competitive inhibitors: $K_i$=apparent $K_i/(1+[ATP]/K_m$ of ATP) where [ATP]=5 µM and $K_m$ of ATP=2.1 µM Morrison equation: $v = v_0 \dfrac{[E] - [I] - K + \sqrt{([E] - [I] - K)^2 + 4[E]K}}{2[E]}$ $v = v_0 \dfrac{[E] - [I] - K + \sqrt{([E] - [I] - K)^2 + 4[E]K}}{2[E]}$

TABLE 2

| EGFR(T790M/L858R) Biochemical activity | |
|---|---|
| Example | EGFR(T790M/L858R) $K_i$ (µM) |
| 1 | 0.6093 |
| 2 | 0.0021 |
| 3 | 0.0014 |
| 4 | 0.0030 |
| 5 | 0.0010 |
| 6 | 0.0009 |
| 7 | 0.2983 |
| 8 | 0.0013 |
| 9 | 0.0052 |
| 10 | 0.0075 |
| 11 | 0.0291 |
| 12 | 0.0022 |
| 13, enantiomer 1 | 0.0014 |
| 13, enantiomer 2 | 0.0016 |
| 14 | 0.0010 |
| 15 | 0.0012 |
| 16 | 0.0011 |
| 17 | 0.0007 |
| 18 | 0.0008 |
| 19 | 0.0049 |
| 20 | 0.0025 |
| 21 | 0.0012 |
| 22 | 0.0054 |
| 23 | 0.0011 |
| 24 | 0.0092 |
| 25 | 0.0010 |
| 26 | 0.0006 |
| 27, enantiomer 1 | 0.0022 |
| 27, enantiomer 2 | 0.0019 |
| 28 | 0.0008 |
| 29 | 0.0019 |
| 30 | 0.0007 |
| 31 | 0.0014 |
| 32 | 0.0356 |
| 33 | 0.0075 |
| 34 | 0.0026 |
| 35 | 0.0007 |
| 36 | 0.0007 |
| 37 | 0.0014 |
| 38 | 0.0011 |
| 39 | 0.0011 |
| 40 | 0.0011 |
| 41 | 0.0013 |
| 42 | 0.0011 |
| 43 | 0.0009 |
| 44 | 0.0071 |
| 45 | 0.0008 |
| 46 | 0.0027 |
| 47 | 0.0008 |
| 48 | 0.0006 |
| 49 | 0.0007 |
| 50 | 0.0235 |
| 51 | 0.0019 |
| 52 | 0.0022 |
| 53 | 0.0012 |
| 54 | 0.0007 |
| 55 | <0.0006 |
| 56 | 0.0012 |
| 57 | <0.0006 |
| 58 | 0.0012 |
| 59 | <0.0006 |
| 60 | <0.0006 |
| 61 | 0.0010 |
| 62 | 0.0120 |
| 63 | <0.0006 |

TABLE 2-continued

| EGFR(T790M/L858R) Biochemical activity | |
|---|---|
| Example | EGFR(T790M/L858R) $K_i$ (µM) |
| 64 | 0.0036 |
| 65 | 0.0036 |
| 66 | 0.0021 |
| 67 | 0.0039 |
| 68 | 0.0032 |
| 69 | 0.0017 |
| 70 | 0.0020 |
| 71 | 0.0047 |
| 72 | 0.0007 |
| 73 | 0.0033 |
| 74 | 0.1286 |
| 75 | 0.0041 |
| 76 | 0.0051 |
| 77 | 0.0187 |
| 78 | 0.0215 |
| 79 | 0.0033 |
| 80 | 0.0041 |
| 81 | 0.0064 |
| 82 | 0.0014 |
| 83 | 0.0013 |
| 84 | 0.0067 |
| 85 | 0.0055 |
| 86 | 0.0133 |
| 87 | 0.0064 |
| 88 | 0.0018 |
| 89 | 0.0265 |
| 91 | 0.0202 |
| 92 | 0.0038 |
| 93 | 0.1101 |
| 94 | 0.8718 |
| 95 | 0.0152 |
| 96 | 0.0046 |
| 97 | 0.0032 |
| 98 | 0.0010 |
| 99 | 0.0032 |
| 100 | 0.0087 |
| 101 | 0.0023 |
| 102 | 0.0022 |
| 103 | 0.0011 |
| 104 | 0.0016 |
| 105 | 0.0012 |
| 106 | 0.0021 |
| 107 | 0.0020 |
| 108 | 0.0019 |
| 109 | 0.0018 |
| 110 | 0.0017 |
| 111 | 0.0017 |
| 112 | 0.0011 |
| 113 | 0.0006 |
| 114 | 0.0008 |
| 115 | 0.0011 |
| 116 | 0.0026 |
| 117 | 0.0013 |
| 118 | 0.0014 |
| 119 | 0.0012 |
| 120 | 0.0014 |
| 121 | 0.0008 |
| 122 | 0.0012 |
| 123 | 0.0006 |
| 124 | 0.0007 |
| 125 | 0.0011 |
| 126 | 0.0053 |
| 127 | 0.0025 |
| 128 | 0.0062 |
| 129 | 0.0027 |
| 130 | 0.0018 |
| 131 | 0.0008 |
| 132 | 0.0049 |
| 133 | 0.0017 |
| 134 | 0.0115 |
| 135 | 0.0103 |
| 136 | 0.0106 |
| 137 | 0.0101 |
| 138 | 0.0046 |
| 139 | 0.0071 |
| 140 | 0.0031 |

TABLE 2-continued

EGFR(T790M/L858R) Biochemical activity

| Example | EGFR(T790M/L858R) $K_i$ (μM) |
|---|---|
| 141 | 0.0016 |
| 142 | 0.0016 |
| 143 | 0.0029 |
| 144 | 0.0018 |
| 145 | 0.0014 |
| 146 | 0.0025 |
| 147 | 0.0024 |
| 148 | 0.0018 |
| 149 | 0.0021 |
| 150 | 0.0049 |
| 151 | 0.0087 |
| 152 | 0.0010 |
| 153 | 0.0021 |
| 154 | 0.0028 |
| 155 | 0.0010 |
| 156 | 0.0011 |
| 157 | 0.0026 |
| 158 | 0.0185 |
| 159 | 0.0116 |
| 160 | 0.0051 |
| 161 | 0.0007 |
| 162 | 0.0010 |
| 163 | 0.0009 |
| 164 | 0.0012 |
| 165 | 0.0019 |
| 166 | 0.0007 |
| 167 | 0.0007 |
| 168 | 0.0015 |
| 169 | 0.0014 |
| 170 | 0.0014 |
| 171 | 0.0062 |
| 172 | 0.0018 |
| 173 | 0.0020 |
| 174 | 0.0018 |
| 175 | 0.0014 |
| 176 | 0.0033 |
| 177 | 0.0017 |
| 178 | 0.0014 |
| 179 | 0.0056 |
| 180 | 0.3022 |
| 181 | 0.0082 |
| 182 | 0.3773 |
| 183 | 0.0347 |
| 193 | 0.0018 |
| 194 | 0.0015 |
| 195 | 0.0010 |
| 196 | 0.0009 |
| 197 | 0.0012 |
| 198 | 0.0015 |
| 199 | 0.0015 |
| 200 | 0.0012 |
| 201 | 0.0058 |
| 202 | 0.0028 |
| 203 | 0.0015 |
| 204 | 0.0022 |
| 205 | 0.0027 |
| 206 | 0.0019 |
| 207 | 0.4691 |
| 208 | 0.0038 |
| 209 | 0.1433 |
| 210 | 0.0031 |

TABLE 3

EGFR(T790M/d746-750) Biochemical activity

| Example | EGFR(T790M/d746-750) $K_i$ (μM) |
|---|---|
| 2 | 0.0097 |
| 3 | 0.0016 |
| 6 | 0.0012 |
| 8 | 0.0013 |
| 10 | 0.0324 |
| 15 | 0.0028 |
| 17 | 0.0008 |
| 18 | 0.0006 |
| 21 | 0.0030 |
| 22 | 0.0205 |
| 23 | 0.0039 |
| 24 | 0.0098 |
| 25 | 0.0025 |
| 35 | 0.0005 |
| 37 | 0.0008 |
| 38 | 0.0024 |
| 53 | 0.0009 |
| 54 | 0.0005 |
| 59 | 0.0005 |
| 60 | 0.0005 |
| 63 | 0.0005 |
| 64 | 0.0161 |
| 65 | 0.0096 |
| 66 | 0.0046 |
| 67 | 0.0111 |
| 68 | 0.0102 |
| 69 | 0.0029 |
| 70 | 0.0023 |
| 71 | 0.0132 |
| 72 | 0.0005 |
| 73 | 0.0031 |
| 74 | 0.1058 |
| 75 | 0.0103 |
| 76 | 0.0138 |
| 77 | 0.0292 |
| 78 | 0.0755 |
| 79 | 0.0059 |
| 80 | 0.0094 |
| 81 | 0.0071 |
| 82 | 0.0012 |
| 83 | 0.0012 |
| 84 | 0.0205 |
| 85 | 0.0155 |
| 86 | 0.0291 |
| 87 | 0.0114 |
| 88 | 0.0043 |
| 89 | 0.0469 |
| 91 | 0.0204 |
| 92 | 0.0095 |
| 93 | 0.0654 |
| 94 | >2.9 |
| 95 | 0.0595 |
| 96 | 0.0172 |
| 97 | 0.0052 |
| 98 | 0.0018 |
| 99 | 0.0056 |
| 100 | 0.0072 |
| 101 | 0.0024 |
| 102 | 0.0124 |
| 103 | 0.0039 |
| 104 | 0.0019 |
| 105 | 0.0027 |
| 106 | 0.0016 |
| 107 | 0.0015 |
| 108 | 0.0017 |
| 109 | 0.0013 |
| 110 | 0.0011 |
| 111 | 0.0010 |
| 112 | 0.0010 |
| 113 | 0.0005 |
| 114 | 0.0007 |
| 115 | 0.0009 |
| 116 | 0.0020 |
| 117 | 0.0011 |
| 118 | 0.0011 |
| 119 | 0.0011 |
| 120 | 0.0013 |
| 121 | 0.0007 |
| 122 | 0.0010 |
| 123 | 0.0006 |
| 124 | 0.0007 |

TABLE 3-continued

EGFR(T790M/d746-750) Biochemical activity

| Example | EGFR(T790M/d746-750) $K_i$ (μM) |
|---|---|
| 125 | 0.0008 |
| 126 | 0.0046 |
| 127 | 0.0060 |
| 128 | 0.0155 |
| 129 | 0.0063 |
| 130 | 0.0033 |
| 131 | 0.0012 |
| 132 | 0.0146 |
| 133 | 0.0043 |
| 134 | 0.0337 |
| 135 | 0.0463 |
| 136 | 0.0399 |
| 137 | 0.0270 |
| 138 | 0.0196 |
| 139 | 0.0183 |
| 140 | 0.0061 |
| 141 | 0.0027 |
| 142 | 0.0031 |
| 143 | 0.0113 |
| 144 | 0.0021 |
| 145 | 0.0016 |
| 146 | 0.0049 |
| 147 | 0.0039 |
| 148 | 0.0025 |
| 149 | 0.0012 |
| 150 | 0.0036 |
| 151 | 0.0063 |
| 152 | 0.0008 |
| 153 | 0.0019 |
| 154 | 0.0029 |
| 155 | 0.0009 |
| 156 | 0.0008 |
| 157 | 0.0049 |
| 158 | 0.0509 |
| 159 | 0.0285 |
| 160 | 0.0097 |
| 161 | 0.0006 |
| 162 | 0.0008 |
| 163 | 0.0009 |
| 164 | 0.0011 |
| 165 | 0.0019 |
| 166 | 0.0007 |
| 167 | 0.0005 |
| 168 | 0.0012 |
| 169 | 0.0012 |
| 170 | 0.0012 |
| 171 | 0.0331 |
| 172 | 0.0025 |
| 173 | 0.0048 |
| 174 | 0.0038 |
| 175 | 0.0026 |
| 176 | 0.0121 |
| 177 | 0.0021 |
| 178 | 0.0047 |
| 179 | 0.0151 |
| 180 | 0.2014 |
| 181 | 0.0108 |
| 182 | 1.1522 |
| 183 | 0.0767 |
| 193 | 0.0056 |
| 194 | 0.0035 |
| 195 | 0.0031 |
| 196 | 0.0011 |
| 197 | 0.0027 |
| 198 | 0.0031 |
| 199 | 0.0015 |
| 200 | 0.0026 |
| 201 | 0.0140 |
| 202 | 0.0048 |
| 203 | 0.0021 |
| 204 | 0.0045 |
| 205 | 0.0090 |
| 206 | 0.0089 |
| 207 | 1.0598 |
| 208 | 0.0101 |
| 209 | 0.1114 |
| 210 | 0.0021 |

H1975 pEGFR MSD Cellular Assays

Background:

These assays are intended for determining cellular. Potency of compounds to inhibit phosphor-EGFR in H1975 (L585R/T790M) mutant EGFR expressing cells is determined using the Meso Scale Discovery 384 well pEGFR Tyr1068 assay kits. (Meso Scale Discovery Catalog# N31CB-1).

Cell Culture:

NCI-H1975 (ATCC Catalog# CRL-5908) cells are maintained in medium containing RPMI 1640, 10% FBS, 4 mM L-Glutamine, 1% Penicillin-Streptomycin, and 4.5 g/L Glucose. All cell culture reagents were purchased from Invitrogen/Gibco. Cells are cultured at 37° C. at 5% $CO_2$ and split as recommended by ATCC.

Cell Plating and Serum Starvation:

H1975 cells are harvested and plated into sterile cell culture treated 384 well plates (Greiner catalog #781091) at a density of 30,000 cells/well in 50 ul culture medium and placed in a 37° C. at 5% $CO_2$ incubator for six hours. After six hours, culture medium is aspirated and replaced with serum-free culture medium. Cells are then incubated with the serum-free medium overnight at 37° C. and 5% $CO_2$.

Assay Procedure:

The following day, test compounds are serially diluted in dimethyl sulfoxide (DMSO) and added to cells in serum free medium (final DMSO concentration 0.5%). Assay plates are then incubated for 1 hour at 37° C. and 5% $CO_2$. Following 1 hour of compound incubation cells are then lysed and processed as per the MSD pEGFR assay kit protocol. Cell lysates are added to assay plates pre-coated with antibodies against phosphorylated EGFR. Phosphorylated EGFR in samples are allowed to bind to the capture antibodies overnight at 4° C. The detection antibody (anti-total EGFR, labeled with an electrochemiluminescent SULFO-TAG) is added to the bound lysate and incubated for 1 hour at room temperature. The MSD Read Buffer is added such that when a voltage is applied to the plate electrodes, the labels bound to the electrode surface emit light. The MSD Sector Instrument measures the intensity of the light, and quantitatively measures the amount of phosphorylated-EGFR in the sample. Percent inhibition of EGFR phosphorylation by varying concentrations of test compounds is calculated relative to untreated controls. $EC_{50}$ values are calculated using the 4 parameter logistic nonlinear regression dose-response model.

H1975 Proliferation Assays

Background:

This assay is intended for determining the potency of compounds H1975 (EGFR T790M/L858R) cell proliferation.

Cell Culture:

NCI-H1975 (ATCC Catalog# CRL-5908) cells are maintained in medium containing RPMI 1640, 10% FBS, 4 mM L-Glutamine, 1% Penicillin-Streptomycin, and 4.5 g/L Glucose. All cell culture reagents were purchased from Invitrogen/Gibco. Cells are cultured at 37° C. at 5% $CO_2$ and split as recommended by ATCC.

Assay Procedure:

H1975 cells are harvested and plated into sterile cell culture treated 384 well plates (Greiner catalog #781091) at a density of 1000 cells/well in 50 μL culture medium and placed in a 37° C. at 5% $CO_2$ incubator overnight. The following day, test compounds are serially diluted in dimethyl sulfoxide (DMSO) and added to cells in culture medium (final DMSO concentration 0.5%, final assay volume 50 Assay plates are then incubated for 72 hour at 37° C. and 5% $CO_2$. After 72 hours, 25 μL of reconstituted Promega Cell Titer-Glo reagent (Promega Catalog# G7572) is added to all wells. Plates are then read on a Perkin Elmer Envision Multi-label plate reader using luminescence mode. Percent inhibition of proliferation by varying concentrations of test compounds is calculated relative to untreated controls. $EC_{50}$ values are calculated using the 4 parameter logistic nonlinear regression dose-response model.

TABLE 4

H1975 pEGFR MSD activity

| Example | H1975 pEGFR $EC_{50}$ (μM) |
|---|---|
| 1 | 0.6062 |
| 2 | 0.0817 |
| 3 | 0.0386 |
| 4 | 0.2187 |
| 5 | 0.0296 |
| 6 | 0.0738 |
| 7 | >10 |
| 8 | 0.0303 |
| 9 | 0.3816 |
| 10 | 0.3492 |
| 11 | |
| 12 | 0.0302 |
| 13, enantiomer 1 | 0.0268 |
| 13, enantiomer 2 | 0.0401 |
| 14 | 0.0193 |
| 15 | 0.0266 |
| 16 | 0.0797 |
| 17 | 0.0192 |
| 18 | 0.0075 |
| 19 | 0.7229 |
| 20 | 0.1349 |
| 21 | 0.0361 |
| 22 | 0.4872 |
| 23 | 0.0231 |
| 24 | 2.0601 |
| 25 | 0.0383 |
| 26 | 0.0144 |
| 27, enantiomer 1 | 0.0403 |
| 27, enantiomer 2 | 0.0982 |
| 28 | 0.0157 |
| 29 | 0.1544 |
| 30 | 0.0513 |
| 31 | 0.1161 |
| 32 | 3.8268 |
| 33 | 1.0157 |
| 34 | 0.1107 |
| 35 | 0.0335 |
| 36 | 0.0158 |
| 37 | 0.0917 |
| 38 | 0.0408 |
| 39 | 0.0711 |
| 40 | 0.0848 |
| 41 | 0.0094 |
| 42 | 0.0125 |
| 43 | 0.0375 |
| 44 | 1.3205 |
| 45 | 0.0638 |
| 46 | 0.1534 |
| 47 | 0.8736 |
| 48 | 1.4646 |
| 49 | 0.0980 |
| 50 | 2.3842 |

TABLE 4-continued

H1975 pEGFR MSD activity

| Example | H1975 pEGFR $EC_{50}$ (μM) |
|---|---|
| 51 | 0.0744 |
| 52 | 0.0901 |
| 53 | 0.0536 |
| 54 | 0.0179 |
| 55 | 0.1437 |
| 56 | 0.0311 |
| 57 | 0.0181 |
| 58 | 0.0094 |
| 59 | 0.0921 |
| 60 | 0.0282 |
| 61 | 0.0689 |
| 62 | 0.4582 |
| 63 | 0.0185 |
| 64 | 0.2228 |
| 65 | 0.1264 |
| 66 | 0.0638 |
| 67 | 0.2573 |
| 68 | 0.1573 |
| 69 | 0.0679 |
| 70 | 0.0830 |
| 71 | 0.2565 |
| 72 | 0.0281 |
| 73 | 0.1245 |
| 74 | 9.2577 |
| 75 | 1.3258 |
| 76 | 0.7519 |
| 77 | >10 |
| 79 | 0.1650 |
| 80 | 4.3728 |
| 81 | 0.2650 |
| 82 | 0.1080 |
| 83 | 0.0216 |
| 84 | 2.1357 |
| 85 | 0.3080 |
| 86 | 1.9355 |
| 87 | 0.4716 |
| 88 | 0.1871 |
| 89 | 5.2565 |
| 92 | 0.7875 |
| 96 | 0.3867 |
| 97 | 0.2334 |
| 98 | 0.0395 |
| 99 | 0.6172 |
| 100 | 1.0578 |
| 101 | 0.5675 |
| 102 | 0.7097 |
| 103 | 0.0231 |
| 104 | 0.0716 |
| 105 | 0.1287 |
| 106 | 0.0578 |
| 107 | 0.3855 |
| 108 | 0.1128 |
| 109 | 0.7883 |
| 110 | 0.1622 |
| 111 | 0.5595 |
| 112 | 0.0626 |
| 113 | 0.0276 |
| 114 | 0.0056 |
| 115 | 0.2207 |
| 116 | 0.6286 |
| 117 | 0.0549 |
| 118 | 0.1336 |
| 119 | 0.0923 |
| 120 | 0.0328 |
| 121 | 0.0196 |
| 122 | 0.0878 |
| 123 | 0.0044 |
| 124 | 0.2476 |
| 125 | 2.8406 |
| 126 | 0.0801 |
| 127 | 0.4657 |
| 128 | 0.9192 |
| 129 | 0.3491 |
| 130 | 0.2608 |
| 131 | 0.1293 |

TABLE 4-continued

HI975 pEGFR MSD activity

| Example | HI975 pEGFR EC$_{50}$ (μM) |
|---|---|
| 132 | 1.4268 |
| 133 | 0.1503 |
| 137 | 0.7154 |
| 138 | 1.4072 |
| 139 | 6.0707 |
| 140 | 0.2877 |
| 141 | 0.0892 |
| 142 | 0.1097 |
| 143 | 0.2188 |
| 144 | 0.9409 |
| 145 | 0.9206 |
| 146 | 0.2766 |
| 147 | 0.0158 |
| 148 | 0.0223 |
| 149 | 0.0519 |
| 150 | 0.2435 |
| 151 | 0.3630 |
| 152 | 0.0209 |
| 153 | 0.1333 |
| 154 | 0.0820 |
| 155 | 0.0289 |
| 156 | 0.0392 |
| 157 | 1.3295 |
| 158 | 1.2965 |
| 159 | 1.1018 |
| 160 | 0.9619 |
| 161 | 0.0543 |
| 162 | 0.0566 |
| 163 | 0.0265 |
| 164 | 0.4304 |
| 165 | 0.0956 |
| 166 | 0.1767 |
| 167 | 0.1887 |
| 168 | 0.0255 |
| 169 | 0.0342 |
| 170 | 0.7314 |
| 171 | 0.7031 |
| 172 | 0.1542 |
| 173 | 1.4058 |
| 174 | 0.1414 |
| 175 | 0.0978 |
| 176 | 3.9819 |
| 177 | 0.0872 |
| 178 | 0.0832 |
| 179 | 0.7456 |
| 180 | >10 |
| 181 | 3.2555 |
| 183 | 1.6509 |
| 184 | 0.0949 |
| 185 | 0.0856 |
| 186 | 0.0749 |
| 187 | 0.0755 |
| 188 | 0.0643 |
| 189 | 0.4735 |
| 190 | 0.0446 |
| 191 | 0.5315 |
| 192 | >10 |
| 193 | 0.1287 |
| 194 | 0.1711 |
| 195 | 0.0449 |
| 196 | 0.0125 |
| 197 | 0.0128 |
| 198 | 0.0164 |
| 199 | 0.2300 |
| 200 | 0.0754 |
| 201 | >10 |
| 202 | 0.1407 |
| 203 | 0.0770 |
| 204 | 0.2236 |
| 205 | 0.2872 |
| 206 | 0.2983 |
| 208 | 1.1995 |
| 210 | 1.8539 |

TABLE 5

HI975 Antiproliferative activity

| Example | H1975 antiproliferative EC$_{50}$ (μM) |
|---|---|
| 1 | 2.0231 |
| 2 | 0.3881 |
| 3 | 0.1591 |
| 4 | 0.7318 |
| 5 | 0.4206 |
| 6 | 0.8774 |
| 7 | >10 |
| 8 | 0.4993 |
| 9 | 1.8368 |
| 10 | 1.7111 |
| 12 | 0.2879 |
| 13, enantiomer 1 | 0.3612 |
| 13, enantiomer 2 | 0.6331 |
| 14 | 0.2157 |
| 15 | 0.3800 |
| 16 | 0.9209 |
| 17 | 0.2362 |
| 18 | 0.2010 |
| 19 | 1.4650 |
| 20 | 1.0750 |
| 21 | 0.3900 |
| 22 | >3 |
| 23 | 0.2481 |
| 24 | >10 |
| 25 | 0.1381 |
| 26 | 0.1076 |
| 27, enantiomer 1 | 0.6096 |
| 27, enantiomer 2 | 1.1414 |
| 28 | 0.1209 |
| 29 | 0.7985 |
| 30 | 1.4521 |
| 31 | 1.0650 |
| 32 | 0.4984 |
| 33 | 0.1100 |
| 34 | 1.4083 |
| 35 | 0.1667 |
| 36 | 0.3966 |
| 37 | 1.1169 |
| 38 | 0.2722 |
| 39 | 0.3733 |
| 40 | 0.7754 |
| 41 | 0.1624 |
| 42 | 0.2402 |
| 43 | 0.2371 |
| 44 | 2.4997 |
| 45 | 0.2470 |
| 46 | 0.9510 |
| 47 | 3.9747 |
| 48 | 5.4438 |
| 49 | 0.9447 |
| 50 | 3.6967 |
| 51 | 0.2664 |
| 52 | 1.1129 |
| 53 | 0.2412 |
| 54 | 0.1581 |
| 55 | 0.9380 |
| 56 | 0.3478 |
| 57 | 0.1588 |
| 58 | 0.1388 |
| 59 | 0.7383 |
| 60 | 0.6082 |
| 61 | 1.1973 |
| 62 | 3.5852 |
| 63 | 0.2711 |
| 64 | 0.7009 |
| 65 | 0.8743 |
| 66 | 0.6310 |
| 67 | 1.1590 |
| 68 | 0.8506 |
| 69 | 0.5210 |
| 70 | 0.3708 |
| 71 | 0.7853 |
| 72 | 0.2063 |
| 73 | 1.2088 |
| 74 | 4.6198 |

TABLE 5-continued

H1975 Antiproliferative activity

| Example | H1975 antiproliferative EC$_{50}$ (μM) |
|---|---|
| 75 | 7.8189 |
| 76 | 1.1774 |
| 77 | >10 |
| 79 | 0.9059 |
| 80 | >10 |
| 81 | 1.4656 |
| 82 | 0.2888 |
| 83 | >10 |
| 84 | >10 |
| 85 | 1.3277 |
| 86 | >10 |
| 87 | 3.2883 |
| 88 | 0.4892 |
| 89 | 9.9760 |
| 92 | 1.7588 |
| 96 | 1.2398 |
| 97 | 1.1279 |
| 98 | 0.2555 |
| 99 | 1.1678 |
| 100 | 1.2643 |
| 101 | 1.8260 |
| 102 | 1.1479 |
| 103 | 0.2481 |
| 104 | 0.4037 |
| 105 | 0.2129 |
| 106 | 0.2323 |
| 107 | 1.6426 |
| 108 | 0.3771 |
| 109 | 4.6247 |
| 110 | 0.8348 |
| 111 | 0.9494 |
| 112 | 0.7405 |
| 113 | 0.2655 |
| 114 | 0.1904 |
| 115 | 1.7878 |
| 116 | 2.0825 |
| 117 | 0.4322 |
| 118 | 1.0119 |
| 119 | 0.7801 |
| 120 | 0.4310 |
| 121 | 0.1835 |
| 122 | 0.6195 |
| 123 | 0.2009 |
| 124 | 0.6603 |
| 125 | >10 |
| 126 | 1.1412 |
| 127 | 1.3763 |
| 128 | 2.0396 |
| 129 | 2.7240 |
| 130 | 1.4277 |
| 131 | 1.4768 |
| 132 | >10 |
| 133 | 0.3321 |
| 137 | 1.0950 |
| 138 | 3.9082 |
| 139 | >10 |
| 140 | 0.6493 |
| 141 | 0.7686 |
| 142 | 1.2845 |
| 143 | 0.9010 |
| 144 | 2.2025 |
| 145 | 7.1741 |
| 146 | 1.6034 |
| 147 | 0.2267 |
| 148 | 0.2254 |
| 149 | 0.4229 |
| 150 | 0.7646 |
| 151 | 0.9293 |
| 152 | 0.2114 |
| 153 | 1.3784 |
| 154 | 0.3125 |
| 155 | 0.1443 |
| 156 | 0.1628 |
| 157 | 2.8612 |
| 158 | 8.1216 |
| 159 | 9.7331 |
| 160 | 3.0925 |
| 161 | 0.6497 |
| 162 | 0.4836 |
| 163 | 0.3440 |
| 164 | 2.5173 |
| 165 | 0.1928 |
| 166 | 1.1601 |
| 167 | 1.8314 |
| 168 | 0.2830 |
| 169 | 0.8253 |
| 170 | >10 |
| 171 | 1.0737 |
| 172 | 0.6994 |
| 173 | >10 |
| 174 | 0.8014 |
| 175 | 0.7662 |
| 176 | >10 |
| 177 | 0.4893 |
| 178 | 0.4829 |
| 179 | 1.4807 |
| 180 | >10 |
| 181 | >10 |
| 183 | 8.2702 |
| 184 | 0.7608 |
| 185 | 0.6964 |
| 186 | 0.5862 |
| 187 | 0.8131 |
| 188 | 1.0942 |
| 189 | 5.5871 |
| 190 | 0.5370 |
| 191 | >10 |
| 192 | >10 |
| 193 | 0.3342 |
| 194 | 0.4287 |
| 195 | 0.2078 |
| 196 | 0.2627 |
| 197 | 0.1487 |
| 198 | 0.3483 |
| 199 | 0.6296 |
| 200 | 0.3003 |
| 201 | >10 |
| 202 | 0.8813 |
| 203 | 0.6191 |
| 204 | 0.5689 |
| 205 | 0.8311 |
| 206 | 1.1057 |
| 208 | 9.1259 |
| 210 | 4.0489 |

The invention claimed is:
1. A compound of Formula (I)

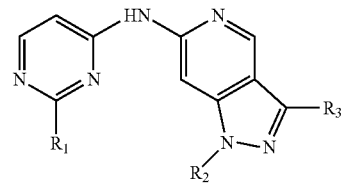

wherein,
R1 is C$_3$-C$_7$heterocycloalkyl, heteroaryl, —O(C$_1$-C$_6$alkyl), or —NR$_a$R$_b$, wherein said C$_3$-C$_7$heterocycloalkyl and heteroaryl may be further substituted with one to five R$_f$ groups;
R2 is hydrogen, C$_3$-C$_7$cycloalkyl, C$_3$-C$_7$heterocycloalkyl or unsubstituted C$_1$-C$_6$alkyl;

R3 is C₁-C₆alkyl, C₃-C₇heterocycloalkyl, C₃-C₇cycloalkyl, —O(C₁-C₆alkyl), CN, —NR$_a$R$_b$, —NHC(O)(C₁-C₃alkyl), —C(O)NR$_a$R$_b$, or heteroaryl; wherein each R$_f$ is independently selected from the group consisting of C₁-C₃alkyl, alkoxy, amino, hydroxy, alkylamino, amide, urea, oxo, halo, pyrazolyl, imidazolyl, triazolyl, CN, —NHC(O)(C₁-C₃alkyl), acyl, sulfonyl, sulfoxide, sulfonamide, sulfoximinyl, —(CH₂)$_m$C₃-C₇heterocycloalkyl, —O(C₁-C₆alkyl), —C(O)OR$_a$; wherein each R$_a$ is independently H or C₁-C₆alkyl, each R$_b$ is independently H, C₁-C₆alkyl, alkoxy, amino, —(CH₂)$_m$C(O)NH₂, —(CH₂)$_m$C₃-C₇cycloalkyl, —(CH₂)$_m$C₃-C₇heterocycloalkyl or —(CH₂)$_m$heteroaryl, or R$_a$ and R$_b$ together may form a C₃-C₇cycloalkyl, C₃-C₇heterocycloalkyl or heteroaryl ring, wherein said C₃-C₇cycloalkyl, C₃-C₇heterocycloalkyl and heteroaryl may each be further substituted with one to three groups selected from the group consisting of halo, hydroxy, C₁-C₃alkyl, amino, oxo, amide, sulfonyl, sulfoxide, sulfoximinyl, sulfonamide, alkoxy, CN and acyl; each m is independently 0, 1, 2 or 3;
or a pharmaceutically acceptable salt thereof.

2. A compound according to claim 1, wherein R1 is C₃-C₇heterocycloalkyl; or a pharmaceutically acceptable salt thereof.

3. A compound according to claim 1, wherein R1 is heteroaryl; or a pharmaceutically acceptable salt thereof.

4. A compound according to claim 1, wherein R1 is —NR$_a$R$_b$; or a pharmaceutically acceptable salt thereof.

5. A compound of claim 1, wherein R1 is heteroaryl or C₃-C₇heterocycloalkyl, R$_f$ is sulfonyl or alkoxy, R3 is —NR$_a$R$_b$ or heteroaryl, R2 is C₁-C₆alkyl, or a pharmaceutically acceptable salt thereof.

6. A compound of claim 5, wherein R1 is piperdinyl or pyrazolyl, or a pharmaceutically acceptable salt thereof.

7. A compound of claim 1, wherein R$_f$ is —SO₂(cyclopropyl), halo, hydroxy, C₁-C₆alkyl or methoxy, or a pharmaceutically acceptable salt thereof.

8. A compound according to claim 1, wherein R2 is unsubstituted C₁-C₆alkyl.

9. A compound according to claim 8, wherein R3 is C₁-C₃alkyl, C₃-C₇heterocycloalkyl, heteroaryl, —NR$_a$R$_b$ or —C(O)NR$_a$R$_b$; or a pharmaceutically acceptable salt thereof.

10. A compound according to claim 1, wherein R1 is a C₃-C₇heterocycloalkyl or heteroaryl selected from the group consisting of piperidinyl and pyrazolyl, wherein said C₃-C₇heterocycloalkyl or heteroaryl may be further substituted with one to three R$_f$ groups selected from C₁-C₆alkyl, alkoxy, hydroxyl, halo, sulfonyl, and sulfonamide; or a pharmaceutically acceptable salt thereof.

11. A compound according claim 1, wherein R2 is isopropyl or sec-butyl; or a pharmaceutically acceptable salt thereof.

12. A pharmaceutical composition comprising a compound of claim 1 and a pharmaceutically acceptable carrier.

13. A method of treating cancer comprising administering to a human in need thereof an effective amount of a compound according to claim 1 or a pharmaceutically acceptable salt thereof in a pharmaceutical composition.

14. A method of claim 13, wherein said cancer is non-small cell lunch cancer.

15. A compound, selected from the group consisting of:
4-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)thiomorpholine 1,1-dioxide;

1-Isopropyl-N-(2-(4-methoxypiperdin-1-yl)pyrimidin-4-yl)-3-(2-oxa-6-azaspiro[3.3]heptan-6-yl)-1H-pyrazolo[4,3-c]pyridine-6-amine;

1-(4-((1-Isopropyl-3-(2-oxa-6-azaspiro[3.3]heptan-6-yl)-1H-pyrazolo[4,3-c]pyridin-6-yl)amino)pyrimidin-2-yl)-3,3-dimethylpiperidin-4-ol;

N-(2-(1-(Cyclopropylmethyl)-1H-pyrazol-4-yl)pyrimidin-4-yl)-1-isopropyl-3-(2-oxa-6-azaspiro[3.3]heptan-6-yl)-1H-pyrazolo[4,3-c]pyridin-6-amine N-(2-(1-(Cyclopropylsulfonyl)-1H-pyrazol-4-yl)pyrimidin-4-yl)-1-isopropyl-3-(2-oxa-6-azaspiro[3.3]heptan-6-yl)-1H-pyrazolo[4,3-c]pyridin-6-amine;

2-((6-((2-(Cyclopropylsulfonyl)-1H-pyrazol-4-yl)pyrimidin-4-yl)amino)-1-isopropyl-1H-pyrazolo[4,3-c]pyridin-3-yl)amino)ethanol;

N-(2-(1-(Cyclopropylsulfonyl)-1H-pyrazol-4-yl)pyrimidin-4-yl)-3-fluoro-1-isopropyl-1H-pyrazolo[4,3-c]pyridin-6-amine;

1-(4-((1-Isopropyl-3-(pyrrolidin-1-yl)-1H-pyrazolo[4,3-c]pyridin-6-yl)amino) pyrimidin-2-yl)-3,3-dimethylpiperidin-4-ol;

N-(2-(1-((Cyclopropylmethyl)-1H-pyrazol-4-yl)pyrimidin-4-yl)-1-isopropyl-3-morpholino-1H-pyrazolo[4,3-c]pyridin-6-amine;

1-(4-((1-Isopropyl-3-(4-methyl-1H-pyrazol-5-yl)-1H-pyrazolo[4,3-c]pyridin-6-yl)amino)pyrimidin-2-yl)-3,3-dimethylpiperidin-4-ol;

1-Isopropyl-6-((2-(4-methoxypiperidin-1-yl)pyrimidin-4-yl)amino)-1H-pyrazolo[4,3-c]pyridine-3-carboxamide;

1-(4-((1-(sec-Butyl)-3-(3-(2-hydroxypropan-2-yl)azetidin-1-yl)-1H-pyrazolo[4,3-c]pyridin-6-yl)amino)pyrimidin-2-yl)-3,3-dimethylpiperidin-4-ol;

2-(1-(1-(sec-Butyl)-6-((2-(1-(cyclopropylsulfonyl)-1H-pyrazol-4-yl)pyrimidin-4-yl)amino)-1H-pyrazolo[4,3-c]pyridin-3-yl)azetidin-3-yl)propan-2-ol;

1-Isopropyl-N-(2-(4-methoxypiperidin-1-yl)pyrimidin-4-yl)-3-(pyrrolidin-1-yl)-1H-pyrazolo[4,3-c]pyridin-6-amine;

N⁶-(2-(1-(Ethylsulfonyl)-1H-pyrazol-4-yl)pyrimidin-4-yl)-1-isopropyl-N³-(oxetan-3-yl)-1H-pyrazolo[4,3-c]pyridine-3,6-diamine;

1-(6-(2-(1-(Ethylsulfonyl)-1H-pyrazol-4-yl) pyrimidin-4-ylamino)-1-isopropyl-1H-pyrazolo[4,3-c] pyridin-3-yl)-N,N-dimethylazetidine-3-carboxamide;

1-(6-(2-(1-(Cyclopropylsulfonyl)-1H-pyrazol-4-yl)pyrimidin-4-ylamino)-1-isopropyl-1H-pyrazolo[4,3-c]pyridin-3-yl) pyrrolidin-3-ol;

N-(2-(1-(Cyclopropylsulfonyl)-1H-pyrazol-4-yl) pyrimidin-4-yl)-1-isopropyl-3-(tetrahydrofuran-3-yl)-1H-pyrazolo [4,3-c] pyridin-6-amine;

(±)-cis-3-Fluoro-1-[4-(1-isopropyl-3-morpholin-4-yl-1H-pyrazolo[4,3-c]pyridin-6-ylamino)pyrimidin-2-yl]piperidin-4-ol;

(±)-cis-3-Fluoro-1-{4-[1-isopropyl-3-(2-oxa-6-azaspiro[3.3]hept-6-yl)-1H-pyrazolo[4,3-c]pyridin-6-ylamino]-pyrimidin-2-yl}piperidin-4-ol;

(±)-1-(6-((2-(cis-3-Fluoro-4-hydroxypiperidin-1-yl)pyrimidin-4-yl)amino)-1-isopropyl-1H-pyrazolo[4,3-c]pyridin-3-yl)imidazolidin-2-one;

(±)-2-(cis-3-Fluoro-4-methoxypiperidin-1-yl)pyrimidin-4-yl]-[1-isopropyl-3-(2-oxa-6-azaspiro[3.3]hept-6-yl)-1H-pyrazolo[4,3-c]pyridin-6-yl]amine;

1-(4-(Aminocyclohexyl)methyl)-N⁶-[2-(4-methoxypiperidin-1-yl)-pyrimidin-4-yl]-1H-pyrazolo[4,3-c]pyridine-3,6-diamine;

1-(1-(sec-Butyl)-6-((2-(1-(cyclopropylsulfonyl)-1H-pyrazol-4-yl)pyrimidin-4-yl)amino)-1H-pyrazolo[4,3-c]pyridin-3-yl)imidazolidin-2-one;
(±)-1-(1-(sec-Butyl)-6-((2-(cis-3-fluoro-4-methoxypiperidin-1-yl)pyrimidin-4-yl)amino)-1H-pyrazolo[4,3-c]pyridin-3-yl)imidazolidin-2-on;
1-(sec-Butyl)-N-(2-(1-(cyclopropylsulfonyl)-1H-pyrazol-4-yl)pyrimidin-4-yl)-3-morpholino-1H-pyrazolo[4,3-c]pyridin-6-amine;
(R)-1-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)pyrrolidine-3-carbonitrile;
N-(2-(1-(Cyclopropylsulfonyl)-1H-pyrazol-4-yl)pyrimidin-4-yl)-1-isopropyl-3-(tetrahydrofuran-3-yloxy)-1H-pyrazolo[4,3-c]pyridin-6-amine;
1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-N-(2-methoxyethyl)azetidine-3-carboxamide;
N-(2-(1-(cyclopropylmethyl)-1H-pyrazol-4-yl)pyrimidin-4-yl)-1-isopropyl-3-(pyrrolidin-1-yl)-1H-pyrazolo[4,3-c]pyridin-6-amine;
N-(2-(1-(cyclopropylmethyl)-1H-pyrazol-4-yl)pyrimidin-4-yl)-1-isopropyl-1H-pyrazolo[4,3-c]pyridin-6-amine;
1-(4-((1-isopropyl-1H-pyrazolo[4,3-c]pyridin-6-yl)amino)pyrimidin-2-yl)-3,3-dimethylpiperidin-4-ol;
1-(4-((1-isopropyl-3-morpholino-1H-pyrazolo[4,3-c]pyridin-6-yl)amino)pyrimidin-2-yl)-3,3-dimethylpiperidin-4-ol;
N6-(2-(1-(cyclopropylsulfonyl)-1H-pyrazol-4-yl)pyrimidin-4-yl)-1-isopropyl-N3-(oxetan-3-yl)-1H-pyrazolo[4,3-c]pyridine-3,6-diamine;
(1-(6-(2-(1-(ethylsulfonyl)-1H-pyrazol-4-yl)pyrimidin-4-ylamino)-1-isopropyl-1H-pyrazolo[4,3-c]pyridin-3-yl)azetidin-3-yl)methanol;
1-(6-(2-(1-(cyclopropylsulfonyl)-1H-pyrazol-4-yl)pyrimidin-4-ylamino)-1-isopropyl-1H-pyrazolo[4,3-c]pyridin-3-yl)azetidin-3-ol;
N6-(2-(1-(ethylsulfonyl)-1H-pyrazol-4-yl)pyrimidin-4-yl)-1-isopropyl-N3-(tetrahydrofuran-3-yl)-1H-pyrazolo[4,3-c]pyridine-3,6-diamine;
(S)—N6-(2-(1-(cyclopropylsulfonyl)-1H-pyrazol-4-yl)pyrimidin-4-yl)-1-isopropyl-N3-(tetrahydrofuran-3-yl)-1H-pyrazolo[4,3-c]pyridine-3,6-diamine;
(R)—N6-(2-(1-(cyclopropylsulfonyl)-1H-pyrazol-4-yl)pyrimidin-4-yl)-1-isopropyl-N3-(tetrahydrofuran-3-yl)-1H-pyrazolo[4,3-c]pyridine-3,6-diamine;
(R)-(1-(6-(2-(1-(cyclopropylsulfonyl)-1H-pyrazol-4-yl)pyrimidin-4-ylamino)-1-isopropyl-1H-pyrazolo[4,3-c]pyridin-3-yl)pyrrolidin-3-yl)methanol;
1-(6-(2-(1-(cyclopropylsulfonyl)-1H-pyrazol-4-yl)pyrimidin-4-ylamino)-1-isopropyl-1H-pyrazolo[4,3-c]pyridin-3-yl)-trans-4-fluoropyrrolidin-3-ol;
1-(6-(2-(1-(cyclopropylsulfonyl)-1H-pyrazol-4-yl)pyrimidin-4-ylamino)-1-isopropyl-1H-pyrazolo[4,3-c]pyridin-3-yl)-4,5-dihydro-1H-imidazol-2-ol;
1-isopropyl-N6-(2-(4-methoxypiperidin-1-yl)pyrimidin-4-yl)-1H-pyrazolo[4,3-c]pyridine-3,6-diamine;
N6-(2-(1-(cyclopropylsulfonyl)-1H-pyrazol-4-yl)pyrimidin-4-yl)-1-isopropyl-1H-pyrazolo[4,3-c]pyridine-3,6-diamine;
N6-(2-(1-(cyclopropylsulfonyl)-1H-pyrazol-4-yl)pyrimidin-4-yl)-N3,1-diisopropyl-1H-pyrazolo[4,3-c]pyridine-3,6-diamine;
3-(6-(2-(1-(cyclopropylsulfonyl)-1H-pyrazol-4-yl)pyrimidin-4-ylamino)-1-isopropyl-1H-pyrazolo[4,3-c]pyridin-3-ylamino)propanamide;
2-(6-(2-(1-(cyclopropylsulfonyl)-1H-pyrazol-4-yl)pyrimidin-4-ylamino)-1-isopropyl-1H-pyrazolo[4,3-c]pyridin-3-ylamino)acetamide;
3-((6-(2-(1-(cyclopropylsulfonyl)-1H-pyrazol-4-yl)pyrimidin-4-ylamino)-1-isopropyl-1H-pyrazolo[4,3-c]pyridin-3-yl)(methyl)amino)propane-1,2-diol;
N-(2-(1-(cyclopropylsulfonyl)-1H-pyrazol-4-yl)pyrimidin-4-yl)-1,3-diisopropyl-1H-pyrazolo[4,3-c]pyridin-6-amine;
N-(2-(1-(cyclopropylsulfonyl)-1H-pyrazol-4-yl)pyrimidin-4-yl)-1-isopropyl-3-morpholino-1H-pyrazolo[4,3-c]pyridin-6-amine;
N6-(2-(1-(cyclopropylsulfonyl)-1H-pyrazol-4-yl)pyrimidin-4-yl)-1-isopropyl-N3-(tetrahydro-2H-pyran-4-yl)-1H-pyrazolo[4,3-c]pyridine-3,6-diamine;
(4-(6-(2-(1-(cyclopropylsulfonyl)-1H-pyrazol-4-yl)pyrimidin-4-ylamino)-1-isopropyl-1H-pyrazolo[4,3-c]pyridin-3-yl)morpholin-2-yl)methanol;
3-(azetidin-1-yl)-N-(2-(1-(cyclopropylsulfonyl)-1H-pyrazol-4-yl)pyrimidin-4-yl)-1-isopropyl-1H-pyrazolo[4,3-c]pyridin-6-amine;
1-(6-(2-(1-(cyclopropylsulfonyl)-1H-pyrazol-4-yl)pyrimidin-4-ylamino)-1-isopropyl-1H-pyrazolo[4,3-c]pyridin-3-yl)azetidine-3-carboxamide;
1-(6-(2-(4-hydroxy-3,3-dimethylpiperidin-1-yl)pyrimidin-4-ylamino)-1-isopropyl-1H-pyrazolo[4,3-c]pyridin-3-yl)-N,N-dimethylazetidine-3-carboxamide;
1-(6-(2-(1-(cyclopropylsulfonyl)-1H-pyrazol-4-yl)pyrimidin-4-ylamino)-1-isopropyl-1H-pyrazolo[4,3-c]pyridin-3-yl)-N,N-dimethylazetidine-3-carboxamide;
(S)-(1-(6-(2-(1-(cyclopropylsulfonyl)-1H-pyrazol-1-yl)pyrimidin-4-ylamino)-1-isopropyl-1H-pyrazolo[4,3-c]pyridin-3-yl)pyrrolidin-3-yl)methanol;
4-(6-(2-(1-(cyclopropylsulfonyl)-1H-pyrazol-4-yl)pyrimidin-4-ylamino)-1-isopropyl-1H-pyrazolo[4,3-c]pyridin-3-yl)piperazin-2-one;
1-(6-(2-(1-(cyclopropylsulfonyl)-1H-pyrazol-4-yl)pyrimidin-4-ylamino)-1-isopropyl-1H-pyrazolo[4,3-c]pyridin-3-yl)pyrrolidine-3-carboxamide;
1-(6-(2-(1-(cyclopropylsulfonyl)-1H-pyrazol-4-yl)pyrimidin-4-ylamino)-1-isopropyl-1H-pyrazolo[4,3-c]pyridin-3-ylamino)-2-methylpropan-2-ol;
N-(2-(1-(cyclopropylsulfonyl)-1H-pyrazol-4-yl)pyrimidin-4-yl)-3-isopropoxy-1-isopropyl-1H-pyrazolo[4,3-c]pyridin-6-amine;
(1-(6-(2-(1-(cyclopropylsulfonyl)-1H-pyrazol-4-yl)pyrimidin-4-ylamino)-1-isopropyl-1H-pyrazolo[4,3-c]pyridin-3-yl)azetidin-3-yl)methanol;
(3RS,4SR)-3-Fluoro-1-{4-[1-isopropyl-3-(2-oxa-6-azaspiro[3.3]hept-6-yl)-1H-pyrazolo[4,3-c]pyridin-6-ylamino]pyrimidin-2-yl)}-4-methylpiperidin-4-ol;
(3R*,4S*)-1-{4-[1-((S)-sec-Butyl)-3-(2-oxa-6-azaspiro[3.3]hept-6-yl)-1H-pyrazolo[4,3-c]pyridin-6-ylamino]pyrimidin-2-yl}-3-fluoro-4-methylpiperidin-4-ol;
(3R*,4S*)-1-{4-[1-((S)-sec-Butyl)-3-(2-oxa-6-azaspiro[3.3]hept-6-yl)-1H-pyrazolo[4,3-c]pyridin-6-ylamino]pyrimidin-2-yl}-3-fluoro-4-methylpiperidin-4-ol;
(3R*,4S*)-1-{4-[1-((S)-sec-Butyl)-3-(2-oxa-6-azaspiro[3.3]hept-6-yl)-1H-pyrazolo[4,3-c]pyridin-6-ylamino]pyrimidin-2-yl}-3-fluoro-4-methylpiperidin-4-ol;
(3R*,4S*)-1-{4-[1-((R)-sec-Butyl)-3-(2-oxa-6-azaspiro[3.3]hept-6-yl)-1H-pyrazolo[4,3-c]pyridin-6-ylamino]pyrimidin-2-yl}-3-fluoro-4-methylpiperidin-4-ol;

(3R*,4S*)-1-{4-[1-((R)-sec-Butyl)-3-(2-oxa-6-azaspiro [3.3]hept-6-yl)-1H-pyrazolo[4,3-c]pyridin-6-ylamino] pyrimidin-2-yl}-3-fluoro-4-methylpiperidin-4-ol;

(3R*,4S*)-1-{4-[1-((S)-sec-Butyl)-3-((R)-3-hydroxypyr rolidin-1-yl)-1H-pyrazolo[4,3-c]pyridin-6-ylamino] pyrimidin-2-yl}-3-fluoro-4-methylpiperidin-4-ol;

(3R*,4S*)-1-{4-[1-((S)-sec-Butyl)-3-((S)-3-hydroxypyr rolidin-1-yl)-1H-pyrazolo[4,3-c]pyridin-6-ylamino] pyrimidin-2-yl}-3-fluoro-4-methylpiperidin-4-ol;

[1-((S)-sec-Butyl)-3-(2-oxa-6-azaspiro[3.3]hept-6-yl)- 1H-pyrazolo[4,3-c]pyridin-6-yl]-[2-(2-methanesulfo nyl-2-methylpropoxy)pyrimidin-4-yl]amine;

3-(6-(2-(1-(Cyclopropylsulfonyl)-1H-pyrazol-4-yl)py rimidin-4-ylamino)-1-isopropyl-1H-pyrazolo[4,3-c] pyridin-3-yl)oxazolidin-2-one;

3-(8-Oxa-3-azabicyclo[3.2.1]octan-3-yl)-N-(2-(1-(cyclo propylsulfonyl)-1H-pyrazol-4-yl)pyrimidin-4-yl)-1- isopropyl-1H-pyrazolo[4,3-c]pyridin-6-amine;

$N^3$-tert-Butyl-$N^6$-(2-(1-(cyclopropylsulfonyl)-1H-pyra zol-4-yl)pyrimidin-4-yl)-1-isopropyl-1H-pyrazolo[4,3- c]pyridine-3,6-diamine;

cis-3-Fluoro-1-(4-(3-((R)-2-(hydroxymethyl)mor pholino)-1-isopropyl-1H-pyrazolo[4,3-c]pyridin-6- ylamino)pyrimidin-2-yl)piperidin-4-ol;

1-(6-(2-(cis-3-Fluoro-4-hydroxypiperidin-1-yl)pyrimi din-4-ylamino)-1-isopropyl-1H-pyrazolo[4,3-c]pyri din-3-yl)-3-methylimidazolidin-2-one;

4-(6-(2-(4-Hydroxy-4-methylpiperidin-1-yl)pyrimidin-4- ylamino)-1-isopropyl-1H-pyrazolo[4,3-c]pyridin-3- ylamino)pyrrolidin-2-one;

2-Hydroxy-1-(4-(6-(2-(4-hydroxy-4-methylpiperidin-1- yl)pyrimidin-4-ylamino)-1-isopropyl-1H-pyrazolo[4, 3-c]pyridin-3-yl)piperazin-1-yl)-2-methylpropan-1- one;

(3RS, 4SR)-3-Fluoro-1-(4-(3-((R)-3-hydroxypyrrolidin- 1-yl)-1-((S*)-1,1,1-trifluoropropan-2-yl)-1H-pyrazolo [4,3-c]pyridin-6-ylamino)pyrimidin-2-yl)-4-methylpi peridin-4-ol;

(±)-1-(4-(1-sec-Butyl-3-(hydroxy-3-(hydroxymethyl) azetidin-1-yl)-1H-pyrazolo[4,3-c]pyridin-6-ylamino) pyrimidin-2-yl)-4-methylpiperidin-4-ol;

2-(1-(4-(1-sec-Butyl-3-((R)-3-hydroxypyrrolidin-1-yl)- 1H-pyrazolo[4,3-c]pyridin-6-ylamino)pyrimidin-2-yl)- 4-methoxypiperidin-4-yl)acetonitrile;

1-(6-(2-(1-(Cyclopropylsulfonyl)-1H-pyrazol-4-yl)py rimidin-4-ylamino)-1-isopropyl-1H-pyrazolo[4,3-c] pyridin-3-yl)-3-methylazetidin-3-ol;

1-(6-(2-(1-(Cyclopropylsulfonyl)-1H-pyrazol-4-yl)py rimidin-4-ylamino)-1-isopropyl-1H-pyrazolo[4,3-c] pyridin-3-yl)-3-methylimidazolidin-2-one;

2-(1-(6-(2-(4-Hydroxy-4-methylpiperidin-1-yl)pyrimi din-4-ylamino)-1-isopropyl-1H-pyrazolo[4,3-c]pyri din-3-yl)azetidin-3-yl)-2-methylpropanamide;

1-(4-(3-(3,3-Difluoro-4-hydroxypyrrolidin-1-yl)-1-iso propyl-1H-pyrazolo[4,3-c]pyridin-6-ylamino)pyrimi din-2-yl)-4-methylpiperidin-4-ol;

4-Amino-1-(6-(2-(4-hydroxy-4-methylpiperidin-1-yl)py rimidin-4-ylamino)-1-isopropyl-1H-pyrazolo[4,3-c] pyridin-3-yl)pyrrolidin-2-one;

4-Methyl-1-[4-[(3-[2-oxa-6-azaspiro[3.3]heptan-6-yl]-1- (1,1,1-trifluoropropan-2-yl)-1H-pyrazolo[4,3-c]pyri din-6-yl)amino]pyrimidin-2-yl]piperidin-4-ol;

(±)-1-(6-(2-(cis-3-Fluoro-4-hydroxypiperidin-1-yl)py rimidin-4-ylamino)-1-isopropyl-1H-pyrazolo[4,3-c] pyridin-3-yl)-4,4-dimethylimidazolidin-2-one;

4-[1-(sec-Butyl)-6-[[2-(4-hydroxy-4-methylpiperidin-1- yl)pyrimidin-4-yl]amino]-1H-pyrazolo[4,3-c]pyridin- 3-yl]-1-imino-4-thiomorpholin-1-one;

1-(1-sec-Butyl-6-(2-(cis-5-fluoro-4-hydroxy-3,3-dimeth ylpiperidin-1-yl)pyrimidin-4-ylamino)-1H-pyrazolo[4, 3-c]pyridine-3-yl)imidazolidin-2-one;

N-(2-(1-(Cyclopropylsulfonyl)-1H-pyrazol-4-yl)pyrimi din-4-yl)-3-(2,5-dimethylpyrrolidin-1-yl)-1-isopropyl- 1H-pyrazolo[4,3-c]pyridin-6-amine;

4-(1-sec-Butyl-6-(2-(4-hydroxy-4-methylpiperidin-1-yl) pyrimidin-4-ylamino)-1H-pyrazolo[4,3-c]pyridin-3-yl) piperazin-2-one;

6-(2-(1-(Cyclopropylsulfonyl)-1H-pyrazol-4-yl)pyrimi din-4-ylamino)-1-isopropyl-1H-pyrazolo[4,3-c]pyri dine-3-carbonitrile;

1-(4-(1-Isopropyl-3-(2-methyltetrahydrofuran-2-yl)-1H- pyrazolo[4,3-c]pyridin-6-ylamino)pyrimidin-2-yl)-4- methylpiperidin-4-ol;

4-(6-(2-(4-Hydroxy-4-methylpiperidin-1-yl)pyrimidin-4- ylamino)-1-isopropyl-1H-pyrazolo[4,3-c]pyridin-3- yl)-2,2-dimethyl-1,2-dihydroimidazol-5-one;

[1-((R)-sec-Butyl)-3-(2-oxa-6-azaspiro[3.3]hept-6-yl)- 1H-pyrazolo[4,3-c]pyridin-6-yl]-[2-(2-methanesulfo nyl-2-methylpropoxy)pyrimidin-4-yl]amine;

[1-(sec-Butyl)-3-(2-oxa-6-azaspiro[3.3]hept-6-yl)-1H- pyrazolo[4,3-c]pyridin-6-yl]-[2-(2-methanesulfonyl-2- methylpropoxy)pyrimidin-4-yl]amine;

1-{1-(sec-Butyl)-6-[2-((3R,4S)-3-fluoro-4-methoxypip eridin-1-yl)pyrimidin-4-ylamino]-1H-pyrazolo[4,3-c] pyridin-3-yl}imidazolidin-2-one;

1-{1-sec-Butyl-6-[2-(2-methanesulfonyl-2-methyl propoxy)pyrimidin-4-ylamino]-1H-pyrazolo[4,3-c] pyridin-3-yl}imidazolidin-2-one;

N4 (1-Isopropyl-3-morpholin-4-yl-1H-pyrazolo[4,3-c] pyridin-6-yl)-N2-(2-methanesulfonyl-2-methylpropyl) pyrimidine-2,4-diamine;

1-{1-sec-Butyl-6-[2-(2-methanesulfonyl-2-methylpropy lamino)pyrimidin-4-ylamino]-1H-pyrazolo[4,3-c]pyri din-3-yl}imidazolidin-2-one;

1-{1-sec-Butyl-6-[2-(4-methanesulfonylpiperidin-1-yl) pyrimidin-4-ylamino]-1H-pyrazolo[4,3-c]pyridin-3- yl}imidazolidin-2-one;

[2-((cis)-(±)-3-Fluoro-4-methoxypiperidin-1-yl)pyrimi din-4-yl]-[1-isopropyl-3-(2-oxa-6-azaspiro[3.3]hept-6- yl)-1H-pyrazolo[4,3-c]pyridin-6-yl]amine;

(3S*,4R*)-3-fluoro-1-(4-((3-(3-hydroxy-3-methylpyrro lidin-1-yl)-1-isopropyl-1H-pyrazolo[4,3-c]pyridin-6- yl)amino)pyrimidin-2-yl)piperidin-4-ol;

(3S*,4R*)-3-fluoro-1-(4-((3-((R)-3-hydroxypyrrolidin-1- yl)-1-isopropyl-1H-pyrazolo[4,3-c]pyridin-6-yl) amino)pyrimidin-2-yl)piperidin-4-ol;

1-(6-(2-(1-(Cyclopropylsulfonyl)-1H-pyrazol-4-yl)py rimidin-4-ylamino)-1-isopropyl-1H-pyrazolo[4,3-c] pyridin-3-yl)pyrrolidin-2-one;

3-((6-((2-(1-(Cyclopropylsulfonyl)-1H-pyrazol-4-yl)py rimidin-4-yl)amino)-1-isopropyl-1H-pyrazolo[4,3-c] pyridin-3-yl)amino)tetrahydrothiophene 1,1-dioxide;

1-(6-(2-(1-(Cyclopropylsulfonyl)-1H-pyrazol-4-yl)py rimidin-4-ylamino)-1-isopropyl-1H-pyrazolo[4,3-c] pyridin-3-yl)-4-methylimidazolidin-2-one;

2-(6-(2-(1-(Cyclopropylsulfonyl)-1H-pyrazol-4-yl)py rimidin-4-ylamino)-1-isopropyl-1H-pyrazolo[4,3-c] pyridin-3-ylamino)propanamide;

4-(6-((2-(1-(Cyclopropylsulfonyl)-1H-pyrazol-4-yl)py rimidin-4-yl)amino)-1-isopropyl-1H-pyrazolo[4,3-c] pyridin-3-yl)thiomorpholine 1-oxide;

4-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)-1-iminothiomorpholine 1-oxide;

7-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)-2,7-diazaspiro[4.4]nonan-1-one;

1-(1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)azetidin-3-yl)ethanol;

(R)-1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)pyrrolidin-3-ol;

7-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)-2,7-diazaspiro[4.4]nonan-3-one;

N-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-2-hydroxy-2-methylpropanamide;

N-(2-(1-(Cyclopropylsulfonyl)-1H-pyrazol-4-yl)pyrimidin-4-yl)-1-isopropyl-3-(3-morpholinoazetidin-1-yl)-1H-pyrazolo[4,3-c]pyridin-6-amine;

N-(2-(1-(Cyclopropylsulfonyl)-1H-pyrazol-4-yl)pyrimidin-4-yl)-3-(4-ethylpiperazin-1-yl)-1-isopropyl-1H-pyrazolo[4,3-c]pyridin-6-amine;

1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)piperidin-4-ol;

N-(2-(1-(Cyclopropylsulfonyl)-1H-pyrazol-4-yl)pyrimidin-4-yl)-1-isopropyl-3-(2-oxa-6-azaspiro[3.4]octan-6-yl)-1H-pyrazolo[4,3-c]pyridin-6-amine;

2-(1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)azetidin-3-yl)acetonitrile;

(1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-3-methylazetidin-3-yl)methanol;

(S)-1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)pyrrolidin-3-ol;

1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-3-(hydroxymethyl)azetidin-3-ol;

N6-(2-(1-(Cyclopropylsulfonyl)-1H-pyrazol-4-yl)pyrimidin-4-yl)-1-isopropyl-N3-(2-(S-methylsulfonimidoyl)ethyl)-1H-pyrazolo[4,3-c]pyridine-3,6-diamine;

N-(2-(1-(Cyclopropylsulfonyl)-1H-pyrazol-4-yl)pyrimidin-4-yl)-1-isopropyl-3-(6-(2,2,2-trifluoroethyl)-2,6-diazaspiro[3.3]heptan-2-yl)-1H-pyrazolo[4,3-c]pyridin-6-amine;

1-(6-(2-(cis-3-Fluoro-4-hydroxypiperidin-1-yl)pyrimidin-4-ylamino)-1-isopropyl-1H-pyrazolo[4,3-c]pyridine-3-yl)-4-methylimidazolidin-2-one;

1-(6-(2-(cis-3-Fluoro-4-hydroxypiperidin-1-yl)pyrimidin-4-ylamino)-1-isopropyl-1H-pyrazolo[4,3-c]pyridin-3-yl)-5-methylimidazolidin-2-one;

(±)cis-3-Fluoro-1-(4-(3-(3-hydroxy-3-(trifluoromethyl)azetidin-1-yl)-1-isopropyl-1H-pyrazolo[4,3-c]pyridin-6-ylamino)pyrimidin-2-yl)piperidin-4-ol;

(±)-cis-3-Fluoro-1-(4-(3-(3-fluoro-3-(hydroxymethyl)azetidin-1-yl)-1-isopropyl-1H-pyrazolo[4,3-c]pyridin-6-ylamino)pyrimidin-2-yl)piperidin-4-ol;

cis-3-Fluoro-1-(4-(3-(trans-3-fluoro-4-hydroxypyrrolidin-1-yl)-1-isopropyl-1H-pyrazolo[4,3-c]pyridin-6-ylamino)pyrimidin-2-yl)piperidin-4-ol;

cis-3-Fluoro-1-(4-(3-((S)-2-(hydroxymethyl)morpholino)-1-isopropyl-1H-pyrazolo[4,3-c]pyridin-6-ylamino)pyrimidin-2-yl)piperidin-4-ol;

(±)-1 (6-(2-(cis-3-Fluoro-4-hydroxypiperidin-1-yl)pyrimidin-4-ylamino)-1-isopropyl-1H-pyrazolo[4,3-c]pyridin-3-yl)pyrrolidin-2-one;

1-(4-(6-(2-(4-Hydroxy-4-methylpiperidin-1-yl)pyrimidin-4-ylamino)-1-isopropyl-1H-pyrazolo[4,3-c]pyridin-3-yl)piperazin-1-yl)propan-1-one;

2-Hydroxy-1-(4-(6-(2-(4-hydroxy-4-methylpiperidin-1-yl)pyrimidin-4-ylamino)-1-isopropyl-1H-pyrazolo[4,3-c]pyridin-3-yl)piperazin-1-yl)ethanone;

2-Hydroxy-1-(4-(6-(2-(4-hydroxy-4-methylpiperidin-1-yl)pyrimidin-4-ylamino)-1-isopropyl-1H-pyrazolo[4,3-c]pyridin-3-yl)piperazin-1-yl)propan-1-one;

1-(6-(2-(4-Hydroxy-4-methylpiperidin-1-yl)pyrimidin-4-ylamino)-1-isopropyl-1H-pyrazolo[4,3-c]pyridin-3-yl)-5-oxopyrrolidine-3-carbonitrile;

6-(6-((2-(4-Hydroxy-1-methylpiperidin-1-yl)pyrimidin-4-yl)amino)-1-isopropyl-1H-pyrazolo[4,3-c]pyridin-3-yl)-2-thia-6-azaspiro[3.3]heptane 2-oxide;

1-(4-(3-(2-(5-Amino-1,3-dioxan-2-yl)ethylamino)-1-isopropyl-1H-pyrazolo[4,3-c]pyridin-6-ylamino)pyrimidin-2-yl)-4-methylpiperidin-4-ol;

(3RS,4SR)-3-Fluoro-1-(4-(3-((R)-3-hydroxypyrrolidin-1-yl)-1-((R*)-1,1,1-trifluoropropan-2-yl)-1H-pyrazolo[4,3-c]pyridin-6-ylamino)pyrimidin-2-yl)-4-methylpiperidin-4-ol;

(±)-cis-3-Fluoro-1-(4-(3-((R)-3-hydroxypyrrolidin-1-yl)-1-((S*)-1,1,1-trifluoropropan-2-yl)-1H-pyrazolo[4,3-c]pyridin-6-ylamino)pyrimidin-2-yl)piperidin-4-ol;

(±)-cis-3-Fluoro-1-(4-(3-((R)-3-hydroxypyrrolidin-1-yl)-1-((R*) 1,1,1-trifluoropropan-2-yl)-1H-pyrazolo[4,3-c]pyridin-6-ylamino)pyrimidin-2-yl)piperidin-4-ol;

1-(4-(3-((R)-3-Hydroxypyrrolidin-1-yl)-1-(1,1,1-trifluoropropan-2-yl)-1H-pyrazolo[4,3-c]pyridin-6-ylamino)pyrimidin-2-yl)-4-methylpiperidin-4-ol;

(3S)-1-(1-sec-Butyl-6-(2-(4-hydroxy-4-methylpiperidin-1l-yl)pyrimidin-4-ylamino)-1H-pyrazolo[4,3-c]pyridin-3-yl)pyrrolidine-3-carboxamide;

(3R)-1-(1-sec-Butyl-6-(2-(4-hydroxy-4-methylpiperidin-1-yl)pyrimidin-4-ylamino)-1H-pyrazolo[4,3-c]pyridin-3-yl)pyrrolidine-3-carboxamide;

1-(4-(1-sec-Butyl-3-(3,3-difluoroazetidin-1-yl)-1H-pyrazolo[4,3-c]pyridin-6-ylamino)pyrimidin-2-yl)-4-methylpiperidin-4-ol;

(4SR,5RS)-1-(4-((1-(sec-Butyl)-3-(2-oxa-6-azaspiro[3.3]heptan-6-yl)-1H-pyrazolo[4,3-c]pyridin-6-ylamino)pyrimidin-2-yl)-5-fluoro-3,3-dimethylpiperidin-4-ol;

cis-5-Fluoro-1-(4-(3-((R)-3-hydroxypyrrolidin-1-yl)-1-isopropyl-1H-pyrazolo[4,3-c]pyridin-6-ylamino)pyrimidin-2-yl)-3,3-dimethylpiperidin-4-ol;

2-(1-(6-(2-(1-(Cyclopropylsulfonyl)-1H-pyrazol-4-yl)pyrimidin-4-ylamino)-1-isopropyl-1H-pyrazolo[4,3-c]pyrindin-3-yl)azetidin-3-yl)propan-2-ol;

3-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-tetrahydropyrimidin-2(1H)-one;

1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-3-ethylimidazolidin-2-one;

N-(2-(1-(Cyclopropylsulfonyl)-1H-pyrazol-4-yl)pyrimidin-4-yl)-1-isopropyl-3-(3-(methoxymethyl)azetidin-1-yl)-1H-pyrazolo[4,3-c]pyridin-6-amine;

2-(1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)azetidin-3-yl)-2-methylpropanenitrile;

N-(2-(1-(Cyclopropylsulfonyl)-1H-pyrazol-4-yl)pyrimidin-4-yl)-3-(3,3-difluoroazetidin-1-yl)-1-isopropyl-1H-pyrazolo[4,3-c]pyridin-6-amine;

1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)azetidine-3-carbonitrile;

1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-N,N-dimethylpyrrolidine-3-carboxamide;

1-(6-(2-(4-Hydroxy-4-methylpiperidin-1-yl)pyrimidin-4-ylamino)-1-isopropyl-1H-pyrazolo[4,3-c]pyridin-3-yl)-3-methylpyrrolidine-3-carboxamide;

(R)-3-Amino-1-(6-(2-(4-hydroxy-4-methylpiperidin-1-yl)pyrimidin-4-ylamino)-1-isopropyl-1H-pyrazolo[4,3-c]pyridin-3-yl)pyrrolidin-2-one;

(S)-3-Amino-1-(6-(2-(4-hydroxy-4-methylpiperidin-1-yl)pyrimidin-4-ylamino)-1-isopropyl-1H-pyrazolo[4,3-c]pyridin-3-yl)pyrrolidin-2-one;

6-(6-((2-(4-Hydroxy-4-methylpiperidin-1-yl)pyrimidin-4-yl)amino)-1-isopropyl-1H-pyrazolo[4,3-c]pyridin-3-yl)-2-thia-6-azaspiro[3.3]heptane 2,2-dioxide;

1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-N-methylazetidine-3-carboxamide;

1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-N-methylazetidine-3-carboxamide;

(1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)azetidin-3-yl)(morpholino)methanone;

(R)-(1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)azetidin-3-yl)(3-hydroxypyrrolidin-1-yl)methanone;

1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-N-(2,2,2-trifluoroethyl)azetidine-3-carboxamide;

(S)-(1-(6-(2-(1-(cyclopropylsulfonyl)-1H-pyrazol-4-yl)pyrimidin-4-ylamino)-1-isopropyl-1H-pyrazolo[4,3-c]pyridin-3-yl)azetidin-3-yl)(3-(hydroxymethyl)pyrrolidin-1-yl)methanone;

(R)-(1-(6-(2-(1-(cyclopropylsulfonyl)-1H-pyrazol-4-yl)pyrimidin-4-ylamino)-1-isopropyl-1H-pyrazolo[4,3-c]pyridin-3-yl)azetidin-3-yl)(3-(hydroxymethyl)pyrrolidin-1-yl)methanone;

8-Oxa-3-azabicyclo[3.2.1]octan-3-yl(1-(6-(2-(1-(cyclopropylsulfonyl)-1H-pyrazol-4-yl)pyrimidin-4-ylamino)-1-isopropyl-1H-pyrazolo[4,3-c]pyridin-3-yl)azetidin-3-yl)methanone;

1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-N-isopropylazetidine-3-carboxamide;

1-(6-(2-(1-(Cyclopropylsulfonyl)-1H-pyrazol-4-yl)pyrimidin-4-ylamino)-1-isopropyl-1H-pyrazolo[4,3-c]pyridin-3-yl)-N-(3-hydroxycyclobutyl)azetidine-3-carboxamide;

1-(6-(2-(4-Hydroxy-4-methylpiperidin-1-yl)pyrimidin-4-ylamino)-1-(1,1,1-trifluoropropan-2-yl)-1H-pyrazolo[4,3-c]pyridin-3-yl)imidazolidin-2-one;

N-(2-(1-Cyclopropylsulfonyl)-1H-pyrazol-4-yl)pyrimidin-4-yl)-3-(2-oxa-6-azaspiro[3.3]heptan-6-yl)-1-(1,1,1-trifluoropropan-2-yl)-1H-pyrazolo[4,3-c]pyridin-6-amine;

(±)-1-(6-(2-(cis)-3-Fluoro-4-hydroxypiperidin-1-yl)pyrimidin-4-ylamino)-1-isopropyl-1H-pyrazolo[4,3-c]pyridin-3-yl)-4-hydroxypyrrolidin-2-one;

(±)-cis-1-(4-(3-(3,3-Difluoroazetidin-1-yl)-1-isopropyl-1H-pyrazolo[4,3-c]pyridin-6-ylamino)pyrimidin-2-yl)-3-fluoropiperidin-4-ol;

(±)-2-(6-((2-((cis)-3-Fluoro-4-hydroxypiperidin-1-yl)pyrimidin-4-yl)amino)-1-isopropyl-1H-pyrazolo[4,3-c]pyridin-3-yl)-2-azaspiro[3.3]heptan-6-ol;

(4S)-1-(1-sec-Butyl-6-(2-(4-hydroxy-4-methylpiperidin-1-yl)pyrimidin-4-ylamino)-1H-pyrazolo[4,3-c]pyridin-3-yl)-4-(hydroxymethyl)imidazolidin-2-one;

1-(4-(3-(cis-3-Amino-4-fluoropyrrolidin-1-yl)-1-sec-butyl-1H-pyrazolo[4,3-c]pyridin-6-ylamino)pyrimidin-2-yl)-4-methylpiperidin-4-ol;

1-(4-(1-sec-Butyl-3-(trans-3-fluoro-4-hydroxypyrrolidin-1-yl)-1H-pyrazolo[4,3-c]pyridin-6-ylamino)pyrimidin-2-yl)-4-methylpiperidin-4-ol;

2-(6-(2-(cis-3-Fluoro-4-hydroxypiperidin-1-yl)pyrimidin-4-ylamino)-1-isopropyl-1H-pyrazolo[4,3-c]pyridin-3-ylamino)propanenitrile;

N-(2-(1-(Cyclopropylsulfonyl)-1H-pyrazol-4-yl)pyrimidin-4-yl)-3-(3,5-dimethylmorpholino)-1-isopropyl-1H-pyrazolo[4,3-c]pyridin-6-amine;

N6-(2-(1-(cyclopropylsulfonyl)-1H-pyrazol-4-yl)pyrimidin-4-yl)-1-isopropyl-N3-(2,2,2-trifluoroethyl)-1H-pyrazolo[4,3-c]pyridine-3,6-diamine;

(±)-2-(6-(2-(cis-3-Fluoro-4-hydroxypiperidin-1-yl)pyrimidin-4-ylamino)-1-isopropyl-1H-pyrazolo[4,3-c]pyridin-3-ylamino)-2-methylpropanamide;

(±)-2-(6-(2-(cis-3-Fluoro-4-hydroxypiperidin-1-yl)pyrimidin-4-ylamino)-1-isopropyl-1H-pyrazolo[4,3-c]pyridin-3-ylamino)-2-methylpropanenitrile;

1-(4-(3-(4-Amino-3,3-difluoropyrrolidin-1-yl)-1-sec-butyl-1H-pyrazolo[4,3-c]pyridin-6-ylamino)pyrimidin-2-yl)-4-methylpiperidin-4-ol;

(3S)-1-(1-sec-Butyl-6-(2-(1-(cyclopropylsulfonyl)-1H-pyrazol-4-yl)pyrimidin-4-ylamino)-1H-pyrazolo[4,3-c]pyridin-3-yl)-3-hydroxypyrrolidin-2-one;

(3R)-1-(1-sec-Butyl-6-(2-(1-(cyclopropylsulfonyl)-1H-pyrazol-4-yl)pyrimidin-4-ylamino)-1H-pyrazolo[4,3-c]pyridin-3-yl)-3-hydroxypyrrolidin-2-one;

(2S)-1-(4-(1-sec-Butyl-6-(2-(1-(cyclopropylsulfonyl)-1H-pyrazol-4-yl)pyrimidin-4-ylamino)-1H-pyrazolo[4,3-c]pyridin-3-yl)piperazin-1-yl)-2-hydroxypropan-1-one;

(2R)-1-(4-(1-sec-Butyl-6-(2-(1-(cyclopropylsulfonyl)-1H-pyrazol-4-yl)pyrimidin-4-ylamino)-1H-pyrazolo[4,3-c]pyridin-3-yl)piperazin-1-yl)-2-hydroxypropan-1-one;

(4S)-1-(1-sec-Butyl-6-(2-(1-(cyclopropylsulfonyl)-1H-pyrazol-4-yl)pyrimidin-4-ylamino)-1H-pyrazolo[4,3-c]pyridin-3-yl)-4-(hydroxymethyl)imidazolidin-2-one;

1-(1-(1-sec-Butyl-6-(2-(1-(cyclopropylsulfonyl)-1H-pyrazol-4-yl)pyrimidin-4-ylamino)-1H-pyrazolo[4,3-c]pyridin-3-yl)azetidin-3-yl)ethanol;

(±)-1-(6-(2-(4-Hydroxy-4-methylpiperidin-1-yl)pyrimidin-4-ylamino)-1-isopropyl-1H-pyrazolo[4,3-c]pyridin-3-yl)pyrrolidine-cis-3,4-diol;

(3S,4S)-1-(6-(2-(4-Hydroxy-4-methylpiperidin-1-yl)pyrimidin-4-ylamino)-1-isopropyl-1H-pyrazolo[4,3-c]pyridin-3-yl)pyrrolidine-3,4-diol;

(3S,4R)-1-((1-((R*)-sec-Butyl)-3-(3-(2-hydroxypropan-2-yl)azetidin-1-yl)-1H-pyrazolo[4,3-c]pyridin-6-yl)amino)pyrimidin-2-yl)-3-fluoropiperidin-4-ol;

(3S,4R)-1-((1-((S*)-sec-Butyl)-3-(3-(2-hydroxypropan-2-yl)azetidin-1-yl)-1H-pyrazolo[4,3-c]pyridin-6-yl)amino)pyrimidin-2-yl)-3-fluoropiperidin-4-ol;

1-(1-(sec-Butyl)-6-((2-((3R,4S)-3-fluoro-4-hydroxypiperidin-1-yl)pyrimidin-4-yl)amino)-1H-pyrazolo[4,3-c]pyridin-3-yl)imidazolidin-2-one;

(3R,4S)-1-(4-((1-(sec-Butyl)-3-((R)-3-hydroxypyrrolidin-1-yl)-1H-pyrazolo[4,3-c]pyridin-6-yl)amino)pyrimidin-2-yl)-3-fluoropiperidin-4-ol;

(3S,4R)-1-(4-((1-((R*)-sec-Butyl)-3-(2-oxa-6-azaspiro[3.3]heptan-6-yl)-1H-pyrazolo[4,3-c]pyridin-6-yl)amino)pyrimidin-2-yl)-3-fluoropiperidin-4-ol;

(3S,4R)-1-(4-((1-((S*)-sec-Butyl)-3-(2-oxa-6-azaspiro[3.3]heptan-6-yl)-1H-pyrazolo[4,3-c]pyridin-6-yl)amino)pyrimidin-2-yl)-3-fluoropiperidin-4-ol;

(S)-1-(6-((2-(1-(Cyclopropylsulfonyl)-1H-pyrazol-4-yl)pyrimidin-4-yl)amino)-1-isopropyl-1H-pyrazolo[4,3-c]pyridin-3-yl)-3-hydroxypyrrolidin-2-one;

1-(1-(sec-Butyl)-6-((2-((3S,4R)-3-fluoro-4-hydroxypiperidin-1-yl)pyrimidin-4-yl)amino)-1H-pyrazolo[4,3-c]pyridin-3-yl)pyrrolidin-2-one;

(3S)-1-(1-(sec-Butyl)-6-((2-((3S,4R)-3-fluoro-4-hydroxypiperidin-1-yl)pyrimidin-4-yl)amino)-1H-pyrazolo[4,3-c]pyridin-3-yl)-3-hydroxypyrrolidin-2-one;

1-(4-((1-(sec-Butyl)-3-(2-oxa-6-azaspiro[3.3]heptan-6-yl)-1H-pyrazolo[4,3-c]pyridin-6-yl)amino)pyrimidin-2-yl)-4-methylpiperidin-4-ol;

1-(4-((1-(sec-Butyl)-3-((R)-3-hydroxypyrrolidin-1-yl)-1H-pyrazolo[4,3-c]pyridin-6-yl)amino)pyrimidin-2-yl)-4-methylpiperidin-4-ol;

1-(1-(sec-Butyl)-6-((2-(4-hydroxy-4-methylpiperidin-1-yl)pyrimidin-4-yl)amino)-1H-pyrazolo[4,3-c]pyridin-3-yl)pyrrolidin-2-one;

(R)-1-(4-((3-(3-Hydroxypyrrolidin-1-yl)-1-isopropyl-1H-pyrazolo[4,3-c]pyridin-6-yl)amino)pyrimidin-2-yl)-4-methylpiperidin-4-ol;

(3R)-1-(1-(sec-Butyl)-6-((2-(4-(methyl sulfonyl)piperidin-1-yl)pyrimidin-4-yl)amino)-1H-pyrazolo[4,3-c]pyridin-3-yl)pyrrolidin-3-ol;

9-(4-((1-((S*)-sec-Butyl)-3-((R)-3-hydroxypyrrolidin-1-yl)-1H-pyrazolo[4,3-c]pyridin-6-yl)amino)pyrimidin-2-yl)-1-oxa-4,9-diazaspiro[5.5]undecan-3-one;

9-(4-((1-((R*)-sec-Butyl)-3-((R)-3-hydroxypyrrolidin-1-yl)-1H-pyrazolo[4,3-c]pyridin-6-yl)amino)pyrimidin-2-yl)-1-oxa-4,9-diazaspiro[5.5]undecan-3-one;

(S*)-1-(4-((1-((S*)-sec-Butyl)-3-((R)-3-hydroxypyrrolidin-1-yl)-1H-pyrazolo[4,3-c]pyridin-6-yl)amino)pyrimidin-2-yl)-3-methylpyrrolidine-3-carboxamide; and (S*)-1-(4-((1-((R*)-sec-Butyl)-3-((R)-3-hydroxypyrrolidin-1-yl)-1H-pyrazolo[4,3-c]pyridin-6-yl)amino)pyrimidin-2-yl)-3-methylpyrrolidine-3-carboxamide.

* * * * *